United States Patent
Reiter et al.

(12)

(10) Patent No.: US 6,541,212 B2
(45) Date of Patent: *Apr. 1, 2003

(54) METHODS FOR DETECTING PROSTATE STEM CELL ANTIGEN PROTEIN

(75) Inventors: Robert E. Reiter, Los Angeles, CA (US); Owen N. Witte, Sherman Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/564,329

(22) Filed: May 3, 2000

(65) Prior Publication Data

US 2001/0055751 A1 Dec. 27, 2001

Related U.S. Application Data

(63) Continuation-in-part of application No. 09/359,326, filed on Jul. 20, 1999, which is a continuation-in-part of application No. 09/318,503, filed on May 25, 1999, now Pat. No. 6,261,791, which is a continuation-in-part of application No. 09/251,835, filed on Feb. 17, 1999, now Pat. No. 6,261,789, which is a continuation-in-part of application No. 09/203,939, filed on Dec. 2, 1998, now Pat. No. 6,258,939, which is a continuation-in-part of application No. 09/038,261, filed on Mar. 10, 1998, now Pat. No. 6,267,960.

(60) Provisional application No. 60/228,816, filed on Mar. 10, 1997, provisional application No. 60/071,141, filed on Jan. 12, 1998, provisional application No. 60/074,675, filed on Feb. 13, 1998, provisional application No. 60/113,230, filed on Dec. 21, 1998, provisional application No. 60/120,536, filed on Feb. 17, 1999, and provisional application No. 60/124,658, filed on Mar. 16, 1999.

(51) Int. Cl.$^7$ ............................................... G01N 33/53
(52) U.S. Cl. .................... 435/7.1; 435/7.94; 530/388.8; 530/388.85
(58) Field of Search .................... 435/7.1, 7.92, 435/7.21, 7.23, 7.94, 188; 530/387.1, 388.1, 388.8, 388.85, 389.1, 391.3

(56) References Cited

U.S. PATENT DOCUMENTS 5,728,815 A * 3/1998 Chung et al.

FOREIGN PATENT DOCUMENTS

| WO | WO 98/00540 | | 1/1998 |
|----|----|----|----|
| WO | WO-98/40403 | * | 9/1998 |
| WO | WO 98/51805 | | 11/1998 |
| WO | WO 98/51824 | | 11/1998 |

OTHER PUBLICATIONS

Paul, Fundamental Immnology, Raven Press, Chapter 8, p. 242, 1993.*

Arlen, Myron et al., "Immunotherapy of Colon Cancer Using Chimeric mAb 31.1," *Critical Review in Immunology*, 1998, 18:133–8. (Exhibit 2).

Arthur, Jill F. et al., "A Comparison of Gene Transfer Methods in Human Dendritic Cells," *Cancer Gene Therapy*, 1997, 4:17–25. (Exhibit 3).

Ashley, David M. et al., "Bone Marrow–generated Dendritic Cells Pulsed with Tumor Extracts or Tumor RNA Induce Antitumor Immunity against Central Nervous System Tumors," *Journal of Experimental Medicine*, Oct. 6, 1997, 186:1177–82 (Exhibit 4).

Bamezai, Anil and Kenneth L. Rock, "Overexpressed Ly–6A.2 Mediates Cell–Cell Adhesion by Binding a Ligand Expressed on Lymphoid Cells," *Proc Nat'l Acad Sci USA*, May 1995, 92:4294–8. (Exhibit 5).

Brakenhoff, Ruud H. et al., "The Human E48 Antigen, Highly Homologous to the Murine Ly–6 Antigen ThB, is a GPI–anchored Molecule Apparently Involved in Keratinocyte Cell–Cell Adhesion," *Journal of Cell Biology*, Jun. 1995, 129:1677–89. (Exhibit 6).

Braun, Benjamin S. et al., "Identification of Target Genes for the Ewing's Sarcoma EWS/FLI Fusion Protein by Representational Difference Analysis," *Molecular and Cell Biology*, Aug. 1995, 15:4623–30. (Exhibit 7).

Cher, Michael L. et al., "Comparative Genomic Hybridization, Allelic Imbalance, and Fluorescence In Situ Hybridization on Chromosome 8 in Prostate Cancer," *Genes, Chromosomes & Cancer*, 1994, 11:153–62. (Exhibit 8).

Cohen, Stanley N. et al., "Nonchromosomal Antibiotic Resistance in Bacteria: Genetic Transformation of *Escherichia coli* by R–Factor DNA," *Proc. Nat'l Acad Sci USA*, Aug. 1972, 69:2110–4. (Exhibit 9).

Cupp, Michael R. and Osterling, Joseph E., "Prostate–Specific Antigen, Digital Rectal Examination and Transrectal Ultrasonography: Their Roles in Diagnosing Early Prostate Cancer," *Mayo Clinic Proceedings*, Mar. 1993, 68:297–306. (Exhibit 10).

Deleersnijder, Willy et al., "Isolation of Markers for Chondro–osteogenic Differentiation Using cDNA Library Subtraction," *Journal of Biological Chemistry*, Aug. 9, 1996, 271:19475–82. (Exhibit 11).

Fields, Stanley and Ok–kyu Song, "A Novel Genetic System to Detect Protein–Protein Interactions," *Nature*, Jul. 20, 1989, 340:245–6. (Exhibit 12).

(List continued on next page.)

*Primary Examiner*—Sheela Huff
*Assistant Examiner*—Larry R. Helms
(74) *Attorney, Agent, or Firm*—Mandel & Adriano

(57) ABSTRACT

The invention provides a novel prostate cell-surface antigen, designated Prostate Stem Cell Antigen (PSCA), which is widely over-expressed across all stages of prostate cancer, including high grade prostatic intraepithelial neoplasia (PIN), androgen-dependent and androgen-independent prostate tumors. The invention also provides a method for detecting a Prostate Stem Cell Antigen (PSCA) protein of bone (SEQ ID NO:2), comprising obtaining a sample; contacting the sample with an antibody that recognizes and binds the PSCA protein; and, detecting binding of the antibody with the PSCA protein in the sample.

13 Claims, 69 Drawing Sheets

OTHER PUBLICATIONS

Fong, Lawrence et al., "Induction of Tissue–Specific Autoimmune Prostatitis with Prostatic Acid Phosphatase Immunization Implications for Immunotherapy of Prostate Cancer," *Journal of Immunology*, 1997, 159:3113–7. (Exhibit 13).

Foon, Kenneth A. et al., "Immune Response to the Carcinoembryonic Antigen in Patients Treated with an Anti–Idiotype Antibody Vaccine," *Journal of Clinical Investigation*, Jul. 1995, 96:334–42. (Exhibit 14).

Fritz, Benjamin A. and Anson W. Lowe, "Polarized GP2 Secretion in MDCK Cells Via GPI Targeting and Apical Membrane–Restricted Proteolysis," *American Journal of Physiology*, Jan. 1996, 270:G176–83. (Exhibit 15).

Funakoshi, Satoshi et al., "Differential In Vitro and In Vivo Antitumor Effects Mediated by Anti–CD40 and AntiCD20 Monoclonal Antibodies Against Human B–Cell Lymphomas," *Journal of Immunotherapy*, 1996, 19(2):93–101. (Exhibit 16).

Graham, F. L. and A. J. Van Der Eb, "A New Technique for the Assay of Infectivity of Human Adenovirus 5 DNA," *Virology*, 1973, 52:456–67. (Exhibit 17).

Liu, He et al., "Constitutive and Antibody–induced Internalization of Prostate–specific Membrane Antigen," *Cancer Research*, Sep. 15, 1998, 58:4055–60 (Exhibit 18).

Henderson, Robert A. et al., "Human Dendritic Cells Genetically Enginerred to Express High Levels of the Human Epithelial Tumor Antigen Mucin (MUC–1)," *Cancer Research*, Aug. 15, 1996, 56:3763–70. (Exhibit 19).

Herlyn, Dorothee et al., "Anti–Idiotype Cancer Vaccines: Past and Future," *Cancer Immunology Immunotherapy*, 1996, 43:65–76. (Exhibit 20).

Hodge, James W. et al., "A Recombinant Vaccinia Virus Expressing Human Prostate–Specific Antigen (PSA): Safety and Immunogenicity in a Non–Human Primate," *International Journal of Cancer*, 1995, 63:231–7 (Exhibit 21).

Israeli, Ron S. et al., "Molecular Cloning of a Complementary DNA Encoding a Prostate–specific Membrane Antigen," *Cancer Research*, Jan. 15, 1993, 53:227–30. (Exhibit 22).

Jenkins, Robert B. et al., "Detection of c–myc Oncogene Amplification and Chromosomal Anomalies in Metastatic Prostatic Carcinoma by Fluorescence in Situ Hybridizaion," *Cancer Research*, Feb. 1, 1997, 57:524–31. (Exhibit 23).

Kasprzyk, Philip G. et al., "Therapy of an Animal Model of Human Gastric Cancer Using a Combination of Anti–erbB–2 Monoclonal Antibodies," *Cancer Research*, May 15, 1992, 52:2771–6. (Exhibit 24).

Katz, Ben–Zion et al., "An Association between High Ly–6A/E Expression on Tumor Cells and a Highly Malignant Phenotype," *International Journal of Cancer*, 1994, 59:684–91. (Exhibit 25).

Kieffer, Bruno et al., "Three–Dimensional Solution Structure of the Extracellular Region of the Complement Regulatory Protein CD59, a New Cell–Surface Protein Domain Related to Snake Venom Neurotoxins," *Biochemistry*, 1994: 33:4471–82. (Exhibit 26).

Klein, Karen A. et al., "Progression of Metastatic Human Prostate Cancer to Androgen Independence in Immunodeficient SCID Mice," *Nature Medicine*, Apr. 1997, 3:402–8. (Exhibit 27).

Lalani, El–Nasir et al., "Molecular and Cellular Biology of Prostate Cancer," *Cancer and Metastasis Reviews*, 1997, 16:29–66. (Exhibit 28).

Lee, Cheryl T. and Joseph E. Oesterling, "Cancer of the Prostate: Diagnosis and Staging," *Urologic Oncology*, 1997, W. B. Saunders Company, Philadelphia, 357–77. (Exhibit 29).

Magi–Galluzzi, C. et al., "Mitogen–Activated Protein Kinase Phosphatase 1 is Overexpresed in Prostate Cancers and is Inversly Related to Apoptosis," *Laboratory Investigation*, Jan. 1997, 76:37–51. (Exhibit 30).

Mao Mao et al., "RIG–E, a Human Homolog of the Murine Ly–6 Family, is Induced by Retinoic Acid During the Differentiation of Acute Promyelocytic Leukemia Cell," *Proc Nat'l Acad Sci USA*, Jun. 1996, 93:5910–4. (Exhibit 31).

Mount, Peter F. et al., "Chimeric (Mouse/Human) Anti–Colon Cancer Antibody c30.6 Inhibits the Growth of Human Colorectal Cancer Xenografts in scid/scid Mice," *Cancer Research*, Dec. 1, 1994, 54:6160–6. (Exhibit 32).

Noda, Satoshi et al., "Protection form Anti–TCR/CD3–induced Apoptosis in Immature Thymocytes by a Signal through Thymic Shared Antigen–1/Stem Cell Antigen–2," *Journal of Experimental Medicine*, May 1996, 183:2355–60. (Exhibit 33).

Ozaki, Shuji et al., "Immunotherapy of Multiple Myeloma with a Monoclonal Antibody Directed Against a Plasma Cell–Specific Antigen, HMI.24," *Blood*, Oct. 15, 1997, 90:3179–3186. (Exhibit 34).

Qian, Junqi et al., "Chromosomal Anomalies in Prostatic Intrepithelial Neoplasia and Carcinoma Detected by Fluorescence in Situ Hybridization," *Cancer Research*, Nov. 15, 1995, 55:5408–14. (Exhibit 35).

Restifo, Nicholas P., "The New Vaccines: Building Viruses That Elicit Antitumor Immunity," *Current Opinion in Immunology*, Oct. 1996, 8:658–63. (Exhibit 36).

Ribas, Antoni et al., "Genetic Immunization for the Melanoma Antigen MART–1/Melan–A Using Recombinant Adenovirus–transduced Murine Dendritic Cells," *Cancer Research*, Jul. 15, 1997, 57:2865–9. (Exhibit 37).

Rowley, Janet D. et al., "Mapping Chromosome Band 11q23 in Human Acute Leukemia with Biotinylated Probes: Identification of 11q23 Translocation Breakpoints with a Yeast Artificial Chromosome," *Proc Natl Acad Sci USA*, Dec. 1990, 87:9358–62. (Exhibit 38).

Shepard, H. Michael et al., "Monoclonal Antibody Therapy of Human Cancer: Taking the HER2 Proto–oncogene to the Clinic," *Journal of Clinical Immunology*, 1991, 11:117–27. (Exhibit 39).

Southern, P. J. and P. Berg, "Transformation of Mammalian Cells to Antibiotic Resistance with a Bacterial Gene Under Control of the SV40 Early Region Promoter," *Journal of Molecular and Applied Genetics*, 1982, 1:327–41. (Exhibit 40).

Southern, E. M., "Detection of Specific Sequences Among DNA Fragments Separated by Gel Electrophoresis," *Journal of Molecular Biology*, 1975, 98:503–17. (Exhibit 41).

Thomas, Pamela M. and Lawrence E. Samelson, "The Glycophosphatidylinositol–anchored Thy–1 Molecule Interacts with the p60$^{fyn}$ Protein Tyrosine Kinase in T Cells," *The Journal of Biological Chemistry*, Jun. 15, 1992, 267:12317–22. (Exhibit 42).

Thorpe, Philip E. and Walter C. J. Ross, "The Preparation and Cytotoxic Properties of Antibody–Toxin Conjugates," *Immunological Review*, 1982, 52:119–58. (Exhibit 43).

Towbin, Harry et al., "Electrophoretic Transfer of Proteins from polyacrylamide Gels to Nitrocellulose Sheets: Procedure and Some Applications," *Proc Nat'l Acad Sci USA*, Sep. 1979, 76:4350–4. (Exhibit 44).

Tsunenari, Toshiaki et al., "New Xenograft Model of Multiple Myeloma and Efficacy of a Humanized Antibody Against Human Interleukin–6 Receptor," *Blood*, Sep. 15, 1997, 90:2437–44. (Exhibit 45).

Udenfriend, Sidney and Krishna Kodukula, "How Glycosyl–Phosphatidylinositol–Anchored Membrane Proteins Are Made," *Annual Review of Biochemistry*, 1995, 64:563–91. (Exhibit 46).

Veis, Deborah J. et al., "Bcl–2–Deficient Mice Demonstrate Fulminant Lymphoid Apoptosis, Polycystic Kidneys and Hypopigmented Hair," *Cell*, Oct. 22, 1993, 75:229–40. (Exhibit 47).

Velders, Markwin P. et al., "Immunotherapy with Low and High Affinity Monoclonal Antibodies 17–1A and 323/A3 in a Nude Mouse Xenograft Carcinoma Model," *Cancer Research*, Oct. 1, 1995, 55:4398–4403 (Exhibit 48).

Wagner, U. et al., "Immunological Responses to the Tumor–Associated Antigen CA 125 in Patients with Advanced Ovarian Cancer Induced by the Murine Monoclonal Anti––Idiotype Vaccine ACA 125," *Hybridoma*, 1997, 16:33–40 (Exhibit 49).

Wigler, Micheal et al., "DNA–Mediated Transfer of the Adenine Phosphoribosyltransferase Locus Into Mammalian Cells," *Proc Nat'l Acad Sci USA*, Mar. 1979, 76:1373–6. (Exhibit 50).

Yang, Yongmin et al., "Differential Expression of Cytokeratin mRNA and Protein in Normal Prostate, Prostatic Intraepithelial Neoplasia and Invasive Carcinoma," *American Journal of Pathology*, Feb. 1997, 150:693–704. (Exhibit 51).

Zhong, Rui–kun et al., "Evaluation of Monoclonal Antibody–Mediated Anti–Acute Myeloid Leukemia Immunotherapy in a SCID/hu Model," *Leukemia Research*, 1996, 20:581–9. (Exhibit 52).

Boulianne, Gabrielle L. et al., "Productions of Functional Chimeric Mouse/Human Antibody," *Nature*, Dec. 1984, 312:643–6. (Exhibit 53).

Fell, H. Perry et al., "Homologous Recombination in Hybridoma Cells: Heavy Chain Chimeric Antibody Produced by Gene Targeting," *Proc. Natl. Acad. Sci. USA*, Nov. 1989, 86:8507–11. (Exhibit 54).

Hellstrom, Ingegerd et al., "Strong Antitumor Activities of IgG3 Antibodies to a Human Melanoma–Associated Ganglioside," *Proc. Natl. Acad. Sci. USA*, Mar. 1985, 82:1499–1502. (Exhibit 55).

Hellstrom, Karl Erik and Ingegerd Hellstrom, "Antibody for Drug Delivery," in Robinson et al., eds, *Controlled Drug Delivery*, 2$^{nd}$ edition, Marcel Dekker, Inc. 1987, 623–53. (Exhibit 56).

Neuberger, Michael S. et al., "Recombinant Antibodies Possessing Novel Effector Functions," *Nature*, Dec. 13, 1984, 312:604–8. (Exhibit 57).

Sahagan, Barbara G. et al., "A Genetically Engineered Murine/Human Chimeric Antibody Retains Specificity for Human Tumor–Associated Antigen," *The Journal of Immunology*, Aug. 1, 1986. 137:1066–74. (Exhibit 58).

Sharon, J. et al., "Expression of $V_H C_K$ Chimeric Protein in Mouse Myeloma Cells," *Nature*, May 1984, 309:364–7. (Exhibit 59).

Shizuya, Hiroaki et al., "Cloning and Stable Maintenance of 300–Kilobase–Pair Fragments of Human DNA in *Escherichia coli* Using an F–Factor–Based Vector," *Proc. Natl. Acad. Sci. USA*, Sep. 1992, 89:8994–7. (Exhibit 60).

Tan, Lee K. et al., "A Human–Mouse Chimeric Immunoglobulin Gene With a Human Variable Region is Expressed in Mouse Myeloma Cells," *The Journal of Immunology*, Nov. 1985, 135:3564–7. (Exhibit 61).

Vitetta, Ellen S. et al., "Immunotoxin Therapy," in De Vita Jr., V.T. et al., eds, Cancer: Principles and Practice of Oncology, 4$^{th}$ edition, J.B. Lippincott Co., Philadelphia 1993, 2624–2636. (Exhibit 62).

Algate, Paul A. et al., "Regulation of the Interleukin–3 (IL–3) Receptor by IL–3 in the Fetal Liver–Derived FL5.12 Cell Line," *Blood*, May 1994, 83(9):2459–68. (Exhibit 63).

Arnon, Ruth et al., "Monoclonal Antibodies for Immunotargeting of Drugs in Cancer Therapy," *Monoclonal Antibodies and Cancer Therapy*, Reisfield, Ralph A. and Stewart Sell (eds.) 1985, 243–56. (Exhibit 64).

Bacchetti, Silvia and Frank L. Graham, "Transfer of the Gene for Thymidine Kinase to Thymidine Kinase–Deficient Human Cells by Purified Herpes Simplex Viral DNA," *Proc. Natl. Acad. Sci. USA*, Apr. 1977, 74(4):1590–4. (Exhibit 65).

Berent, Susan L. et al., "Comparison of Oligonucleotide and Long DNA Fragments as Probes in DNA and RNA Dot, Southeran, Northern, Colony and Plaque Hybridizations," *BioTechniques*, May/Jun. 1985, 3:208–19. (Exhibit 66).

Bekner, kathleen L., "Development of Adenovirus Vectors for the Expression of Heterologous Genes," *BioTechniques*, Jul./Aug. 1988, 6(7):616–29. (Exhibit 67).

Bonkhoff, Helmut and Klaus Remberger, "Differentiation Pathways and Histogenetic Aspects of Normal and Abnormal Prostatic Growth: A Stem Cell Model," *The Prostate*, Feb. 1996, 28(2):98–106. (Exhibit 68).

Bonkhoff, Helmut et al., "The Proliferative Function of Basal Cells in the Normal and Hyperplastic Human Prostate," *The Prostate*, Jan. 1994, 24(1):114–8. (Exhibit 69).

Boshart, Michael et al., "A Very Strong Enhancer is Located Upstream of an Immediate Early Gene of Human Cytomegalovirus," *Cell*, Jun. 1985, 41(2):521–30. (Exhibit 70).

Breviario, Ferruccio et al., "Interleukin–1–Inducible Genes in Endothelial Cells Cloning of a New Gene Related to C–Reactive Protein and Serum Amyloid P Component," *The Journal of Biological Chemistry*, Nov. 5, 1992, 267(31):22190–7. (Exhibit 71).

Brinster, Ralph L. et al., "Transgenic Mice Harboring SV40 T–Antigen Genes Develop Characteristic Brain Tumors," *Cell*, Jun. 1984, 37:367–79. (Exhibit 72).

Brinster, Ralph L. et al., "Introns Increase Transcriptional Efficiency in Transgenic Mice," *Proc. Natl. Acad. Sci. USA*, Feb. 1988, 85:836–40. (Exhibit 73).

Cluitmans, F.H.M. et al., "IL–4 Down–Regulates IL–2–, IL–3–, and GM–CSF–Induced Cytokine Gene Expression in Peripheral Blood Monocytes," *Annals of Hematology*, 1994, 68:293–8. (Exhibit 74).

De Wit, Harry et al., "Differential Regulation of M–CSF and IL–6 Gene Expression in Monocytic Cells," *British Journal of Hematology*, 1994, 86:259–64. (Exhibit 75).

DePamphilis, M.L. et al., "Microinjecting DNA into Mouse Ova to Study DNA Replication and Gene Expression and to Produce Transgenic Animals," *BioTechniques*, Jul./Aug. 1988, 6(7):662–80. (Exhibit 76).

Espinoza–Delgado, Igor et al., "Regulation of IL–2 Receptor Subunit Genes in Human Monocytes Differential Effects of IL–2 and IFN–γ," *The Journal of Immunology,* Nov. 1, 1992, 149(9):2961–8. (Exhibit 77).

Felgner, Philip L. et al., "Lipofection: A Highly Efficient, Lipid–Mediated DNA–Transfection Procedure," *Proc. Natl. Acad. Sci. USA,* Nov. 1987, 84:7413–7. (Exhibit 78).

Felgner, P.L. et al., "Cationic Liposome Mediated Transfection," *Proceedings of the Western Pharmacology Society,* 1989, 32:115–21. (Exhibit 79).

Freireich, Emil J. et al., "Quantitative Comparison of Toxicity of Anticancer Agents in Mouse, Rat, Hamster, Dog, Monkey and Man," *Cancer Chemotherapy Reports,* May 1966, 50(4):219–44. (Exhibit 80).

Gao, Xiang et al., "Diagnostic and Prognostic Markers for Human Prostate Cancer," *The Prostate,* Apr. 1, 1997, 31:264–81. (Exhibit 81).

Garabedian, Emily M. et al., "A Transgenic Mouse Model of Metastatic Prostate Cancer Originating From Neuroendocine Cells (Prostatic Intraepithelial Neoplasia)," *Proc. Natl. Acad. Sci. USA,* Dec. 1998, 95:15382–7. (Exhibit 82).

Geller, Alfred I. et al., "An Efficient Deletion Mutant Packaging System for Defective Herpes Simplex Virus Vectors: Potential Applications to Human Gene Therapy and Neuronal Physiology," *Proc. Natl. Acad. Sci. USA,* Nov. 1990, 87:8950–4. (Exhibit 83).

Ghosh–Choudhury, Coutam et al., "Human Adenovirus Cloning Vectors Based on Infectious Bacterial Plasmids (Recombinant DNA; Ad5 Insertion Mutants; Shuttle Vectors; Gene Transfer; DNA Transfection; Bacteriophage λ cos Site; Neomycin Resistance," *Gene,* 1986, 50(1–3):161–71. (Exhibit 84).

Greenberg, N. M. et al., "Prostate Cancer in a Transgenic Mouse," *Proc. Natl. Acad. Sci. USA,* Apr. 1995, 92:3439–43. (Exhibit 85).

Hock, Randy A. and A. Dusty Miller, "Retrovirus–Mediated Transfer and Expression of Drug Resistance Genes in Human Haematopoietic Progenitor Cells," *Nature,* Mar. 1986, 320:275–7. (Exhibit 86).

Horisberger, Michel A. et al., "Cloning and Sequence Analyses of cDNAs for Interferon– and Virus–Induced Human Mx Proteins Reveal that They Contain Putative Guanine Nucleotide–Binding Sites: Functional Study of the Corresponding Gene Promoter," *Journal of Virology,* Mar. 1990, 64(3):1171–81. (Exhibit 87).

Jenkins, Robert B. et al., "Detection of c–myc Oncogene Amplification and Chromosomal Anomalies in Metastatic Prostatic Carcinoma by Fluorescence in Situ Hybridization," *Cancer Research,* Feb. 1, 1997, 57:524–31. (Exhibit 88).

Kaufman, Randal J., "Identification of the Components Necessary for Adenovirus Translational Control and Their Utilization in cDNA Expression Vectors," *Proc. Natl. Acad. Sci. USA,* Feb. 1985, 82:689–93. (Exhibit 89).

Kaufman, Randal J., "Vectors Used for Expression in Mammalian Cells," *Methods in Enzymology,* Gene Expression Technology, David V. Goeddel, ed., 1990, 185:487–511. (Exhibit 90).

Kay, A. B. et al., "Messenger RNA Expression of the Cytokine Gene Cluster, Interleukin 3 (IL–3), IL–4, IL–5 and Granulocyte/Macrophage Colony–stimulating Factor, In Allergen–Induced Late–Phase Cutaneous Reactions in Atopic Subjects," *Journal of Experimental Medicine,* Mar. 1991, 173:775–8. (Exhibit 91).

Lagoo, Anand S. et al., "IL–2, IL–4 and IFN–γ Gene Expression Versus Secretion in Superantigen–Activated T Cells," *The Journal of Immunology,* Feb. 15, 1994, 152(4):1641–52. (Exhibit 92).

Li, Yi–Ping and Philip Stashenko, "Proinflammatory Cytokines Tumor Necrosis Factor–α and IL–6, But Not IL–1 Down–Regulate the Osteocalcin Gene Promoter," *The Journal of Immunology,* Feb. 1, 1992, 148(3):788–94. (Exhibit 93).

Martinez, Olivia M. et al., "IL–2 and IL–5 Gene Expression in Response to Alloantigen in Liver Allograft Recipients and In Vitro," *Transplantation,* May 1993, 55(5):1159–66. (Exhibit 94).

Mauviel, Alain et al., "Leukoregulin, A T Cell–Derived Cytokine, Induces IL–8 Gene Expression and Secretion in Human Skin Fibroblasts Demonstration of Enhanced NFγB–Driven Promoter Activity," *The Journal of Immunology,* Nov. 1, 1992, 149(9):2969–76. (Exhibit 95).

Maxam Allan M. and Walter Gilbert, "Sequencing End–Labeled DNA with Base–Specific Chemical Cleavages," *Methods in Enzymology,* (Lawrence Grossman, ed.) 1980, 65:499–560. (Exhibit 96).

Maroulakou, Ioanna G. et al., "Prostate and Mammary Adenocarcinoma in Transgenic Mice Carrying a Rat CD(1) Simian Virus 40 Large Tumor Antigen Fusion Gene," *Proc. Natl. Acad. Sci. USA,* Nov. 1994, 91:11236–40. (Exhibit 97).

Murphy, G. et al., "Phase I Clinical Trial: T–Cell Therapy for Prostate Cancer Using Autologous Dendritic Cells Pulsed With HLA–A0201–Specific Peptides from Prostate–Specific Membrane Antigen," *The Prostate,* 1996, 29:371–80. (Exhibit 98).

Pang, G. et al., "GM–CSF, IL–1χ, IL–1β, IL–6, IL–8, IL–10, ICAM–1 and VCAM–1 Gene Expression and Cytokine Production in Human Duodenal Fibroblasts Stimulated with Lipopolysaccharide, IL–1χ and TNF–χ," *Clinical and Experimental Immunology,* Apr. 1994, 96(1):437–43. (Exhibit 99).

Panicali, Dennis and Enzo Paoletti, "Construction of Poxviruses as Cloning Vectors: Insertion of the Thymidine Kinase Gene From Herpes Simplex Virus into the DNA of Infectious Vaccinia Virus," *Proc. Natl. Acad. Sci. USA,* Aug. 1982, 79:4927–31. (Exhibit 100).

Pizarro, Theresa T. et al., "Induction of TNFα and the TNFβ Gene Expression in Rat Cardiac Transplants During Allograft Rejection," *Transplantation,* Aug. 1993, 56(2):399–404. (Exhibit 101).

Rosenfeld, Melissa A. et al., "Adenovirus–Mediated Transfer of a Recombinant α1–Antitrypsin Gene to the Lung Epithelium in Vivo," *Science,* Apr. 19, 1991, 252:431–4. (Exhibit 102).

Sarver, Nava et al., "Bovine Papilloma Virus Deoxyribonucleic Acid: A Novel Eucaryotic Cloning Vector," *Molecular and Cellular Biology,* Jun. 1981, 1(6):486–96. (Exhibit 103).

Schaefer–Ridder, Maria et al., "Liposomes as Gene Carriers: Efficient Transformation of Mouse L. Cells by Thymidine Kinase Gene," *Science,* Jan. 8, 1982, 215:166–8. (Exhibit 104).

Shimane, Miyuki et al., "Molecular Cloning and Characterization of G–CSF Induced Gene cDNA," *Biochemical and Biophysical Research Communications,* Feb. 28, 1994, 199(1):26–32. (Exhibit 105).

Smith, Geoffrey L. et al., "Infectious Vaccinia Virus Recombinants that Express Hepatitis B Virus Surface Antigen," *Nature,* Apr. 1993, 302:490–5. (Exhibit 106).

Sprecher, E. and Y. Becker, "Detection of IL–1β, TNF–α and IL–6 Gene Transcription by the Polymerase Chain Reaction in Keratinocytes, Langerhans Cells and Peritoneal Exudate Cells During Infection with Herples Simplex Virus–1," *Archives of Virology,* 1992, 126(1–4):253–69. (Exhibit 107).

Stavridis, J.C. et al., "Construction of Transferrin–Coated Liposomes for In Vivo Transport of Exogenous DNA to Bone Marrow Erythroblasts in Rabbits," *Experimental Cell Research,* Jun. 1986, 164(2):568–72. (Exhibit 108).

Tjoa, Benjamin et al., "Presentation of Prostate Tumor Antigens by Dendritic Cells Stimulates T–Cell Proliferation and Cytotoxicity," *The Prostate,* 1986, 28:65–9. (Exhibit 109).

Ulich, Thomas R. et al., "Endotoxin–Induced Cytokine Gene Expression In Vivo III. IL–6 mRNA and Serum Protein Expression and the In Vivo Hematologic Effects of IL–6," *The Journal of Immunology,* Apr. 1, 1991, 146(7):2316–23. (Exhibit 110).

Wong, Gordon G. et al., "Human GM–CSF: Molecular Cloning of the Complementary DNA and Purification of the Natural and Recombinant Proteins," *Science,* May 17, 1985, 228:810–5. (Exhibit 111).

Bzdega, Tomasz et al., "Molecular Cloning of a Peptidase Against N–Acetylaspartylglutamate from a Rat Hippocampal cDNA Library," *Journal of Neurochemistry,* Dec. 1997, 69(6):2270–7. (Exhibit 113).

Caron, Philip C. et al., "Enginerred Humanized Dimeric Forms of IgG Are More Effective Antibodies," *Journal of Experimental Medicine,* Oct. 1, 1992, 176(4):1191–5. (Exhibit 114).

Carter, Paul et al., "Humanization of an Anti–p185$^{HER2}$ Antibody for Human Cancer Therapy," *Proc. Natl. Acad. Sci. USA,* May 1992, 89:4285–9. (Exhibit 115).

Carter, Ruth E. et al., "Prostate–specific Membrane Antigen is a Hydrolase with Substrate and Pharmacologic Characteristics of a Neuropeptidase," *Proc. Natl. Acad. Sci. USA,* Jan. 1996, 93:749–53 (Exhibit 116).

Coloma, M. Josefina et al., "Novel Vectors for the Expression of Antibody Molecules Using Variable Regions Generated by Polymerase Chain Reaction," *Journal of Immunological Methds,* 1992, 152:89–104. (Exhibit 117).

Graham, F. L. and A. J. Van Der Eb, "A New Technique for the Assay of Infectivity of Human Adenovirus 5 DNA," *Virology,* 1973, 52:456–67. (Exhibit 118).

Hooijberg, Erik et al., "Eradication of Large Human B Cell Tumors in Nude Mice with Unconjugated CD20 Monoclonal Antibodies and Interleukin 2," *Cancer Research,* Jun. 15, 1995, 55:2627–34. (Exhibit 119).

Huang, Yi–Wu et al., "Anti–CD54 (ICAM–1) Has Antitumor Activity in SCID Mice with Human Myeloma Cells," *Cancer Research,* Feb. 1, 1995, 55:610–6 (Exhibit 120).

Israeli, Ron S. et al., "Expression of the Prostate–Specific Membrane Antigen," *Cancer Research,* Apr. 1, 1994, 54(7):1807–11. (Exhibit 121).

Jenkins, Robert B. et al., "Detection of c–myc Oncogene Amplification and Chromosomal Anomalies in Metastatic Prostatic Carcinoma by Fluorescence in Situ Hybridization," *Cancer Research,* Feb. 1, 1997, 57(3):524–31. (Exhibit 122).

Jones, Peter T. et al., "Replacing the Complementarity–Determining Regions in a Human Antibody with Those From a Mouse," *Nature,* 1986, 321(6069):522–5. (Exhibit 123).

Larson, L. N. et al., "Mouse Monoclonal Antibodies for Experimental Immunotherapy Promotes Killing of Tumor Cells," *International Journal of Cancer,* Dec. 15, 1988, 42(6):877–82. (Exhibit 124).

Morton, Thomas A. and David G. Myszka, "Kinetic Analysis of Macromolecular Interactions Using Surface Plasmon Resonance Biosensors," *Methods in Enzymology,* 1998, 295:268–94. (Exhibit 125).

Riechmann, Lutz et al., "Reshaping Human Antibodies for Therapy," *Nature,* Mar. 1988, 332:323–7. (Exhibit 126).

Shopes, Bob, "A Genetically Engineered Human IgG Mutant With Enhanced Cytolytic Activity," *The Journal of Immunology,* May 1992, 148:2918–22. (Exhibit 127).

Shizuya, Hiroaki et al., "Cloning and Stable Maintenance of 300–kilobase–pair Fragments of Human DNA in *Escherichia coli* Using an F–factor–based Vector," *Proc. Natl. Acad. Sci. USA,* Sep. 1992, 89:8794–7. (Exhibit 128).

Sims, Martin J. et al., "A Humanized CD18 Antibody Can Block Function without Cell Destruction," *The Journal of Immunology,* Aug. 1993, 151(4):2296–308. (Exhibit 129).

Slovin, S. F. et al., "Epidermal Growth Factor Receptor (EGFr) Monoclonal Antibody (MoAb) C225 and Doxorubicin (DOC) In Androgen–Independent (AI) Prostate Cancer (PC): Results of a Ib/ILa Study," *Progam/Proceedings American Soceity of Clinical Oncology,* May 1997, 16:311a. (Exhibit 130).

Su, Zao–Zhong et al., "Surface–epitope Masking and Expression Cloning Identifies the Human Prostate Carcinoma Tumor Antigen Gene PCTA–1 a Member of the Galectin Gene Family," *Proc. Natl. Acad Sci. USA,* Jul. 1996, 93:7252–7. (Exhibit 131).

Towbin, Harry et al., "Electrophoretic Transfer of Proteins From Polyacrylamide Gels to Nitrocellulose Sheets: Procedure and Some Applications," *Proc. Natl. Acad. Sci. USA,* Sep. 1979, 76(9):4350–4. (Exhibit 132).

Vaughan, Tristan J. et al., "Human Antibodies by Design," *Nature Biotechnology,* Jun. 1998, 16(6):535–9. (Exhibit 133).

Verhoeyen, Martine et al., "Reshaping Human Antibodies: Grafting and Antilysozyme Activity," *Science,* Mar. 1988, 239:1534–6. (Exhibit 134).

Wolff, Edith A. et al., "Monoclonal Antibody Homodimers: Enhanced Antitumor Activity in Nude Mice," *Cancer Research,* Jun. 1993, 53(11):2560–5. (Exhibit 135).

Yang, Xiao–Dong et al., "Eradication of Established Tumors by a Fully Human Monoclonal Antibody to the Epidermal Growth Factor Receptor without Concomitant Chemotherapy," *Cancer Research,* Mar. 1999, 59(6):1236–43. (Exhibit 136).

Cama, C., et al., "Molecular Staging of Prostate Cancer: II. A comparison of the Application of an Enhance Reverse Transriptase Polymerase Chain Reaction Assay for Prostate Specific Antigen Versus Prostate Specific Membrane Antigen", *The Journal of Urology,* 1995, 153:1373–1378 (Exhibit 137).

Horoszewicz, J. S., et al., "Monoclonal Antibodies to a New Antigenic Marker in Epithelial Prostatic Cells and Serum of Prostatic Cancer Patients", *Anticancer Research,* 1987, 7:927–936 (Exhibit 138).

Israeli, R. S., et al., "Sensitive Nested Reverse Transcription Polymerase Chain Reaction Detection of Circulating Prostatic Tumor Cells: Comparison of Prostate–specific Membrane Antigen and Prostate–specific Antigen–based Assays", *Cancer Research,* 1994, 54:6306–6310 (Exhibit 139).

Smith, M. R., et al., "Prostate–specific Antigen Messenger RNA is Expressed in Non–Prostate Cells: Implications for Detection of Micrometastases", *Cancer Research,* 1995, 55:2640–2644 (Exhibit 140).

Sodee, D. B., et al., "Preliminary Imaging Results Using In–11 Labeled CYT–356 (Prostacing™) in the Detection of Recurrent Prostate Cancer", *Clinical Nuclear Medicine,* 1996, 21:759–767 (Exhibit 141).

Wu, J. T., et al., "Assay for Prostate Specific Antigen (PSA): Problems and Possible Solutions", *Journal of Clinical Laboratory Analysis,* 1994, 8:51–62 (Exhibit 142).

Colowick, et al., *Methods in Enzymology* 65:499–560 (Exhibit 144).

Muller, et al., 1991 *Molec. Cell. Biol.,* 11:1785–1792 (Exhibit 145).

\* cited by examiner

FIG. 1A

```
  1  agggagaggc agtgaccatg aaggctgtgc tgcttgccct gttgatggca
 51  ggcttggccc tgcagccagg cactgccctg ctgtgctact cctgcaaagc
101  ccaggtgagc aacgaggact gcctgcaggt ggagaactgc acccagctgg
151  gggagcagtg ctggaccgcg cgcatccgcg cagttggcct cctgaccgtc
201  atcagcaaag gctgcagctt gaactgcgtg gatgactcac aggactacta
251  cgtgggcaag aagaacatca cgtgctgtga caccgacttg tgcaacgcca
301  gcggggccca tgccctgcag ccggctgccg ccatccttgc gctgctccct
351  gcactcggcc tgctgctctg ggacccggc cagctatagg ctctgggggg
401  ccccgctgca gcccacactg ggtgtggtgc cccaggcctt tgtgccactc
451  ctcacagaac ctggcccagt gggagcctgt cctggttcct gaggcacatc
501  ctaacgcaag tttgaccatg tatgtttgca ccccttttcc ccnaaccctg
551  accttcccat gggccttttc caggattccn accnggcaga tcagttttag
601  tganacanat ccgcntgcag atggcccctc caaccntttn tgttgntgtt
651  tccatggccc agcattttcc accttaacc ctgtgttcag gcacttnttc
701  ccccaggaag ccttccctgc cacccccatt tatgaattga gccaggtttg
751  gtccgtggtg tcccccgcac ccagcagggg acaggcaatc aggagggccc
801  agtaaaggct gagatgaagt ggactgagta gaactggagg acaagagttg
851  acgtgagttc ctgggagttt ccagagatgg ggcctggagg cctggaggaa
901  ggggccaggc ctcacatttg tggggntccc gaatggcagc ctgagcacag
951  cgtaggccct taataaacac ctgttggata agccaaaaaa aaaaaaaa
```

FIG. 1B

MKAVLLALLMAGLALQPGTALLCYSCKAQVSNEDCLQV

ENCTQLGEQCWTARIRAVGLLTVISKGCSLNCVDDS

QDYYVGKKNITCCDTDLCNASGAHALQPAAAILALLPAL

GLLLWGPGQL

FIG. 2

```
    ATGAAGACAGTTTTTTTTATCCTGCTGGCCACCTACTTAGCCCTGCATCCAGGTGCTGCT
1   ---------+---------+---------+---------+---------+---------+ 60
    TACTTCTGTCAAAAAAAATAGGACGACCGGTGGATGAATCGGGACGTAGGTCCACGACGA

M  K  T  V  F  F  I  L  L  A  T  Y  L  A  L  H  P  G  A  A

CTGCAGTGCTATTCATGCACAGCACAGATGAACAACAGAGACTGTCTGAATGTACAGAAC
61  ---------+---------+---------+---------+---------+---------+ 120
    GACGTCACGATAAGTACGTGTCGTGTCTACTTGTTGTCTCTGACAGACTTACATGTCTTG

L  Q  C  Y  S  C  T  A  Q  M  N  N  R  D  C  L  N  V  Q  N

TGCAGCCTGGACCAGCACAGTTGCTTTACATCGCGCATCCGGGCCATTGGACTCGTGACA
121 ---------+---------+---------+---------+---------+---------+ 180
    ACGTCGGACCTGGTCGTGTCAACGAAATGTAGCGCGTAGGCCCGGTAACCTGAGCACTGT

C  S  L  D  Q  H  S  C  F  T  S  R  I  R  A  I  G  L  V  T

GTTATCAGTAAGGGCTGCAGCTCACAGTGTGAGGATGACTCGGAGAACTACTATTTGGGC
181 ---------+---------+---------+---------+---------+---------+ 240
    CAATAGTCATTCCCGACGTCGAGTGTCACACTCCTACTGAGCCTCTTGATGATAAACCCG

V  I  S  K  G  C  S  S  Q  C  E  D  D  S  E  N  Y  Y  L  G

AAGAAGAACATCACGTGCTGCTACTCTGACCTGTGCAATGTCAACGGGGCCCACACCCTG
241 ---------+---------+---------+---------+---------+---------+ 300
    TTCTTCTTGTAGTGCACGACGATGAGACTGGACACGTTACAGTTGCCCCGGGTGTGGGAC

K  K  N  I  T  C  C  Y  S  D  L  C  N  V  N  G  A  H  T  L

AAGCCACCCACCACCCTGGGGCTGCTGACCGTGCTCTGCAGCCTGTTGCTGTGGGGCTCC
301 ---------+---------+---------+---------+---------+---------+ 360
    TTCGGTGGGTGGTGGGACCCCGACGACTGGCACGAGACGTCGGACAACGACACCCCGAGG

K  P  P  T  T  L  G  L  L  T  V  L  C  S  L  L  L  W  G  S

AGCCGTCTGTAGGCTCTGGGAGAGCCTACCATAGCCCGATTGTGAAGGGATGAGCTGCAC
361 ---------+---------+---------+---------+---------+---------+ 420
    TCGGCAGACATCCGAGACCCTCTCGGATGGTATCGGGCTAACACTTCCCTACTCGACGTG

S  R  L  *

TCCACCCCACCCCCACACAGG
421 ---------+---------+- 441
    AGGTGGGGTGGGGGTGTGTCC
```

FIG. 3

```
  1  M K I F L P V L L A A L L G V E R A S S      hSCA-2
  1  M K A V L L A L L M A G L A L Q P G T A      hPSCA
  1  M K T V L F L L L A T Y L A L H P G A A      mPSCA

21  L M C F S C L N Q K S N*L Y C L K P T I
 21  L L C Y S C K A Q V S N*E D C L Q V E N*
 21  L Q C Y S C T A Q M N N*R D C L N V Q N*

41  C S D Q D N Y C V T V S A S A G I G N L
 41  C T Q L G E Q C W T A R I R A V G L L T
 41  C S L D Q H S C F T S R I R A I G L V T

61  V T F G H S L S K T C S P A C P I P E G
 61  V - - - - - I S K G C S L N C V D D S Q
 61  V - - - - - I S K G C S S Q C E D D S E

81  V N V G V A S M G I S C C Q S F L C N*F
 76  D Y Y V G K K - N*I T C C D T D L C N*A
 76  N Y Y L G K K - N*I T C C Y S D L C N*V

101  S A A D G G L R A S V T L L G A G L L L
 95  S G A H A L Q P A A A I L A L L P A L G
 95  N G A H T L K P P T T L G L L T V L C S

121  S L L P A L L R F G P
115  L L L W G P G Q L - -
115  L L L W G S S R L - -
```

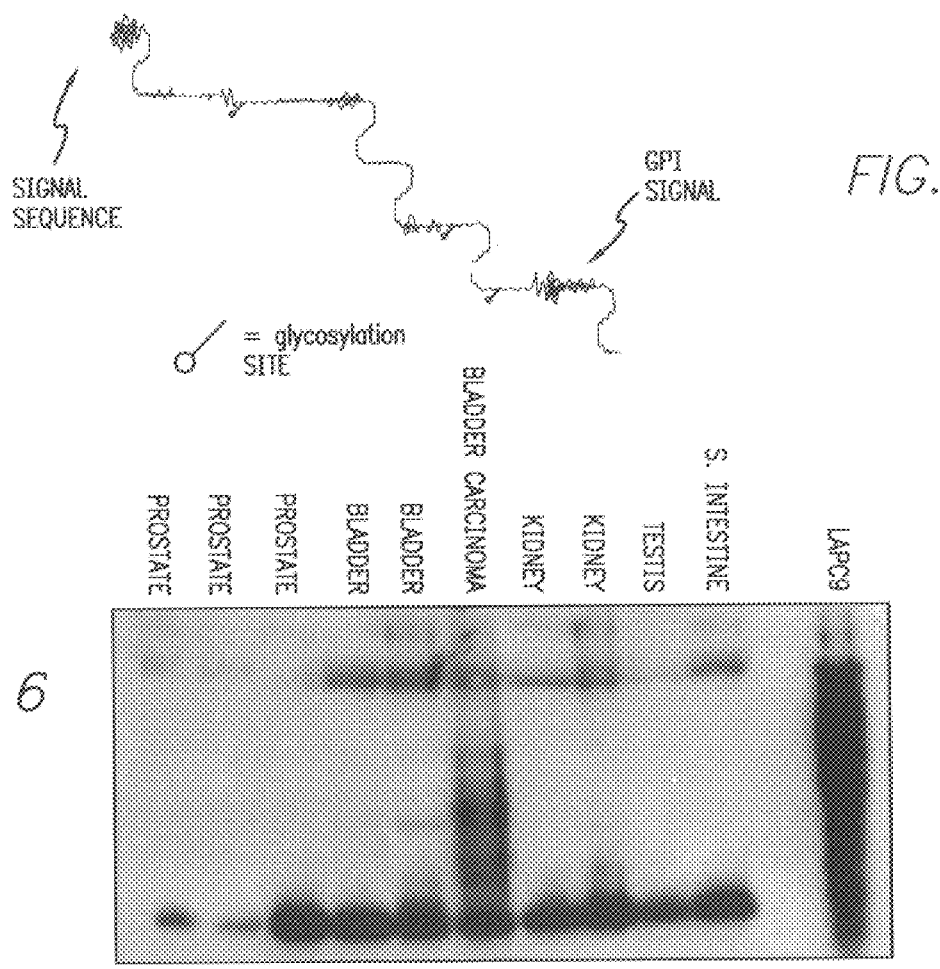

FIG. 11A
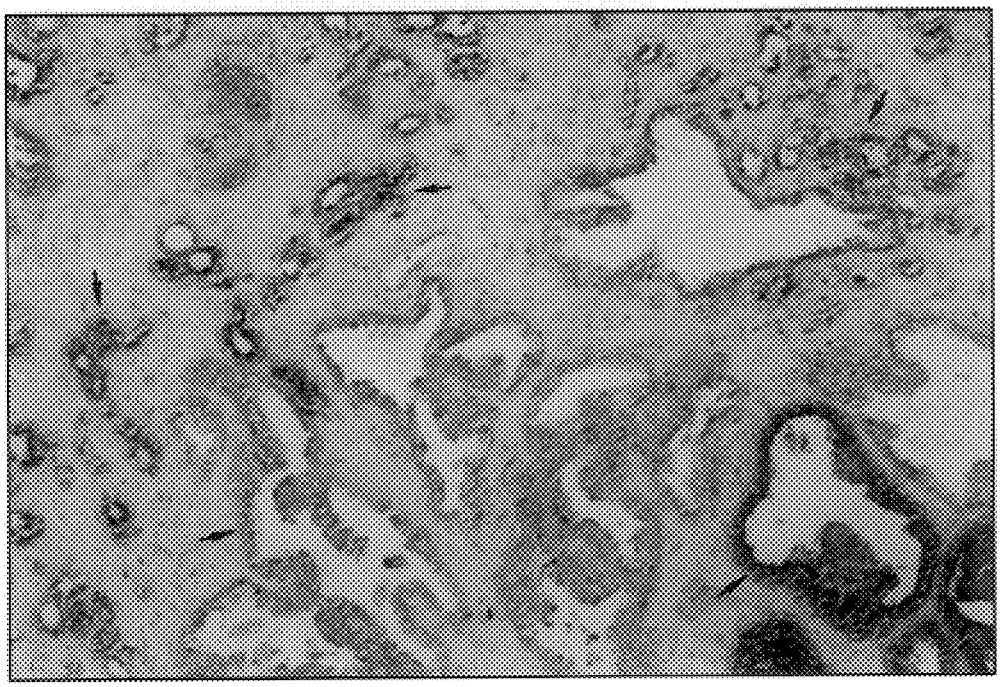
FIG. 11B

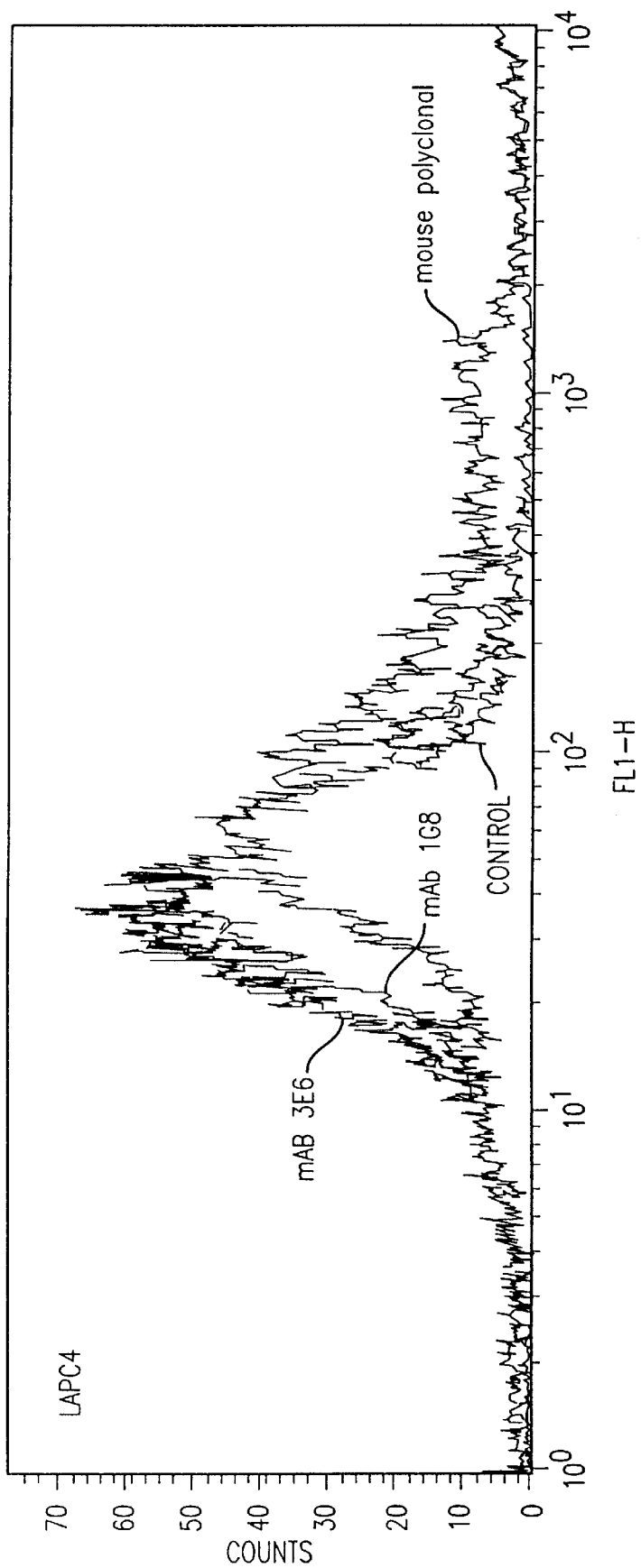

PROSTATE STEM CELL ANTIGEN (PSCA) IS A GPI-ANCHORED PROTEIN

|  | | | | | | | | | | | | | | | | | | | | |
|---|---|---|---|---|---|---|---|---|---|---|---|---|---|---|---|---|---|---|---|---|
| 1 | M | K | I | F | L | P | V | L | L | A | A | L | L | G | V | E | R | A | S | S | hSCA-2 |
| 1 | M | K | A | V | L | L | A | L | L | M | A | G | C | A | L | Q | P | G | T | A | hPSCA |
| 1 | M | K | T | V | L | F | L | L | A | T | L | Y | A | L | H | P | G | A | A | | mPSCA |
| 21 | L | M | C | F | S | C | L | N | Q | K | S | N* | L | Y | C | L | K | P | T | I | |
| 21 | L | C | Y | S | C | K | A | Q | V | S | N* | E | D | C | L | Q | V | E | N* | | |
| 21 | L | Q | C | Y | S | C | T | A | Q | M | N* | R | D | C | L | N | V | Q | N* | | |
| 41 | C | S | D | Q | D | N | Y | C | V | T | V | S | A | S | A | G | I | G | N | L | |
| 41 | T | Q | L | G | E | Q | C | W | T | A | R | I | R | A | V | Q | L | T | | | |
| 41 | C | S | L | D | Q | H | S | C | F | I | S | R | I | R | T | I | G | L | V | T | |
| 61 | V | T | F | G | H | S | L | S | K | T | C | S | P | A | C | P | I | P | E | G | |
| 61 | V | — | — | — | — | I | S | K | G | C | C | S | L | N | C | V | D | D | S | Q | |
| 61 | V | — | — | — | — | I | S | K | G | C | S | S | Q | C | G | E | D | D | S | E | |
| 81 | V | N | V | G | V | A | S | M | G | T | S | C | C | Q | S | F | C | N* | F | | |
| 76 | D | Y | Y | V | G | K | K | — | N | I | T | C | C | D | T | D | L | C | N | A | |
| 76 | N | Y | L | G | K | K | — | N | I | T | C | C | Y | S | D | L | C | N | V | | |
| 101 | S | A | A | D | G | G | L | R | A | S | V | T | L | L | G | A | G | L | L | L | |
| 95 | S | A | H | T | L | Q | P | A | A | A | I | L | A | L | L | P | A | L | G | | |
| 95 | N | G | A | H | T | L | K | P | T | T | L | G | L | L | T | V | L | C | S | | |
| 121 | S | L | L | P | A | L | L | R | F | G | P | | | | | | | | | | |
| 115 | L | L | W | G | P | G | Q | L | — | — | — | | | | | | | | | | |
| 115 | L | L | W | G | S | S | R | L | — | — | — | | | | | | | | | | |

FIG. 16A

FIG. 17
FISH ANALYSIS OF PSCA AND c-myc IN PROSTATE CANCER
GAIN CHROMOSOME 8
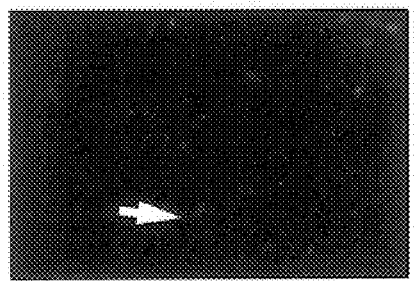
34 c-myc
AMPLIFICATION
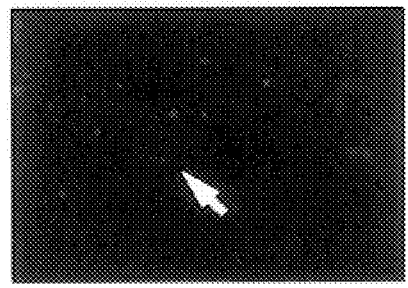
75 c-myc
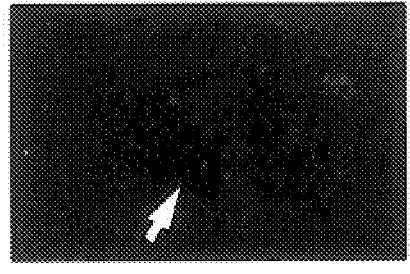
34 PSCA
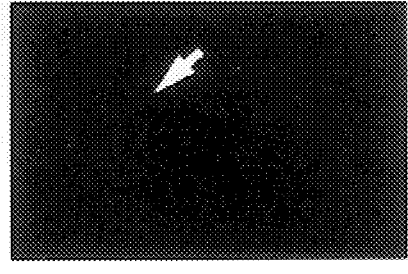
75 PSCA
FIG. 18
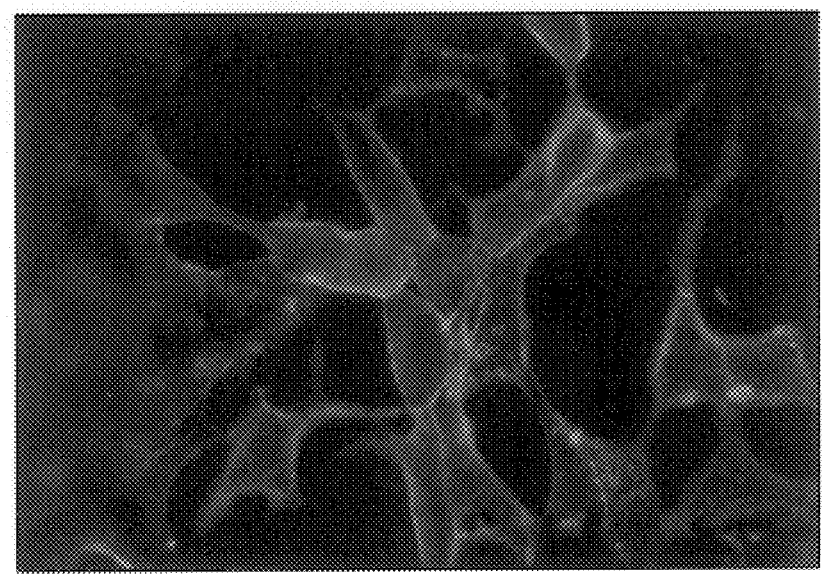

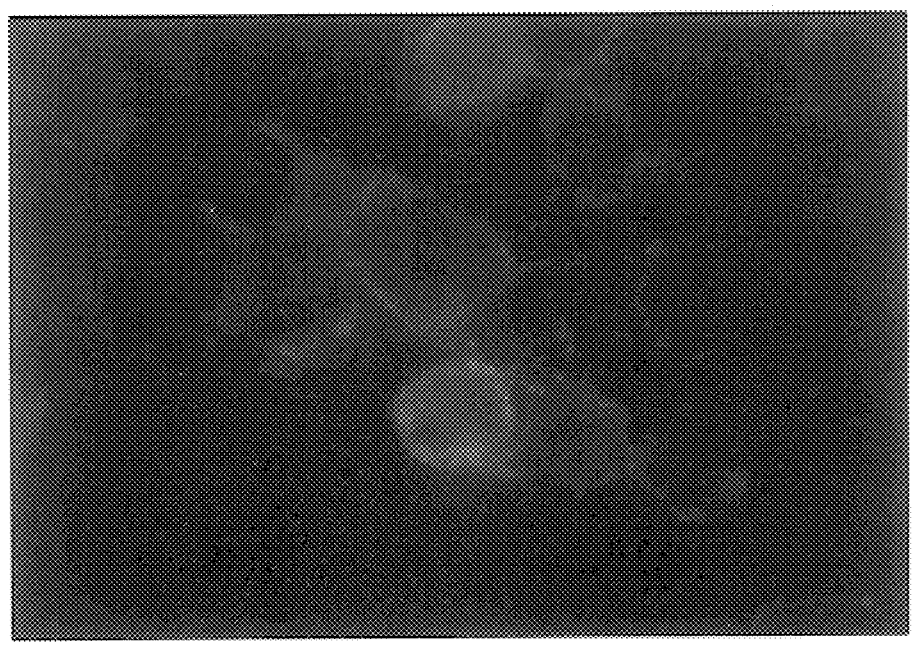
FIG. 19
FIG. 20

PSCA IMMUNOSTAINING OF PRIMARY TUMORS

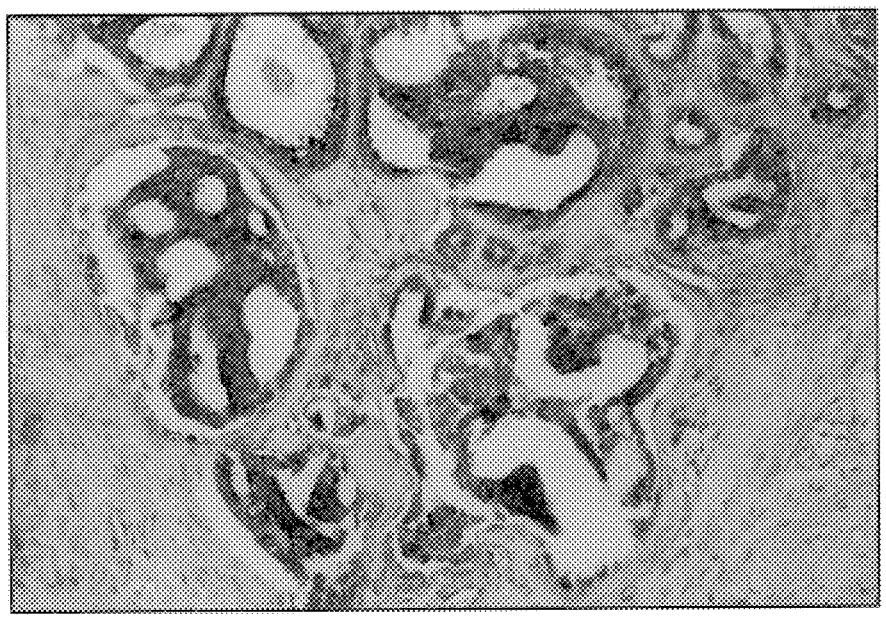
FIG. 23
FIG. 24

PSCA NORTHERN

FIG. 27
PSCA IMMUNOSTAINING OF BONY METASTASES
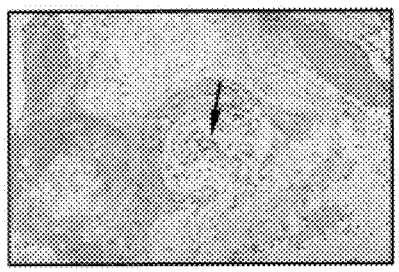 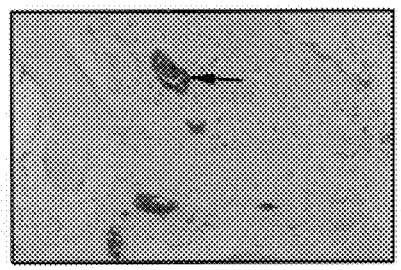 Patient 5: H and E and mAb 1G8
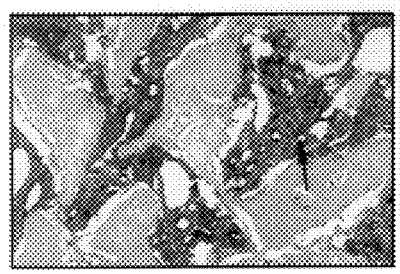 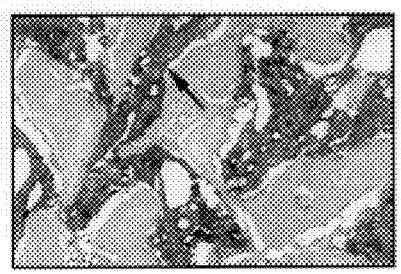 Patient 4: H and E and mAb 3E6
FIG. 28

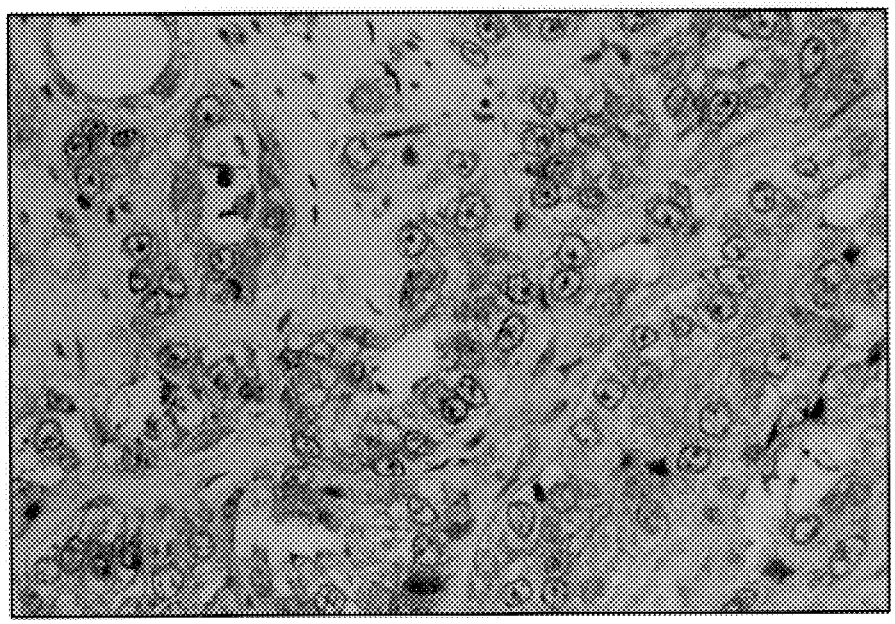
FIG. 29
FIG. 30
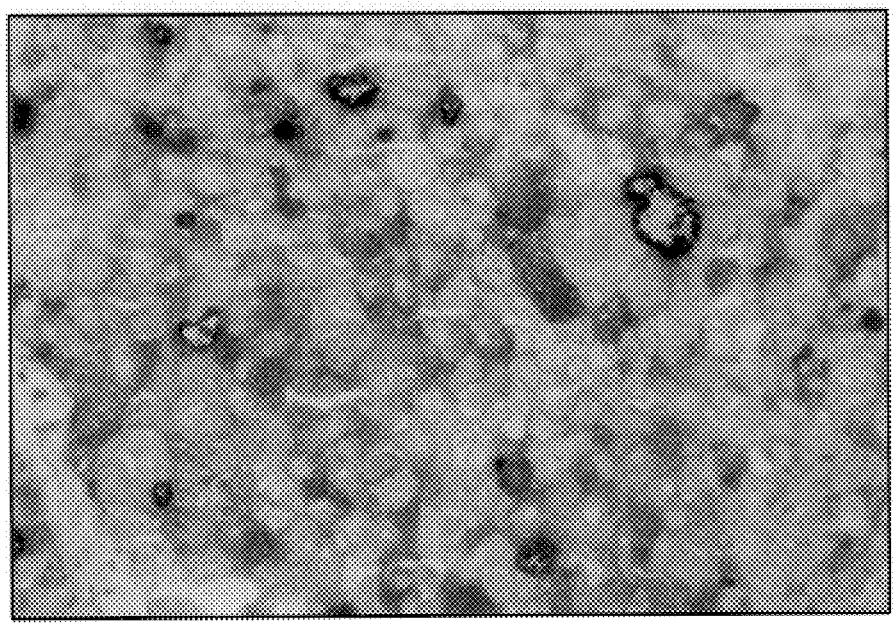

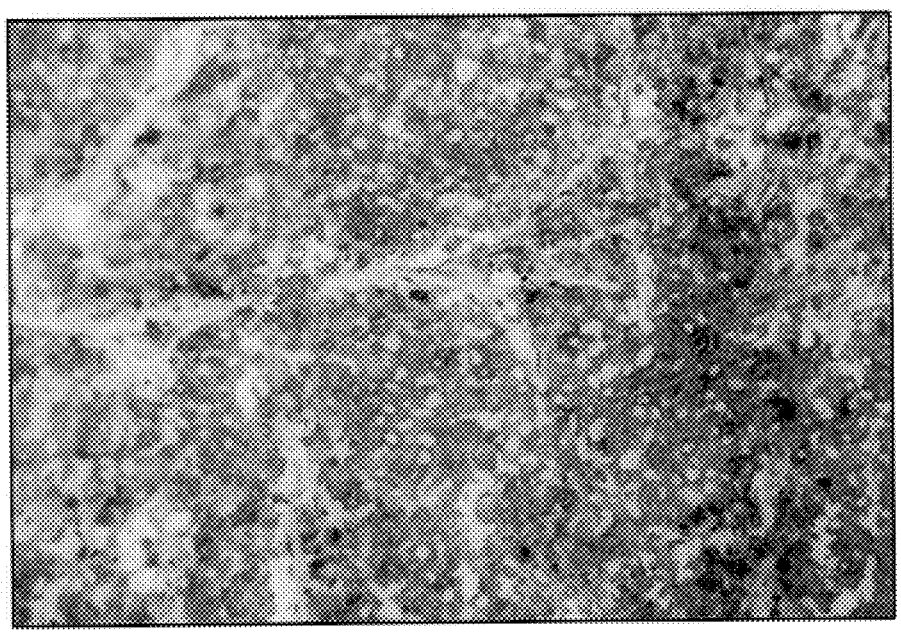
FIG. 31
FIG. 32
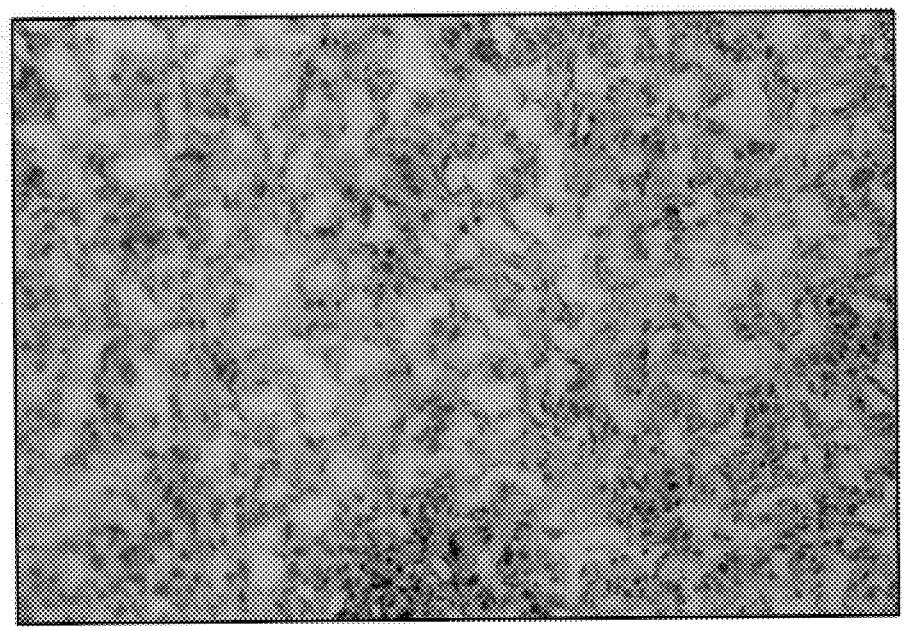

IMMUNOFLUORESCENT STAINING OF LNCaP-PSCA CELLS

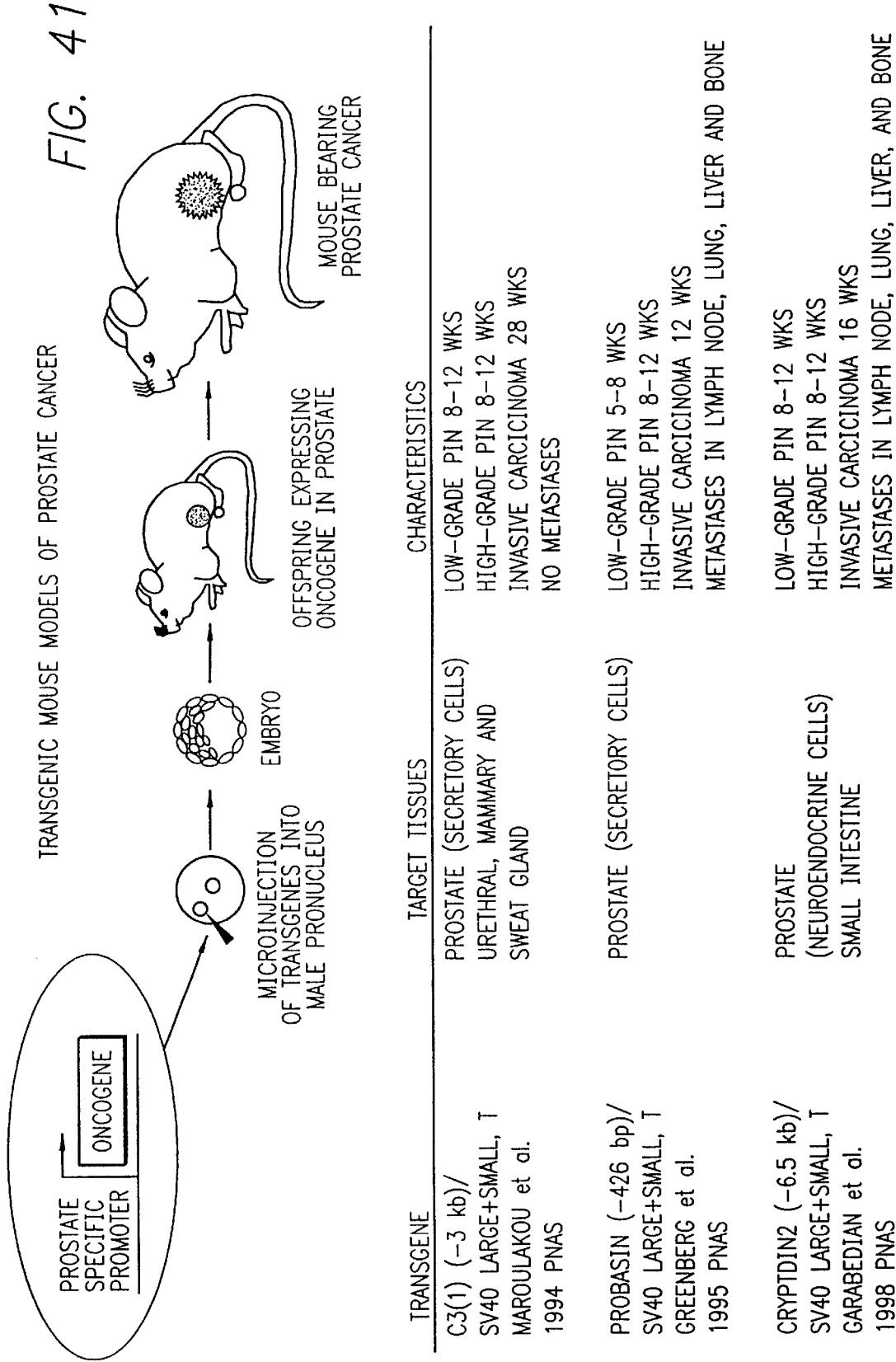

FIG. 48
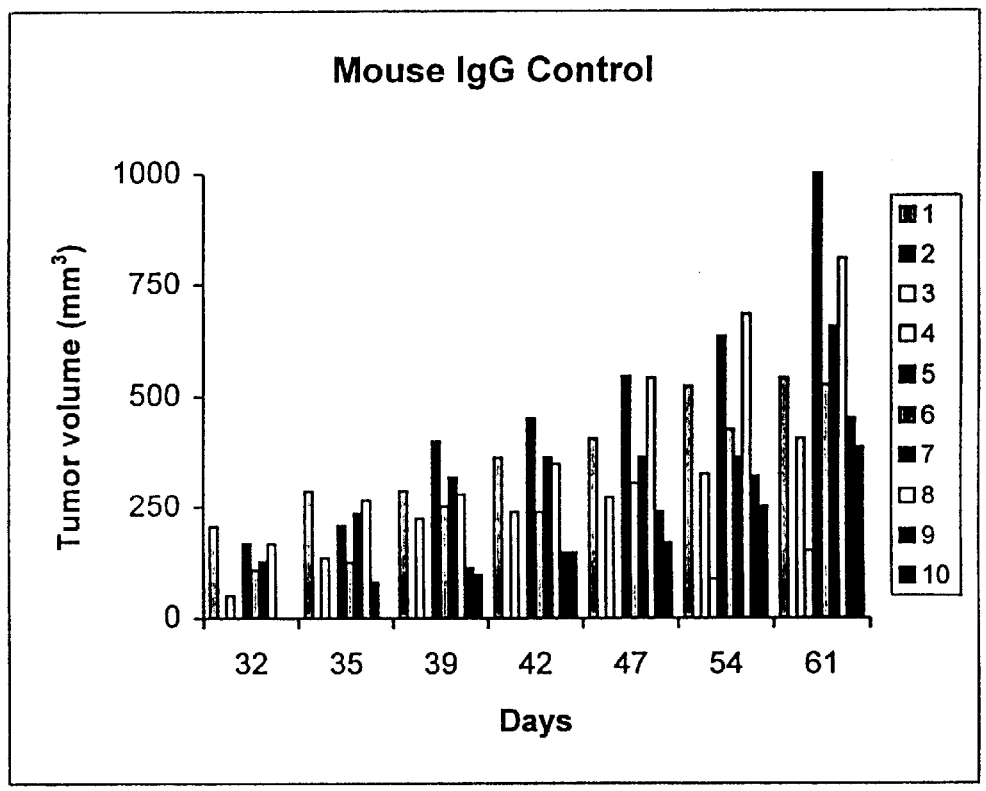
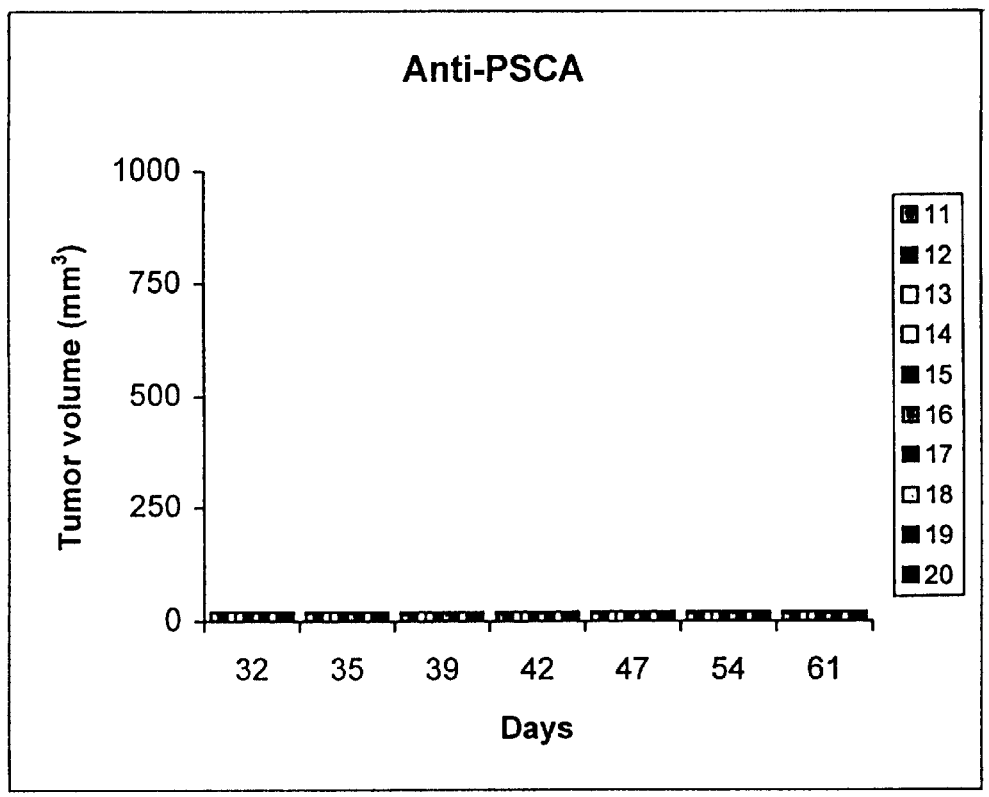

A
| mAb | Isotype | Epitope recognized (OD 450 nm) | | | |
|---|---|---|---|---|---|
| | | F (18-98) | N (2-50) | M (46-109) | C (85-123) |
| 1G8 | IgG1 k | 1.485 | 0.004 | 1.273 | 0.003 |
| 2A2 | IgG2a k | 0.873 | 0.631 | 0.023 | 0.010 |
| 2H9 | IgG1 k | 1.069 | 1.026 | 0.002 | 0.001 |
| 3C5 | IgG2a k | 1.916 | 1.709 | 0.006 | 0.002 |
| 3E6 | IgG3 k | 1.609 | 0.036 | 1.133 | 2.118 |
| 3G3 | IgG2a k | 2.895 | 1.731 | 0.004 | 0.000 |
| 4A10 | IgG2a k | 1.053 | 0.493 | 0.000 | 0.001 |
FIG. 49
B
1G8
F N M C
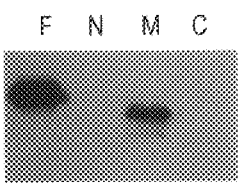
2A2
F N M C
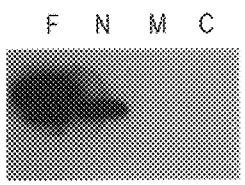
2H9
F N M C
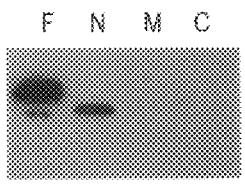
3C5
F N M C
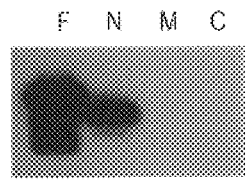
3E6
F N M C
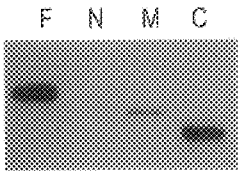
3G3
F N M C
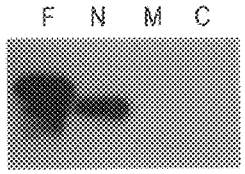
4A10
F N M C
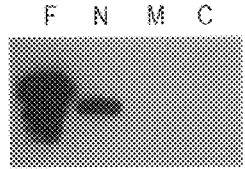

FIG. 50
A
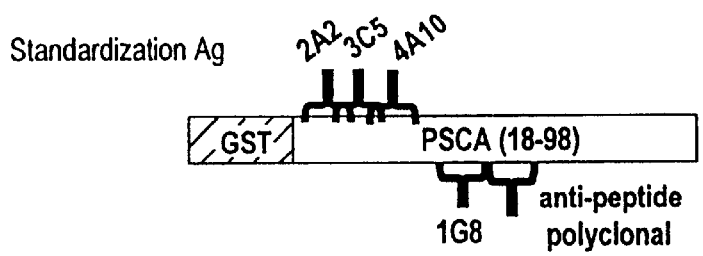
Standardization Ag
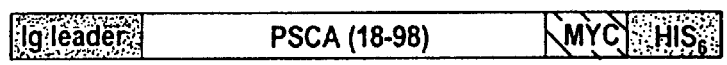
Engineered mammalian secreted form
B
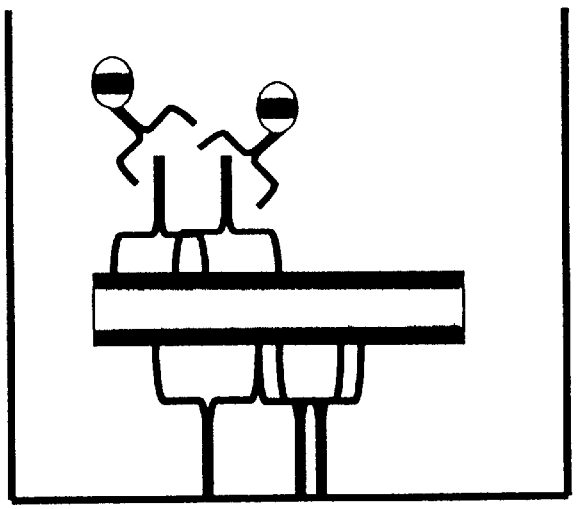
Anti-IgG2a HRP
Anti-PSCA mAbs 3C5+4A10+2A2 (IgG2a)
PSCA
Affinity purified anti-peptide polyclonal + mAb 1G8 (IgG1)

| Sample | OD+range (n=2) | ng/ml |
|---|---|---|
| vector | 0.005+0.001 | ND |
| vector+hu serum | 0.004+0.001 | ND |
| secPSCA | 2.695+0.031 | 32.92 |
| secPSCA+hu serum | 2.187+0.029 | 26.55 |

FIG. 54
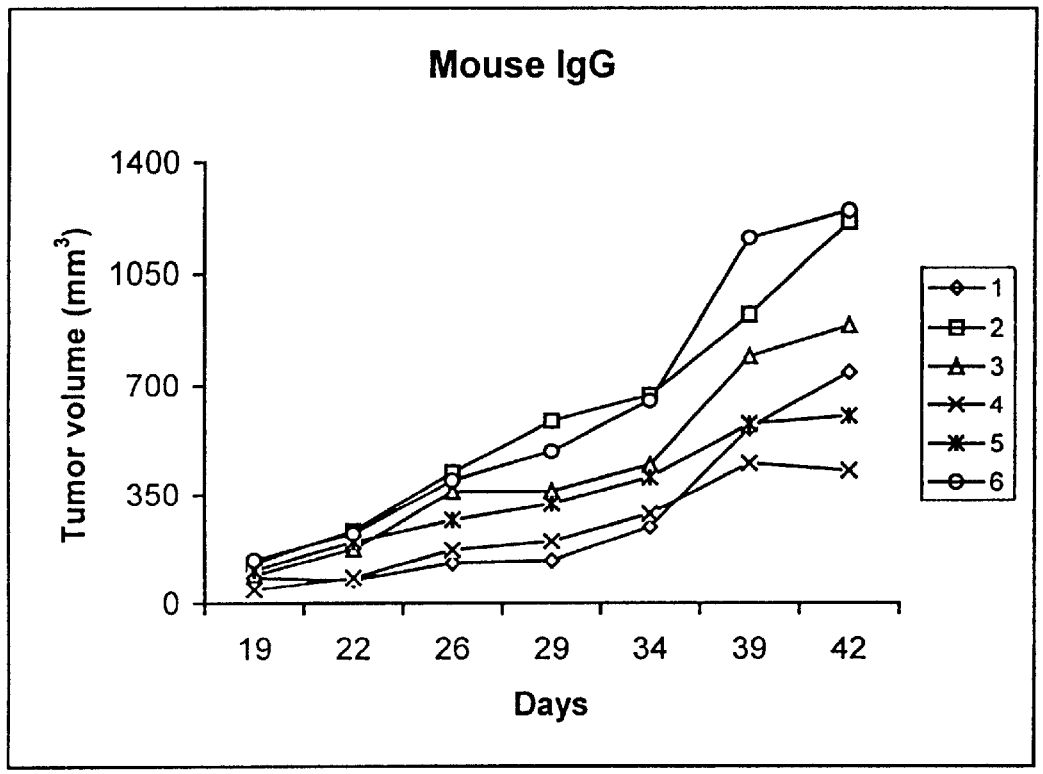
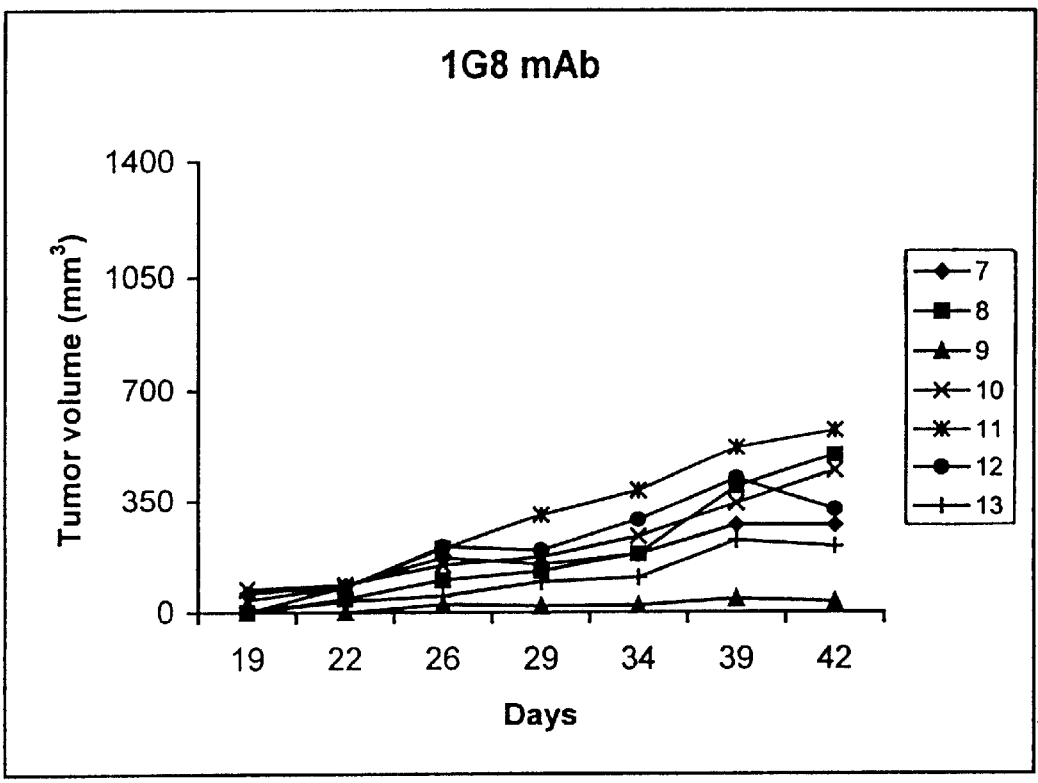

FIG. 55
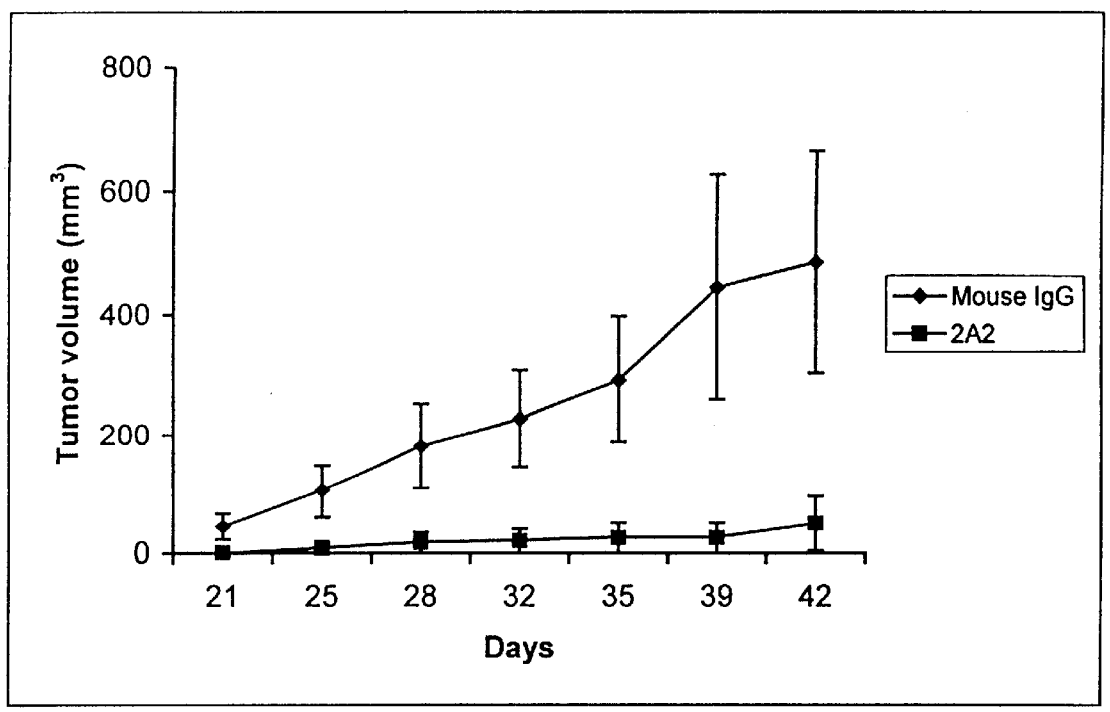
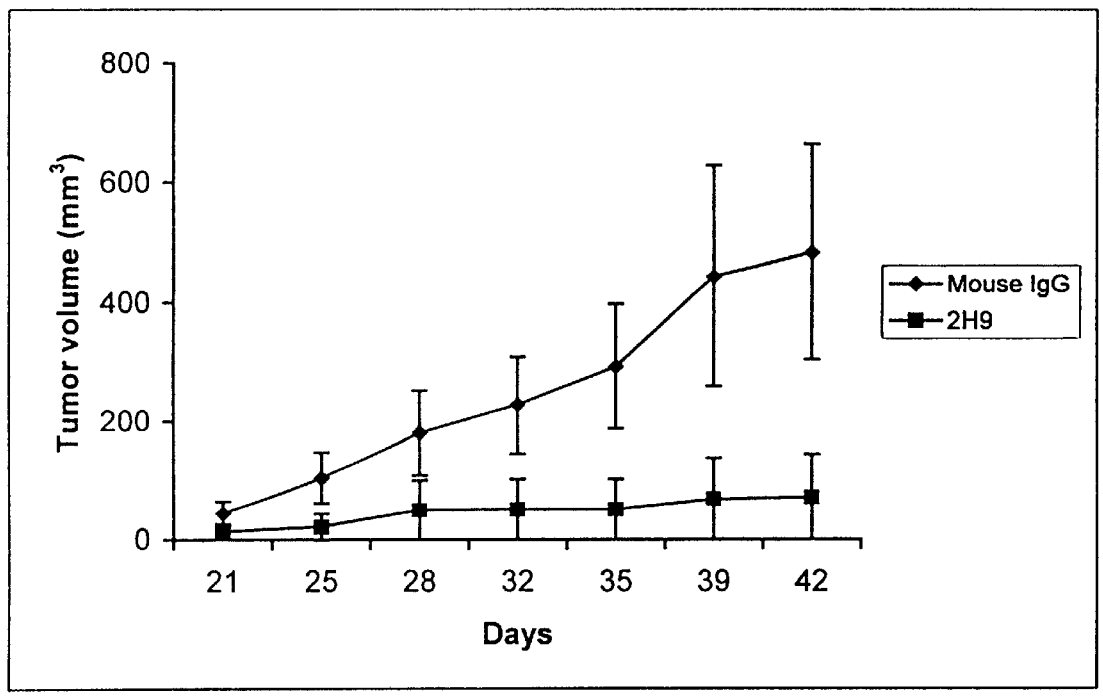

FIG. 56
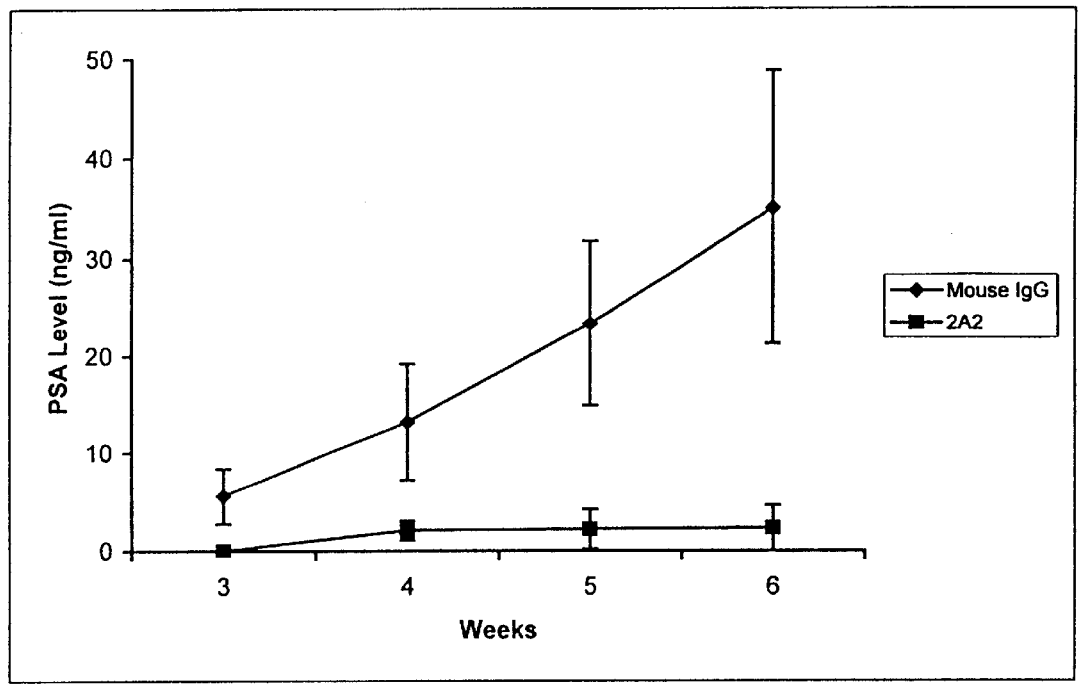
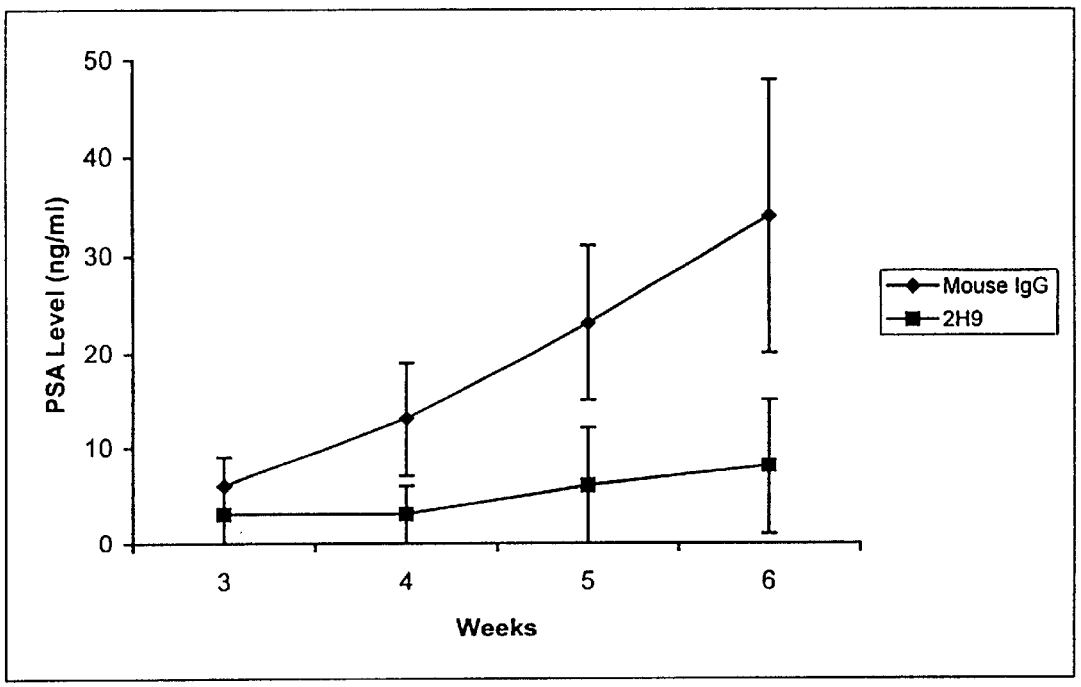

FIG. 58

```
TGCTTCTTCCTGATGGCAGTGGTTATAGGAGTCAATTCAGAGGTTCAGTGCAGCAGTCT    60
 C  F  F  L  M  A  V  V  I  G  V  N  S  E  V  Q  L  Q  Q  S    20
                                                  ┌─────
GGGGCAGAACTTGTGAGGTCAGGGGCCCTCAGTCAAGTTGTCCTGCACAGCTTCTGGCTTC  120
 G  A  E  L  V  R  S  G  A  S  V  K  L  S  C  T  A  S  G  F    40
       ─── CDR1 ─────────────────────────────
AACATTAAAGACTACTATATACACTGGGTGAATCAGAGGCCTGACCAGGGCCTGGAGTGG  180
 N  I  K  D  Y  Y  I  H  W  V  N  Q  R  P  D  Q  G  L  E  W    60
                                       ┌─── CDR2 ──────────
ATTGGATGGATTGATCCTGAGAATGGTGACACTGAATTTGTCCCGAAGTTCCAGGGCAAG  240
 I  G  W  I  D  P  E  N  G  D  T  E  F  V  P  K  F  Q  G  K    80
  ─────────────────────────────────────
GCCACTATGACTGCAGACATTTCTCCAACACAGCCTACCTGCACCTCAGCAGCCTGACA  300
 A  T  M  T  A  D  I  F  S  N  T  A  Y  L  H  L  S  S  L  T   100
                                     ┌─── CDR3 ─────
TCTGAAGACACTGCCGTCTATTACTGTAAAACGGGGGTTTCTGGGGCCAAGGGACTCTG  360
 S  E  D  T  A  V  Y  Y  C  K  T  G  G  F  W  G  Q  G  T  L   120
                                    ──────

GTCACTGTCTCTGCAGCCAAAACGACACCCCCATCTGTCTATCCACTG
 V  T  V  S  A  A  K  T  T  P  P  S  V  Y  P  L
```

FIG. 59

```
TTGGTAGCAACAGCCTCAGATGTCCACTCCCAGGTCCAGCTGCAGCAACTGGGTCTGAA     60
 L  V  A  T  A  S  D  V  H  S  Q  V  Q  L  Q  Q  P  G  S  E     20

CTGGTGAGGCCTGGAACTTCAGTGAAGCTGTCCTGCAAGGCTTCTGGCTATACATTCTCC    120
 L  V  R  P  G  T  S  V  K  L  S  C  K  A  S  G  Y  T  F  S     40
                                              ―――――――――――――
                                                   CDR1

AGCTACTGGATGCACTGGGTGAAGCAGAGGCCTGGACAAGGCCTTGAGTGGATTGGAAAT    180
 S  Y  W  M  H  W  V  K  Q  R  P  G  Q  G  L  E  W  I  G  N     60
 ――――――――

ATTGACCCTGGTAGTGGTTACACTAACTACGCTGAGAACCTCAAGACCAAGGCCACACTG    240
 I  D  P  G  S  G  Y  T  N  Y  A  E  N  L  K  T  K  A  T  L     80
 ―――――――――――――――――――――――――――――――――
              CDR2

ACTGTAGACACATCCTCCAGCACAGCCTACATGCAGCTCAGCAGCCTGACATCTGAGGAC    300
 T  V  D  T  S  S  S  T  A  Y  M  Q  L  S  S  L  T  S  E  D    100

TCTGCAGTCTATTACTGTACAAGCCGATCTACTATGATTACGACGGGATTTGCTTACTGG    360
 S  A  V  Y  Y  C  T  S  R  S  T  M  I  T  T  G  F  A  Y  W    120
                     ―――――――――――――――――――――――――――――――――
                                    CDR3

GGCCAAGGGACTCTGGTCACTGTCTCTGCAGCTACAACAGCCCCATCTGTCTATCCA      420
 G  Q  G  T  L  V  T  V  S  A  A  T  T  T  A  P  S  V  Y  P    160

CTGGCC
 L  A
```

FIG. 60

```
AATGACTTCGGGTTGAGCTGGGTTTTATTATTGTCTCTTTAAAGGGGTCCGGAGTGAA    60
 N  D  F  G  L  S  W  V  F  I  I  V  L  L  K  G  V  R  S  E   20

GTGAGGCTTGAAGGAGTCTGGAGGAGGCTGGGTGCAACCTGGAGGATCCATGAAACTCTCC  120
 V  R  L  E  E  S  G  G  G  W  V  Q  P  G  G  S  M  K  L  S   40

TGTGTAGCCTCTGGATTCACTTTCAGTAATTACTGGATGACTTGGGTCCGCCAGTCTCCA  180
 C  V  A  S  G  F  T  F  S  N  Y  W  M  T  W  V  R  Q  S  P   60
              ─────────────────────
                     CDR1

GAGAAGGGGCTTGAGTGGGTTGCTGAAATTCGATTGAGATCTGAAAATTATGCAACACAT  240
 E  K  G  L  E  W  V  A  E  I  R  L  R  S  E  N  Y  A  T  H   80
                       ──────────────────────────────
                                    CDR2

TATGCGGAGTCTGTGAAAGGGAAATTCACCATCTCAAGAGATGATTCCAGAAGTCGTCTC  300
 Y  A  E  S  V  K  G  K  F  T  I  S  R  D  D  S  R  S  R  L  100
 ─────────────

TACCTGCAAATGAACAACTTAAGACCTGAAGACAGTGGAATTTATTACTGTACAGATGGT  360
 Y  L  Q  M  N  N  L  R  P  E  D  S  G  I  Y  Y  C  T  D  G  120

CTGGGACGACCTAACTGGGGCCAAGGACTCTGTGGTCACTGTCTCTGCAGCCAAAACGACA  420
 L  G  R  P  N  W  G  Q  G  T  L  V  T  V  S  A  A  K  T  T  140
 ──────────────────
       CDR3

CCCCCATCTGTCTATCCACTGGCCCCTTGTGTA
 P  P  S  V  Y  P  L  A  P  C  V
```

FIG. 61

CDR1 Comparisons

| | | | | | | | | | | | |
|---|---|---|---|---|---|---|---|---|---|---|---|
| 1G8 | 1gG$_{1k}$ | Middle | G | F | N | I | K | D | Y | Y | I | H |
| 2H9 | 1gG$_{1k}$ | N-Term. | G | F | T | F | S | N | Y | W | M | T |
| 4A10 | 1gG$_{2ak}$ | N-Term. | G | Y | T | F | S | S | Y | W | M | H |

CDR2 Comparisons

| | | | | | | | | | | | | | | | |
|---|---|---|---|---|---|---|---|---|---|---|---|---|---|---|---|
| 1G8 | 1gG$_{1k}$ | W | I | D | P | E | N | G | D | T | E | F | V | P | K | F | Q | G |
| 2H9 | 1gG$_{1k}$ | E | I | R | L | R | S | E | N | Y | A | T | H | Y | A | E | S | V | K | G |
| 4A10 | 1gG$_{2ak}$ | N | I | D | P | G | S | G | Y | T | N | | | Y | A | E | N | L | K | T |

CDR3 Comparisons

| | | | | | | | | | | | |
|---|---|---|---|---|---|---|---|---|---|---|---|
| 1G8 | 1gG$_{1k}$ | G | G | F | | | | | | | |
| 2H9 | 1gG$_{1k}$ | L | G | R | P | N | | | | | |
| 4A10 | 1gG$_{2ak}$ | R | S | T | M | I | T | T | G | F | A | Y | anti-1G8

1. LAPC-4 AD
2. LAPC-9 AI
3. LNCaP
4. LNCaP-PSCA

5. HPAC
6. Capan-1
7. ASPC-1

FIG. 65
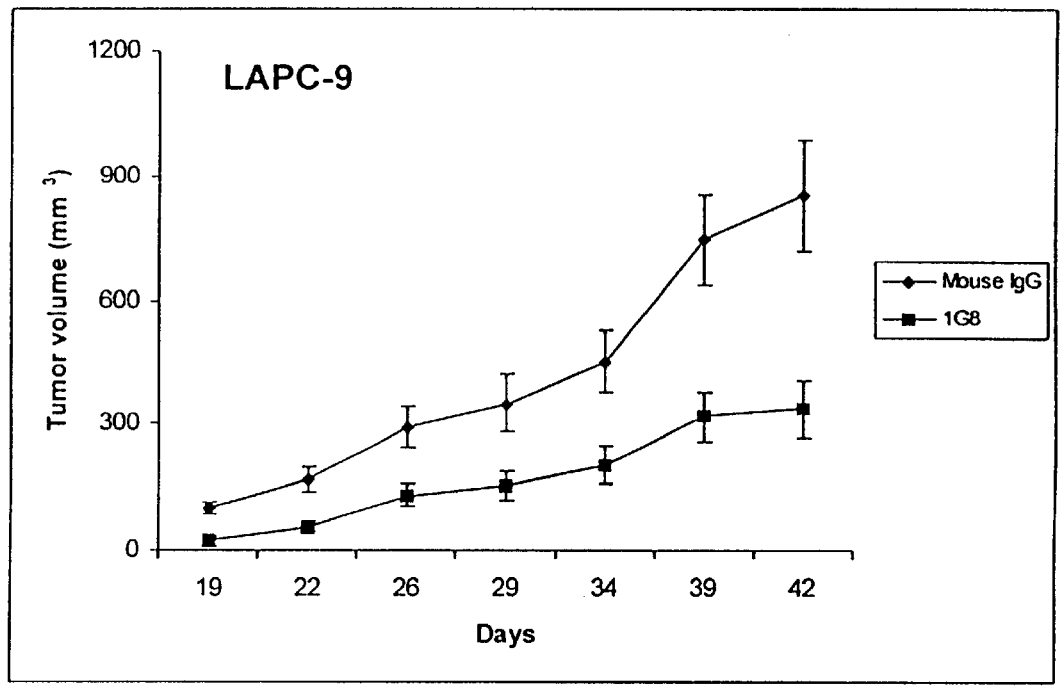
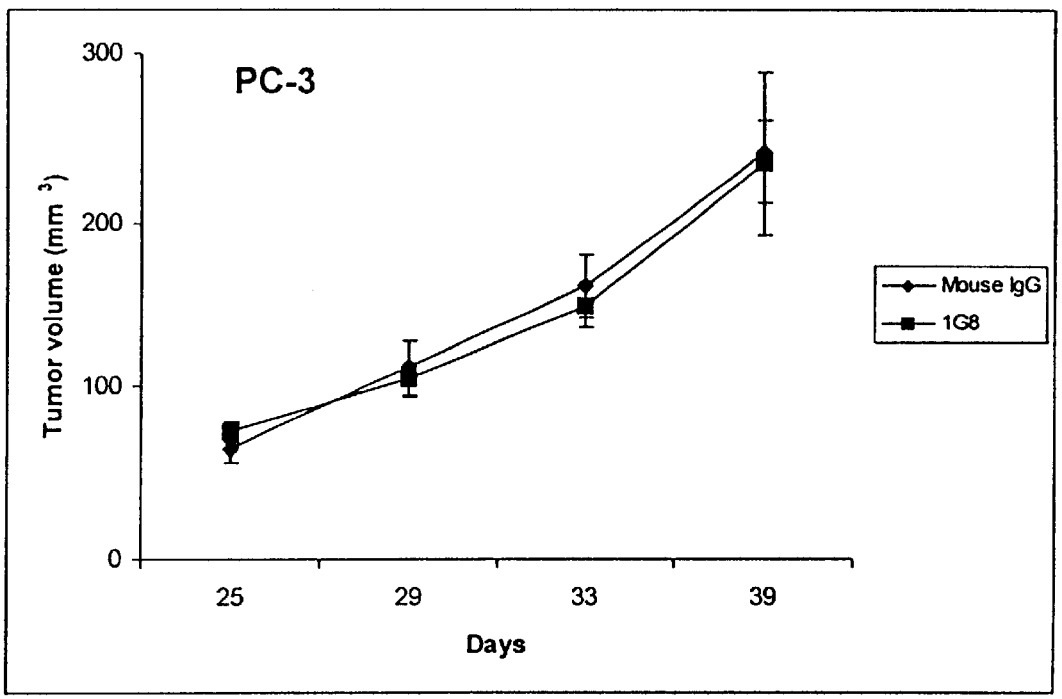

FIG. 66
A)
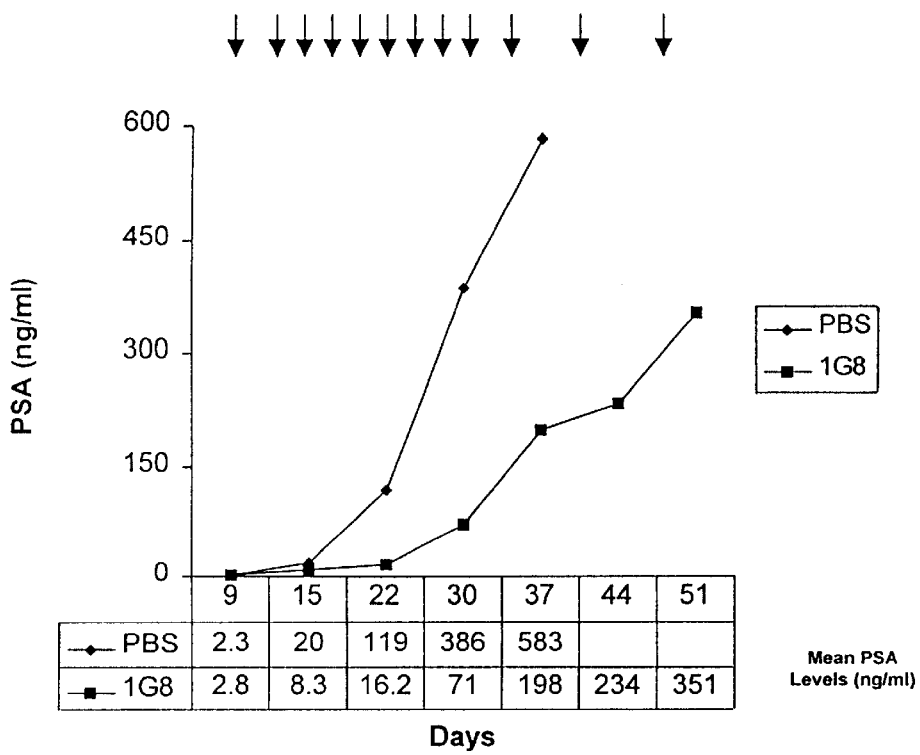
B)
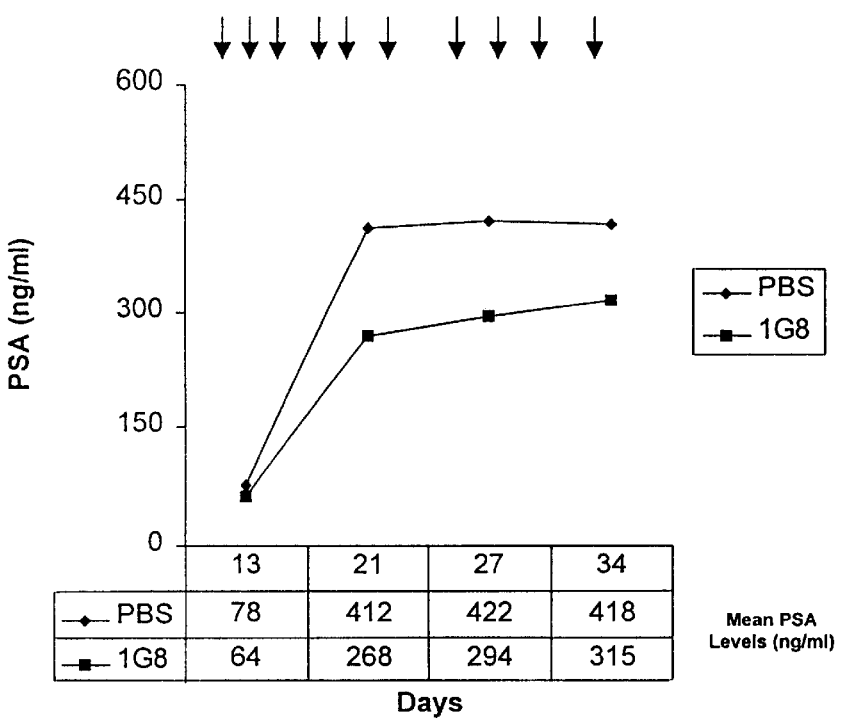

FIG. 67
A)
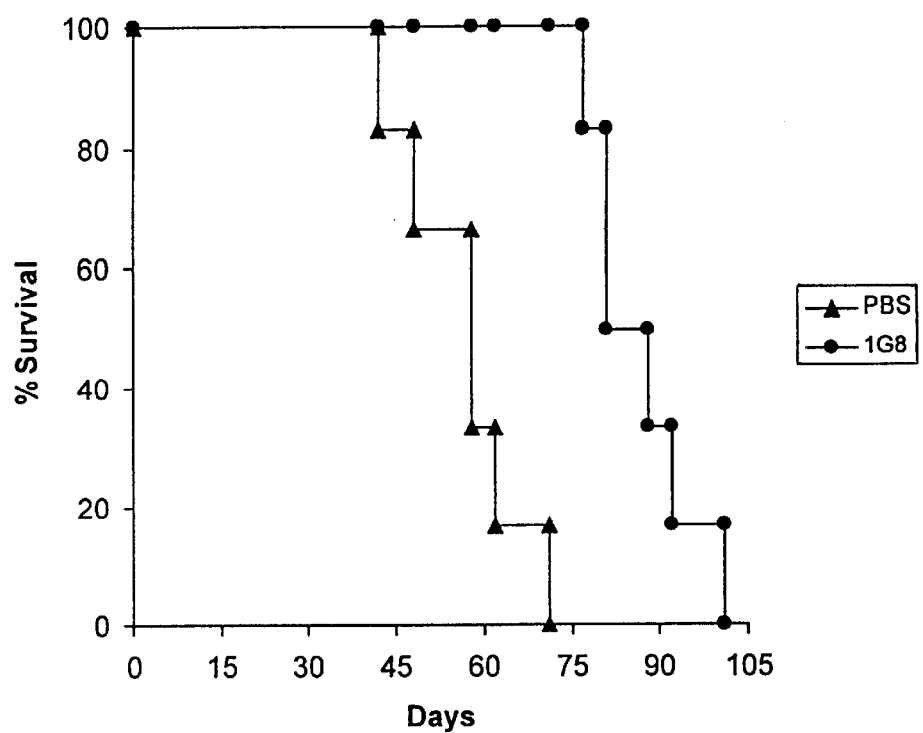
B)
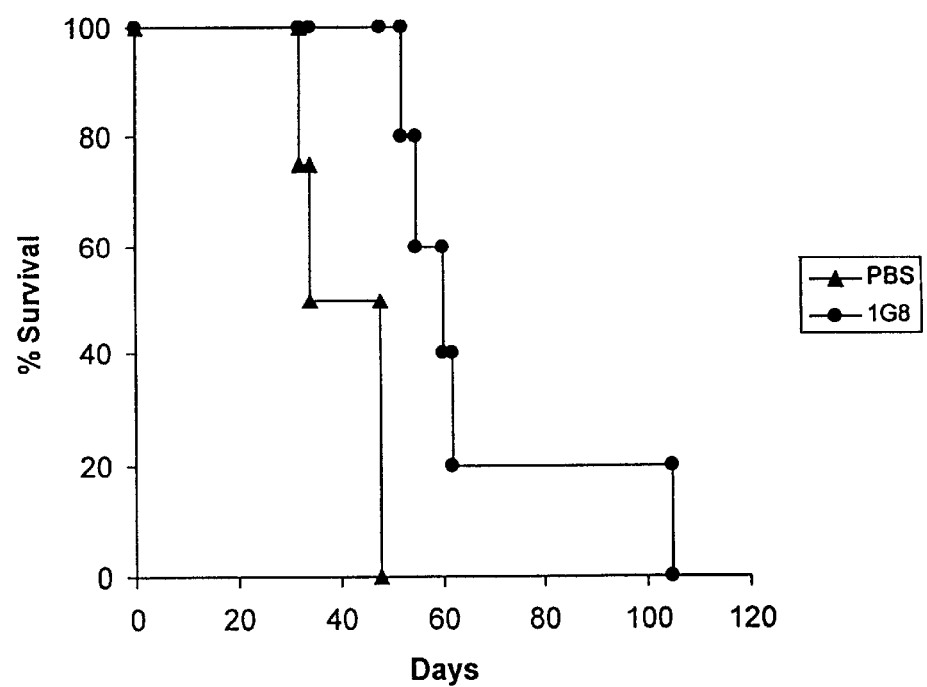

FIG. 68
A)
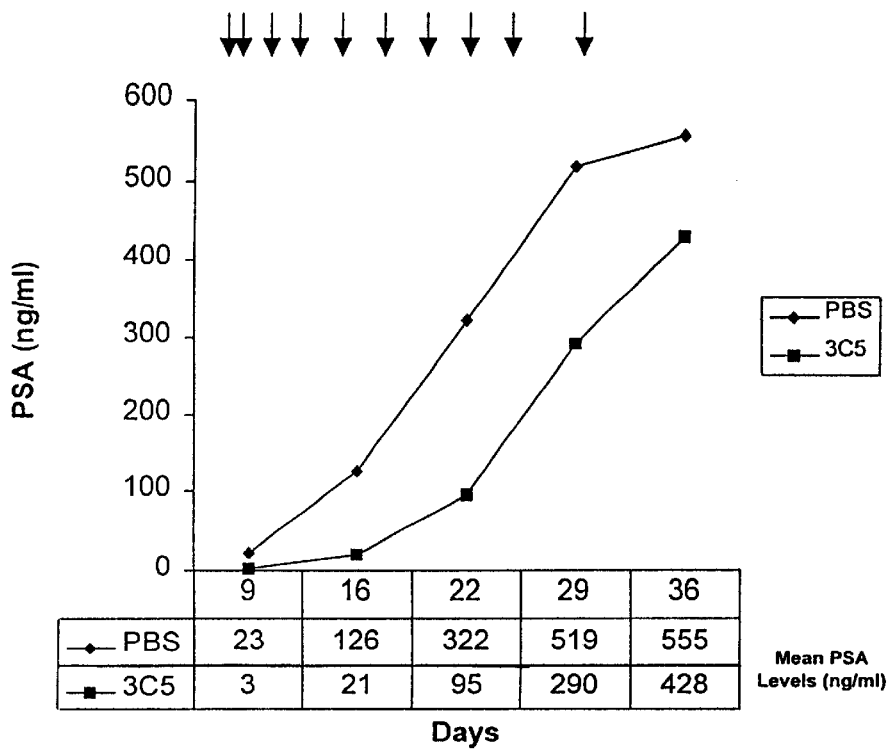
B)
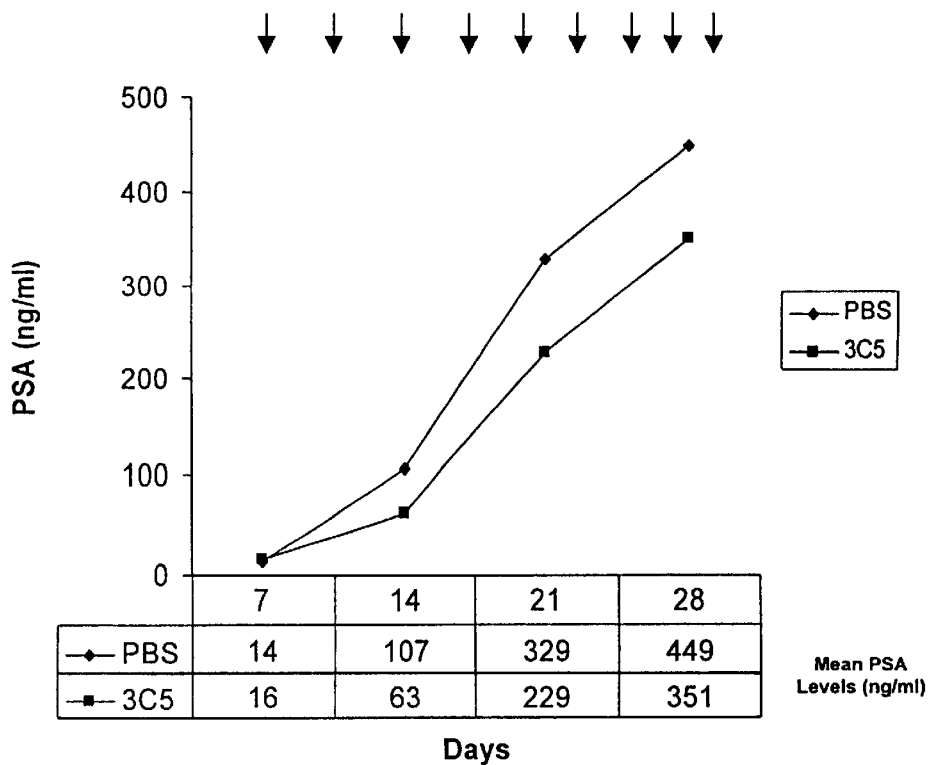

FIG. 69
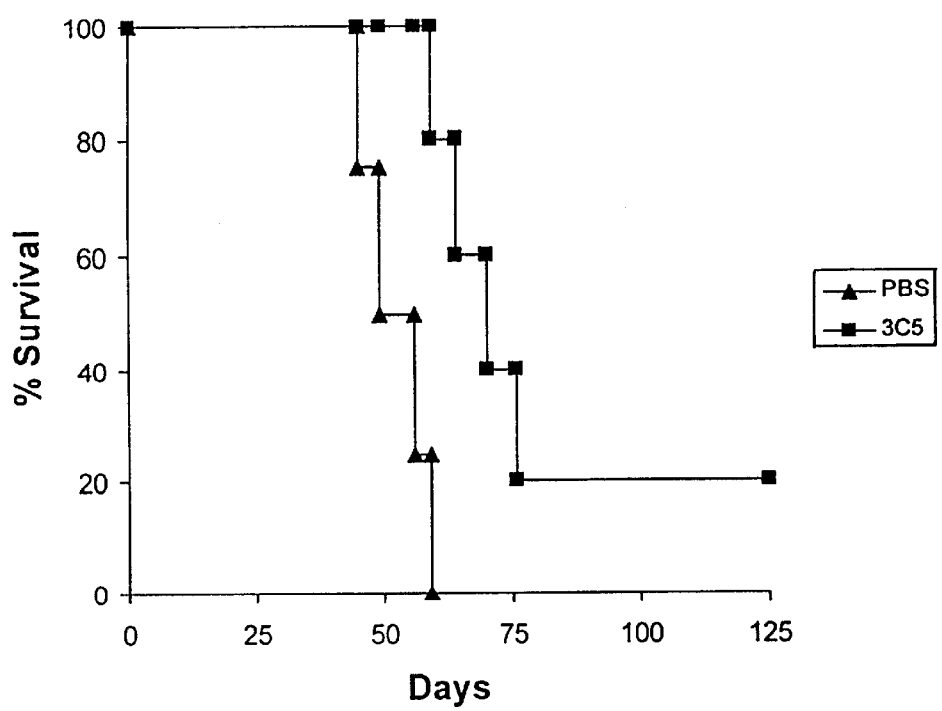
A)
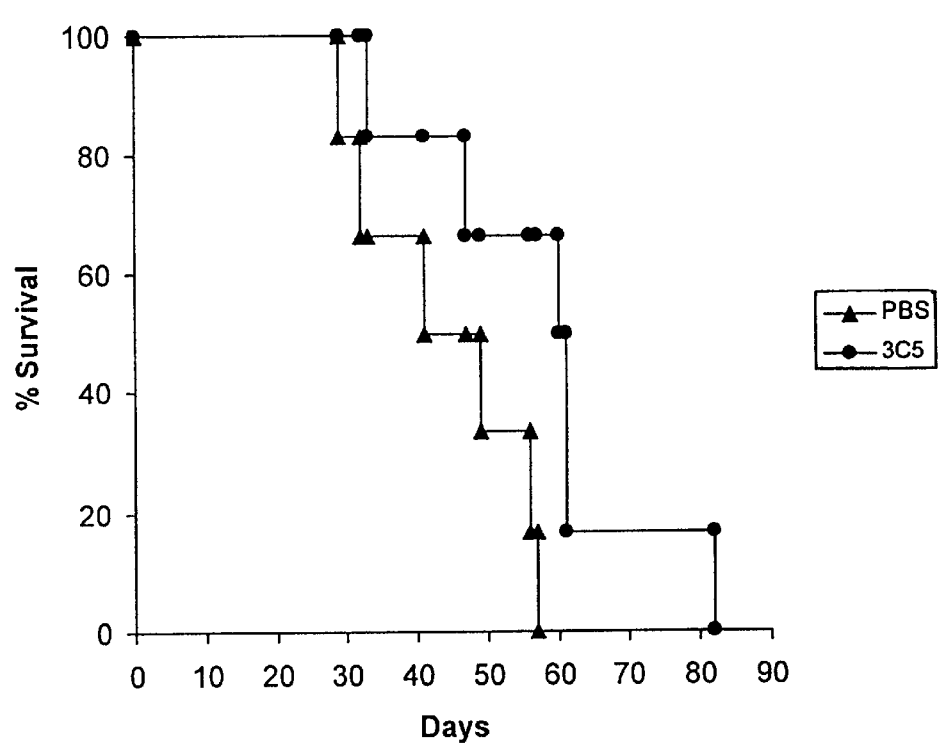
B)

FIG. 71
PSCA 3C5 MAb Localizes within LAPC9AD Xenograft Tissue
3C5 Treated
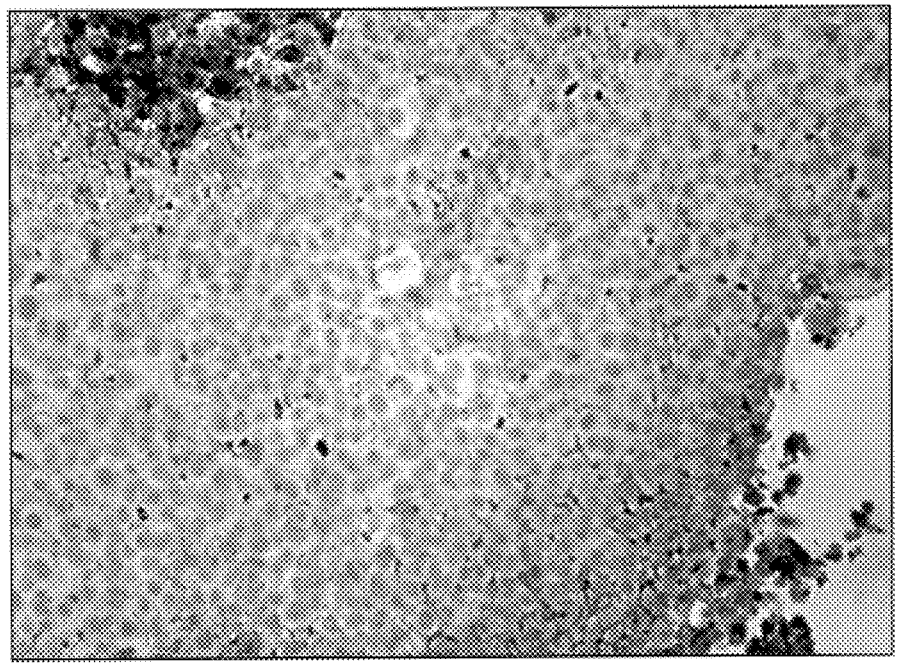
mIgG Treated
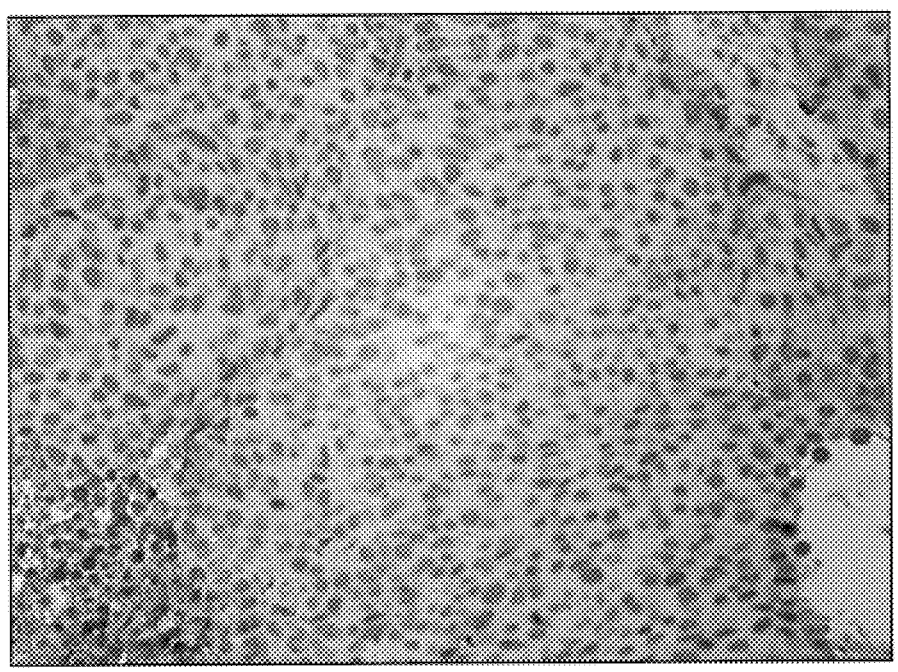

SEQUENCE LISTING

```
<160> NUMBER OF SEQ ID NOS: 27

<210> SEQ ID NO 1
<211> LENGTH: 998
<212> TYPE: DNA
<213> ORGANISM: HUMAN PSCA (hPSCA)
<220> FEATURE:
<221> NAME/KEY: misc_feature
<222> LOCATION: (543)
<223> OTHER INFORMATION: any nucleotide (i.e., a, c, g or t)
<221> NAME/KEY: misc_feature
<222> LOCATION: (580)
<223> OTHER INFORMATION: any nucleotide (i.e., a, c, g or t)
<221> NAME/KEY: misc_feature
<222> LOCATION: (584)
<223> OTHER INFORMATION: any nucleotide (i.e., a, c, g or t)
<221> NAME/KEY: misc_feature
<222> LOCATION: (604)
<223> OTHER INFORMATION: any nucleotide (i.e., a, c, g or t)
<221> NAME/KEY: misc_feature
<222> LOCATION: (608)
<223> OTHER INFORMATION: any nucleotide (i.e, a, c, g or t)
<221> NAME/KEY: misc_feature
<222> LOCATION: (615)
<223> OTHER INFORMATION: any nucleotide (i.e., a, c, g or t)
<221> NAME/KEY: misc_feature
<222> LOCATION: (636)
<223> OTHER INFORMATION: any nucleotide (i.e., a, c, g or t)
<221> NAME/KEY: misc_feature
<222> LOCATION: (640)
<223> OTHER INFORMATION: any nucleotide (i.e., a, c, g or t)
<221> NAME/KEY: misc_feature
<222> LOCATION: (646)
<223> OTHER INFORMATION: any nucleotide (i.e., a, c, g or t)
<221> NAME/KEY: misc_feature
<222> LOCATION: (697)
<223> OTHER INFORMATION: any nucleotide (i.e., a, c, g or t)
<221> NAME/KEY: misc_feature
<222> LOCATION: (926)
<223> OTHER INFORMATION: any nucleotide (i.e., a, c, g or t)

<400> SEQUENCE: 1
agggagaggc agtgaccatg aaggctgtgc tgcttgccct gttgatggca ggcttggccc      60
tgcagccagg cactgccctg ctgtgctact cctgcaaagc ccaggtgagc aacgaggact     120
gcctgcaggt ggagaactgc acccagctgg gggagcagtg ctggaccgcg cgcatccgcg     180
cagttggcct cctgaccgtc atcagcaaag gctgcagctt gaactgcgtg gatgactcac     240
aggactacta cgtgggcaag aagaacatca cgtgctgtga caccgacttg tgcaacgcca     300 gcgggggccca tgccctgcag ccggctgccg ccatccttgc gctgctccct gcactcggcc     360
tgctgctctg gggacccggc cagctatagg ctctgggggg ccccgctgca gcccacactg     420
ggtgtggtgc cccaggcctt tgtgccactc ctcacagaac ctgcccagt gggagcctgt       480
```

-continued

```
cctggttcct gaggcacatc ctaacgcaag tttgaccatg tatgtttgca ccccttttcc      540
ccnaaccctg accttcccat gggccttttc caggattccn accnggcaga tcagttttag      600
tganacanat ccgcntgcag atggcccctc caaccntttn tgttgntgtt tccatggccc      660
agcattttcc acccttaacc ctgtgttcag gcacttnttc ccccaggaag ccttccctgc      720
ccaccccatt tatgaattga gccaggtttg gtccgtggtg tcccccgcac ccagcagggg      780
acaggcaatc aggagggccc agtaaaggct gagatgaagt ggactgagta gaactggagg      840
acaagagttg acgtgagttc ctgggagttt ccagagatgg ggcctggagg cctggaggaa      900
ggggccaggc ctcacatttg tggggntccc gaatggcagc ctgagcacag cgtaggccct      960
taataaacac ctgttggata agccaaaaaa aaaaaaaa                              998
```

<210> SEQ ID NO 2
<211> LENGTH: 123
<212> TYPE: PRT
<213> ORGANISM: HUMAN PSCA (hPSCA)
<220> FEATURE:
<221> NAME/KEY: SITE
<222> LOCATION: (50)..(64)
<221> NAME/KEY: SITE
<222> LOCATION: (71)..(82)
<221> NAME/KEY: SITE
<222> LOCATION: (67)..(81)

<400> SEQUENCE: 2

```
Met Lys Ala Val Leu Leu Ala Leu Leu Met Ala Gly Leu Ala Leu Gln
 1               5                  10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ile Leu Ala Leu Leu Pro Ala
            100                 105                 110

Leu Gly Leu Leu Leu Trp Gly Pro Gly Gln Leu
        115                 120
```

<210> SEQ ID NO 3
<211> LENGTH: 441
<212> TYPE: DNA
<213> ORGANISM: MURINE PSCA (mPSCA)

<400> SEQUENCE: 3

```
atgaagacag tttttttttat cctgctggcc acctacttag ccctgcatcc aggtgctgct      60
ctgcagtgct attcatgcac agcacagatg aacaacagag actgtctgaa tgtacagaac     120
tgcagcctgg accagcacag ttgctttaca tcgcgcatcc gggccattgg actcgtgaca     180
gttatcagta agggctgcag ctcacagtgt gaggatgact cggagaacta ctatttgggc     240
aagaagaaca tcacgtgctg ctactctgac ctgtgcaatg tcaacggggc ccacaccctg     300 aagccacccca ccaccctggg gctgctgacc gtgctctgca gcctgttgct gtggggctcc     360
agccgtctgt aggctctggg agagcctacc atagcccgat tgtgaaggga tgagctgcac     420
```
tccaccccac ccccacacag g         441

<210> SEQ ID NO 4
<211> LENGTH: 123
<212> TYPE: PRT
<213> ORGANISM: MURINE PSCA (mPSCA)

<400> SEQUENCE: 4

```
Met Lys Thr Val Phe Phe Ile Leu Leu Ala Thr Tyr Leu Ala Leu His
 1               5                  10                  15

Pro Gly Ala Ala Leu Gln Cys Tyr Ser Cys Thr Ala Gln Met Asn Asn
            20                  25                  30

Arg Asp Cys Leu Asn Val Gln Asn Cys Ser Leu Asp Gln His Ser Cys
        35                  40                  45

Phe Thr Ser Arg Ile Arg Ala Ile Gly Leu Val Thr Val Ile Ser Lys
    50                  55                  60

Gly Cys Ser Ser Gln Cys Glu Asp Asp Ser Glu Asn Tyr Tyr Leu Gly
 65                  70                  75                  80

Lys Lys Asn Ile Thr Cys Cys Tyr Ser Asp Leu Cys Asn Val Asn Gly
                85                  90                  95

Ala His Thr Leu Lys Pro Pro Thr Thr Leu Gly Leu Leu Thr Val Leu
            100                 105                 110

Cys Ser Leu Leu Leu Trp Gly Ser Ser Arg Leu
        115                 120
```

<210> SEQ ID NO 5
<211> LENGTH: 131
<212> TYPE: PRT
<213> ORGANISM: HUMAN STEM CELL ANTIGEN (hSCA-2)

<400> SEQUENCE: 5

```
Met Lys Ile Phe Leu Pro Val Leu Leu Ala Ala Leu Leu Gly Val Glu
 1               5                  10                  15

Arg Ala Ser Ser Leu Met Cys Phe Ser Cys Leu Asn Gln Lys Ser Asn
            20                  25                  30

Leu Tyr Cys Leu Lys Pro Thr Ile Cys Ser Asp Gln Asp Asn Tyr Cys
        35                  40                  45

Val Thr Val Ser Ala Ser Ala Gly Ile Gly Asn Leu Val Thr Phe Gly
    50                  55                  60

His Ser Leu Ser Lys Thr Cys Ser Pro Ala Cys Pro Ile Pro Glu Gly
 65                  70                  75                  80

Val Asn Val Gly Val Ala Ser Met Gly Ile Ser Cys Cys Gln Ser Phe
                85                  90                  95

Leu Cys Asn Phe Ser Ala Ala Asp Gly Gly Leu Arg Ala Ser Val Thr
            100                 105                 110

Leu Leu Gly Ala Gly Leu Leu Leu Ser Leu Leu Pro Ala Leu Leu Arg
        115                 120                 125

Phe Gly Pro
    130
```

<210> SEQ ID NO 6
<211> LENGTH: 123
<212> TYPE: PRT
<213> ORGANISM: HUMAN PSCA (hPSCA)

<400> SEQUENCE: 6

```
Met Lys Ala Val Leu Leu Ala Leu Leu Met Ala Gly Leu Ala Leu Gln
 1               5                  10                  15
```

Pro Gly Thr Ala Leu Leu Cys Tyr Ser Cys Lys Ala Gln Val Ser Asn
           20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ile Leu Ala Leu Leu Pro Ala
            100                 105                 110

Leu Gly Leu Leu Leu Trp Gly Pro Gly Gln Leu
            115                 120

<210> SEQ ID NO 7
<211> LENGTH: 123
<212> TYPE: PRT
<213> ORGANISM: MURINE PSCA (mPSCA)

<400> SEQUENCE: 7

Met Lys Thr Val Leu Phe Leu Leu Leu Ala Thr Tyr Leu Ala Leu His
1               5                   10                  15

Pro Gly Ala Ala Leu Gln Cys Tyr Ser Cys Thr Ala Gln Met Asn Asn
            20                  25                  30

Arg Asp Cys Leu Asn Val Gln Asn Cys Ser Leu Asp Gln His Ser Cys
        35                  40                  45

Phe Thr Ser Arg Ile Arg Ala Ile Gly Leu Val Thr Val Ile Ser Lys
    50                  55                  60

Gly Cys Ser Ser Gln Cys Glu Asp Asp Ser Glu Asn Tyr Tyr Leu Gly
65                  70                  75                  80

Lys Lys Asn Ile Thr Cys Cys Tyr Ser Asp Leu Cys Asn Val Asn Gly
                85                  90                  95

Ala His Thr Leu Lys Pro Pro Thr Thr Leu Gly Leu Leu Thr Val Leu
            100                 105                 110

Cys Ser Leu Leu Leu Trp Gly Ser Ser Arg Leu
            115                 120

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: RT-PCR
      PRIMER

<400> SEQUENCE: 8
ttctcctgct ggccacctac                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: RT-PCR
      PRIMER

<400> SEQUENCE: 9
gcagctcatc ccttcacaat                                              20

<210> SEQ ID NO 10
<211> LENGTH: 408
<212> TYPE: DNA
<213> ORGANISM: SCID Mice

<400> SEQUENCE: 10

```
tgcttcttcc tgatggcagt ggttatagga gtcaattcag aggttcagct gcagcagtct      60
ggggcagaac ttgtgaggtc aggggcctca gtcaagttgt cctgcacagc ttctggcttc     120
aacattaaag actactatat acactgggtg aatcagaggc ctgaccaggg cctggagtgg     180
attggatgga ttgatcctga gaatggtgac actgaatttg tcccgaagtt ccagggcaag     240
gccactatga ctgcagacat tttctccaac acagcctacc tgcacctcag cagcctgaca     300
tctgaagaca ctgccgtcta ttactgtaaa acggggggtt tctggggcca agggactctg     360
gtcactgtct ctgcagccaa aacgacaccc ccatctgtct atccactg                  408
```

<210> SEQ ID NO 11
<211> LENGTH: 136
<212> TYPE: PRT
<213> ORGANISM: SCID Mice

<400> SEQUENCE: 11

```
Cys Phe Phe Leu Met Ala Val Val Ile Gly Val Asn Ser Glu Val Gln
  1               5                  10                  15

Leu Gln Gln Ser Gly Ala Glu Leu Val Arg Ser Gly Ala Ser Val Lys
             20                  25                  30

Leu Ser Cys Thr Ala Ser Gly Phe Asn Ile Lys Asp Tyr Tyr Ile His
         35                  40                  45

Trp Val Asn Gln Arg Pro Asp Gln Gly Leu Glu Trp Ile Gly Trp Ile
     50                  55                  60

Asp Pro Glu Asn Gly Asp Thr Glu Phe Val Pro Lys Phe Gln Gly Lys
 65                  70                  75                  80

Ala Thr Met Thr Ala Asp Ile Phe Ser Asn Thr Ala Tyr Leu His Leu
                 85                  90                  95

Ser Ser Leu Thr Ser Glu Asp Thr Ala Val Tyr Tyr Cys Lys Thr Gly
            100                 105                 110

Gly Phe Trp Gly Gln Gly Thr Leu Val Thr Val Ser Ala Ala Lys Thr
        115                 120                 125

Thr Pro Pro Ser Val Tyr Pro Leu
    130                 135
```

<210> SEQ ID NO 12
<211> LENGTH: 426
<212> TYPE: DNA
<213> ORGANISM: SCID Mice

<400> SEQUENCE: 12

```
ttggtagcaa cagcctcaga gtccactcc caggtccaac tgcagcaacc tgggtctgaa       60
ctggtgaggc ctggaacttc agtgaagctg tcctgcaagg cttctggcta tacattctcc     120
agctactgga tgcactgggt gaagcagagg cctggacaag ccttgagtg gattggaaat     180 attgaccctg gtagtggtta cactaactac gctgagaacc tcaagaccaa ggccacactg     240
actgtagaca catcctccag cacagcctac atgcagctca gcagcctgac atctgaggac     300
tctgcagtct attactgtac aagccgatct actatgatta cgacgggatt tgcttactgg     360
ggccaaggga ctctggtcac tgtctctgca gctacaacaa cagccccatc tgtctatcca     420
``` ctggcc                                                                  426

<210> SEQ ID NO 13
<211> LENGTH: 142
<212> TYPE: PRT
<213> ORGANISM: SCID Mice

<400> SEQUENCE: 13

Leu Val Ala Thr Ala Ser Asp Val His Ser Gln Val Gln Leu Gln Gln
 1               5                  10                  15

Pro Gly Ser Glu Leu Val Arg Pro Gly Thr Ser Val Lys Leu Ser Cys
            20                  25                  30

Lys Ala Ser Gly Tyr Thr Phe Ser Ser Tyr Trp Met His Trp Val Lys
        35                  40                  45

Gln Arg Pro Gly Gln Gly Leu Glu Trp Ile Gly Asn Ile Asp Pro Gly
    50                  55                  60

Ser Gly Tyr Thr Asn Tyr Ala Glu Asn Leu Lys Thr Lys Ala Thr Leu
65                  70                  75                  80

Thr Val Asp Thr Ser Ser Thr Ala Tyr Met Gln Leu Ser Ser Leu
                85                  90                  95

Thr Ser Glu Asp Ser Ala Val Tyr Tyr Cys Thr Ser Arg Ser Thr Met
            100                 105                 110

Ile Thr Thr Gly Phe Ala Tyr Trp Gly Gln Gly Thr Leu Val Thr Val
        115                 120                 125

Ser Ala Ala Thr Thr Thr Ala Pro Ser Val Tyr Pro Leu Ala
    130                 135                 140

<210> SEQ ID NO 14
<211> LENGTH: 453
<212> TYPE: DNA
<213> ORGANISM: SCID Mice

<400> SEQUENCE: 14
aatgacttcg ggttgagctg ggttttatt attgttcttt taaaagggt ccggagtgaa      60 gtgaggcttg aggagtctgg aggaggctgg gtgcaacctg gaggatccat gaaactctcc    120
tgtgtagcct ctggatttac tttcagtaat tactggatga cttgggtccg ccagtctcca    180 gagaagggc ttgagtgggt tgctgaaatt cgattgagat ctgaaaatta tgcaacacat    240
tatgcggagt ctgtgaaagg gaaattcacc atctcaagag atgattccag aagtcgtctc    300
tacctgcaaa tgaacaactt aagacctgaa gacagtggaa tttattactg tacagatggt    360
ctgggacgac taactggggg ccaagggact ctggtcactg tctctgcagc caaaacgaca    420
cccccatctg tctatccact ggccccttgt gta                                 453

<210> SEQ ID NO 15
<211> LENGTH: 151
<212> TYPE: PRT
<213> ORGANISM: SCID Mice

<400> SEQUENCE: 15

Asn Asp Phe Gly Leu Ser Trp Val Phe Ile Ile Val Leu Leu Lys Gly
 1               5                  10                  15

Val Arg Ser Glu Val Arg Leu Glu Glu Ser Gly Gly Gly Trp Val Gln
            20                  25                  30

Pro Gly Gly Ser Met Lys Leu Ser Cys Val Ala Ser Gly Phe Thr Phe
        35                  40                  45

```
Ser Asn Tyr Trp Met Thr Trp Val Arg Gln Ser Pro Glu Lys Gly Leu
    50                  55                  60

Glu Trp Val Ala Glu Ile Arg Leu Arg Ser Glu Asn Tyr Ala Thr His
 65                  70                  75                  80

Tyr Ala Glu Ser Val Lys Gly Lys Phe Thr Ile Ser Arg Asp Asp Ser
                 85                  90                  95

Arg Ser Arg Leu Tyr Leu Gln Met Asn Asn Leu Arg Pro Glu Asp Ser
                100                 105                 110

Gly Ile Tyr Tyr Cys Thr Asp Gly Leu Gly Arg Pro Asn Trp Gly Gln
                115                 120                 125

Gly Thr Leu Val Thr Val Ser Ala Ala Lys Thr Thr Pro Pro Ser Val
        130                 135                 140

Tyr Pro Leu Ala Pro Cys Val
145                 150

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: RT-PCR
      PRIMER

<400> SEQUENCE: 16

Thr Ala Arg Ile Arg Ala Val Gly Leu Leu Thr Val Ile Ser Lys
  1               5                  10                  15

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: RT-PCR
      PRIMER

<400> SEQUENCE: 17

Val Asp Asp Ser Gln Asp Tyr Tyr Val Gly Lys Lys
  1               5                  10

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: RT-PCR
      PRIMER

<400> SEQUENCE: 18

Ser Leu Asn Cys Val Asp Asp Ser Gln Asp Tyr Tyr Val Gly Lys
  1               5                  10                  15

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: RT-PCR
      PRIMER

<400> SEQUENCE: 19
tgcttgccct gttgatggca g                                              21

<210> SEQ ID NO 20
<211> LENGTH: 22
```

```
<212> TYPE: DNA
<213> ORGANISM: Artificial Sequence
<220> FEATURE:
<223> OTHER INFORMATION: Description of Artificial Sequence: RT-PCR
      PRIMER

<400> SEQUENCE: 20
ccagagcagc aggccgagtg ca                                         22

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: RT-PCR
      PRIMER

<400> SEQUENCE: 21
gggaattcgc acagccttca gggtc                                      25

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: RT-PCR
      PRIMER

<400> SEQUENCE: 22
ggagaattca tggcactgcc ctgctgtgct ac                              32

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: RT-PCR
      PRIMER

<400> SEQUENCE: 23
ggagaattcc taatgggccc cgctggcgtt                                 30

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: RT-PCR
      PRIMER

<400> SEQUENCE: 24
gggaagcttg cacagccttc agggtc                                     26

<210> SEQ ID NO 25
<211> LENGTH: 39
<212> TYPE: DNA
<213> ORGANISM: Artificial Sequence
<220> FEATURE:
<221> NAME/KEY: misc_feature
<222> LOCATION: (18)
<223> OTHER INFORMATION: a or g
<221> NAME/KEY: misc_feature
<222> LOCATION: (22)
<223> OTHER INFORMATION: g or c
<221> NAME/KEY: misc_difference
<222> LOCATION: (28)
<223> OTHER INFORMATION: g or t
<221> NAME/KEY: misc_feature
<222> LOCATION: (31)
```

```
<223> OTHER INFORMATION: a or c
<221> NAME/KEY: misc_feature
<222> LOCATION: (34)
<223> OTHER INFORMATION: g or c
<223> OTHER INFORMATION: Description of Artificial Sequence: RT-PCR
      PRIMER

<400> SEQUENCE: 25
ggcgatatcc accatggrat gsagctgkgt matsctctt                             39

<210> SEQ ID NO 26
<211> LENGTH: 39
<212> TYPE: DNA
<213> ORGANISM: Artificial Sequence
<220> FEATURE:
<221> NAME/KEY: misc_feature
<222> LOCATION: (11)
<223> OTHER INFORMATION: c or t
<221> NAME/KEY: misc_feature
<222> LOCATION: (25)..(26)
<223> OTHER INFORMATION: a or g
<223> OTHER INFORMATION: Description of Artificial Sequence: RT-PCR
      PRIMER

<400> SEQUENCE: 26
agggaattca yctccacaca caggrrccag tggatagac                             39

<210> SEQ ID NO 27
<211> LENGTH: 39
<212> TYPE: DNA
<213> ORGANISM: Artificial Sequence
<220> FEATURE:
<221> NAME/KEY: misc_feature
<222> LOCATION: (17)
<223> OTHER INFORMATION: a or g
<221> NAME/KEY: misc_feature
<222> LOCATION: (26)
<223> OTHER INFORMATION: c or t
<221> NAME/KEY: misc_feature
<222> LOCATION: (33)
<223> OTHER INFORMATION: g or t
<223> OTHER INFORMATION: Description of Artificial Sequence: RT-PCR
      PRIMER

<400> SEQUENCE: 27
ggggatatcc accatgract tcgggytgag ctkggtttt                             39
```

METHODS FOR DETECTING PROSTATE STEM CELL ANTIGEN PROTEIN

This application is a continuation-in-part (CIP) of U.S. Ser. No. 09/359,326, filed Jul. 20, 1999, which is a CIP of U.S. Pat. No. 6,261,791, issued Jul. 17, 2001, based on U.S. Ser. No. 09/318,503, filed May 25, 1999, now U.S. Pat. No. 6,261,791, which is a CIP of U.S. Pat. No. 6,261,789, issued Jul. 17, 2001, based on U.S. Ser. No. 09/251,835, filed Feb. 17, 1999, which is a CIP of U.S. Pat. No. 6,258,939, issued Jul. 10, 2001, based on U.S. Ser. No. 09/203,939, filed Dec. 2, 1998, which is a CIP of U.S. Pat. No. 6,267,960, issued Jul. 31, 2001, based on U.S. Ser. No. 09/038,261, filed Mar. 10, 1998; claiming the priority of provisional applications, U.S. Ser. No. 60/228,816, filed Mar. 10, 1997; U.S. Ser. No. 60/071,141 filed Jan. 12, 1998 and; U.S. Ser. No. 60/074,675, filed Feb. 13, 1998. This application further claims the benefit of the filing dates of U.S. Ser. Nos. 60/124,658 filed Mar. 16, 1999; 60/120,536 filed Feb. 17, 1999; and 60/113,230 filed Dec. 21, 1998. The contents of all of the foregoing applications are incorporated by reference into the present application.

Throughout this application, various publications are referenced within parentheses. The disclosures of these publications are hereby incorporated by reference herein in their entireties.

BACKGROUND OF THE INVENTION

Cancer is the second leading cause of human death next to coronary disease. Worldwide, millions of people die from cancer every year. In the United States alone, cancer cause the death of well over a half-million people each year, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the leading causes of cancer death. These and virtually all other carcinomas share a common lethal feature. With very few exceptions, metastatic disease from a carcinoma is fatal. Moreover, even for those cancer patients that initially survive their primary cancers, common experience has shown that their lives are dramatically altered. Many cancer patients experience strong anxieties driven by the awareness of the potential for recurrence or treatment failure. Many cancer patients experience significant physical debilitations following treatment.

Generally speaking, the fundamental problem in the management of the deadliest cancers is the lack of effective and non-toxic systemic therapies. Molecular medicine, still very much in its infancy, promises to redefine the ways in which these cancers are managed. Unquestionably, there is an intensive worldwide effort aimed at the development of novel molecular approaches to cancer diagnosis and treatment. For example, there is a great interest in identifying truly tumor-specific genes and proteins that could be used as diagnostic and prognostic markers and/or therapeutic targets or agents. Research efforts in these areas are encouraging, and the increasing availability of useful molecular technologies has accelerated the acquisition of meaningful knowledge about cancer. Nevertheless, progress is slow and generally uneven.

Recently, there has been a particularly strong interest in identifying cell surface tumor-specific antigens which might be useful as targets for various immunotherapeutic or small molecule treatment strategies. A large number of such cell-surface antigens have been reported, and some have proven to be reliably associated with one or more cancers. Much attention has been focused on the development of novel therapeutic strategies which target these antigens. However, few truly effective immunological cancer treatments have resulted.

The use of monoclonal antibodies to tumor-specific or over-expressed antigens in the treatment of solid cancers is instructive. Although antibody therapy has been well researched for some 20 years, only very recently have corresponding pharmaceuticals materialized. One example is the humanized anti-HER2/neu monoclonal antibody, Herceptin, recently approved for use in the treatment of metastatic breast cancers overexpressing the HER2/neu receptor. Another is the human/mouse chimeric anti-CD20/B cell lymphoma antibody, Rituxan, approved for the treatment of non-Hodgkin's lymphoma. Several other antibodies are being evaluated for the treatment of cancer in clinical trials or in pre-clinical research, including a chimeric and a fully human IgG2 monoclonal antibody specific for the epidermal growth factor receptor (Slovin et al., 1997, Proc. Am. Soc. Clin. Oncol. 16:311; Falcey et al., 1997, Proc. Am. Soc. Clin. Oncol. 16:383; Yang et al., 1999, Cancer Res. 59: 1236). Evidently, antibody therapy is finally emerging from a long embryonic phase. Nevertheless, there is still a very great need for new, more-specific tumor antigens for the application of antibody and other biological therapies. In addition, there is a corresponding need for tumor antigens which may be useful as markers for antibody-based diagnostic and imaging methods, hopefully leading to the development of earlier diagnosis and greater prognostic precision.

As discussed below, the management of prostate cancer serves as a good example of the limited extent to which molecular biology has translated into real progress in the clinic. With limited exceptions, the situation is more or less the same for the other major carcinomas mentioned above.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease, second only to lung cancer. Despite the magnitude of these figures, there is still no effective treatment for metastatic prostate cancer. Surgical prostatectomy, radiation therapy, hormone ablation therapy, and chemotherapy remain as the main treatment modalities. Unfortunately, these treatments are clearly ineffective for many. Moreover, these treatments are often associated with significant undesirable consequences.

On the diagnostic front, the serum PSA assay has been a very useful tool. Nevertheless, the specificity and general utility of PSA is widely regarded as lacking in several respects. Neither PSA testing, nor any other test nor biological marker has been proven capable of reliably identifying early-stage disease. Similarly, there is no marker available for predicting the emergence of the typically fatal metastatic stage of the disease. Diagnosis of metastatic prostate cancer is achieved by open surgical or laparoscopic pelvic lymphadenectomy, whole body radionuclide scans, skeletal radiography, and/or bone lesion biopsy analysis. Clearly, better imaging and other less invasive diagnostic methods offer the promise of easing the difficulty those procedures place on a patient, as well as improving therapeutic options. However, until there are prostate tumor markers capable of reliably identifying early-stage disease, predicting susceptibility to metastasis, and precisely imaging tumors, the management of prostate cancer will continue to be extremely difficult. Accordingly, more specific molecular tumor markers are clearly needed in the management of prostate cancer.

There are some known markers which are expressed predominantly in prostate, such as prostate specific membrane antigen (PSM), a hydrolase with 85% identity to a rat neuropeptidase (Carter et al., 1996, Proc. Natl. Acad. Sci. USA 93: 749; Bzdega et al., 1997, J. Neurochem. 69: 2270). However, the expression of PSM in small intestine and brain (Israeli et al., 1994, Cancer Res. 54: 1807), as well its potential role in neuropeptide catabolism in brain, raises concern of potential neurotoxicity with anti-PSM therapies. Preliminary results using an Indium-111 labeled, anti-PSM monoclonal antibody to image recurrent prostate cancer show some promise (Sodee et al., 1996, Clin Nuc Med 21: 759–766). More recently identified prostate cancer markers include PCTA-1 (Su et al., 1996, Proc. Natl. Acad. Sci. USA 93: 7252). PCTA-1, a novel galectin, is largely secreted into the media of expressing cells and may hold promise as a diagnostic serum marker for prostate cancer (Su et al., 1996). Vaccines for prostate cancer are also being actively explored with a variety of antigens, including PSM and PSA.

SUMMARY OF THE INVENTION

The invention provides a novel prostate cell-surface antigen, designated Prostate Stem Cell Antigen (PSCA), which is widely over-expressed across all stages of prostate cancer, including high grade prostatic intraepithelial neoplasia (PIN), androgen-dependent and androgen-independent prostate tumors. The PSCA gene shows 30% homology to stem cell antigen-2 (SCA-2), a member of the Thy-1/Ly-6 family of glycosylphosphatidylinositol (GPI)-anchored cell surface antigens, and encodes a 123 amino acid protein with an amino-terminal signal sequence, a carboxy-terminal GPI-anchoring sequence, and multiple N-glycosylation sites. PSCA mRNA expression is highly upregulated in both androgen dependent and androgen independent prostate cancer xenografts. In situ mRNA analysis localizes PSCA expression to the basal cell epithelium, the putative stem cell compartment of the prostate. Flow cytometric analysis demonstrates that PSCA is expressed predominantly on the cell surface and is anchored by a GPI linkage. Fluorescent in situ hybridization analysis localizes the PSCA gene to chromosome 8q24.2, a region of allelic gain in more than 80% of prostate cancers.

PSCA may be an optimal therapeutic target in view of its cell surface location, greatly upregulated expression in certain types of cancer such as prostate cancer cells. In this regard, the invention provides antibodies capable of binding to PSCA which can be used therapeutically to destroy or inhibit the growth of such cancer cells, or to block PSCA activity. In addition, PSCA proteins and PSCA-encoding nucleic acid molecules may be used in various immunotherapeutic methods to promote immune-mediated destruction or growth inhibition of tumors expressing PSCA.

PSCA also may represent an ideal prostate cancer marker, which can be used to discriminate between malignant prostate cancers, normal prostate glands and non-malignant neoplasias. For example, PSCA is expressed at very high levels in prostate cancer in relation to benign prostatic hyperplasia (BPH). In contrast, the widely used prostate cancer marker PSA is expressed at high levels in both normal prostate and BPH, but at lower levels in prostate cancer, rendering PSA expression useless for distinguishing malignant prostate cancer from BPH or normal glands. Because PSCA expression is essentially the reverse of PSA expression, analysis of PSCA expression can be employed to distinguish prostate cancer from non-malignant conditions.

The genes encoding both human and murine PSCA have been isolated and their coding sequences elucidated and provided herein. Also provided are the amino acid sequences of both human and murine PSCA. The invention further provides various diagnostic assays for the detection, monitoring, and prognosis of prostate cancer, including nucleic acid-based and immunological assays. PSCA-specific monoclonal and polyclonal antibodies and immunotherapeutic and other therapeutic methods of treating prostate cancer are also provided. These and other aspects of the invention are further described below.

BRIEF DESCRIPTION OF THE FIGURES

FIG. 1A. Nucleotide sequences (SEQ. ID NO:1, ATCC Designation 209612) of a cDNA encoding human PSCA.

FIG. 1B. Translated amino acid sequence (SEQ ID NO:2) of human PSCA.

FIG. 2. Nucleotide sequence (SEQ ID NO:3), of a murine cDNA PSCA homologue and the translated amino acid sequence (SEQ. ID NO:4) of murine PSCA.

FIG. 3. Alignment of amino acid sequences of human PSCA (SEQ. ID NO:5), murine PSCA (SEQ. ID NO:6), and human stem cell antigen-2 (hSCA-2) (SEQ. ID NO:7). Shaded regions highlight conserved amino acids. Conserved cysteines are indicated by bold lettering. Four predicted N-glycosylation sites in PSCA are indicated by asterisks. The underlined amino acids at the beginning and end of the protein represent N terminal hydrophobic signal sequences and C terminal GPI-anchoring sequences, respectively.

FIG. 5. Chou-Fassman analysis of human PSCA.

FIG. 6. A western blot showing that monoclonal antibody 1G8 binds LAPC9 (PSCA positive control) and a transitional cell carcinoma (bladder carcinoma) designated bladder (Rob).

FIG. 11A. In situ hybridization with antisense riboprobe for human PSCA on normal prostate specimens. PSCA is expressed by a subset of basal cells within the basal cell epithelium (black arrows), but not by the terminally differentiated secretory cells lining the prostatic ducts (400× magnification).

FIG. 11B. In situ hybridization with antisense riboprobe for human PSCA on normal and malignant prostate specimens. PSCA is expressed strongly by a high grade prostatic intraepithelial neoplasia (PIN) (black arrow) and by invasive prostate cancer glands (yellow arrows), but is not detectable in normal epithelium (green arrow) at 40× magnification.

FIG. 14B. Flow Cytometric analysis of cell surface PSCA expression on prostate cancer cell line (LAPC-4) using anti-PSCA monoclonal antibodies 1G8 and 3E6, mouse anti-PSCA polyclonal serum, or control secondary antibody. See Example 5 for details.

FIG. 16A. Alignment of amino acid sequences of human PSCA, murine PSCA, and human stem cell antigen-2 (hSCA-2). Shaded regions highlight conserved amino acids.

FIG. 17. A photograph showing a FISH analysis of PSCA and c-myc Gene Copy No. in prostate cancer.

FIG. 18. A photograph showing FITC labeled 1G8 antibodies strongly bind PSCA protein on PSCA transfected LNCAP cells.

FIG. 19. A photograph showing FITC labeled 1G8 antibodies weakly bind PreC cells.

FIG. 20. A photograph showing in situ RNA hybridization of PSCA in normal prostate basal cells.

Figure 22:

FIG. 22. A photograph of a bone sample showing bone metastases of prostate cancer as determined by biotinylated 1G8 monoclonal antibody linked to horseradish peroxidase-conjugated streptavidin.

FIG. 23. A photograph of a bone sample showing bone metastases of prostate cancer as determined by biotinylated 1G8 monoclonal antibody linked to horseradish peroxidase-conjugated streptavidin.

FIG. 24. A photograph of a bone sample showing bone metastases of prostate cancer as determined by biotinylated 3E6 monoclonal antibody linked to horseradish peroxidase-conjugated streptavidin.

Figure 25:
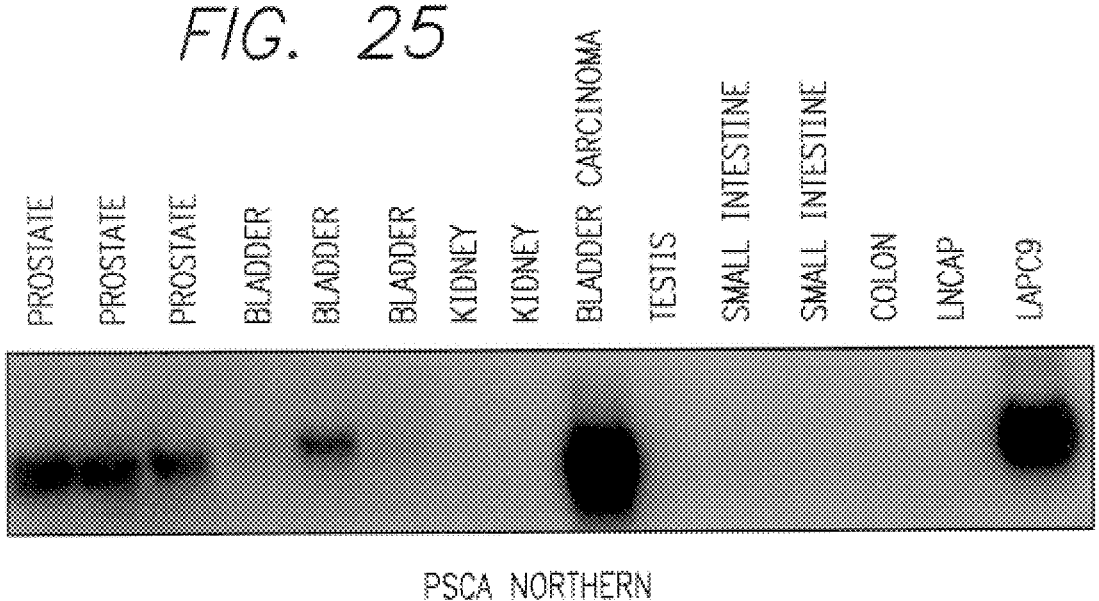

FIG. 25. A northern blot showing increased level of PSCA RNA in LAPC9 and transitional cell carcinoma of an advanced bladder carcinoma.

Figure 26:
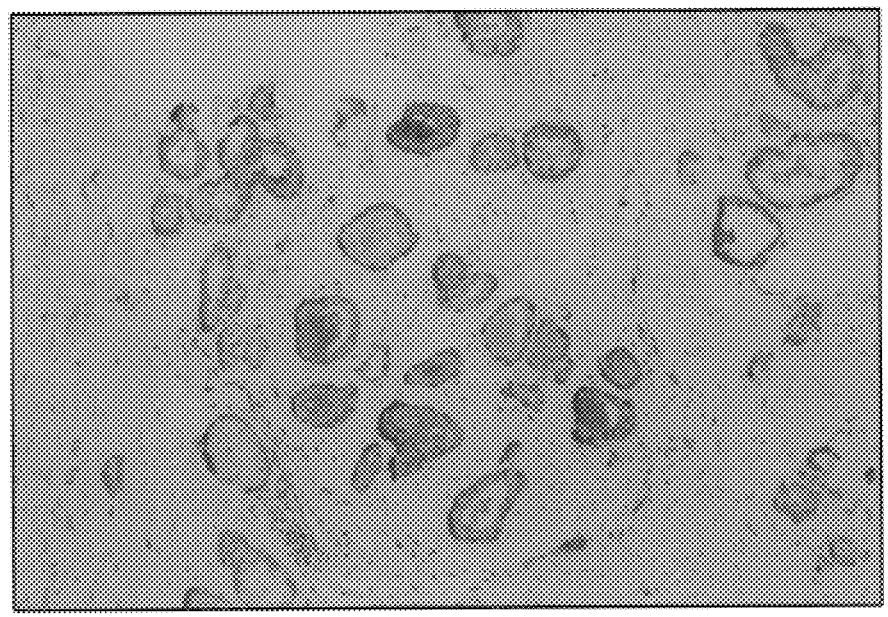

FIG. 26. A photograph of a tissue undergoing early stage prostate cancer as determined by biotinylated 3E6 monoclonal antibody linked to horseradish peroxidase-conjugated streptavidin.

FIG. 27. A photograph of a bone sample showing bone metastases of prostate cancer as determined by hematoxylin stained 3E6 monoclonal antibody.

Figure 21:
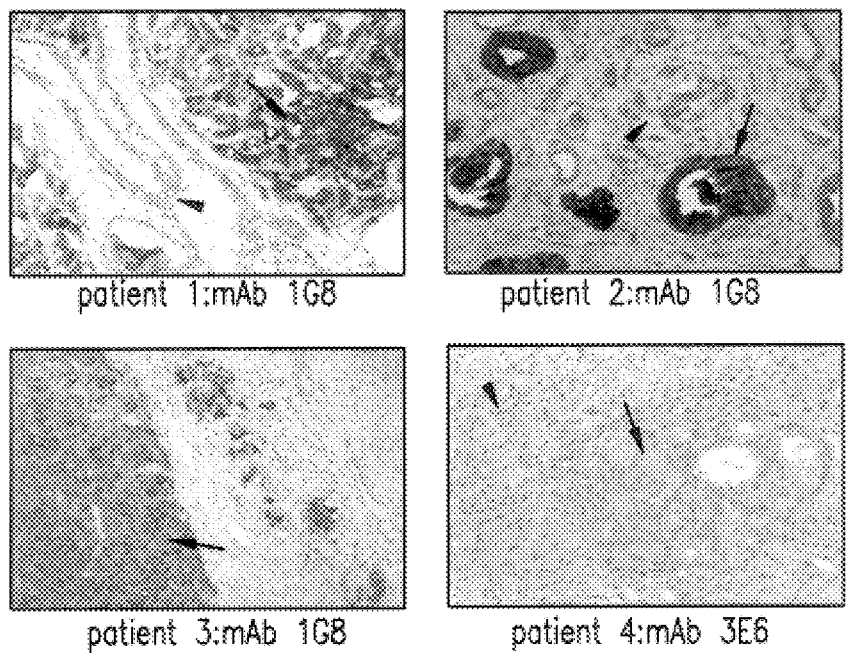
FIG. 21. PSCA immunostaining in primary prostate cancers. Representative paraffin-embedded sections from four patients were stained with anti-PSCA mAbs. The specimen from patient 1 demonstrates overexpression of PSCA protein in a Gleason grade 4 tumor (arrow) and undetectable expression of PSCA in adjacent normal glands (arrowhead) using PSCA mAb 1G8. The positively staining cancer completely surrounds the normal glands. The specimen from patient 2 demonstrates heterogeneous staining in a Gleason grade 3+¾ cancer. The Gleason pattern 3 glands (arrowhead) stain weakly compared with the larger, more cribriform appearing Gleason pattern ¾ glands (arrow). The specimen from patient 3 demonstrates strong expression of PSCA by a poorly differentiated Gleason 5 (arrow) tumor with mAb 1G8. Patient 4 is a biopsy specimen showing no PSCA staining in the majority of a poorly differentiated tumor (arrowhead) and extremely weak staining in a cribriform focus identified in the specimen. The matched bone metastasis from patient 4 is shown in FIG. 28.

FIG. 28. PSCA immunostaining in prostate cancer bone metastases. The top panel shows the hematoxylin and eosin (left) and PSCA (right) staining of a bony lesion from patient 5. A single focus suspicious for cancer (arrow) was identified in the H and E section and confirmed by intense staining with anti-PSCA mAb 1G8 (arrow). The bottom panel shows the H and E (left) and PSCA staining of a bone lesion from patient 4. The primary lesion from patient 4 is depicted in FIG. 21. Both the H and E and PSCA stains show diffuse bony involvement by prostate cancer (arrows). Again, PSCA immunostaining in the bone metastasis is uniform and intense.

FIG. 29. A photograph of a tissue undergoing early stage prostate cancer as determined by biotinylated 1G8 monoclonal antibody linked to horseradish peroxidase-conjugated streptavidin.

FIG. 30. A photograph showing that 1G8 binds LAPC9 cells as determined by hematoxylin staining.

FIG. 31. A photograph showing that 1G8 binds PSCA-transfected LnCaP cells.

FIG. 32. A photograph showing that 1G8 does not bind LnCaP cells (not transfected with PSCA).

Figure 33:
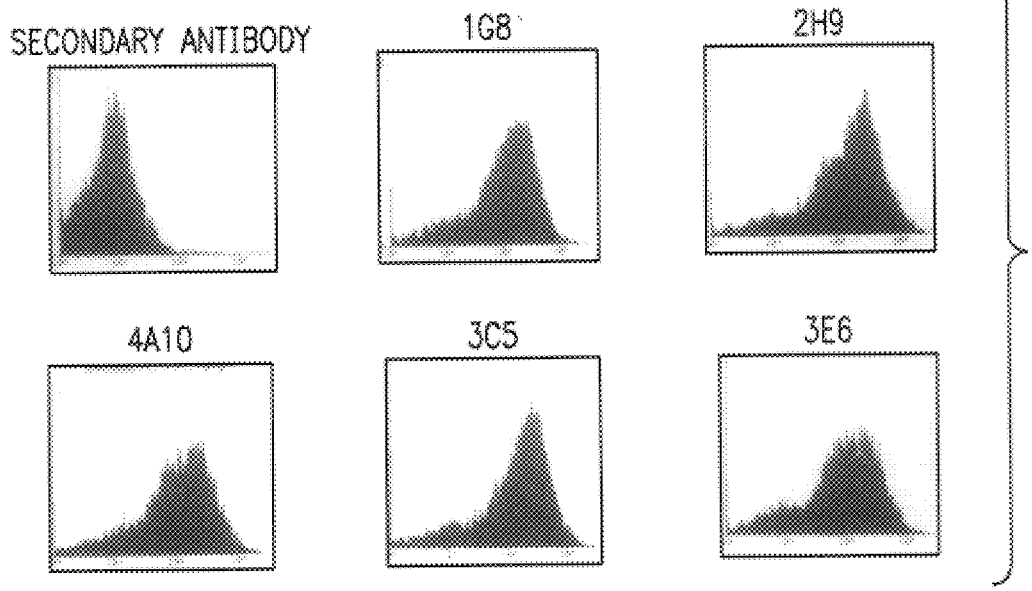

FIG. 33. Flow cytometric recognition of PSCA on the cell surface of nonpermeabilized LAPC-9 human prostate cancer cells using mAbs 1G8, 2H9, 3E6, 3C5 and 4A10. Staining was compared to an irrelevant isotype control antibody.

Figure 34:
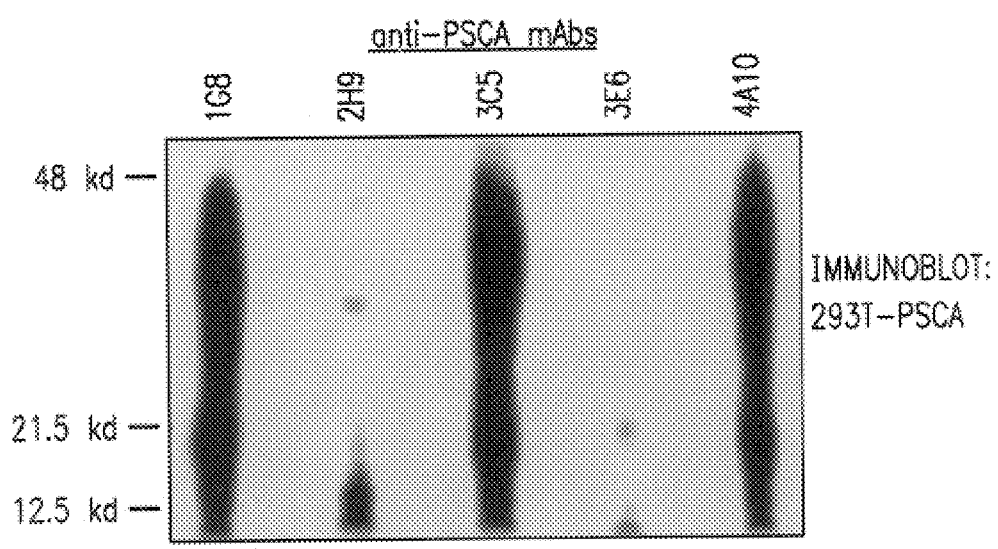

FIG. 34. A photograph showing 293T cells transiently transfected with PSCA and immunoblotted with PSCA monoclonal antibodies. Monoclonal antibodies 2H9 and 3E6 binds deglycosylated PSCA but does not bind glycosylated PSCA in 293T cells. In contrast, monoclonal antibodies 1G8, 3C5,and 4A10 recognizes glycosylated PSCA.

Figure 35:
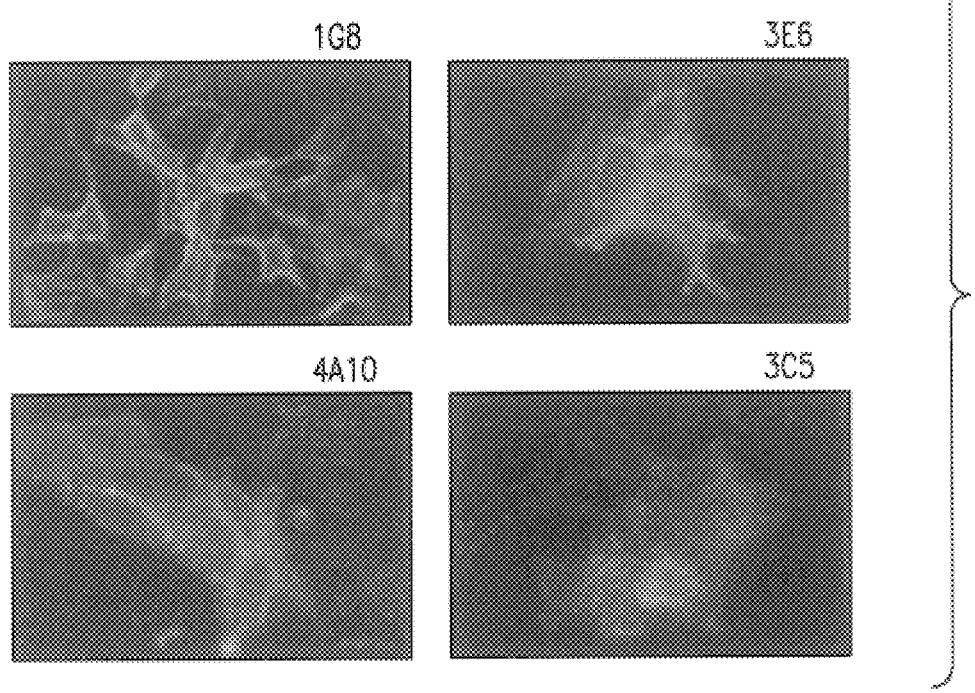

FIG. 35. Immunofluorescent analysis demonstrating cell surface expression of PSCA in nonpermeabilized prostate cancer cells. LNCaP cells were stably transfected with PSCA and stained with mAbs 1G8, 3E6, 3C5 and 4A10. Negative controls included irrelevant isotype antibody and LNCaP cells transfected with control vector, all of which showed no staining even after prolonged exposures.

Figure 36:
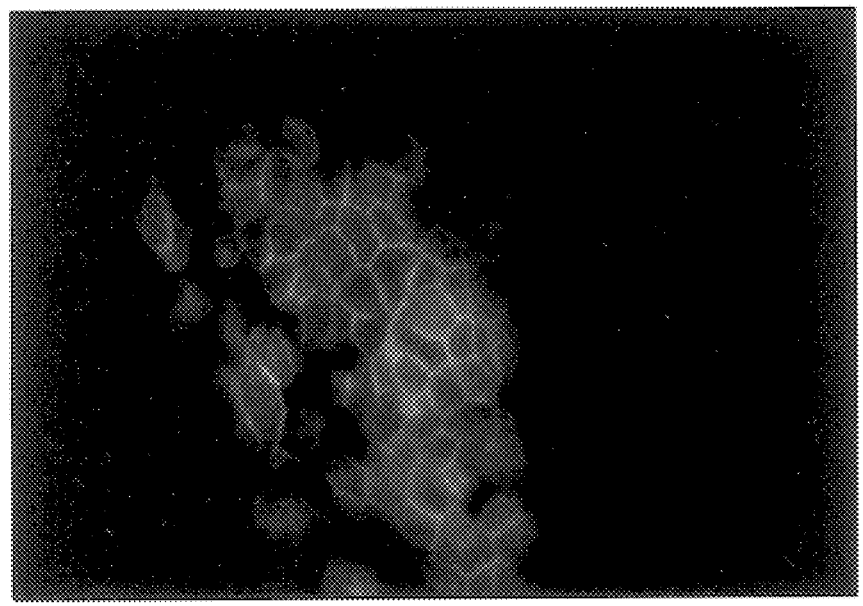

FIG. 36. A photograph showing monoclonal antibody 2H9 binds LAPC9 cells.

Figure 37:
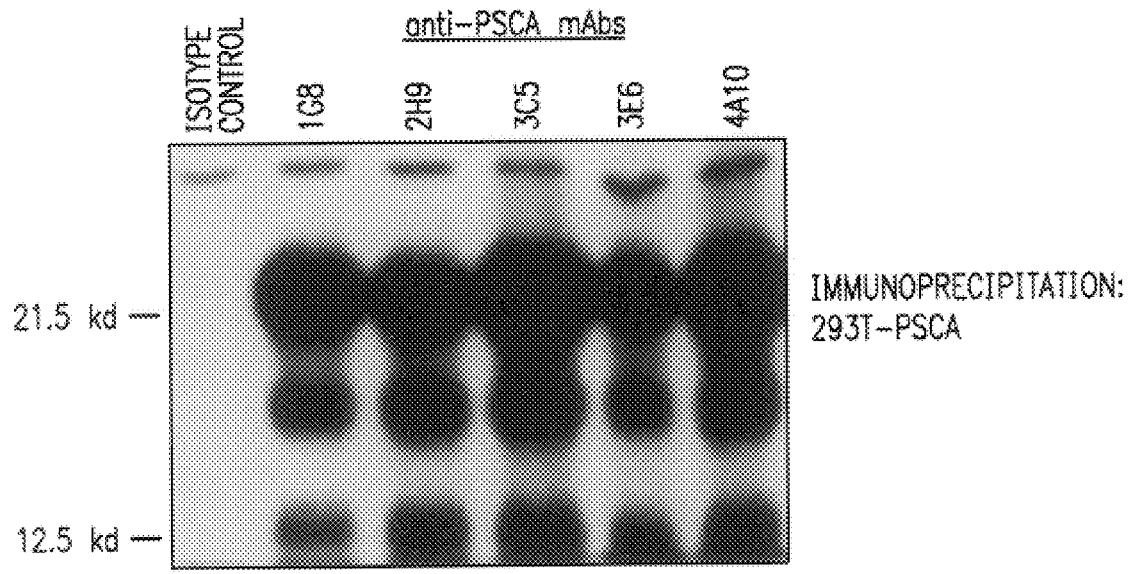

FIG. 37. A photograph showing immunological reactivity of anti-mAbs. Immunoprecipitation of PSCA from 293T cells transiently transfected with PSCA using mAbs 1G8, 2H9, 3C5, 3E6 and 4A10. The control was an irrelevant murine IgG mAb.

Figure 38:
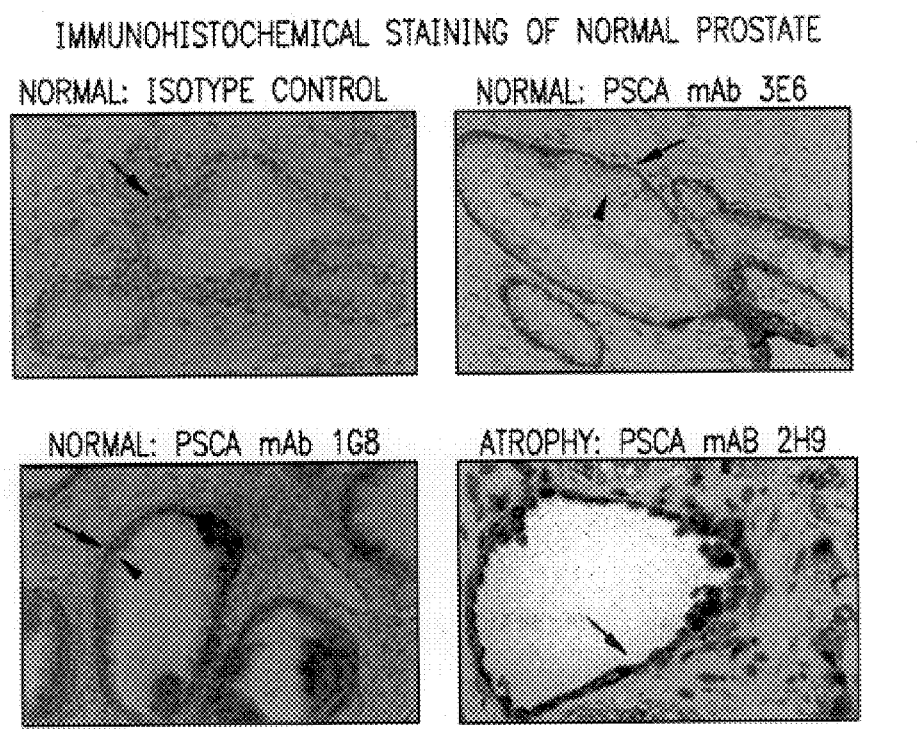

FIG. 38. Immunohistochemical staining of normal prostate with anti-PSCA mAbs. Examples shown include a normal gland stained with an irrelevant isotype antibody as a negative control (arrow), PSCA mAb 3E6 and mAb 1G8. PSCA mAb 3E6 preferentially stains basal cells (arrow) when compared with secretory cells (arrowhead), whereas mAb 1G8 stains both basal (arrow) and secretory (arrowhead) cells equally. Also shown is strong staining of an atrophic single-layered gland from a normal prostate specimen stained with PSCA mAb 2H9.

Figure 39A:
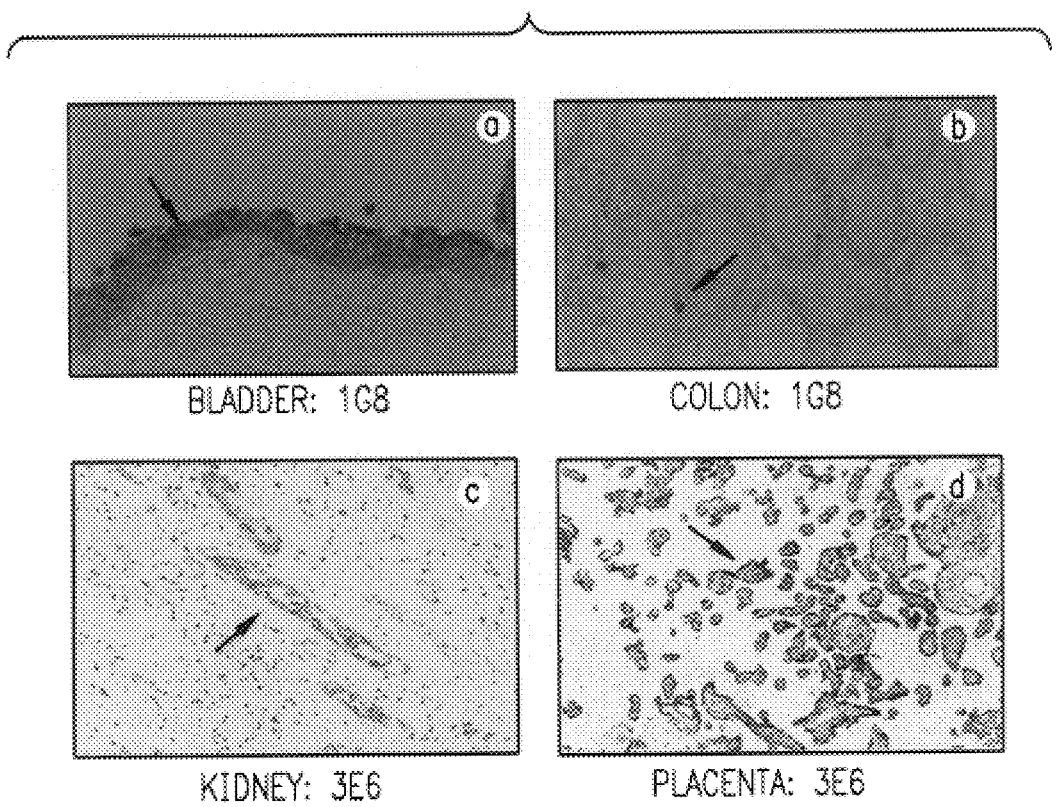

FIG. 39A. Expression of PSCA in normal tissues. Panel a shows staining of bladder transitional epithelium with mAb 1G8. Panel b shows colonic neuroendocrine cell staining with mAb 1G8. Double staining with chromogranin confirmed that the positive cells are of neuroendocrine origin (not shown). Panel c shows staining of collecting ducts (arrow) and tubules with mAb 3E6. Panel d show staining of placental trophoblasts with mAb 3E6.

Figure 39B:
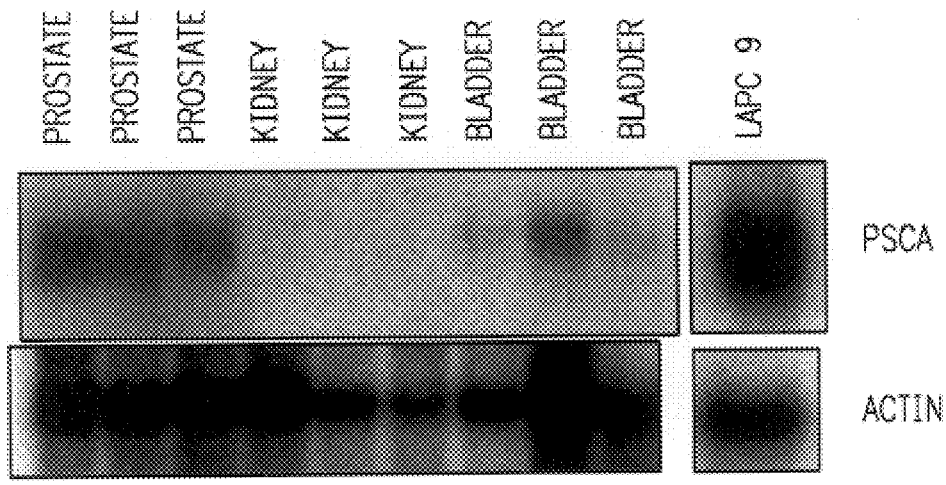

FIG. 39B. Expression of PSCA in normal tissues. Northern blot analysis of PSCA mRNA expression. Total RNA from normal prostate, kidney, bladder and the LAPC-9 prostate cancer xenograft was analyzed using a PSCA specific probe (top panel). The same membrane was probed with actin to control of loading differences (bottom panel).

Figure 40A:
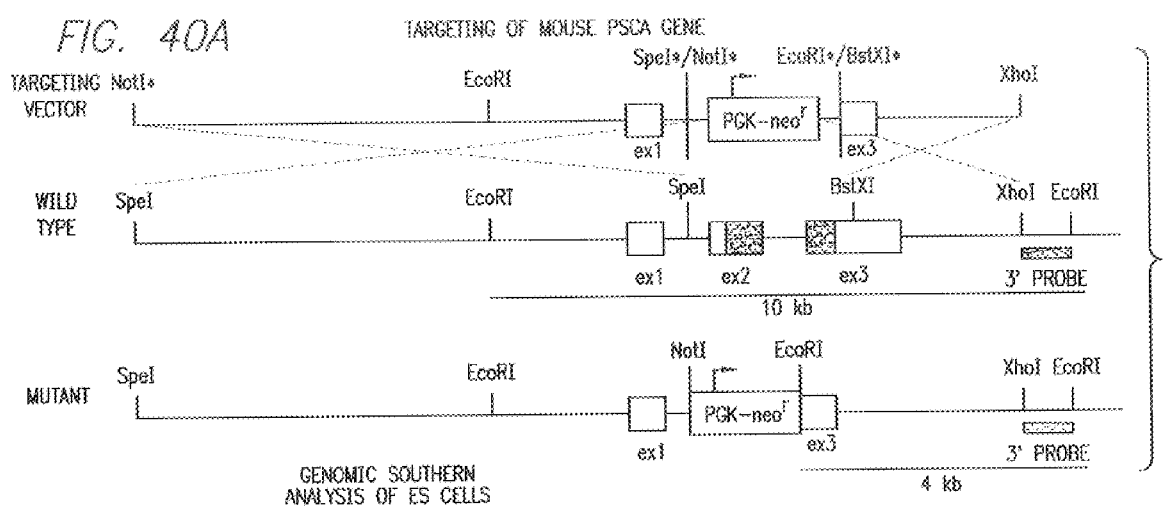

FIG. 40A. Targeting of mouse PSCA gene. A schematic drawing showing a strategy for creating a PSCA targeting vector.

Figure 40B:
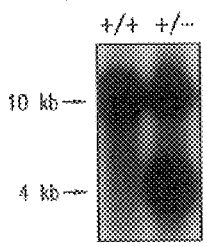

FIG. 40B. Targeting of mouse PSCA gene. A photograph of a Southern blot analysis of genomic DNA using 3' probe showing recovery of wild-type (+/+) and heterozygous (+/−) ES cells.

FIG. 41. The upper panel is a schematic drawing of a strategy for generating transgenic mouse models of prostate cancer. The lower panel is a list of existing transgenic mouse models of prostate cancer.

Figure 42:
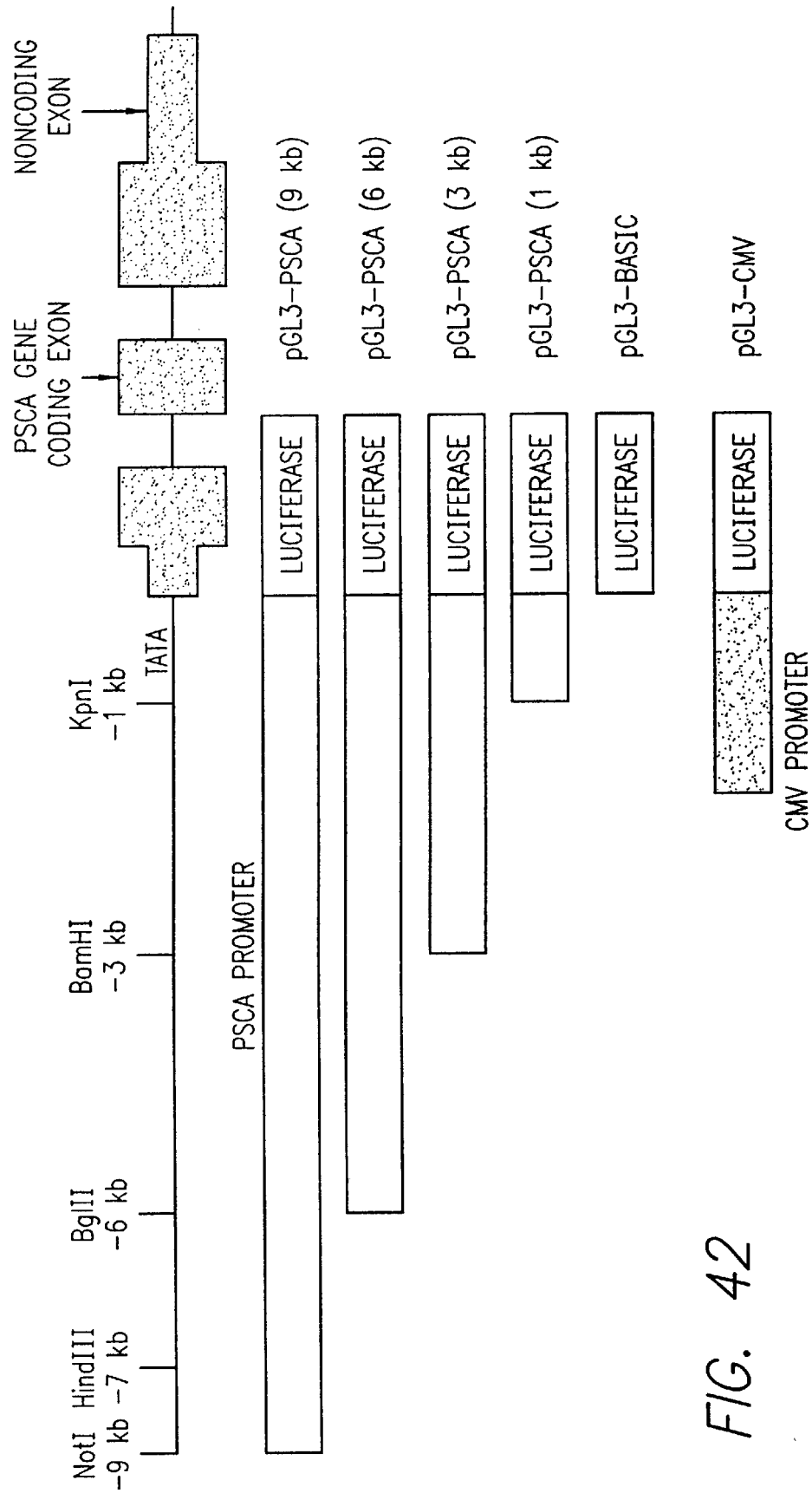

FIG. 42. A schematic drawing showing reporter gene constructs for transfection assay.

Figure 43:
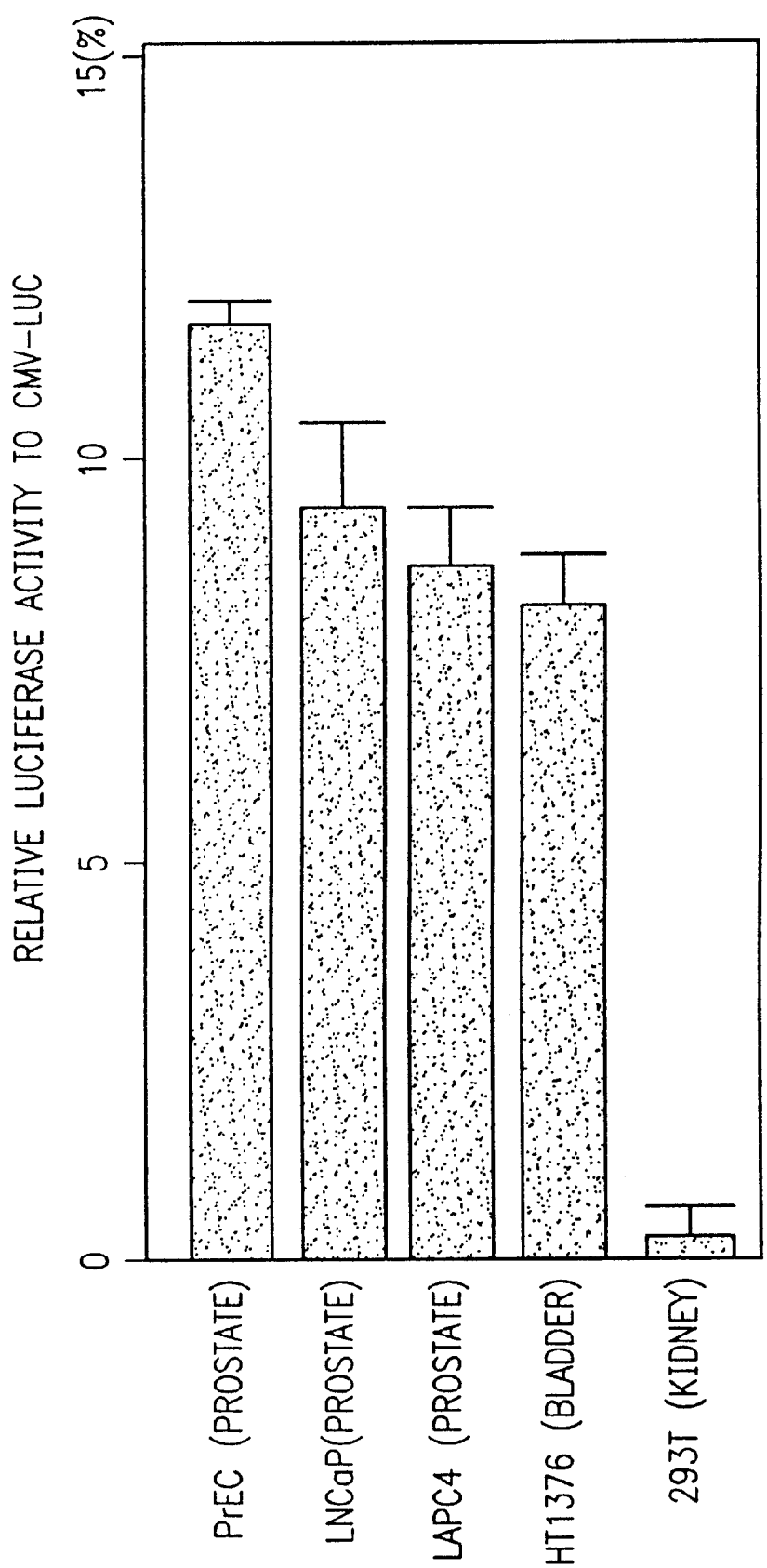

FIG. 43. A bar graph showing the tissue-predominant expression (prostate and bladder cells) of the 9 kb human PSCA upstream regulatory region having increased gene expression activity.

Figure 44:
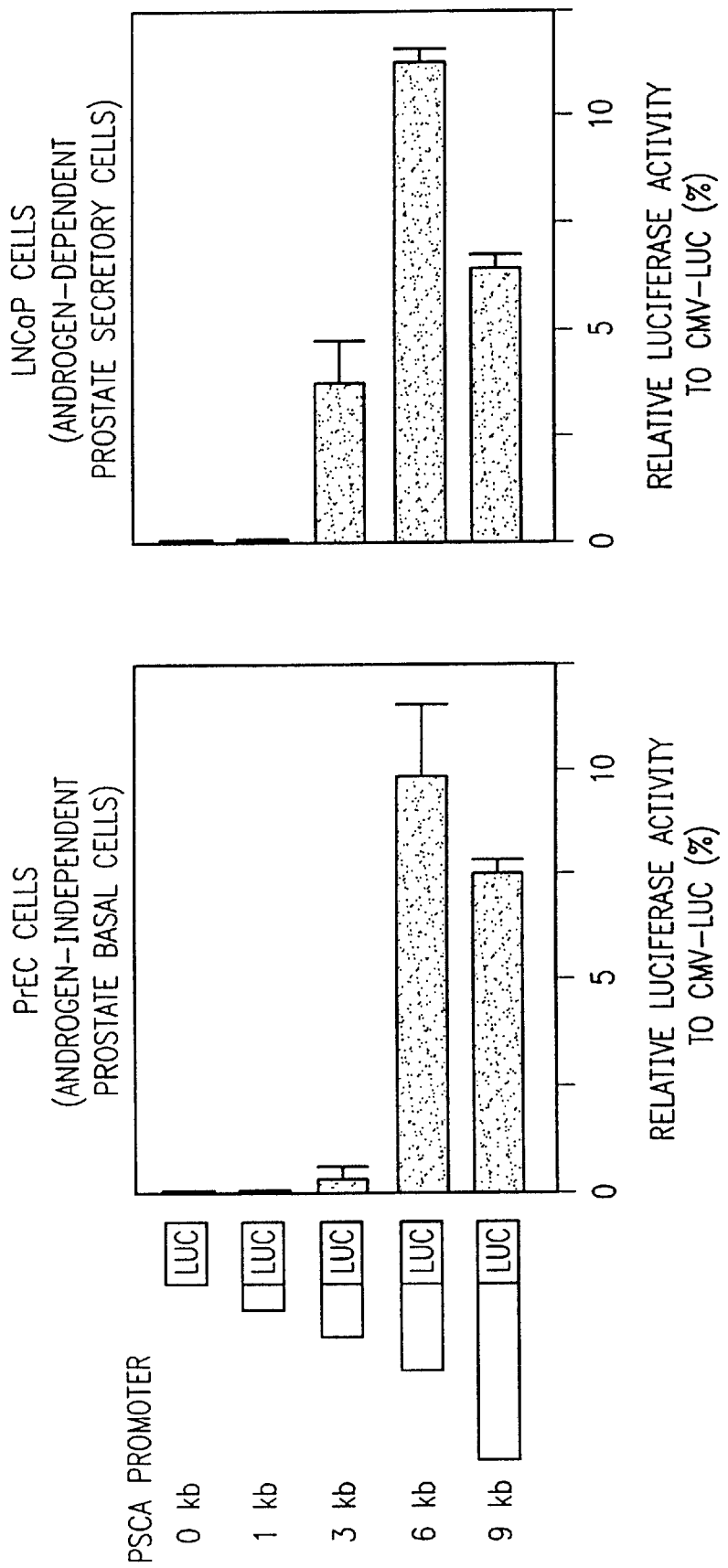

FIG. 44. Bar graphs identifying prostate-predominant expression elements within PSCA upstream regions having increased gene expression activity, i.e., the 9 kb, 6 kb, 3 kb, and 1 kb PSCA regions.

Figure 45:
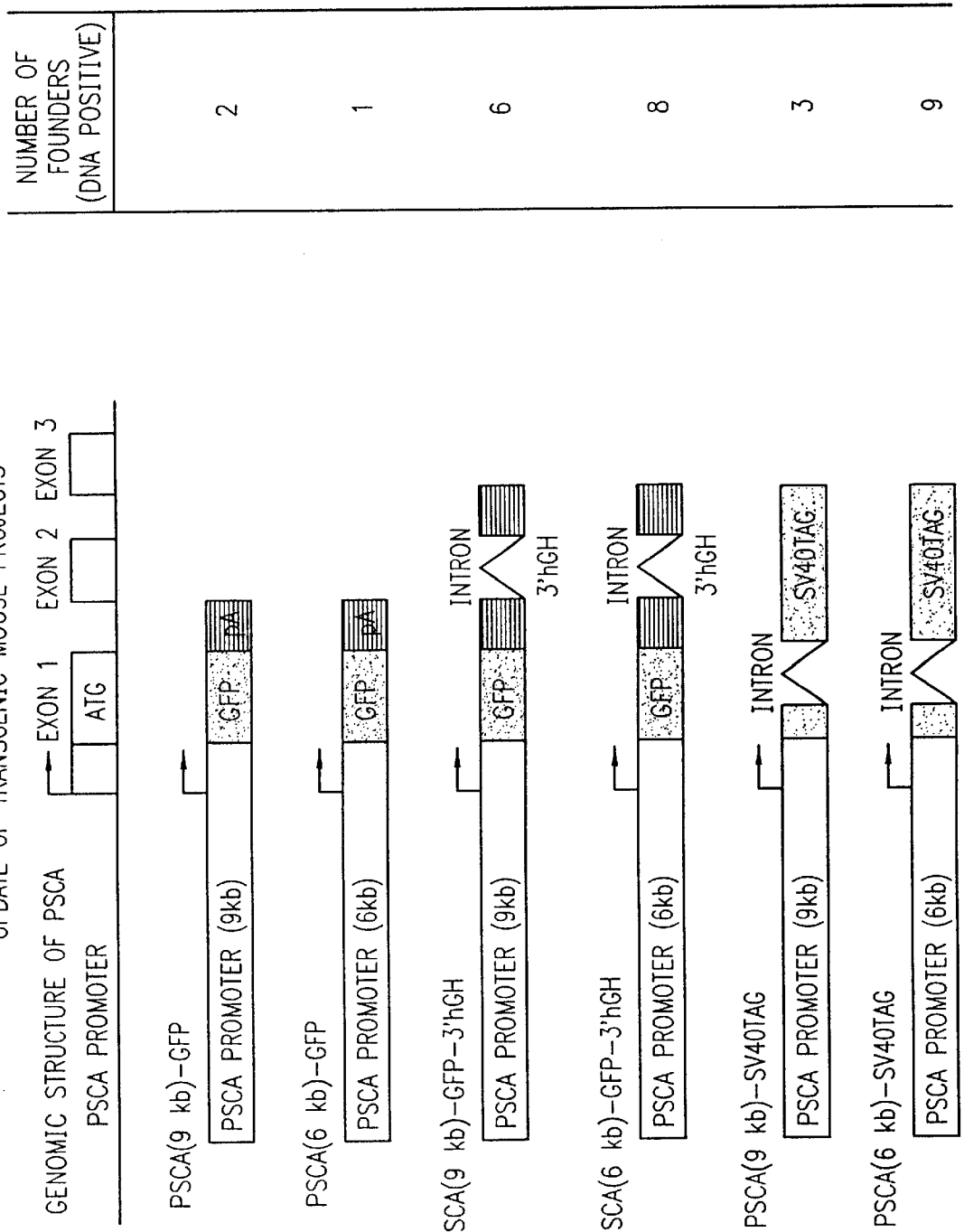

FIG. 45. A schematic drawing showing the design of transgenic vectors containing either a 9 kb or 6 kb human PSCA upstream region operatively linked to a detectable marker.

Figure 46:
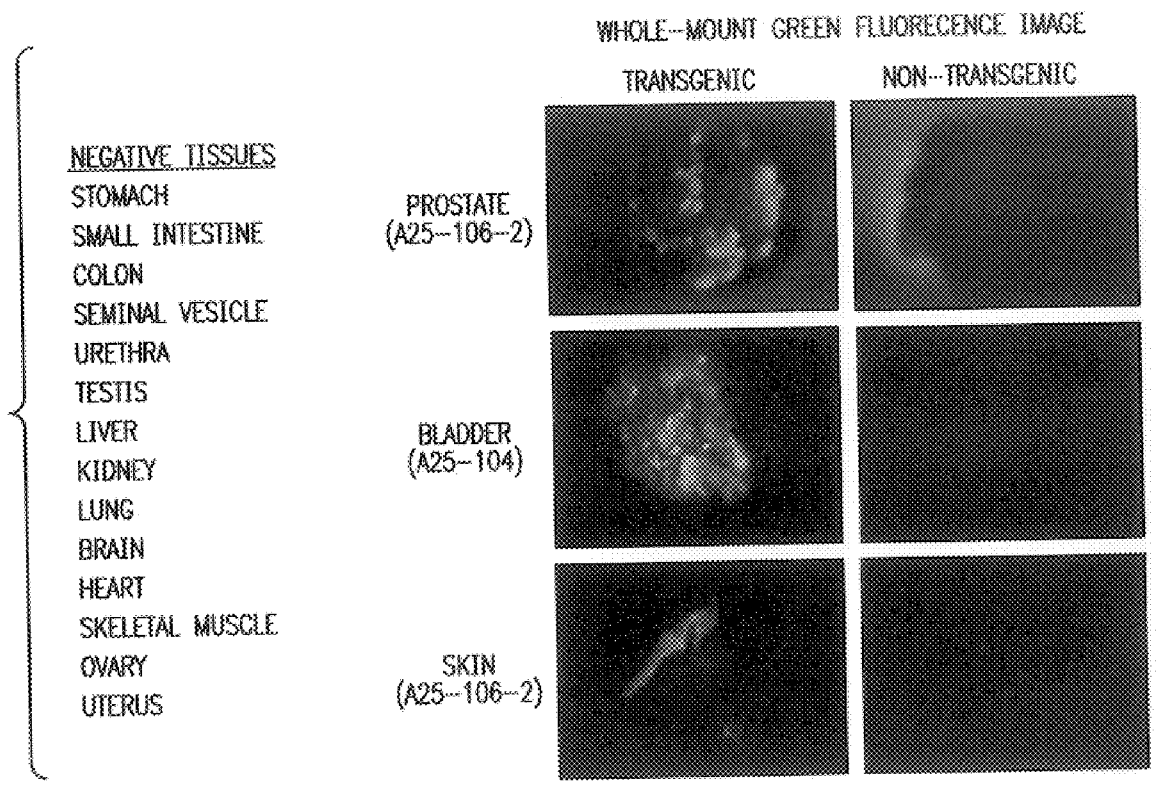

FIG. 46. Photographs showing that the 9 kb PSCA upstream region drives reporter gene expression in prostate, bladder and skin in vivo.

Figure 47:
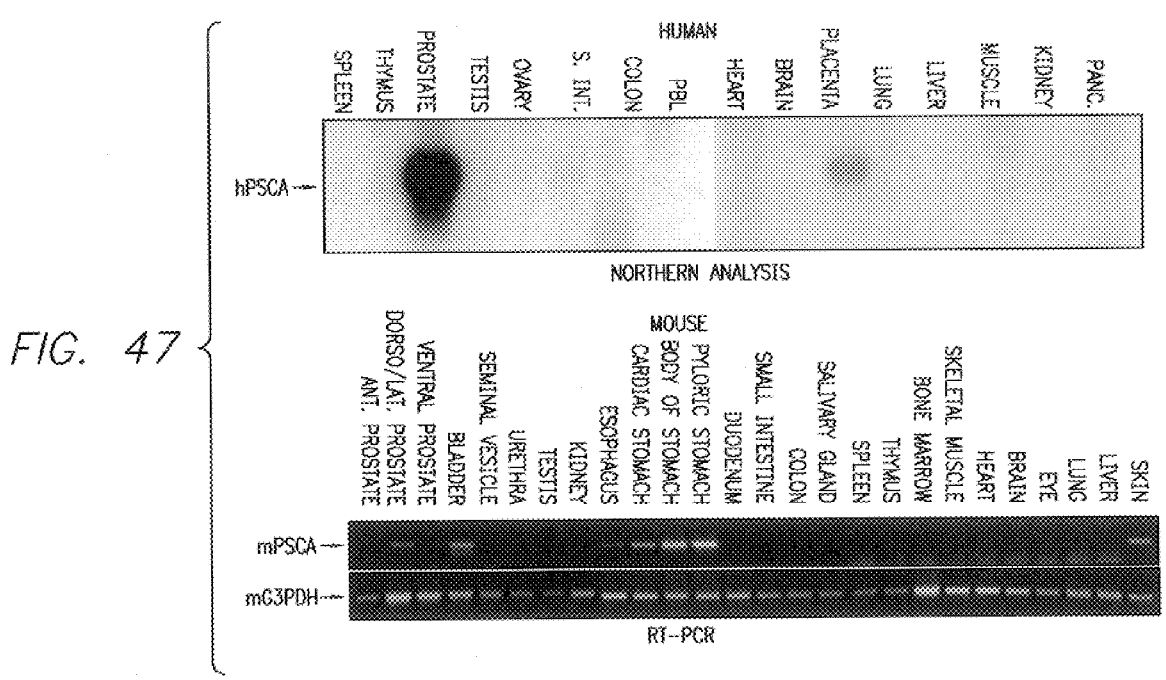

FIG. 47. Photographs of multiple tissue northern blot analysis showing tissue specific expression patterns of human PSCA RNA. Photographs of a multiple issue Northen blot analysis showing tissue specific expression patterns of murine PSCA RNA.

FIG. 48. Complete inhibition of LAPC-9 prostate tumor growth in SCID mice by treatment with anti-PSCA monoclonal antibodies. Mice were injected with LAPC-9 s.c. and treated with a mouse IgG control. Each data point represents the ellipsoidal volume of tumors at specified time points as described in Example 18-A, infra. Complete inhibition of LAPC-9 prostate tumor growth in SCID mice by treatment with anti-PSCA monoclonal antibodies. Mice were injected with LAPC-9 s.c. and treated with the anti-PSCA mAb cocktail. Each data point represents the ellipsoidal volume of tumors at specified time points as described in Example 18-A, infra. In the anti-PSCA group, an arbitrary value of 20 was given for all data points to create a line, although the actual tumor volume was 0 (Example 18-A, infra).

FIG. 49A. Characteristics of anti-PSCA monoclonal antibodies utilized in the in vivo tumor challenge study described in Example 18. Isotype and epitope map: The region of PSCA protein recognized by the anti-PSCA mAbs was determined by ELISA analysis using GST-fusion proteins (50 ng/well) encoding the indicated amino acids of PSCA. Following incubation of wells with hybridoma supernatants, anti-mouse-HRP conjugate antibody was added and reactivity was determined by the addition of 3,3' 5,5'-Tetramethylbenzidine base (TMB) substrate. Optical densities (450 nm) are the means of duplicate determinations.

FIG. 49B. Characteristics of anti-PSCA monoclonal antibodies utilized in the in vivo tumor challenge study described in Example 18. Epitope map determined by Western analysis: 50 ng of the indicated GST-PSCA fusion protein was separated by SDS-PAGE and transferred to nitrocellulose. Western analysis was carried out by incubation of blots with hybridoma supernatants followed by anti-mouse-HRP secondary Ab and visualized by enhanced chemiluminesence.

FIG. 50A. Schematic representations of PSCA Capture ELISA. Standardization and control antigens: A GST-fusion protein encoding amino acids 18–98 of the PSCA protein is used for generating a standard curve for quantification of unknown samples. Also depicted are approximate epitope binding regions of the anti-PSCA monoclonal and polyclonal antibodies used in the ELISA. A secreted recombinant mammalian expressed form of PSCA is used for quality control of the ELISA assay. This protein contains an Ig leader sequence to direct secretion of the recombinant protein and MYC and 6XHIS epitope tags for affinity purification.

FIG. 50B. Schematic representations of PSCA Capture ELISA. An ELISA format schematic.

FIG. 51A. Quantification of recombinant secreted PSCA protein. PSCA capture ELISA standard curve.

FIG. 51B. Quantification of PSCA protein secreted by mammalian cells. 2 day conditioned tissue culture supernatants from either 293T cells transfected with empty vector or with vector encoding recombinant secreted PSCA (secPSCA) was mixed with an equal volume of either PBS or normal human serum (Omega Scientific) and analyzed for the presence of PSCA protein. Data are the means of duplicate determinations ± range. ND not detectable.

Figure 52:
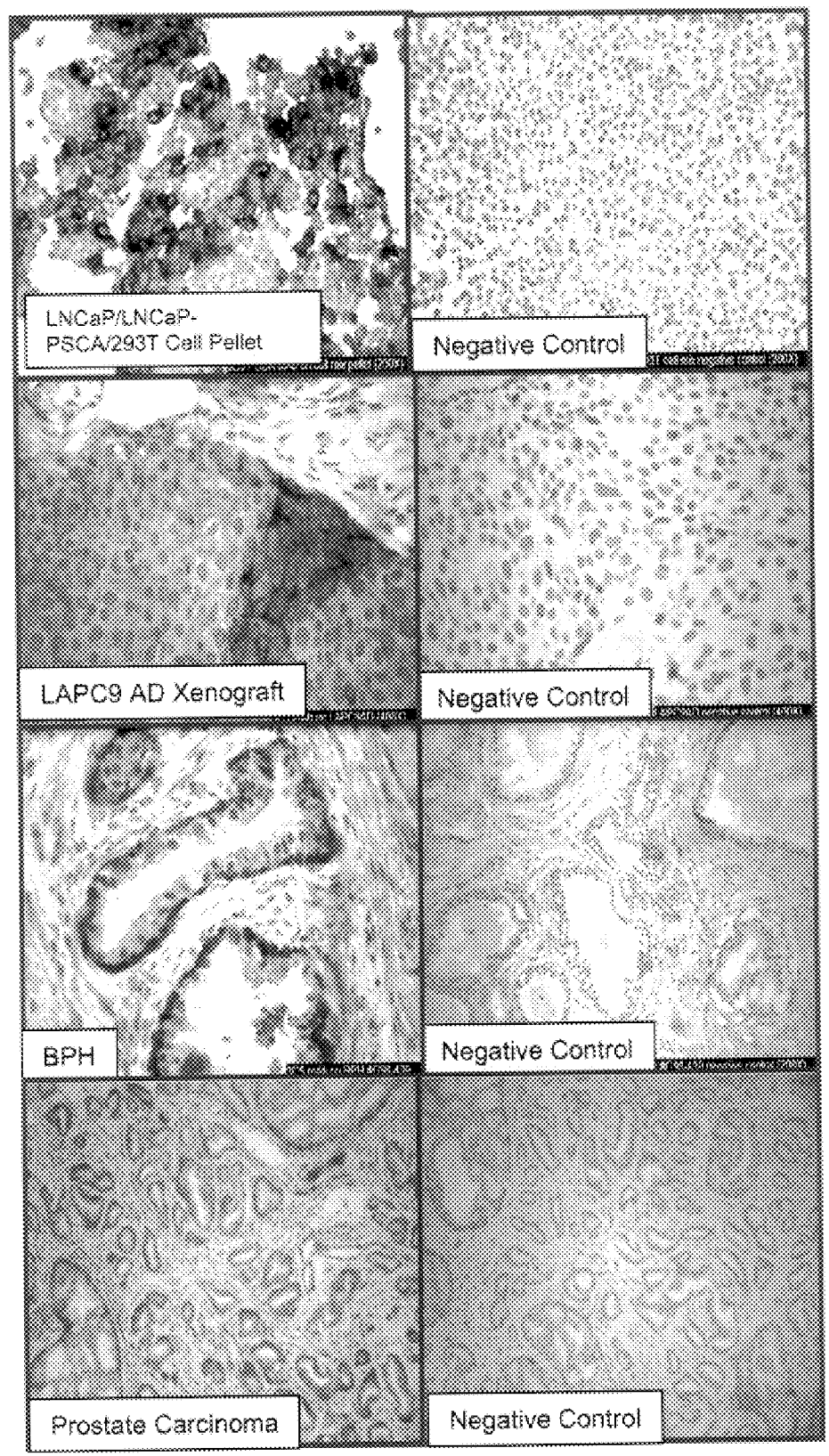

FIG. 52. Immunohistochemical Analysis of cell pellet, LAPC9AD xenograft, a BPH sample, and a prostate carcinoma tissue using anti-PSCA monoclonal antibody 3C5.

Figure 53:
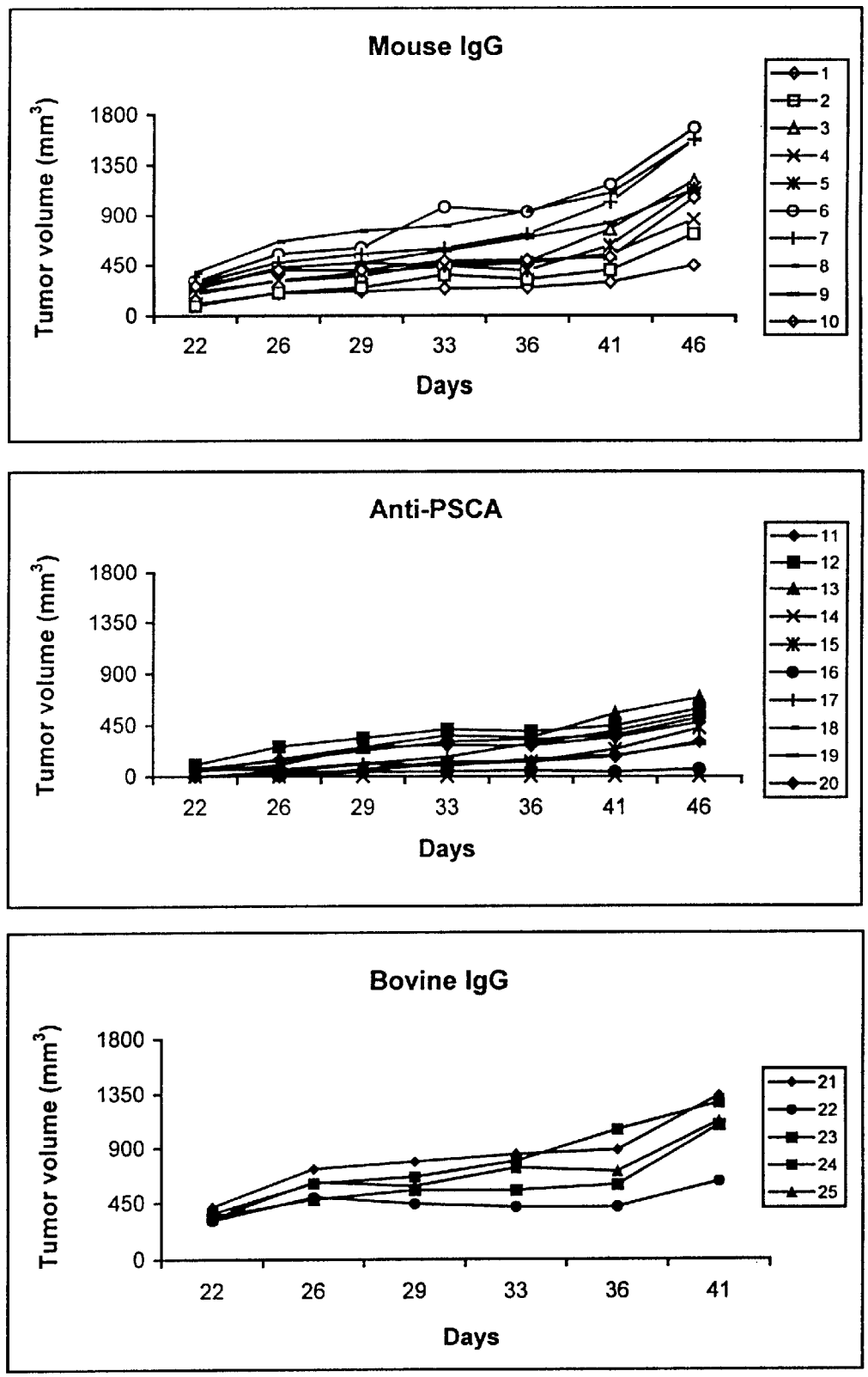

FIG. 53. Inhibition of LAPC-9 tumor growth by anti-PSCA monoclonal antibodies. Mice were injected with $1\times10^6$ LAPC-9 s.c. and treated with a mouse IgG control (n=10). Each data point represents the ellipsoidal volume of tumors at specified time points as described in Example 18-B. Inhibition of LAPC-9 tumor growth by anti-PSCA monoclonal antibodies. Mice were injected with LAPC-9 s.c. and treated with anti-PSCA mAb cocktail (n=10). Each data point represents the ellipsoidal volume of tumors at specified time points as described in Example 18-B. Inhibition of LAPC-9 tumor growth by anti-PSCA monoclonal antibodies. Mice were injected with LAPC-9 s.c. and treated with bovine IgC (n=5). Each data point represents the ellipsoidal volume of tumors at specified time points as described in Example 18-B.

FIG. 54. Inhibition of LAPC-9 tumor growth by the anti-PSCA monoclonal antibody 1G8. Mice injected with $1\times10^6$ LAPC-9 s.c. and treated with a mouse IgG control (n=6). Each data point represents the ellipsoidal volume of tumors at specified time points. Inhibition of LAPC-9 tumor growth by the anti-PSCA monoclonal antibody 1G8. Mice injected with LAPC-9 s.c. and treated with the anti-PSCA mAb 1G8 (n=7). Each data point represents the ellipsoidal volume of tumors at specified time points.

FIG. 55. Inhibition of LAPC-9 tumor growth by anti-PSCA monoclonal antibodies 2A2 and 2H9. Mice were injected with $1\times10^6$ LAPC-9 s.c. and treated with either a mouse IgG control (n=7) or the 2A2 mAb (n=7). All data points represent the mean ellipsoidal volume of tumors ($mm^3$) at the specified time points. Error bars represent standard error of the mean (SEM). Inhibition of LAPC-9 tumor growth by anti-PSCA monoclonal antibodies 2A2 and 2H9. Mice were injected with LAPC-9 s.c. and treated with the same mouse IgG control (n=6) or the 2H9 mAb (n=7). All data points represent the mean ellipsoidal volume of tumors ($mm^3$) at the specified time points. Error bars represent standard error of the mean (SEM).

FIG. 56. Circulating PSA levels in LAPC-9 tumor-injected mice after treatment with anti-PSCA mAbs 2A2 and 2H9. Mice were injected with $1\times10^6$ LAPC-9 s.c. and treated with either the mouse IgG control (n=6) or the 2A2 mAb (n=7). Each data point represents the mean PSA level determined from the serum of mice at weekly time points. Error bars represent standard error of the mean (SEM). Circulating PSA levels in LAPC-9 tumor-injected mice after treatment with anti-PSCA mAbs 2A2 and 2H9. Mice were injected with LAPC-9 s.c. and treated with either the mouse IgG control (n=6) or the 2A2 mAb (n=7). Each data point represents the mean PSA level determined from the serum of mice at weekly time points. Error bars represent standard error of the mean (SEM).

Figure 57:
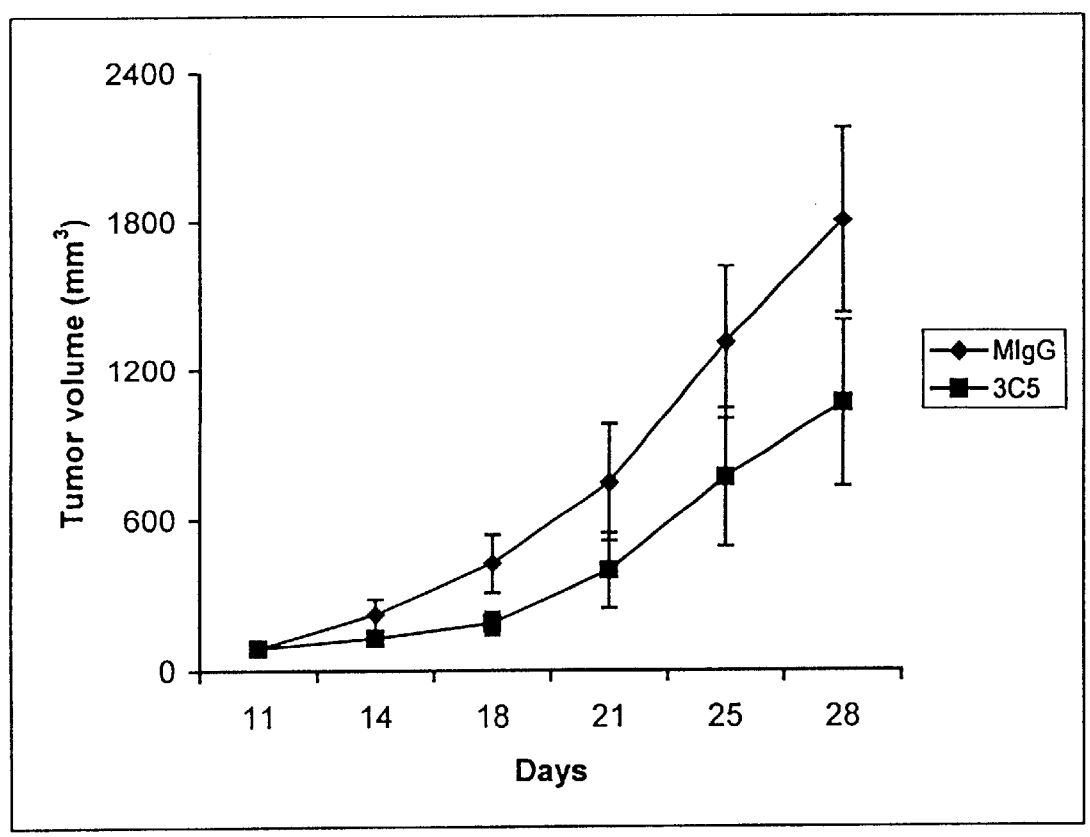

FIG. 57. Inhibition of established LAPC-9 prostate cancer xenografts by PSCA monoclonal antibody 3C5. See Example 18-C4 for details.

FIG. 58. Nucleotide sequence (SEQ ID NO:10) and amino acid sequence (SEQ ID NO:11) of the heavy chain variable domain regions of PSCA monoclonal antibodies 1G8. CDRs are labeled and underlined.

FIG. 59. Nucleotide sequence (SEQ ID NO:12) and amino acid sequence (SEQ ID NO:13) of the heavy chain variable domain regions of PSCA monoclonal antibodies 4A10. CDRs are labeled and underlined.

FIG. 60. Nucleotide sequence (SEQ ID NO:14) and amino acid sequence (SEQ ID NO:15) of the heavy chain variable domain regions of PSCA monoclonal antibodies 2H9. CDRs are labeled and underlined.

FIG. 61. Amino acid sequence alignments of CDRs of PSCA mAbs 1G8, 4A10 and 2H9.

FIG. 62A. Photographs showing PSCA protein expression in normal bladder tissue using immunohistochemical staining of paraffin-embedded samples with PSCA mAb 1G8.

FIG. 62B. Photograph showing PSCA protein expression in non-invasive superficial papillar tissue using immunohistochemical staining of paraffin-embedded samples with PSCA mAb 1G8.

FIG. 62C. Photograph showing PSCA protein expression in carcinoma in situ, a high grade pre-cancerous lesion, using immunohistochemical staining of paraffin-embedded samples with PSCA mAb 1G8.

FIG. 62D. Photograph showing PSCA protein expression in invasive bladder cancer tissue using immunohistochemical staining of paraffin-embedded samples with PSCA mAb 1G8.

Figure 63:
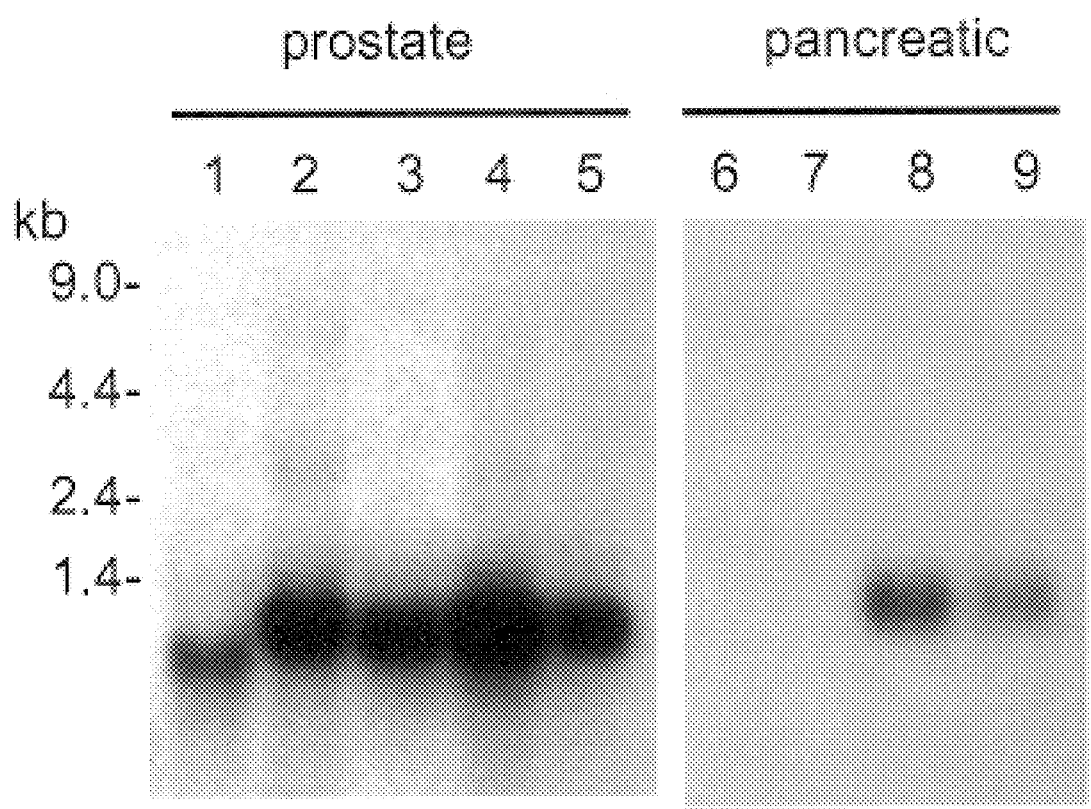

FIG. 63. Northern blot analysis of PSCA expression in several pancreatic cancer cells lines. Northern blot analysis of PSCA expression in normal prostate and several prostate cancer xenografts are shown alongside for comparison. RNA levels between all samples were normalized.

Figure 64:
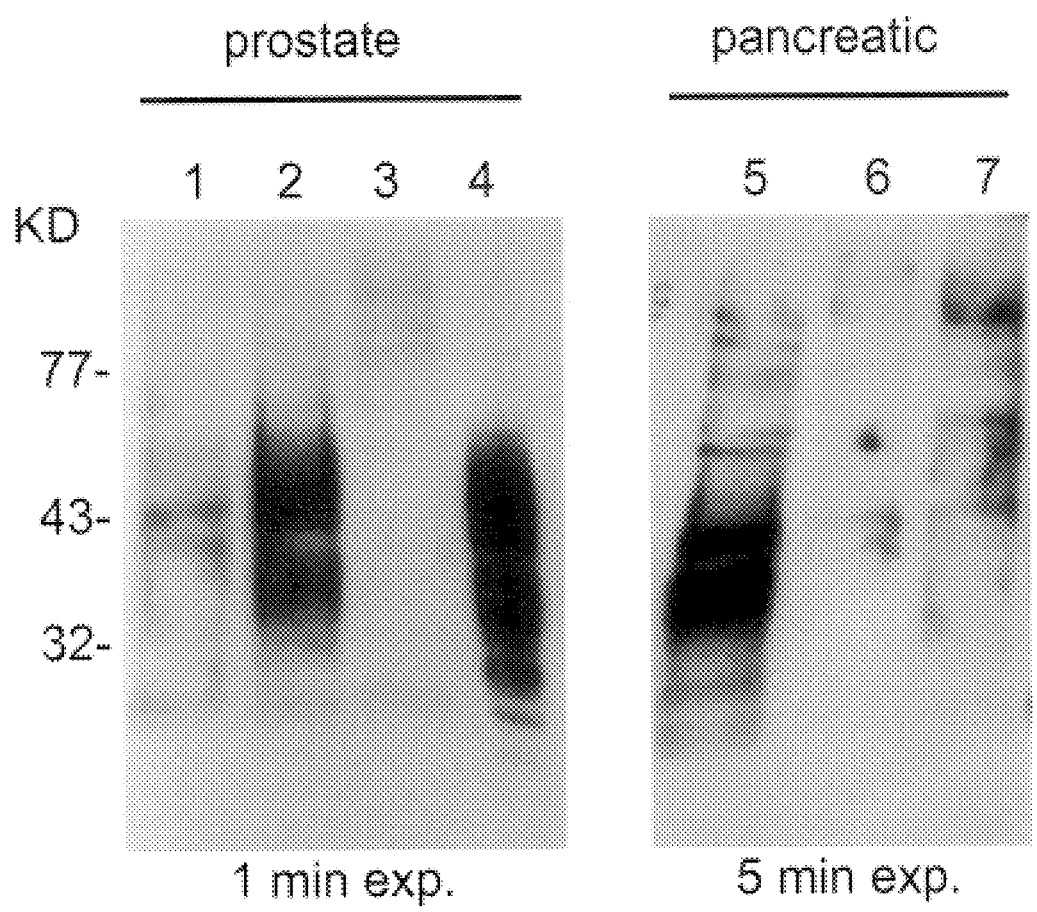

FIG. 64. Western blot analysis of PSCA protein expression in prostate and pancreatic cancer cell line using PSCA mab 1G8.

FIG. 65. PSCA mAbs exert growth inhibitory effect through PSCA protein. The growth inhibitory effect of PSCA mAb 1G8 on LAPC-9 prostate tumors showing significant growth inhibition in LAPC-9 tumors, which express PSCA antigen. See Examples 18-C1, -C3 for details. PSCA mAbs exert growth inhibitory effect through PSCA protein. The growth inhibitory effect of PSCA mAb 1G8 on PC-3 prostate tumors, showing no effect on PC-3 tumors, which do not express PSCA antigens. See Examples 18-C1, -C3 for details.

FIG. 66A. Growth inhibition of established LAPC-9 (AD) orthotopic tumors by the anti-PSCA mAb 1G8. Mice having low levels of serum PSA. Two mg of 1G8 was administered to these mice on days 10, 13, and 15, followed by one mg on days 17, 20, 22, 25, 27, 29, 34, 41, and 49 as indicated by the arrows.

FIG. 66B. Growth inhibition of established LAPC-9 (AD) orthotopic tumors by the anti-PSCA mAb 1G8. Mice having moderate levels of serum PSA. One mg of 1G8 was administered on days 12, 13, 14, 19, 20, 22, 25, 27, 29, and 33 as indicated by the arrows.

FIG. 67A. Treatment with the anti-PSCA mAb, 1G8, increases survival of mice bearing established LAPC-9 (AD) orthotopic tumors. Mice treated with 1G8 exhibited an increase in survival compared to mice treated with PBS.

FIG. 67B. Treatment with the anti-PSCA mAb, 1G8, increases survival of mice bearing established LAPC-9 (AD) orthotopic tumors. Mice treated with PBS.

FIG. 68A. Growth inhibition of established LAPC-9 AD orthotopic tumors by the anti-PSCA mAb 3C5. One mg of 3C5 was administered to tumor-bearing mice on days 6, 8, 10, 13, 15, 17, 20, 22, 24, and 29 as indicated by the arrows. The mice were bled on the days indicated on the X-axis for PSA determinations.

FIG. 68B. Growth inhibition of established LAPC-9 AD orthotopic tumors by the anti-PSCA mAb 3C5. Two mg of 3C5 was administered to tumor-bearing mice on days 9, 12, and 15, followed by one mg on days 18, 20, 22, 25, 27, and 29 as indicated by the arrows. The mice were bled on the days indicated on the X-axis for PSA determinations.

FIG. 69A. Treatment with the anti-PSCA mAb, 3C5, increases survival of mice bearing LAPC-9 AD orthotopic tumors. Mice treated with 3C5 exhibited an increase in survival compared to mice treated with PBS. There were 4 mice in the PBS-treated group and 5 mice in the 3C5-treated group.

FIG. 69B. Treatment with the anti-PSCA mAb, 3C5, increases survival of mice bearing LAPC-9 AD orthotopic tumors. Mice treated with 3C5 exhibited an increase in survival compared to mice treated with PBS. There were 6 mice in both the PBS-treated and then 3C5-treated groups.

Figure 70:
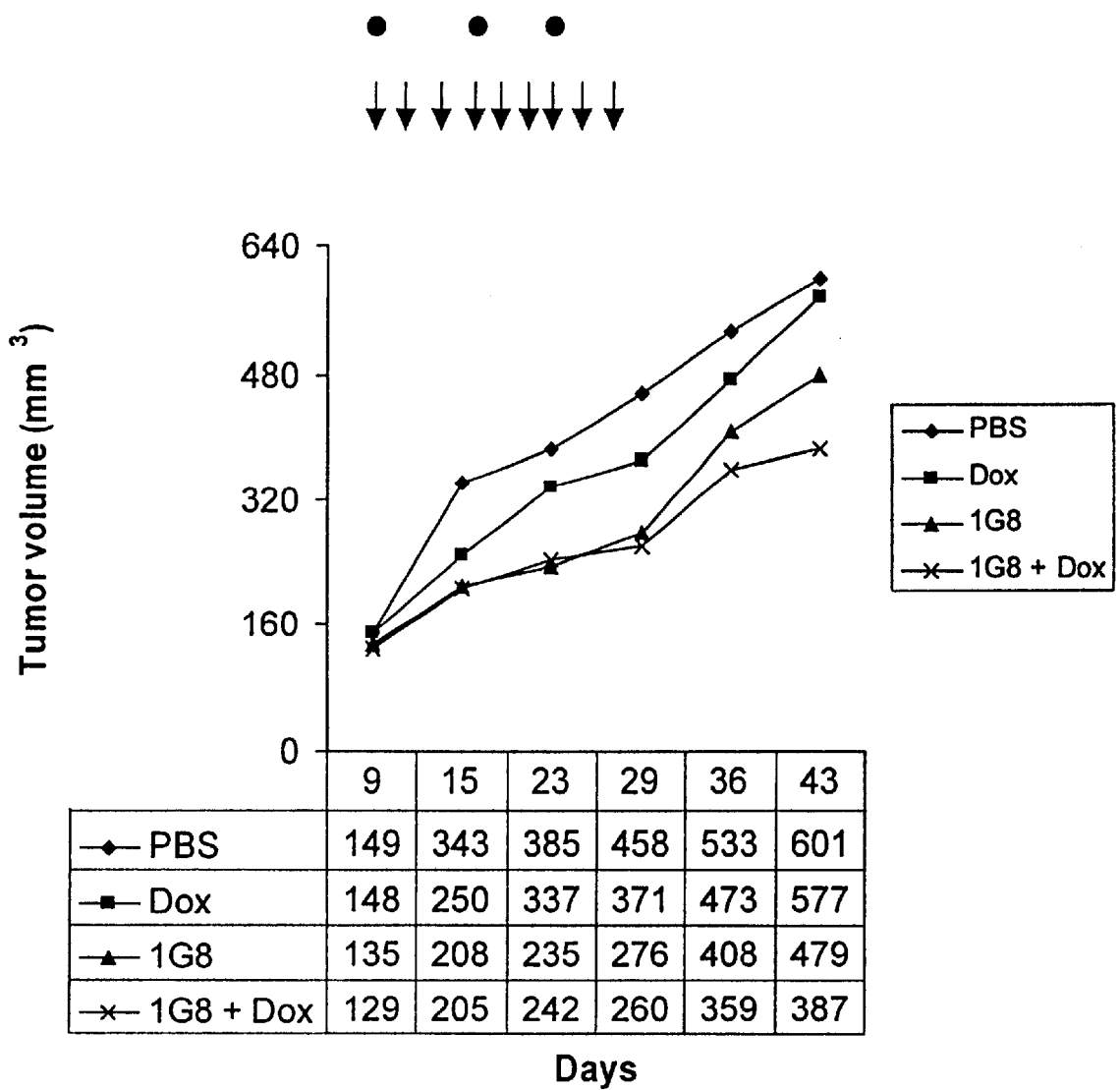

FIG. 70. Growth inhibition of established PC3-PSCA tumors by 1G8 alone or in combination with doxorubicin. One mg of 1G8 was administered to tumor-bearing mice on days 9, 11, 14, 16, 18, 21, 23, 25, and 28 as indicated by the arrows. Twenty-five micrograms of doxorubicin was administered on days 9, 16, and 23 as indicated by the (•) symbol.

FIG. 71. Anti-PSCA antibody administered to tumor-bearing mice circulates and targets tumors expressing PSCA. Immunohistochemistry of a tumor explant from a mouse, bearing an established PSCA-expressing tumor, treated with 3C5. Anti-PSCA antibody administered to tumor-bearing mice circulates and targets tumors expressing PSCA. Immunohistochemistry of a tumor explant from a mouse, bearing an established PSCA-expressing tumor, treated with mouse IgG.

Figure 72:
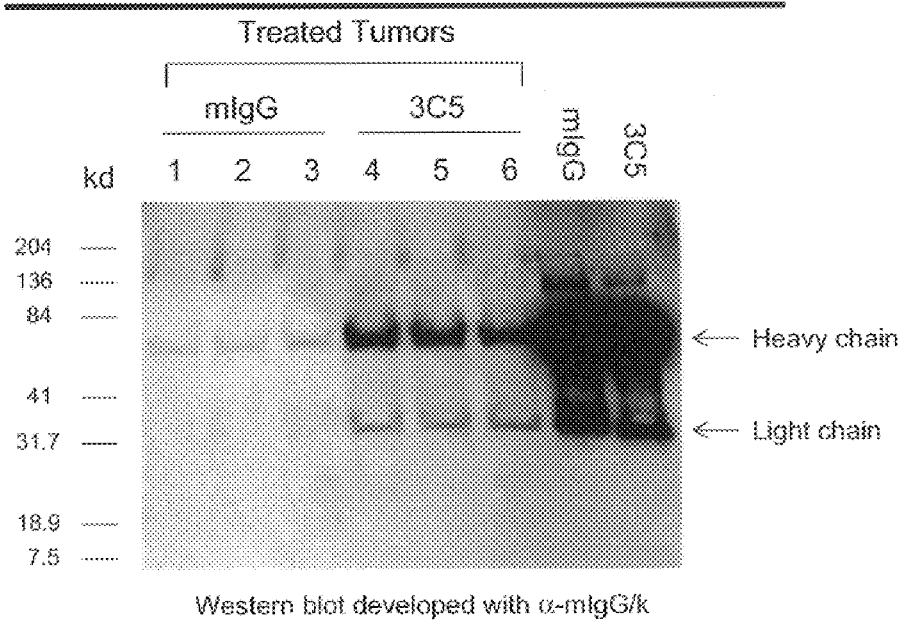

FIG. 72. Anti-PSCA antibody administered to a tumor-bearing mouse circulates and targets tumors expressing PSCA. A Western blot analysis of tumor lysates from tumors explanted from mice described in FIG. 71, probed with goat anti-mouse IgG-HRP antibody.

Figure 73:
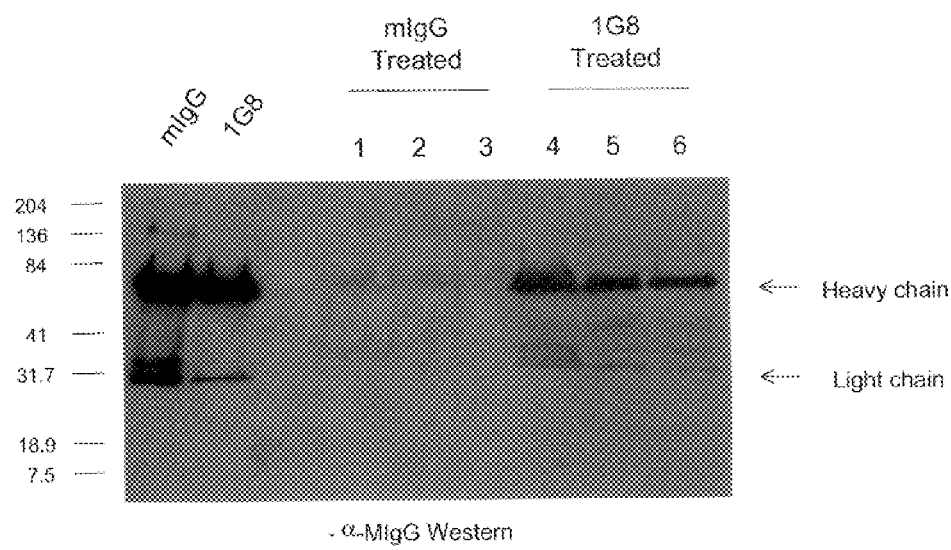

FIG. 73. Anti-PSCA antibody administered to a tumor-bearing mouse circulates and targets tumors expressing PSCA. A Western blot analysis of tumor lysates from tumors explanted from mice bearing established PSCA-expressing tumors, treated with 1G8. The blot was probed with goat anti-mouse IgG-HRP antibody.

DETAILED DESCRIPTION OF THE INVENTION

Figure 16B:
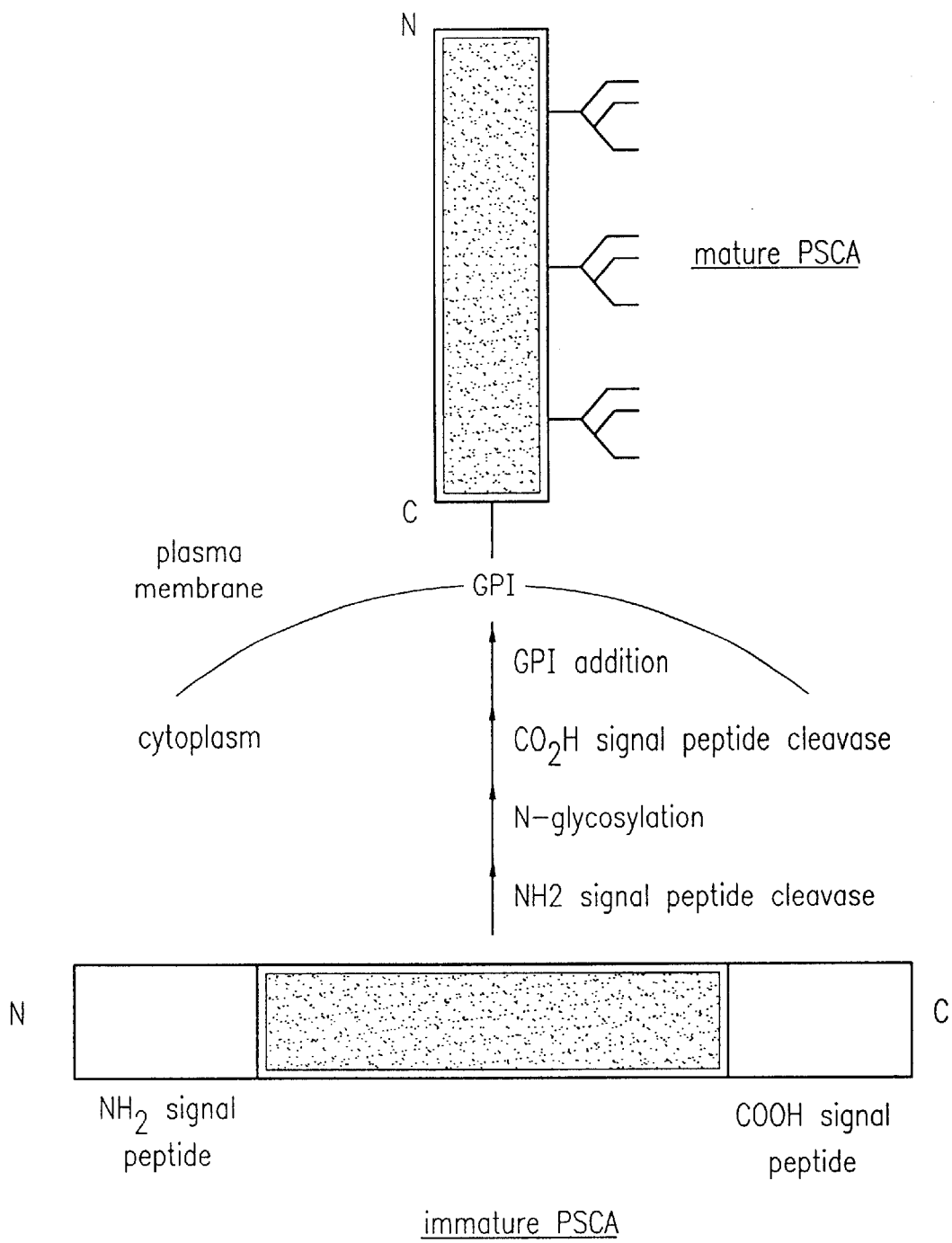
FIG. 16B. A schematic diagram showing that PSCA is a GPI-anchored protein.

The present invention relates to Prostate Stem Cell Antigen (hereinafter "PSCA"). PSCA is a novel, glycosylphosphatidylinositol (GPI)-anchored cell surface antigen which is expressed in normal cells such prostate cells, urothelium, renal collecting ducts, colonic neuroendocrine cells, placenta, normal bladder and urethral transitional epithelial cells (FIG. 16). PSCA, in addition to normal cells, is also overexpressed by both androgen-dependent and androgen-independent prostate cancer cells (FIG. 9-11), prostate cancer metastases to bone (FIG. 20-24 and 26-32), bladder carcinomas (FIG. 6, 25 and 62), and pancreatic carcinomas (FIGS. 63 and 64). The expression of PSCA in cancer, e.g., prostate cancer and bladder cancer, appears to correlate with increasing grade. Further, overexpression of PSCA (i.e. higher expression than found in normal cells) in patients suffering from cancer, e.g., prostate cancer, appears to be indicative of poor prognosis.

PSCA mRNA is also expressed by a subset of basal cells in normal prostate. The basal cell epithelium is believed to contain the progenitor cells for the terminally differentiated secretory cells (Bonkhoff et al., 1994, Prostate 24: 114–118). Recent studies using cytokeratin markers suggest that the basal cell epithelium contains at least two distinct cellular subpopulations, one expressing cytokeratins 5 and 14 and the other cytokeratins 5, 8 and 18 (Bonkhoff and Remberger, 1996, Prostate 28: 98–106). The finding that PSCA is expressed by only a subset of basal cells suggests that PSCA may be a marker for one of these two basal cell lineages.

The biological function of PSCA is unknown. The Ly-6 gene family is involved in diverse cellular functions, including signal transduction and cell-cell adhesion. Signaling through SCA-2 has been demonstrated to prevent apoptosis in immature thymocytes (Noda et al., 1996, J. Exp. Med. 183: 2355–2360). Thy-1 is involved in T cell activation and transmits signals through src-like tyrosine kinases (Thomas et al., 1992, J. Biol. Chem. 267: 12317–12322). Ly-6 genes have been implicated both in tumorigenesis and in homotypic cell adhesion (Bamezai and Rock, 1995, Proc. Natl. Acad. Sci. USA 92: 4294-4298; Katz et al., 1994, Int. J. Cancer 59: 684–691; Brakenhoff et al., 1995, J. Cell Biol. 129: 1677–1689). Based on its restricted expression in basal cells and its homology to Sca-2, we hypothesize that PSCA may play a role in stem/progenitor cell functions such as self-renewal (anti-apoptosis) and/or proliferation.

PSCA is highly conserved in mice and humans. The identification of a conserved gene which is predominantly restricted to prostate supports the hypothesis that PSCA may play an important role in normal prostate development.

In its various aspects, as described in detail below, the present invention provides PSCA proteins, antibodies, nucleic acid molecules, recombinant DNA molecules, transformed host cells, generation methods, assays, immunotherapeutic methods, transgenic animals, immunological and nucleic acid-based assays, and compositions.

PSCA Proteins

One aspect of the invention provides various PSCA proteins and peptide fragments thereof. As used herein, PSCA refers to a protein that has the amino acid sequence of human PSCA (SEQ ID NO:2) as provided in FIGS. 1B and 3, the amino acid sequence of the murine PSCA homologue (SEQ ID NO:4) as provided in FIG. 3, or the amino acid sequence of other mammalian PSCA homologues, as well as allelic variants and conservative substitution mutants of these proteins that have PSCA activity. The PSCA proteins of the invention include the specifically identified and characterized variants herein described, as well as allelic variants, conservative substitution variants and homologs that can be isolated/generated and characterized without undue experimentation following the methods outlined below. For the sake of convenience, all PSCA proteins will be collectively referred to as the PSCA proteins, the proteins of the invention, or PSCA.

The term "PSCA" includes all naturally occurring allelic variants, isoforms, and precursors of human PSCA (SEQ ID NO:2) as provided in FIGS. 1B and 3 and murine PSCA (SEQ ID NO:4) as provided in FIG. 3. In general, for example, naturally occurring allelic variants of human PSCA will share significant homology (e.g., 70–90%) to the PSCA amino acid sequence provided in FIGS. 1B and 3. Allelic variants, though possessing a slightly different amino acid sequence, may be expressed on the surface of prostate cells as a GPI linked protein or may be secreted or shed. Typically, allelic variants of the PSCA protein will contain conservative amino acid substitutions from the PSCA sequence herein described or will contain a substitution of an amino acid from a corresponding position in a PSCA homologue such as, for example, the murine PSCA homologue described herein.

One class of PSCA allelic variants will be proteins that share a high degree of homology with at least a small region of the PSCA amino acid sequences presented in FIGS. 1B (SEQ ID NO:2) and 3 (SEQ ID NO:2 or 4), but will further contain a radical departure from the sequence, such as a non-conservative substitution, truncation, insertion or frame shift. Such alleles are termed mutant alleles of PSCA and represent proteins that typically do not perform the same biological functions.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

The amino acid sequence of human PSCA protein (SEQ ID NO:2) is provided in FIGS. 1B and 3. Human PSCA is comprised of a single subunit of 123 amino acids and contains an amino-terminal signal sequence, a carboxy-terminal GPI-anchoring sequence, and multiple N-glycosylation sites. PSCA shows 30% homology to stem cell antigen-2 (SCA-2), a member of the Thy-1/Ly-6 gene family, a group of cell surface proteins which mark the earliest phases of hematopoetic development. The amino acid sequence of a murine PSCA homologue (SEQ ID NO:4) is shown in FIG. 3. Murine PSCA is a single subunit protein of 123 amino acids having approximately 70% homology to human PSCA and similar structural organization.

PSCA proteins may be embodied in many forms, preferably in isolated form. As used herein, a protein is said to be isolated when physical, mechanical or chemical methods are employed to remove the PSCA protein from cellular constituents that are normally associated with the protein. A skilled artisan can readily employ standard purification methods to obtain an isolated PSCA protein. A purified PSCA protein molecule will be substantially free of other proteins or molecules that impair the binding of PSCA to antibody or other ligand. The nature and degree of isolation and purification will depend on the intended use. Embodiments of the PSCA protein include a purified PSCA protein and a functional, soluble PSCA protein. One example of a functional soluble PSCA protein has the amino acid sequence shown in FIG. 1B (SEQ ID NO:2) or a fragment thereof. In one form, such functional, soluble PSCA proteins or fragments thereof retain the ability to bind antibody or other ligand.

The invention also provides peptides comprising biologically active fragments of the human (SEQ ID NO:2) and murine (SEQ ID NO:4) PSCA amino acid sequences shown in FIGS. 1B and 3. For example, the invention provides a peptide fragment having the amino acid sequence TARIRAVGLLTVISK (SEQ ID NO:16), a peptide fragment having the amino acid sequence VDDSQDYYVGKK (SEQ ID NO:17), and SLNCVDDSQDYYVGK (SEQ ID NO:18).

The peptides of the invention exhibit properties of PSCA, such as the ability to elicit the generation of antibodies that specifically bind an epitope associated with PSCA. Such peptide fragments of the PSCA proteins can be generated using standard peptide synthesis technology and the amino acid sequences of the human or murine PSCA proteins disclosed herein. Alternatively, recombinant methods can be used to generate nucleic acid molecules that encode a fragment of the PSCA protein. In this regard, the PSCA-encoding nucleic acid molecules described herein provide means for generating defined fragments of PSCA.

Figure 4:
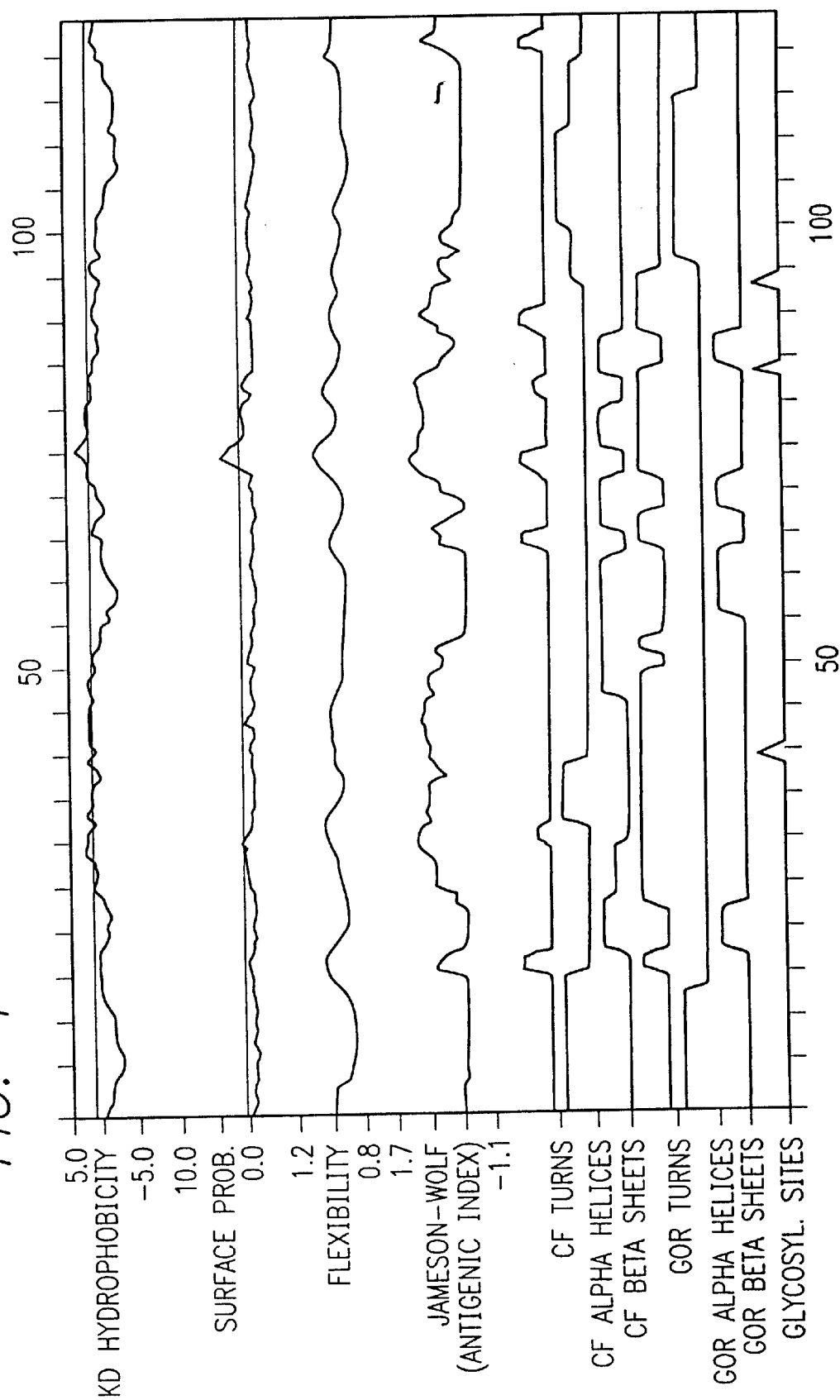
FIG. 4. Hydrophobicity plot of human PSCA.

As discussed below, peptide fragments of PSCA are particularly useful in: generating domain specific antibodies; identifying agents that bind to PSCA or a PSCA domain; identifying cellular factors that bind to PSCA or a PSCA domain; and isolating homologs or other allelic forms of human PSCA. PSCA peptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. As examples, hydrophobicity and Chou-Fasman plots of human PSCA are provided in FIGS. 4 and 5, respectively. Fragments containing such residues are particularly useful in generating subunit specific anti-PSCA antibodies or in identifying cellular factors that bind to PSCA.

Various regions of the PSCA protein can bind to anti-PSCA antibodies. The regions of the PSCA protein may include, for example, the N-terminal region, middle region, and C-terminal region (Example 18, FIG. 49). The N-terminal region includes any portion of the PSCA protein encompassed by amino acid residues 2–50, preferably residues 18–50. The middle region includes any portion of the PSCA protein encompassed by amino acid residues 46–109, preferably residues 46–98. The C-terminal region includes any portion of the PSCA protein encompassed by amino acid residues 85–123, preferably residues 85–98.

The PSCA proteins of the invention may be useful for a variety of purposes, including but not limited to their use as diagnostic and/or prognostic markers of prostate cancer, the ability to elicit the generation of antibodies, and as targets for various therapeutic modalities, as further described below. PSCA proteins may also be used to identify and isolate ligands and other agents that bind to PSCA. In the normal prostate, PSCA is expressed exclusively in a subset of basal cells, suggesting that PSCA may be used as a marker for a specific cell lineage within basal epithelium. In addition, the results herein suggest that this set of basal cells represent the target of neoplastic transformation. Accordingly for example, therapeutic strategies designed to eliminate or modulate the molecular factors responsible for transformation may be specifically directed to this population of cells via the PSCA cell surface protein.

PSCA Antibodies

The invention further provides antibodies (e.g., polyclonal, monoclonal, chimeric, and humanized antibodies) that bind to PSCA. The most preferred antibodies will selectively bind to PSCA and will not bind (or will bind weakly) to non-PSCA proteins. The most preferred antibodies will specifically bind to PSCA. It is intended that the term "specifically bind" means that the antibody predominantly binds to PSCA. Anti-PSCA antibodies that are particularly contemplated include monoclonal and polyclonal antibodies as well as fragments thereof (e.g., recombinant proteins) containing the antigen binding domain and/or one or more complement determining regions of these antibodies. These antibodies can be from any source, e.g., rat, dog, cat, pig, horse, mouse or human.

In one embodiment, the PSCA antibodies specifically bind to the extracellular domain of a PSCA protein, e.g., on the cell surface of prostate cancer cells from primary lesions and prostate cancer bone metastases. It is intended that the term "extracellular domain" means any portion of the PSCA protein which is exterior to the plasma membrane of the cell. In other embodiments, the PSCA antibodies specifically bind to other domains of a PSCA protein or precursor (such as a portion of the N-terminal region, the middle region, or the C-terminal region; FIG. 49). As will be understood by those skilled in the art, the regions or epitopes of a PSCA protein to which an antibody is directed may vary with the intended application. For example, antibodies intended for use in an immunoassay for the detection of membrane-bound PSCA on viable prostate cancer cells should be directed to an accessible epitope on membrane-bound PSCA. Examples of such antibodies are described the Examples which follow. Antibodies that recognize other epitopes may be useful for the identification of PSCA within damaged or dying cells, for the detection of secreted PSCA proteins or fragments thereof. The invention also encompasses antibody fragments that specifically recognize a PSCA protein. As used herein, an antibody fragment is defined as at least a portion of the variable region of the immunoglobulin molecule that binds to its target, i.e., the antigen binding region. Some of the constant region of the immunoglobulin may be included.

For example, the overexpression of PSCA in both androgen-dependent and androgen-independent prostate cancer cells, and the cell surface location of PSCA represent characteristics of an excellent marker for screening, diagnosis, prognosis, and follow-up assays and imaging methods. In addition, these characteristics indicate that PSCA may be an excellent target for therapeutic methods such as targeted antibody therapy, immunotherapy, and gene therapy.

PSCA antibodies of the invention may be particularly useful in diagnostic assays, imaging methodologies, and therapeutic methods in the management of prostate cancer. The invention provides various immunological assays useful for the detection of PSCA proteins and for the diagnosis of prostate cancer. Such assays generally comprise one or more PSCA antibodies capable of recognizing and binding a PSCA protein, and include various immunological assay formats well known in the art, including but not limited to various types of precipitation, agglutination, complement fixation, radioimmunoassays (RIA), enzyme-linked immunosorbent assays (ELISA), enzyme-linked immunofluorescent assays (ELIFA) (H. Liu et al. Cancer Research 58: 4055–4060 (1998), immunohistochemical analysis and the like. In addition, immunological imaging methods capable of detecting prostate cancer are also provided by the invention, including but limited to radioscintigraphic imaging methods using labeled PSCA antibodies. Such assays may be clinically useful in the detection, monitoring, and prognosis of prostate cancer.

In one embodiment, PSCA antibodies and fragments thereof (e.g., Fv, Fab', F(ab')2) are used for detecting the presence of a prostate cancer, bladder carcinoma, pancreatic carcinoma, bone metastases of prostate cancer, PIN, or basal epithelial cell expressing a PSCA protein. The presence of such PSCA positive (+) cells within various biological samples, including serum, prostate and other tissue biopsy specimens, other tissues such as bone, urine, etc., may be detected with PSCA antibodies. In addition, PSCA antibodies may be used in various imaging methodologies, such as immunoscintigraphy with Induim-111 (or other isotope) conjugated antibody. For example, an imaging protocol similar to the one recently described using an In-111 conjugated anti-PSMA antibody may be used to detect recurrent and metastatic prostate carcinomas (Sodee et al., 1997, Clin Nuc Med 21: 759–766). In relation to other markers of prostate cancer, such as PSMA for example, PSCA may be particularly useful for targeting androgen independent prostate cancer cells. PSCA antibodies may also be used therapeutically to inhibit PSCA function.

PSCA antibodies may also be used in methods for purifying PSCA proteins and peptides and for isolating PSCA homologues and related molecules. For example, in one embodiment, the method of purifying a PSCA protein comprises incubating a PSCA antibody, which has been coupled to a solid matrix, with a lysate or other solution containing PSCA under conditions which permit the PSCA antibody to bind to PSCA; washing the solid matrix to eliminate impurities; and eluting the PSCA from the coupled antibody. Additionally, PSCA antibodies may be used to isolate PSCA positive cells using cell sorting and purification techniques. The presence of PSCA on prostate tumor cells (alone or in combination with other cell surface markers) may be used to distinguish and isolate human prostate cancer cells from other cells. In particular, PSCA antibodies may be used to isolate prostate cancer cells from xenograft tumor tissue, from cells in culture, etc., using antibody-based cell sorting or affinity purification techniques. Other uses of the PSCA antibodies of the invention include generating anti-idiotypic antibodies that mimic the PSCA protein, e.g., a monoclonal anti-idiotypic antibody reactive with an idiotype on any of the monoclonal antibodies of the invention such as 1G8, 2A2, 2H9, 3C5, 3E6, 3G3, and 4A10.

The ability to generate large quantities of relatively pure human PSCA positive prostate cancer cells which can be grown in tissue culture or as xenograft tumors in animal models (e.g., SCID or other immune deficient mice) provides many advantages, including, for example, permitting the evaluation of various transgenes or candidate therapeutic compounds on the growth or other phenotypic characteristics of a relatively homogeneous population of prostate cancer cells. Additionally, this feature of the invention also permits the isolation of highly enriched preparations of human PSCA positive prostate cancer specific nucleic acids in quantities sufficient for various molecular manipulations. For example, large quantities of such nucleic acid preparations will assist in the identification of rare genes with biological relevance to prostate cancer disease progression.

Another valuable application of this aspect of the invention is the ability to isolate, analyze and experiment with relatively pure preparations of viable PSCA positive prostate tumor cells cloned from individual patients with locally advanced or metastatic disease. In this way, for example, an individual patient's prostate cancer cells may be expanded from a limited biopsy sample and then tested for the presence of diagnostic and prognostic genes, proteins, chromosomal aberrations, gene expression profiles, or other relevant genotypic and phenotypic characteristics, without the potentially confounding variable of contaminating cells. In addition, such cells may be evaluated for neoplastic aggressiveness and metastatic potential in animal models. Similarly, patient-specific prostate cancer vaccines and cellular immunotherapeutics may be created from such cell preparations.

Various methods for the preparation of antibodies are well known in the art. For example, antibodies may be prepared by immunizing a suitable mammalian host using a PSCA protein, peptide, or fragment, in isolated or immunoconjugated form (Harlow, Antibodies, Cold Spring Harbor Press, NY (1989)). In addition, fusion proteins of PSCA may also be used, such as a PSCA GST-fusion protein. Cells expressing or overexpressing PSCA may also be used for immunizations. Similarly, any cell engineered to express PSCA may be used. This strategy may result in the production of monoclonal antibodies with enhanced capacities for recognizing endogenous PSCA. For example, using standard technologies described in Example 5 and standard hybridoma protocols (Harlow and Lane, 1988, Antibodies: A Laboratory Manual. (Cold Spring Harbor Press)), hybridomas producing monoclonal antibodies designated 1G8 (ATCC No. HB-12612), 2A2 (ATCC No. HB-12613), 2H9 (ATCC No. HB-12614), 3C5 (ATCC No. HB-12616), 3E6 (ATCC No. HB-12618), and 3G3 (ATCC No. HB-12615), 4A10 (ATCC No. HB-12617) were generated. These antibody were deposited on Dec. 11, 1998 with the American Type Culture Collection (ATCC), 10801 University Boulevard, Manassas, Va. 20110–2209.

Chimeric antibodies of the invention are immunoglobulin molecules that comprise a human and non-human portion. The antigen combining region (variable region) of a chimeric antibody can be derived from a non-human source (e.g. murine) and the constant region of the chimeric antibody which confers biological effector function to the immunoglobulin can be derived from a human source. The chimeric antibody should have the antigen binding specificity of the non-human antibody molecule and the effector function conferred by the human antibody molecule.

In general, the procedures used to produce chimeric antibodies can involve the following steps:

a) identifying and cloning the correct gene segment encoding the antigen binding portion of the antibody molecule; this gene segment (known as the VDJ, variable, diversity and joining regions for heavy chains or VJ, variable, joining regions for light chains or simply as the V or variable region) may be in either the cDNA or genomic form;

b) cloning the gene segments encoding the constant region or desired part thereof;

c) ligating the variable region with the constant region so that the complete chimeric antibody is encoded in a form that can be transcribed and translated;

d) ligating this construct into a vector containing a selectable marker and gene control regions such as promoters, enhancers and poly(A) addition signals;

e) amplifying this construct in bacteria;

f) introducing this DNA into eukaryotic cells (transfection) most often mammalian lymphocytes;

g) selecting for cells expressing the selectable marker;

h) screening for cells expressing the desired chimeric antibody; and k) testing the antibody for appropriate binding specificity and effector functions.

Antibodies of several distinct antigen binding specificities have been manipulated by these protocols to produce chimeric proteins [e.g. anti-TNP: Boulianne et al., *Nature* 312:643 (1984); and anti-tumor antigens: Sahagan et al., *J. Immunol.* 137:1066 (1986)]. Likewise, several different effector functions have been achieved by linking new sequences to those encoding the antigen binding region. Some of these include enzymes [Neuberger et al., *Nature* 312:604 (1984)], immunoglobulin constant regions from another species and constant regions of another immunoglobulin chain [Sharon et al., *Nature* 309:364 (1984); Tan et al., *J. Immunol.* 135:3565–3567 (1985)]. Additionally, procedures for modifying antibody molecules and for producing chimeric antibody molecules using homologous recombination to target gene modification have been described (Fell et al., *Proc. Natl. Acad. Sci. USA* 86:8507–8511 (1989)).

These antibodies are capable of binding to PSCA, e.g., on the cell surface of prostate cancer cells, thereby confirming the cell surface localization of PSCA. Because these mAbs recognize epitopes on the exterior of the cell surface, they have utility for prostate cancer diagnosis and therapy. For example, these mAbs were used to locate sites of metastatic disease (Example 6). Another possibility is that they may be used (e.g., systemically) to target prostate cancer cells therapeutically when used alone or conjugated to a radioisotope or other toxin.

PSCA mAbs stain the cell surface in a punctate manner (see Example 5), suggesting that PSCA may be localized to specific regions of the cell surface. GPI-anchored proteins are known to cluster in detergent-insoluble glycolipid-enriched microdomains (DIGS) of the cell surface. These microdomains, which include caveolae and shingolipid-cholesterol rafts, are believed to play critical roles in signal transduction and molecular transport. Thy-1, a homologue of PSCA, has previously been shown to transmit signals to src kinases through interaction in lipid-microdomains. Subcellular fractionation experiments in our laboratory confirm the presence of PSCA in DIGS.

Additionally, some of the antibodies of the invention are internalizing antibodies, i.e., the antibodies are internalized into the cell upon or after binding. It is intended that the term "internalize" means that the antibody is taken into the cell. Further, some of the antibodies induce inhibition of PSCA positive cancer cell growth.

A characterization of these antibodies, e.g., in prostate cancer specimens, demonstrates that PSCA protein is overexpressed in prostate cancers relative to normal cells and its expression appears to be upregulated during prostate cancer progression and metastasis. These antibodies are useful in studies of PSCA biology and function, as well as in vivo targeting of PSCA associated cancers, including, without limitation, human prostate cancer, prostate cancer metastases to bone, bladder carcinomas, and pancreatic carcinomas.

PSCA mAbs which specifically recognize and bind to the extracellular domain of the PSCA protein are described herein. Some of these have been shown to bind to native PSCA as expressed on the cell surface and some have been shown to inhibit the in vivo growth of prostate tumor cells.

The amino acid sequence of PSCA presented herein may be used to select specific regions of the PSCA protein for generating antibodies. For example, hydrophobicity and hydrophilicity analyses of the PSCA amino acid sequence may be used to identify hydrophilic regions in the PSCA structure. Regions of the PSCA protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Fragments containing these residues are particularly suited in generating specific classes of anti-PSCA antibodies. Particularly useful fragments include, but are not limited to, the sequences TARIRAVGLLTVISK and SLNCVDDSQDYYVGK.

As described in Example 2, below, a rabbit polyclonal antibody was generated against the former fragment, prepared as a synthetic peptide, and affinity purified using a PSCA-glutathione S transferase fusion protein. Recognition of PSCA by this antibody was established by immunoblot and immunoprecipitation analysis of extracts of 293T cells transfected with PSCA and a GST-PSCA fusion protein. This antibody also identified the cell surface expression of PSCA in PSCA-transfected 293T and LAPC-4 cells using fluorescence activated cell sorting (FACS).

Additionally, a sheep polyclonal antibody was generated against the latter fragment, prepared as a synthetic peptide, and affinity purified using a peptide Affi-gel column (also by the method of Example 2). Recognition of PSCA by this antibody was established by immunoblot and immunoprecipitation analysis of extracts of LNCaP cells transfected with PSCA. This antibody also identified the cell surface expression of PSCA in PSCA-transfected LNCaP cells using fluorescence activated cell sorting (FACS) and immunohistochemistry analysis.

Methods for preparing a protein for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a PSCA immunogen is conducted generally by injection over a suitable time period and with use of a suitable adjuvant, as is generally understood in the art. During the immunization schedule, titers of antibodies can be taken to determine adequacy of antibody formation.

While the polyclonal antisera produced in this way may be satisfactory for some applications, for pharmaceutical compositions, monoclonal antibody preparations are preferred. Immortalized cell lines which secrete a desired monoclonal antibody may be prepared using the standard method of Kohler and Milstein or modifications which effect immortalization of lymphocytes or spleen cells, as is generally known. The immortalized cell lines secreting the desired antibodies are screened by immunoassay in which the antigen is the PSCA protein or PSCA fragment. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonal antibodies of the invention or the polyclonal antisera (e.g., Fab, F(ab')$_2$, Fv fragments, fusion proteins) which contain the immunologically significant portion (i.e., a portion that recognizes and binds PSCA) can be used as antagonists, as well as the intact antibodies. Humanized antibodies directed against PSCA is also useful. As used herein, a humanized PSCA antibody is an immunoglobulin molecule which is capable of binding to PSCA and which comprises a FR region having substantially the amino acid sequence of a human immunoglobulin and a CDR having substantially the amino acid sequence of non-human immunoglobulin or a sequence engineered to bind PSCA. Methods for humanizing murine and other non-human antibodies by substituting one or more of the non-human antibody CDRs for corresponding human antibody sequences are well known (see for example, Jones et al., 1986, Nature 321: 522–525; Riechmnan et al., 1988, Nature 332: 323–327; Verhoeyen et al., 1988, Science 239: 1534–1536). See also, Carter et al., 1993, Proc. Natl. Acad. Sci. USA 89: 4285 and Sims et al., 1993, J. Immunol. 151: 2296.

Use of immunologically reactive fragments, such as the Fab, Fab', or F(ab')$_2$ fragments is often preferable, especially in a therapeutic context, as these fragments are generally less immunogenic than the whole immunoglobulin. Further, bi-specific antibodies specific for two or more epitopes may be generated using methods generally known in the art. Further, antibody effector functions may be modified so as to enhance the therapeutic effect of PSCA antibodies on cancers. For example, cysteine residues may be engineered into the Fc region, permitting the formation of interchain disulfide bonds and the generation of homodimers which may have enhanced capacities for internalization, ADCC and/or complement-mediated cell killing (see, for example, Caron et al., 1992, J. Exp. Med. 176: 1191–1195; Shopes, 1992, J. Immunol. 148: 2918–2922). Homodimeric antibodies may also be generated by cross-linking techniques known in the art (e.g., Wolff et al., Cancer Res. 53: 2560–2565). The invention also provides pharmaceutical compositions having the monoclonal antibodies or anti-idiotypic monoclonal antibodies of the invention.

The generation of monoclonal antibodies (mAbs) capable of binding to cell surface PSCA are described in Example 5. Epitope mapping of these mAbs indicates that they recognize different epitopes on the PSCA protein. For example, one recognizes an epitope within the carboxy-terminal region and the other recognizing an epitope within the amino-terminal region. Such PSCA antibodies may be particularly well suited to use in a sandwich-formatted ELISA, given their differing epitope binding characteristics.

The antibodies or fragments may also be produced, using current technology, by recombinant means. Regions that bind specifically to the desired regions of the PSCA protein can also be produced in the context of chimeric or CDR grafted antibodies of multiple species origin. The invention includes an antibody, e.g., a monoclonal antibody which competitively inhibits the immunospecific binding of any of the monoclonal antibodies of the invention to PSCA.

Alternatively, methods for producing fully human monoclonal antibodies, include phage display and transgenic methods, are known and may be used for the generation of human mAbs (for review, see Vaughan et al., 1998, Nature Biotechnology 16: 535–539). For example, fully human anti-PSCA monoclonal antibodies may be generated using cloning technologies employing large human Ig gene combinatorial libraries (i.e., phage display)(Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human anti-PSCA monoclonal antibodies may also be produced using transgenic mice engineered to contain human immunoglobulin gene loci as described in PCT Patent Application WO98/24893, Jakobovits et al., published Dec. 3, 1997 (see also, Jakobovits, 1998, Exp. Opin. Invest. Drugs 7(4): 607–614). This method avoids the in vitro manipulation required with phage display technology and efficiently produces high affinity authentic human antibodies.

Reactivity of anti-PSCA mAbs against the target antigen may be established by a number of well known means, including Western blot, immunoprecipitation, ELISA, and FACS analyses using, as appropriate, PSCA proteins, peptides, PSCA-expressing cells or extracts thereof. Anti-PSCA mAbs may also be characterized in various in vitro assays, including complement-mediated tumor cell lysis, antibody-dependent cell cytotoxicity (ADCC), antibody-dependent macrophage-mediated cytotoxicity (ADMMC), tumor cell proliferation, etc. Examples of such in vitro assays are presented in Example 19, infra.

The antibody or fragment thereof of the invention may be cytostatic to the cell, to which it binds. It is intended that the term "cytostatic" means that the antibody can inhibit growth, but not necessarily kill, PSCA-positive cells.

The antibody or fragment thereof of the invention may be labeled with a detectable marker or conjugated to a second molecule, such as a therapeutic agent (e.g., a cytotoxic agent) thereby resulting in an immunoconjugate. For example, the therapeutic agent includes, but is not limited to, an anti-tumor drug, a toxin, a radioactive agent, a cytokine, a second antibody or an enzyme. Further, the invention provides an embodiment wherein the antibody of the invention is linked to an enzyme that converts a prodrug into a cytotoxic drug.

The immunoconjugate can be used for targeting the second molecule to a PSCA positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624–2636).

Examples of cytotoxic agents include, but are not limited to ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas exotoxin* (PE) A, PE40, abrin, arbrin A chain, modeccin A chain, alpha-sarcin, gelonin, mitogellin, retstrictocin, phenomycin, enomycin, curicin, crotin, calicheamicin, sapaonaria officinalis inhibitor, maytansinoids, and glucocorticoid and other chemotherapeutic agents, as well as radioisotopes such as $^{212}$Bi, $^{131}$I, $^{131}$In, $^{90}$Y, and $^{186}$Re. Suitable detectable markers include, but are not limited to, a radioisotope, a fluorescent compound, a bioluminescent compound, chemiluminescent compound, a metal chelator or an enzyme. Antibodies may also be conjugated to an anti-cancer pro-drug activating enzyme capable of converting the pro-drug to its active form. See, for example, U.S. Pat. No. 4,975,287.

Additionally, the recombinant protein of the invention comprising the antigen-binding region of any of the monoclonal antibodies of the invention can be used to treat cancer. In such a situation, the antigen-binding region of the recombinant protein is joined to at least a functionally active portion of a second protein having therapeutic activity. The second protein can include, but is not limited to, an enzyme, lymphokine, oncostatin or toxin. Suitable toxins include those described above.

Techniques for conjugating or joining therapeutic agents to antibodies are well known (see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243–56 (Alan R. Liss, Inc. 1985); Hellstrom et al., "Antibodies For Drug Delivery", in *Controlled Drug Delivery* (2nd Ed.), Robinson et al. (eds.), pp. 623–53 (Marcel Dekker, Inc. 1987); Thorpe, "Antibody Carriers Of Cytotoxic Agents In Cancer Therapy: A Review", in *Monoclonal Antibodies '84: Biological And Clinical Applications,* Pinchera et al. (eds.), pp. 475–506 (1985); and Thorpe et al., "The Preparation And Cytotoxic Properties Of Antibody-Toxin Conjugates", *Immunol. Rev.,* 62:119–58 (1982)). The use of PSCA antibodies as therapeutic agents is further described in the subsection "PROSTATE CANCER IMMUNOTHERAPY" below.

PSCA-Encoding Nucleic Acid Molecules

Another aspect of the invention provides various nucleic acid molecules encoding PSCA proteins and fragments thereof, preferably in isolated form, including DNA, RNA, DNA/RNA hybrid, and related molecules, nucleic acid molecules complementary to the PSCA coding sequence or a part thereof, and those which hybridize to the PSCA gene or to PSCA-encoding nucleic acids. Particularly preferred nucleic acid molecules will have a nucleotide sequence substantially identical to or complementary to the human or murine DNA sequences herein disclosed. Specifically contemplated are genomic DNA, cDNAs, ribozymes, and antisense molecules, as well as nucleic acids based on an alternative backbone or including alternative bases, whether derived from natural sources or synthesized.

For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the herein described PSCA sequences. For convenience, PSCA-encoding nucleic acid molecules will be referred to herein as PSCA-encoding nucleic acid molecules, PSCA genes, or PSCA sequences.

Figure 8A:
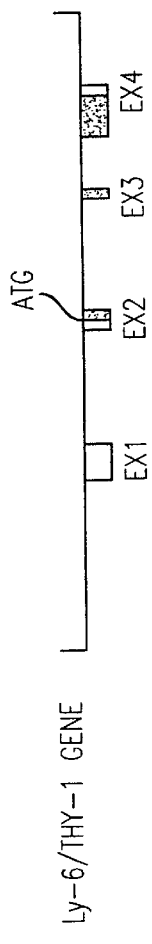
FIG. 8A. Schematic representation of human Thy-1/Ly-6 gene structures.
Figure 8B:
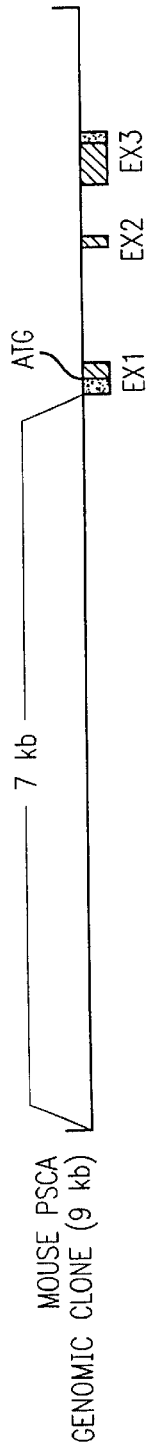
FIG. 8B. Schematic representation of murine PSCA gene structure.
Figure 8C:
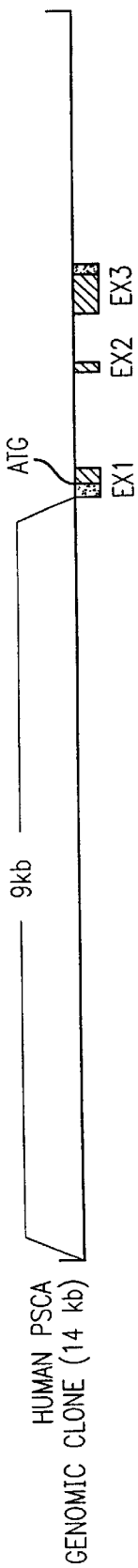
FIG. 8C. Schematic representation of human PSCA gene structure.

The nucleotide sequence of a cDNA (SEQ ID NO:1) encoding one allelic form of human PSCA is provided in FIG. 1A. The nucleotide sequence of a cDNA (SEQ ID NO:3) encoding a murine PSCA homologue ("murine PSCA") is provided in FIG. 2. Genomic clones of human and murine PSCA have also been isolated, as described in Example 4. Both the human and murine genomic clones contain three exons encoding the translated and 3' untranslated regions of the PSCA gene. A fourth exon encoding a 5' untranslated region is presumed to exist based on PSCA's homology to other members of the Ly-6 and Thy-1 gene families (FIG. 8).

The human PSCA gene maps to chromosome 8q24.2. Human stem cell antigen 2 (RIG-E), as well as one other recently identified human Ly-6 homologue (E48) are also localized to this region, suggesting that a large family of related genes may exist at this locus (Brakenhoff et al., 1995, supra; Mao et al., 1996, Proc. Natl. Acad. Sci. USA 93: 5910–5914). Intriguingly, chromosome 8q has been reported to be a region of allelic gain and amplification in a majority of advanced and recurrent prostate cancers (Cher et al., 1994, Genes Chrom. Cancer 11: 153–162). c-myc localizes proximal to PSCA at chromosome 8q24 and extra copies of c-myc (either through allelic gain or amplification) have been found in 68% of primary prostate tumors and 96% of metastases (Jenkins et al., 1997, Cancer Res. 57: 524–531).

Embodiments of the PSCA-encoding nucleic acid molecules of the invention include primers, which allow the specific amplification of nucleic acid molecules of the invention or of any specific parts thereof, and probes that selectively or specifically hybridize to nucleic acid molecules of the invention or to any part thereof. The nucleic acid probes can be labeled with a detectable marker. Examples of a detectable marker include, but are not limited to, a radioisotope, a fluorescent compound, a bioluminescent compound, a chemiluminescent compound, a metal chelator or an enzyme. Such labeled probes can be used to diagnosis the presence of a PSCA protein as a means for diagnosing cell expressing a PSCA protein. Technologies for generating DNA and RNA probes are well known.

As used herein, a nucleic acid molecule is said to be "isolated" when the nucleic acid molecule is substantially separated from contaminant nucleic acid molecules that encode polypeptides other than PSCA. A skilled artisan can readily employ nucleic acid isolation procedures to obtain an isolated PSCA-encoding nucleic acid molecule.

The invention further provides fragments of the PSCA-encoding nucleic acid molecules of the present invention. As used herein, a fragment of a PSCA-encoding nucleic acid molecule refers to a small portion of the entire PSCA-encoding sequence. The size of the fragment will be determined by its intended use.

For example, if the fragment is chosen so as to encode an active portion of the PSCA protein, such an active domain, effector binding site or GPI binding domain, then the fragment will need to be large enough to encode the functional region(s) of the PSCA protein. If the fragment is to be used as a nucleic acid probe or PCR primer, then the fragment length is chosen so as to obtain a relatively small number of false positives during probing/priming.

Fragments of human PSCA that are particularly useful as selective hybridization probes or PCR primers can be readily identified from the entire PSCA sequence using art-known methods. One set of PCR primers that are useful for RT-PCR analysis comprise 5'-TGCTTGCCCTGTTGATGGCAG- and 3'-CCAGAGCAGCAGGCCGAGTGCA-.

Methods for Isolating Other PSCA-Encoding Nucleic Acid Molecules

The PSCA-encoding nucleic acid molecules described herein enable the isolation of PSCA homologues, alternatively sliced isoforms, allelic variants, and mutant forms of the PSCA protein as well as their coding and gene sequences. The most preferred source of PSCA homologs are mammalian organisms.

For example, a portion of the PSCA-encoding sequence herein described can be synthesized and used as a probe to retrieve DNA encoding a member of the PSCA family of proteins from organisms other than human, allelic variants of the human PSCA protein herein described, and genomic sequence containing the PSCA gene. Oligomers containing approximately 18–20 nucleotides (encoding about a 6–7 amino acid stretch) are prepared and used to screen genomic DNA or cDNA libraries to obtain hybridization under stringent conditions or conditions of sufficient stringency to eliminate an undue level of false positives. In a particular embodiment, cDNA encoding human PSCA was used to isolate a full length cDNA encoding the murine PSCA homologue as described in Example 3 herein. The murine clone encodes a protein with 70% amino acid identity to human PSCA.

In addition, the amino acid sequence of the human PSCA protein may be used to generate antibody probes to screen expression libraries prepared from cells. Typically, polyclonal antiserum from mammals such as rabbits immunized with the purified protein (as described below) or monoclonal antibodies can be used to probe an expression library, prepared from a target organism, to obtain the appropriate coding sequence for a PSCA homologue. The cloned cDNA sequence can be expressed as a fusion protein, expressed directly using its own control sequences, or expressed by constructing an expression cassette using control sequences appropriate to the particular host used for expression of the enzyme.

Genomic clones containing PSCA genes may be obtained using molecular cloning methods well known in the art. In one embodiment, a human genomic clone of approximately 14 kb containing exons 1–4 of the PSCA gene was obtained by screening a lambda phage library with a human PSCA cDNA probe, as more completely described in Example 4 herein. In another embodiment, a genomic clone of approximately 10 kb containing the murine PSCA gene was obtained by screening a murine BAC (bacterial artificial chromosome) library with a murine PSCA cDNA (also described in Example 4).

Additionally, pairs of oligonucleotide primers can be prepared for use in a polymerase chain reaction (PCR) to selectively amplify/clone a PSCA-encoding nucleic acid molecule, or fragment thereof. A PCR denature/anneal/extend cycle for using such PCR primers is well known in the art and can readily be adapted for use in isolating other PSCA-encoding nucleic acid molecules. Regions of the human PSCA gene that are particularly well suited for use as a probe or as primers can be readily identified.

Non-human homologues of PSCA, naturally occurring allelic variants of PSCA and genomic PSCA sequences will share a high degree of homology to the human PSCA sequences herein described. In general, such nucleic acid molecules will hybridize to the human PSCA sequence under stringent conditions. Such sequences will typically contain at least 70% homology, preferably at least 80%, most preferably at least 90% homology to the human PSCA sequence.

Stringent conditions are those that (1) employ low ionic strength and high temperature for washing, for example, 0.015M NaCl/0.0015M sodium nitrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

Another example is use of 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

Recombinant DNA Molecules Containing PSCA-Encoding Nucleic Acids

Also provided are recombinant DNA molecules (rDNAs) that contain a PSCA-encoding sequences as herein described, or a fragment thereof. As used herein, a rDNA molecule is a DNA molecule that has been subjected to molecular manipulation in vitro. Methods for generating rDNA molecules are well known in the art, for example, see Sambrook et al., *Molecular Cloning* (1989). In the preferred rDNA molecules of the present invention, a PSCA-encoding DNA sequence that encodes a PSCA protein or a fragment of PSCA, is operably linked to one or more expression control sequences and/or vector sequences. The rDNA molecule can encode either the entire PSCA protein, or can encode a fragment of the PSCA protein.

The choice of vector and/or expression control sequences to which the PSCA-encoding sequence is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the PSCA-encoding sequence included in the rDNA molecule.

Expression control elements that are used for regulating the expression of an operably linked protein encoding sequence are known in the art and include, but are not limited to, inducible promoters, constitutive promoters, secretion signals, enhancers, transcription terminators and other regulatory elements. Preferably, an inducible promoter that is readily controlled, such as being responsive to a nutrient in the host cell's medium, is used.

In one embodiment, the vector containing a PSCA-encoding nucleic acid molecule will include a prokaryotic replicon, i.e., a DNA sequence having the ability to direct autonomous replication and maintenance of the recombinant DNA molecule intrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or viral promoter capable of directing the expression (transcription and translation) of the PSCA-encoding sequence in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Various viral vectors well known to those skilled in the art may also be used, such as, for example, a number of well known retroviral vectors.

Expression vectors compatible with eukaryotic cells, preferably those compatible with vertebrate cells, can also be used to variant rDNA molecules that contain a PSCA-encoding sequence. Eukaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. Southern et al., *J Mol Anal Genet* (1982) 1:327–341. Alternatively, the selectable marker can be present on a separate plasmid, and the two vectors are introduced by cotransfection of the host cell, and selected by culturing in the presence of the appropriate drug for the selectable marker.

In accordance with the practice of the invention, the vector can be a plasmid, cosmid or phage vector encoding the cDNA molecule discussed above. Additionally, the invention provides a host-vector system comprising the plasmid, cosmid or phage vector transfected into a suitable eukaryotic host cell. Examples of suitable eukaryotic host cells include a yeast cell, a plant cell, or an animal cell, such as a mammalian cell. Examples of suitable cells include the LnCaP, LAPC-4, and other prostate cancer cell lines. The host-vector system is useful for the production of a PSCA protein. Alternatively, the host cell can be prokaryotic, such as a bacterial cell.

Transformed Host Cells

The invention further provides host cells transformed with a nucleic acid molecule that encodes a PSCA protein or a fragment thereof The host cell can be either prokaryotic or eukaryotic. Eukaryotic cells useful for expression of a PSCA protein are not limited, so long as the cell line is compatible with cell culture methods and compatible with the propagation of the expression vector and expression of a PSCA gene. Preferred eukaryotic host cells include, but are not limited to, yeast, insect and mammalian cells, preferably vertebrate cells such as those from a mouse, rat, monkey or human fibroblastic cell line. Prostate cancer cell lines, such as the LnCaP and LAPC4 cell lines may also be used. Any prokaryotic host can be used to express a PSCA-encoding rDNA molecule. The preferred prokaryotic host is *E. coli*.

Transformation of appropriate cell hosts with an rDNA molecule of the present invention is accomplished by well known methods that typically depend on the type of vector used and host system employed. With regard to transformation of prokaryotic host cells, electroporation and salt treatment methods are typically employed, see, for example, Cohen et al., *Proc Acad Sci USA* (1972) 69:2110; and Maniatis et al., *Molecular Cloning, A Laboratory Manual*, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol* (1973) 52:456; Wigler et al., *Proc Natl Acad Sci USA* (1979) 76:1373–76.

Successfully transformed cells, i.e., cells that contain an rDNA molecule of the present invention, can be identified by well known techniques. For example, cells resulting from the introduction of an rDNA of the present invention can be cloned to produce single colonies. Cells from those colonies can be harvested, lysed and their DNA content examined for the presence of the rDNA using a method such as that described by Southern, *J Mol Biol* (1975) 98:503, or Berent et al., *Biotech* (1985) 3:208 or the proteins produced from the cell assayed via an immunological method.

Recombinant Methods of Generating PSCA Proteins

The invention further provides methods for producing a PSCA protein using one of the PSCA-encoding nucleic acid molecules herein described. In general terms, the production of a recombinant PSCA protein typically can involve the following steps (Maniatis, supra).

First, a nucleic acid molecule is obtained that encodes a PSCA protein (SEQ ID NO:2 or 4) or a fragment thereof, such as the nucleic acid molecule depicted in FIG. 1A. The PSCA-encoding nucleic acid molecule is then preferably placed in an operable linkage with suitable control sequences, as described above, to generate an expression unit containing the PSCA-encoding sequence. The expression unit is used to transform a suitable host and the transformed host is cultured under conditions that allow the production of the PSCA protein. Optionally the PSCA protein is isolated from the medium or from the cells; recovery and purification of the protein may not be necessary in some instances where some impurities may be tolerated.

Each of the foregoing steps may be done in a variety of ways. For example, the desired coding sequences may be obtained from genomic fragments and used directly in an appropriate host. The construction of expression vectors that are operable in a variety of hosts is accomplished using an appropriate combination of replicons and control sequences. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with PSCA-encoding sequences to produce a PSCA protein.

In a specific embodiment described in the examples which follow, a secreted form of PSCA may be conveniently expressed in 293T cells transfected with a CMV-driven expression vector encoding PSCA with a C-terminal 6XHis and MYC tag (pcDNA3.1/mycHIS, Invitrogen). The secreted HIS-tagged PSCA in the culture media may be purified using a nickel column using standard techniques.

Assays for Identifying PSCA Ligands and Other Binding Agents

Another aspect of the invention relates to assays and methods that can be used to detect and identify PSCA ligands and other agents and cellular constituents that bind to PSCA. Specifically, PSCA ligands and other agents and cellular constituents that bind to PSCA can be identified by the ability of the PSCA ligand or other agent or constituent to bind to PSCA and/or the ability to inhibit/stimulate PSCA activity. Assays for PSCA activity (e.g., binding) using a PSCA protein are suitable for use in high through-put screening methods.

In one embodiment, the assay comprises mixing PSCA with a test agent or cellular extract. After mixing under conditions that allow association of PSCA with the agent or component of the extract, the mixture is analyzed to determine if the agent/component is bound to PSCA. Binding agents/components are identified as being able to bind to PSCA. Alternatively or consecutively, PSCA activity can be directly assessed as a means for identifying agonists and antagonists of PSCA activity.

Alternatively, targets that bind to a PSCA protein can be identified using a yeast two-hybrid system (Fields, S. and Song, O. (1989), Nature 340:245–246) or using a binding-capture assay (Harlow, supra). In the yeast two hybrid system, an expression unit encoding a fusion protein made up of one subunit of a two subunit transcription factor and the PSCA protein is introduced and expressed in a yeast cell. The cell is further modified to contain (1) an expression unit encoding a detectable marker whose expression requires the two subunit transcription factor for expression and (2) an expression unit that encodes a fusion protein made up of the second subunit of the transcription factor and a cloned segment of DNA. If the cloned segment of DNA encodes a protein that binds to the PSCA protein, the expression results in the interaction of the PSCA and the encoded protein. This brings the two subunits of the transcription factor into binding proximity, allowing reconstitution of the transcription factor. This results in the expression of the detectable marker. The yeast two hybrid system is particularly useful in screening a library of cDNA encoding segments for cellular binding partners of PSCA.

PSCA proteins which may be used in the above assays include, but are not limited to, an isolated PSCA protein, a fragment of a PSCA protein, a cell that has been altered to express a PSCA protein, or a fraction of a cell that has been altered to express a PSCA protein. Further, the PSCA protein can be the entire PSCA protein or a defined fragment of the PSCA protein. It will be apparent to one of ordinary skill in the art that so long as the PSCA protein can be assayed for agent binding, e.g., by a shift in molecular weight or activity, the present assay can be used.

The method used to identify whether an agent/cellular component binds to a PSCA protein will be based primarily on the nature of the PSCA protein used. For example, a gel retardation assay can be used to determine whether an agent binds to PSCA or a fragment thereof. Alternatively, immunodetection and biochip technologies can be adopted for use with the PSCA protein. A skilled artisan can readily employ numerous art-known techniques for determining whether a particular agent binds to a PSCA protein.

Agents and cellular components can be further tested for the ability to modulate the activity of a PSCA protein using a cell-free assay system or a cellular assay system. As the activities of the PSCA protein become more defined, functional assays based on the identified activity can be employed.

As used herein, an agent is said to antagonize PSCA activity when the agent reduces PSCA activity. The preferred antagonist will selectively antagonize PSCA, not affecting any other cellular proteins. Further, the preferred antagonist will reduce PSCA activity by more than 50%, more preferably by more than 90%, most preferably eliminating all PSCA activity.

As used herein, an agent is said to agonize PSCA activity when the agent increases PSCA activity. The preferred agonist will selectively agonize PSCA, not affecting any other cellular proteins. Further, the preferred antagonist will increase PSCA activity by more than 50%, more preferably by more than 90%, most preferably more than doubling PSCA activity.

Agents that are assayed in the above method can be randomly selected or rationally selected or designed. As used herein, an agent is said to be randomly selected when the agent is chosen randomly without considering the specific sequences of the PSCA protein. An example of randomly selected agents is the use of a chemical library or a peptide combinatorial library, or a growth broth of an organism or plant extract.

As used herein, an agent is said to be rationally selected or designed when the agent is chosen on a nonrandom basis that takes into account the sequence of the target site and/or its conformation in connection with the agent's action. Agents can be rationally selected or rationally designed by utilizing the peptide sequences that make up the PSCA protein. For example, a rationally selected peptide agent can be a peptide whose amino acid sequence is identical to a fragment of a PSCA protein.

The agents tested in the methods of the present invention can be, as examples, peptides, small molecules, and vitamin derivatives, as well as carbohydrates. A skilled artisan can readily recognize that there is no limit as to the structural nature of the agents used in the present screening method. One class of agents of the present invention are peptide agents whose amino acid sequences are chosen based on the amino acid sequence of the PSCA protein. Small peptide agents can serve as competitive inhibitors of PSCA protein assembly.

Peptide agents can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies inmunoreactive with critical positions of the PSCA protein. As described above, antibodies are obtained by immunization of suitable mammalian subjects with peptides, containing as antigenic regions, those portions of the PSCA protein intended to be targeted by the antibodies. Critical regions may include the domains identified in FIG. 15. Such agents can be used in competitive binding studies to identify second generation inhibitory agents.

The cellular extracts tested in the methods of the present invention can be, as examples, aqueous extracts of cells or tissues, organic extracts of cells or tissues or partially purified cellular fractions. A skilled artisan can readily recognize that there is no limit as to the source of the cellular extract used in the screening method of the present invention.

Agents that bind a PSCA protein, such as a PSCA antibody, can be used to modulate the activity of PSCA, to target anticancer agents to appropriate mammalian cells, or to identify agents that block the interaction with PSCA. Cells expressing PSCA can be targeted or identified by using an agent that binds to PSCA.

How the PSCA binding agents will be used depends on the nature of the PSCA binding agent. For example, a PSCA binding agent can be used to: deliver conjugated toxins, such a diphtheria toxin, cholera toxin, ricin or pseudomonas exotoxin, to a PSCA expressing cell; modulate PSCA activity; to directly kill PSCA expressing cells; or in screens to identify competitive binding agents. For example, a PSCA inhibitory agent can be used to directly inhibit the growth of PSCA expressing cells whereas a PSCA binding agent can be used as a diagnostic agent.

There are multiple diagnostic uses of the invention. For example, the invention provides methods for diagnosing in a subject, e.g., an animal or human subject, a cancer associated with the presence of the PSCA protein. In one embodiment, the method comprises quantitatively determining the number of PSCA protein in the sample (e.g., cell or biological fluid sample) using any one or combination of the antibodies of the invention. Then the number so determined can be compared with the amount in a sample from a normal subject. The presence of a measurably different amount (i.e., the number of PSCA in the test sample exceeds the number from a normal sample) in the samples indicating the presence of the cancer. PSCA is overexpressed on a cell when the number of PSCA in the test sample exceeds the number from a normal sample.

In another embodiment, diagnosis involves quantitatively determining in a sample from the subject the amount of RNA encoding the PSCA protein using the nucleic acid of the invention. The amount so determined can be compared with the amount of RNA in a sample from a normal subject. Once again, the presence of a measurable different amount indicating the presence of the cancer.

Additionally, the invention provides methods for monitoring the course of cancer (e.g., prostate, bone metastases of prostate cancer, bladder, pancreatic cancer) or disorders associated with PSCA in a subject by measuring the amount of PSCA in a sample from the subject at various points in time. This is done for purposes of determining a change in the amount of PSCA in the sample e.g., to determine whether the change is a small change in the amount or a large change, i.e., overexpression of PSCA. In one embodiment, the method comprises quantitatively determining in a first sample from the subject the presence of a PSCA protein and comparing the amount so determined with the amount present in a second sample from the subject, such samples being taken at different points in time, a difference in the amounts determined being indicative of the course of the cancer.

In another embodiment, monitoring is effected by quantitatively determining in a first sample from the subject the presence of a PSCA RNA and comparing the amount so determined with the amount present in a second sample from the subject, such samples being taken at different points in time, a difference in the amounts determined being indicative of the course of the cancer (e.g., prostate, bone metastases of prostate cancer, bladder and pancreatic cancer).

As a further embodiment, the diseases or disorders associated with PSCA can be monitored in a sample by detecting an increase in or increased PSCA gene copy number. An increase in or increased PSCA gene copy number is important because it may correlate with poor outcome.

The sample can be from an animal or a human. Further, the sample can be a cell sample. For example, using the methods of the invention, organ tissues such as prostate tissue, bladder tissue, pancreatic tissue, neuroendocrine tissue, and bone (any tissue where carcinomas can metastasize, e.g., node, lung, liver, pancreas) can be evaluated for the presence of cancer or metastatic lesion. Alternatively, the sample can be a biological fluid, e.g., urine, blood sera or plasma.

In accordance with the practice of the invention, detection can be effected by immunologic detection means involving histology, blotting, ELISA, and ELIFA. When the sample is a tissue or cell sample it can be formalin-fixed, paraffin-embedded or frozen.

The invention additionally provides methods of determining a difference in the amount and distribution of PSCA in tissue sections from a neoplastic tissue to be tested relative to the amount and distribution of PSCA in tissue sections from a normal tissue. In one embodiment, the method comprises contacting both the tissue to be tested and the normal tissue with a monoclonal antibody that specifically forms a complex with PSCA and thereby detecting the difference in the amount and distribution of PSCA.

Further, the invention provides a method for diagnosing a neoplastic or preneoplastic condition in a subject. This method comprises obtaining from the subject a sample of a tissue, detecting a difference in the amount and distribution of PSCA in the using the method above, a distinct measurable difference being indicative of such neoplastic or preneoplastic condition.

In accordance with the practice of the invention, the antibody can be directed to the epitope to which any of the monoclonal antibodies of the invention is directed. Further, the tissue section can be from the bladder, prostate, bone, lymphatic tissues, pancreas, other organs, or muscle.

The invention also provides methods of detecting and quantitatively determining the concentration of PSCA in a biological fluid sample. In one embodiment the method comprises contacting a solid support with an excess of one or more monoclonal antibodies which forms (preferably specifically forms) a complex with PSCA under conditions permitting the monoclonal antibody to attach to the surface of the solid support. The resulting solid support to which the monoclonal antibody is attached is then contacted with a biological fluid sample so that the PSCA in the biological fluid binds to the antibody and forms a PSCA-antibody complex. The complexed can be labeled directly or indirectly with a detectable marker. Alternatively, either the PSCA or the antibody can be labeled before the formation the complex. The complex can then be detected and quantitatively determined thereby detecting and quantitatively determining the concentration of PSCA in the biological fluid sample. A high concentration of PSCA in the sample relative to normal cells being indicative of a neoplastic or preneoplastic condition.

In accordance with the practice of the invention, the biological fluid includes but is not limited to tissue extract, urine, blood, serum, and phlegm. Further, the detectable marker includes but is not limited to an enzyme, biotin, a fluorophore, a chromophore, a heavy metal, a paramagnetic isotope, or a radioisotope.

Further, the invention provides a diagnostic kit comprising an antibody that recognizes and binds PSCA (an anti-PSCA antibody); and a conjugate of a detectable label and a specific binding partner of the anti-PSCA antibody. In accordance with the practice of the invention the label includes, but is not limited to, enzymes, radiolabels, chromophores and fluorescers.

Cancer Immunotherapy

Since PSCA protein is expressed or overexpressed in many cancers, including but not limited to prostate tumors, metastases of prostate tumors (such as bone metastases), bladder cancer and pancreatic cancer, it is a target for cancer immunotherapy. These immunotherapeutic methods include the use of antibody therapy, in vivo vaccines, and ex vivo immunotherapy approaches.

In one approach, the invention provides PSCA antibodies that may be used systemically to treat cancer, such as prostate, bladder and pancreatic cancer. PSCA antibodies may also be useful in the treatment of various other benign and malignant tumors. Antibodies which bind specifically to the extracellular domain of PSCA are preferred. Antibodies which target the tumor cells but not the surrounding non-tumor cells and tissue are preferred. Thus, the invention provides a method of treating a patient susceptible to or having a cancer which expresses PSCA antigen, comprising administering to said patient an effective amount of an antibody which binds specifically to the extracellular domain of PSCA. In another approach, the invention provides a method of inhibiting the growth of tumor cells expressing PSCA, comprising administering to a patient an antibody which binds specifically to the extracellular domain of PSCA in an amount effective to inhibit growth of the tumor cells. PSCA mAbs may also be used in a method for selectively inhibiting the growth of or killing a cell expressing PSCA antigen comprising reacting a PSCA antibody immunoconjugate or immunotoxin with the cell in an amount sufficient to inhibit the growth of or kill the cell.

For example, unconjugated PSCA antibody (including monoclonal, polyclonal, chimeric, humanized, fully human and fragments thereof (e.g., recombinant proteins)) may be introduced into a patient such that the antibody binds to PSCA on cancer cells and mediates growth inhibition of such cells (including the destruction thereof), and the tumor, by mechanisms which may include complement-mediated cytolysis, antibody-dependent cellular cytotoxicity, altering the physiologic function of PSCA, and/or the inhibition of ligand binding or signal transduction pathways. In addition to unconjugated PSCA antibodies, fragments thereof, and recombinant proteins of the invention, PSCA antibodies conjugated to toxic agents such as ricin may also be used therapeutically to deliver the toxic agent directly to PSCA-bearing tumor cells and thereby destroy the tumor.

Cancer immunotherapy using PSCA antibodies may follow the teachings generated from various approaches which have been successfully employed with respect to other types of cancer, including but not limited to colon cancer (Arlen et al., 1998, Crit Rev Immunol 18: 133–138), multiple myeloma (Ozaki et al., 1997, Blood 90: 3179–3186; Tsunenari et al., 1997, Blood 90: 2437–2444), gastric cancer (Kasprzyk et al., 1992, Cancer Res 52: 2771–2776), B-cell lymphoma (Funakoshi et al., 1996, J Immunther Emphasis Tumor Immunol 19: 93–101), leukemia (Zhong et al., 1996, Leuk Res 20: 581–589), colorectal cancer (Moun et al., 1994, Cancer Res 54: 6160–6166); Velders et al., 1995, Cancer Res 55: 4398–4403), and breast cancer (Shepard et al., 1991, J Clin Immunol 11: 117–127).

For example, one way to apply antitumor monoclonal antibodies clinically is to administer them in unmodified form, using monoclonal antibodies of the invention which display antitumor activity (e.g., ADCC and CDC activity) and/or internalizing ability in vitro and/or in animal models (see, e.g. Hellstrom et al., *Proc. Natl. Acad. Sci. USA* 82:1499–1502 (1985). To detect ADCC and CDC activity monoclonal antibodies can be tested for lysing cultured $^{51}$Cr-labeled tumor target cells over a 4-hour incubation period. Target cells are labeled with $^{51}$Cr and then can be exposed for 4 hours to a combination of effector cells (in the form of human lymphocytes purified by the use of a lymphocyte-separation medium) and antibody, which is added in concentrations, e.g., varying between 0.1 μg/ml and 10 μg/ml. The release of $^{51}$Cr from the target cells is measured as evidence of tumor-cell lysis (cytotoxicity). Controls include the incubation of target cells alone or with either lymphocytes or monoclonal antibody separately. The total amount of $^{51}$Cr that can be released is measured and ADCC is calculated as the percent killing of target cells observed with monoclonal antibody plus effector cells as compared to target cells being incubated alone. The procedure for CDC is identical to the one used to detect ADCC except that human serum, as a source of complement, (diluted 1:3 to 1:6) is added in place of the effector cells.

In the practice of the method of the invention, anti-PSCA antibodies capable of inhibiting the growth of cancer cells expressing PSCA on the cell surface are administered in a therapeutically effective amount to cancer patients whose tumors express or overexpress PSCA. The anti-PSCA mAb therapy method of the invention demonstrates remarkable tumor growth inhibition of prostate tumors in vivo. Accordingly, the invention provides a specific, effective and long-needed treatment for prostate cancer. The method of the invention may also be useful for the treatment of other cancers which express or overexpress PSCA, including but not limited to bladder carcinoma and pancreatic carcinomas, since both of these cancers express elevated levels of PSCA. The antibody therapy methods of the invention may be combined with a chemotherapeutic, radiation, and/or other therapeutic regimen.

As described in Example 18A below, individual mouse anti-PSCA mAbs, as well as combinations of these anti-PSCA monoclonal antibodies, are capable of significantly inhibiting prostate tumor growth in vivo using a xenogenic prostate cancer SCID mouse model. In one study, a cohort of SCID mice receiving injections of a human prostate tumor xenograft were treated with a combination of several murine anti-PSCA mAbs. The results of this study showed that the treatment was able to completely block the formation of tumors in all of these mice—even after 61 days post tumor injection. In contrast, all animals in a control group of SCID mice receiving the same prostate tumor xenograft, but treated with control murine IgG, developed significant and progressively more massive tumors during the study. There was no apparent toxicity associated with the treatment of these animals with the anti-PSCA mAb preparation, as all mice in the treatment group remained lively and healthy throughout the experiment. The xenograft used in the study, LAPC-9, was generated from a bone tumor biopsy of a patient with hormone-refractory metastatic prostate cancer, is characterized by an extremely androgen-sensitive phenotype (PSA levels drop to zero after castration in recipient SCID mice), particularly aggressive growth properties, and high level overexpression of PSCA. LAPC-9 and is described further elsewhere (Published PCT Application WO98/16628, Sawyers et al., Apr. 23, 1998). These results were confirmed in a second in vivo study described in Example 18B. In addition, further in vivo studies demonstrated that anti-PSCA mAbs are therapeutically effective when used alone (Example 18C1, C2). In all of these in vivo studies, tumors in mice receiving the anti-PSCA mAb treatments had significantly slower growth rates, longer latency periods, and were smaller in size compared to tumors in mice receiving control antibody treatments. Serum PSA levels were also lower in relation to control treated animals and correlated with tumor inhibition. Moreover, antibodies recognizing different PSCA epitopes, as well as antibodies having different IgG isotypes, are therapeutically effective. In one study, anti-PSCA mAbs effectively inhibited the growth of established prostate tumors in vivo (Example 18, C4). Some of the mice treated in this particular study showed tumor regression following PSCA treatment (Example 18).

Additionally, the 3C5 antibody, administered to a tumor-bearing mouse, targeted the tumor cells that express PSCA. A SCID mouse bearing an LAPC-9 tumor (e.g., expressed PSCA), was treated with 3C5 antibody. The tumor was explanted and examined for the presence of the 3C5 antibody, by immunohistochemistry analysis (Example 26, FIG. 71). The fixed tissue slices were probed with goat anti-mouse IgG. The 3C5 antibody was localized to the mass of PSCA-expressing tumor cells (FIG. 71) and could be detected throughout the tumor. Because SCID mice produce no immunoglobulin, the antibody detected in the tumor tissue most likely originated from the 3C5 treatment. To confirm the localization of the 3C5 antibody, Western blot analysis was performed on tumor explants from the same mouse. The blot included protein extracts from the tumor explant, control IgG antibody, and 3C5 antibody, and the blot was probed with goat anti-mouse IgG-HRP antibodies. The IgG heavy and light chains were readily detected in the tumor lysates from the 3C5-treated mouse (FIG. 72).

The results of a different study also indicate that anti-PSCA antibodies can target PSCA-expressing tumors. A SCID mouse bearing an established LAPC-9 tumor was treated with 1G8 antibody. The explanted tumor was examined for the presence of the 1G8 antibody, by Western blot analysis (Example 26, FIG. 72) using goat anti-mouse IgG-HRP antibodies as a probe. The heavy and light chains were readily detectable in the 1G8-treated mouse. These results indicate that anti-PSCA antibodies administered to an subject, can circulate and target a PSCA-expressing tumor. This suggests that anti-PSCA monoclonal antibodies can circulate and target PSCA-expressing cells in tumors that are local, locally recurring, and metastatic. Furthermore, this suggests that conjugated anti-PSCA monoclonal antibodies can target and kill tumors cells expressing PSCA.

As described in Example 24 below, individual anti-PSCA mAbs are capable of inhibiting prostate tumor growth in vivo, in a xenogenic prostate cancer SCID mouse model. For example, two cohorts of SCID mice received injections of LAPC-9, and were treated with 1G8 or 3C5. The results showed that treatment with 1G8 or 3C5 alone inhibited tumor growth in the tumor-bearing mice. In contrast, the mice in a control group that received the same prostate tumor xenograft, but treated with murine IgG or phosphate buffer, developed larger tumors during the study. In addition, the anti-PSCA treatment significantly prolonged the life of the mice receiving the antibody treatment, compared to the control mice. The prolonged life of the antibody-treated mice correlated with a decrease in tumor growth, and effected the level of serum PSA levels. These results indicate that treatment with anti-PSCA antibody can prolong the life of a tumor-bearing animal, by inhibiting tumor growth.

The effect of anti-PSCA mAbs in combination with an cytotoxic agent was also tested. As described in Example 25 below, two cohorts of SCID mice received injections of PC3 cells which were engineered to express PSCA, and the mice were treated with 1G8 alone or in combination with doxorubicin. The results showed that treatment with 1G8 inhibited tumor growth of the PSCA-positive PC3 cells, and the combination of 1G8 and doxorubicin had a synergetic effect on inhibiting tumor growth, compared to the tumors in mice treated with phosphate buffer or doxorubicin alone.

Thus, the results of Example 24 show that anti-PSCA monoclonal antibodies, having different isotypes, are effective in inhibiting the growth of established androgen-dependent tumors. For example, the LAPC-9 xenograft was generated from a bone tumor biopsy of a patient with hormone-refractory metastatic prostate cancer. The 1G8 antibody is a mouse gamma-1, isotypic, neutral antibody, which interacts directly with the PSCA antigen. The 3C5 antibody is a mouse gamma-2A isotypic, antibody, which binds to cells and complement. Thus, the 1G8 antibody may direct cell cytotoxicity of androgen-dependent tumors, through an antibody-dependent cell cytotoxicity (ADCC) mechanism, and the 3C5 antibody may initiate a potent immune response against the tumor. In a similar manner, the results of Example 25 show that anti-PSCA antibodies are effective in treating established androgen-independent tumors.

Patients may be evaluated for the presence and level of PSCA overexpression in tumors, preferably using immunohistochemical assessments of tumor tissue, quantitative PSCA imaging, or other techniques capable of reliably indicating the presence and degree of PSCA expression. Immunohistochemical analysis of tumor biopsies or surgical specimens may be preferred for this purpose. Methods for immunohistochemical analysis of tumor tissues are well known in the art. An example of an immunohistochemical analytical technique useful for determining the level of PSCA overexpression in a sample is described in the example sections below.

Anti-PSCA monoclonal antibodies useful in treating cancer include those which are capable of initiating a potent immune response against the tumor and those which are capable of direct cytotoxicity. In this regard, anti-PSCA mAbs may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-PSCA mAbs which exert a direct biological effect on tumor growth are useful in the practice of the invention. Such mAbs may not require the complete immunoglobulin to exert the effect. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-PSCA mAb exerts an anti-tumor effect may be evaluated using any number of in vitro assays designed to determine ADCC, ADMMC, complement-mediated cell lysis, and so forth, such as those described in Example 19, below.

The anti-tumor activity of a particular anti-PSCA mAb, or combination of anti-PSCA mAbs, is preferably evaluated in vivo using a suitable animal model. Xenogenic cancer models, wherein human cancer explants or passaged xenograft tissues are introduced into immune compromised animals, such as nude or SCID mice, are particularly appropriate and are known. Examples of xenograft models of human prostate cancer (capable of recapitulating the development of primary tumors, micrometastasis, and the formation of osteoblastic metastases characteristic of late stage disease) are described in Klein et al., 1997, Nature Medicine 3: 402–408 and in PCT Patent Application WO98/16628, Sawyers et al., published Apr. 23, 1998. The examples herein provide detailed experimental protocols for evaluating the anti-tumor potential of anti-PSCA mAb preparations in vivo. Other in vivo assays are contemplated, such as those which measure regression of established tumors, interference with the development of metastasis, and the like.

It should be noted that the use of murine or other non-human monoclonal antibodies and chimeric mAbs may induce moderate to strong immune responses in some patients. In the most severe cases, such an immune response may lead to the extensive formation of immune complexes which, potentially, can cause renal failure. Accordingly, preferred monoclonal antibodies used in the practice of the therapeutic methods of the invention are those which are either fully human or humanized and which bind specifically to the target PSCA antigen with high affinity but exhibit low or no antigenicity in the patient.

The method of the invention contemplate the administration of single anti-PSCA mAbs as well as combinations, or "cocktails, of different individual mAbs such as those recognizing different epitopes. Such mAb cocktails may have certain advantages inasmuch as they contain mAbs which bind to different epitopes and/or exploit different effector mechanisms or combine directly cytotoxic mAbs with mAbs that rely on immune effector functionality. Such mAbs in combination may exhibit synergistic therapeutic effects. In addition, the administration of anti-PSCA mAbs may be combined with other therapeutic agents, including but not limited to various chemotherapeutic agents, androgen-blockers, and immune modulators (e.g., IL-2, GM-CSF). The anti-PSCA mAbs may be administered in their "naked" or unconjugated form, or may have therapeutic agents conjugated to them.

The anti-PSCA monoclonal antibodies used in the practice of the method of the invention may be formulated into pharmaceutical compositions comprising a carrier suitable for the desired delivery method. Suitable carriers include any material which when combined with the anti-PSCA mAbs retains the anti-tumor function of the antibody and is non-reactive with the subject's immune systems. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

The anti-PSCA antibody formulations may be administered via any route capable of delivering the antibodies to the tumor site. Potentially effective routes of administration include, but are not limited to, intravenous, intraperitoneal, intramuscular, intratumor, intradermal, and the like. The preferred route of administration is by intravenous injection. A preferred formulation for intravenous injection comprises the anti-PSCA mAbs in a solution of preserved bacteriostatic water, sterile unpreserved water, and/or diluted in polyvinylchloride or polyethylene bags containing 0.9% sterile Sodium Chloride for Injection, USP. The anti-PSCA mAb preparation may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the anti-PSCA antibody preparation via an acceptable route of administration such as intravenous injection (IV), at an effective dose. Dosages will depend upon various factors generally appreciated by those of skill in the art, including without limitation the type of cancer and the severity, grade, or stage of the cancer, the binding affinity and half life of the mAb or mAbs used, the degree of PSCA expression in the patient, the extent of circulating shed PSCA antigen, the desired steady-state antibody concentration level, frequency of treatment, and the influence of chemotherapeutic agents used in combination with the treatment method of the invention. Typical daily doses may range from about 0.1 to 100 mg/kg. Doses in the range of 10–500 mg mAb per week may be effective and well tolerated, although even higher weekly doses may be appropriate and/or well tolerated. The principal determining factor in defining the appropriate dose is the amount of a particular antibody necessary to be therapeutically effective in a particular context. Repeated administrations may be required in order to achieve tumor inhibition or regression. Initial loading doses may be higher. The initial loading dose may be administered as an infusion. Periodic maintenance doses may be administered similarly, provided the initial dose is well tolerated.

Direct administration of PSCA mAbs is also possible and may have advantages in certain contexts. For example, for the treatment of bladder carcinoma, PSCA mAbs may be injected directly into the bladder. Because PSCA mAbs administered directly to bladder will be cleared from the patient rapidly, it may be possible to use non-human or chimeric antibodies effectively without significant complications of antigenicity.

Patients may be evaluated for serum PSCA in order to assist in the determination of the most effective dosing regimen and related factors. The PSCA Capture ELISA described in Example 20 infra, or a similar assay, may be used for quantitating circulating PSCA levels in patients prior to treatment. Such assays may also be used for monitoring purposes throughout therapy, and may be useful to gauge therapeutic success in combination with evaluating other parameters such as serum PSA levels.

The invention further provides vaccines formulated to contain a PSCA protein or fragment thereof. The use of a tumor antigen in a vaccine for generating humoral and cell-mediated immunity for use in anti-cancer therapy is well known in the art and, for example, has been employed in prostate cancer using human PSMA and rodent PAP immunogens (Hodge et al., 1995, Int. J. Cancer 63: 231–237; Fong et al., 1997, J. Immunol. 159: 3113–3117). Such methods can be readily practiced by employing a PSCA protein, or fragment thereof, or a PSCA-encoding nucleic acid molecule and recombinant vectors capable of expressing and appropriately presenting the PSCA immunogen.

For example, viral gene delivery systems may be used to deliver a PSCA-encoding nucleic acid molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658–663). Non-viral delivery systems may also be employed by using naked DNA encoding a PSCA protein or fragment thereof introduced into the patient (e.g., intramuscularly) to induce an anti-tumor response. In one embodiment, the full-length human PSCA cDNA may be employed. In another embodiment, PSCA nucleic acid molecules encoding specific cytotoxic T lymphocyte (CTL) epitopes may be employed. CTL epitopes can be determined using specific algorithms (e.g., Epimer, Brown University) to identify peptides within a PSCA protein which are capable of optimally binding to specified HLA alleles.

Various ex vivo strategies may also be employed. One approach involves the use of dendritic cells to present PSCA antigen to a patient's immune system. Dendritic cells express MHC class I and II, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65–69; Murphy et al., 1996, Prostate 29: 371–380). Dendritic cells can be used to present PSCA peptides to T cells in the context of MHC class I and II molecules. In one embodiment, autologous dendritic cells are pulsed with PSCA peptides capable of binding to MHC molecules. In another embodiment, dendritic cells are pulsed with the complete PSCA protein. Yet another embodiment involves engineering the overexpression of the PSCA gene in dendritic cells using various implementing vectors known in the art, such as adenovirus (Arthur et al., 1997, Cancer Gene Ther. 4: 17–25), retrovirus (Henderson et al., 1996, Cancer Res. 56: 3763–3770), lentivirus, adeno-associated virus, DNA transfection (Ribas et al., 1997, Cancer Res. 57: 2865–2869), and tumor-derived RNA transfection (Ashley et al., 1997, J. Exp. Med. 186: 1177–1182).

Anti-idiotypic anti-PSCA antibodies can also be used in anti-cancer therapy as a vaccine for inducing an immune response to cells expressing a PSCA protein. Specifically, the generation of anti-idiotypic antibodies is well known in the art and can readily be adapted to generate anti-idiotypic anti-PSCA antibodies that mimic an epitope on a PSCA protein (see, for example, Wagner et al., 1997, Hybridoma 16: 33–40; Foon et al., 1995, J Clin Invest 96: 334–342; Herlyn et al., 1996, Cancer Immunol Immunother 43: 65–76). Such an anti-idiotypic antibody can be used in anti-idiotypic therapy as presently practiced with other anti-idiotypic antibodies directed against tumor antigens.

Genetic immunization methods may be employed to generate prophylactic or therapeutic humoral and cellular immune responses directed against cancer cells expressing PSCA. Using the PSCA-encoding DNA molecules described herein, constructs comprising DNA encoding a PSCA protein/immunogen and appropriate regulatory sequences may be injected directly into muscle or skin of an individual, such that the cells of the muscle or skin take-up the construct and express the encoded PSCA protein/immunogen. The PSCA protein/immunogen may be expressed as a cell surface protein or be secreted. Expression of the PSCA protein/immunogen results in the generation of prophylactic or therapeutic humoral and cellular immunity against prostate cancer. Various prophylactic and therapeutic genetic immunization techniques known in the art may be used (for review, see information and references published at internet address www.genweb.com).

The invention further provides methods for inhibiting cellular activity (e.g., cell proliferation, activation, or propagation) of a cell expressing multiple PSCA antigens on its cell surface. This method comprises reacting the immunoconjugates of the invention (e.g., a heterogeneous or homogenous mixture) with the cell so that the PSCA antigens on the cell surface forms a complex with the immunoconjugates. The greater the number of PSCA antigens on the cell surface, the greater the number of PSCA-antibody complexes can be used. The greater the number of PSCA-antibody complexes the greater the cellular activity that is inhibited. A subject with a neoplastic or preneoplastic condition can be treated in accordance with this method when the inhibition of cellular activity results in cell death.

A heterogeneous mixture includes PSCA antibodies that recognize different or the same epitope, each antibody being conjugated to the same or different therapeutic agent. A homogenous mixture includes antibodies that recognize the same epitope, each antibody being conjugated to the same therapeutic agent.

The invention further provides methods for inhibiting the biological activity of PSCA by blocking PSCA from binding its ligand. The methods comprises contacting an amount of PSCA with an antibody or immunoconjugate of the invention under conditions that permit a PSCA-immunoconjugate or PSCA-antibody complex thereby blocking PSCA from binding its ligand and inhibiting the activity of PSCA.

In another embodiment, the invention provides methods for selectively inhibiting a cell expressing PSCA antigen by reacting any one or a combination of the immunoconjugates of the invention with the cell in an amount sufficient to inhibit the cell. Such amounts include an amount to kill the cell or an amount sufficient to inhibit cell growth or proliferation. As discussed supra the dose and dosage regimen will depend on the nature of the disease or disorder to be treated associated with PSCA, its population, the site to which the antibodies are to be directed, the characteristics of the particular immunotoxin, and the patient. For example, the amount of immunoconjugate can be in the range of 0.1 to 200 mg/kg of patient weight.

Methods for Identifying PSCA Proteins and PSCA Genes and RNA

The invention provides methods for identifying cells, tissues or organisms expressing a PSCA protein or a PSCA gene. Such methods can be used to diagnose the presence of cells or an organism that expresses a PSCA protein in vivo or in vitro. The methods of the present invention are particularly useful in the determining the presence of cells that mediate pathological conditions of the prostate. Specifically, the presence of a PSCA protein can be identified by determining whether a PSCA protein, or nucleic acid encoding a PSCA protein, is expressed. The expression of a PSCA protein can be used as a means for diagnosing the presence of cells, tissues or an organism that expresses a PSCA protein or gene.

A variety of immunological and molecular genetic techniques can be used to determine if a PSCA protein is expressed/produced in a particular cell or sample. In general, an extract containing nucleic acid molecules or an extract containing proteins is prepared. The extract is then assayed to determine whether a PSCA protein, or a PSCA-encoding nucleic acid molecule, is produced in the cell.

Various polynucleotide-based detection methods well known in the art may be employed for the detection of PSCA-encoding nucleic acid molecules and for the detection of PSCA expressing cells in a biological specimen. For example, RT-PCR methods may be used to selectively amplify a PSCA mRNA or fragment thereof, and such methods may be employed to identify cells expressing PSCA, as described in Example 1 below. In a particular embodiment, RT-PCR is used to detect micrometastatic prostate, bladder or pancreatic cancer cells or circulating prostate, bladder or pancreatic cancer cells. Various other amplification type detection methods, such as, for example, branched DNA methods, and various well known hybridization assays using DNA or RNA probes may also be used for the detection of PSCA-encoding polynucleotides or PSCA expressing cells.

Various methods for the detection of proteins are well known in the art and may be employed for the detection of PSCA proteins and PSCA expressing cells. To perform a diagnostic test based on proteins, a suitable protein sample is obtained and prepared using conventional techniques. Protein samples can be prepared, for example, simply by boiling a sample with SDS. The extracted protein can then be analyzed to determine the presence of a PSCA protein using known methods. For example, the presence of specific sized or charged variants of a protein can be identified using mobility in an electric filed. Alternatively, antibodies can be used for detection purposes. A skilled artisan can readily adapt known protein analytical methods to determine if a sample contains a PSCA protein.

Alternatively, PSCA expression can also be used in methods to identify agents that decrease the level of expression of the PSCA gene. For example, cells or tissues expressing a PSCA protein can be contacted with a test agent to determine the effects of the agent on PSCA expression. Agents that activate PSCA expression can be used as an agonist of PSCA activity whereas agents that decrease PSCA expression can be used as an antagonist of PSCA activity.

PSCA Promoter and Other Expression Regulatory Elements

The invention further provides expression control sequences found 5' of the of the newly identified PSCA gene in a form that can be used to generate expression vectors and transgenic animals. Specifically, the PSCA expression control elements, such as the PSCA promoter that can readily be identified as being 5' from the ATG start codon in the PSCA gene, and can be used to direct the expression of an operably linked protein encoding DNA sequence. Since PSCA expression is predominantly expressed in prostate cells, the expression control elements are particularly useful in directing the expression of an introduced transgene in a tissue specific fashion. A skilled artisan can readily use the PSCA gene promoter and other regulatory elements in expression vectors using methods known in the art.

In eukaryotic cells, the regulatory sequences can be found upstream, downstream and within the coding region of the gene. The eukaryotic regulatory sequences comprise a promoter sequence and sometimes at least one enhancer sequence. In a typical eukaryotic gene, the promoter sequence resides upstream and proximal to the coding region of the gene, and must be oriented in one direction to control expression of the gene. In a typical eukaryotic gene, the enhancer sequences can reside in the upstream, downstream and even within the coding region of the gene, and can be oriented in either direction to enhance or suppress expression of the gene.

The present invention provides a DNA fragment containing 9 kb of sequences upstream of the PSCA coding region.

The ability of this PSCA fragment to drive expression of an operatively linked transgene has been tested using a series of chimeric reporter constructs transfected into cells. The chimeric reporter constructs demonstrate an expression pattern similar to that of native endogenous PSCA, and the PSCA fragment drives expression of the transgene when linked in the forward orientation. Thus, this PSCA fragment comprises a PSCA upstream regulatory region that exhibits promoter-like activity.

PSCA transcripts are also present at a significantly higher level in prostate tumor cells but not in benign prostatic hyperplasia. Thus PSCA transcripts are detectable in a prostate-predominant manner, and are detectable at a higher level in prostate tumor samples. The significantly higher level of PSCA transcripts, or over-expression as is known in the art, can be determined by measuring and comparing the amount of detectable PSCA transcripts in a normal prostate with a prostate tumor sample. This comparison can be performed by methods well known in the art, including Northern analysis and RT-PCR assays, and the differences in transcript levels can be quantitated. Thus, the presence of a measurably different amount of PSCA transcripts (i.e., the number of PSCA transcripts in the test sample exceeds the number from a normal sample) in the samples can be used to indicate the presence of prostate cancer.

PSCA expression is also observed in other human cancers, particularly bladder and pancreatic carcinomas. In the case of bladder carcinoma, the degree of PSCA expression appears to correlate with the severity of the disease, reaching the highest level of overexpression in invasive bladder cancer (See Example 17, below).

The pattern of PSCA transcript and protein accumulation is known, and the PSCA upstream regulatory region has been isolated and characterized. A series of chimeric constructs comprising the PSCA upstream regulatory region operatively linked to a transgene has been tested. The PSCA upstream regulatory region drives expression of the transgene in various prostate cells and cell lines, and in bladder, and to a lesser extent in kidney. Thus, the PSCA upstream region drives expression of a transgene in a prostate-predominant manner.

In preferred embodiments, DNA fragments of 9 kb, 6 kb, 3 kb, and 1 kb derived from the 5' upstream region of the PSCA gene, as shown in FIG. 42, were produced by techniques described herein. The 9 kb PSCA upstream region (pEGFP-PSCA) is involved with gene regulatory activity and was deposited on May 17, 1999 with the American Type Culture Collection (ATCC), 12301 Parklawn Drive, Rockville, Md. 20852 and has there been identified as follows ATCC No. PTA-80. The 9 kb fragment was obtained by amplification using a T7 primer and RIhPSCA3'-5 (5'-gggaattcgcacagccttcagggtc-3').

Uses of the Fragment having Gene Regulatory Activity

This invention provides methods (e.g., gene therapy methods) for targeting a gene-of-interest to a cancer cell/site so that the protein encoded by the gene can be expressed thereby directly or indirectly ameliorating the diseased state.

A susceptible cell is introduced with an expression vector that expresses a transgene (e.g., a therapeutic gene) under the control of a PSCA upstream region having significantly increased gene expression activity in tumor cells. The use of an expression vector that expresses a therapeutic gene predominantly in tumor cells will allow expression of the therapeutic genes in target cell, such as prostate, bladder and pancreatic tumor cells.

After infecting a susceptible cell, a transgene (e.g., a therapeutic gene) is driven by a PSCA upstream region having increased gene expression activity in a vector, that expresses the protein encoded by the transgene. The use of a fairly specific prostate specific gene vector will allow selective expression of the specific genes in target cells, e.g., prostate cancer cells.

PSCA regions having increased gene expression activity may be modified, e.g., by sequence mutations, deletions, and insertions, so as to produce derivative molecules. Modifications include multiplying the number of sequences that can bind prostate cell specific regulatory proteins and deleting sequences that are nonfunctional in the PSCA region having gene expression activity. Other modifications include adding enhancers thereby improving the efficiency of the PSCA region having promoter activity. Enhancers may function in a position-independent manner and can be located upstream, within or downstream of the transcribed region.

Derivative molecules would retain the functional property of the PSCA upstream region having increased gene expression activity, namely, the molecule having such substitutions will still permit substantially prostate tissue specific expression of a gene of interest located 3' to the fragment. Modification is permitted so long as the derivative molecules retain its ability to drive gene expression in a substantially prostate specific manner compared to a PSCA fragment having promoter activity alone.

In a preferred embodiment, a vector was constructed by inserting a heterologous sequence (therapeutic gene) downstream of the PSCA upstream region having promoter activity.

Examples of therapeutic genes include suicide genes. These are genes sequences the expression of which produces a protein or agent that inhibits tumor cell growth or tumor cell death (e.g., prostate tumor cells). Suicide genes include genes encoding enzymes (e.g., prodrug enzymes), oncogenes, tumor suppressor genes, genes encoding toxins, genes encoding cytokines, or a gene encoding oncostatin. The purpose of the therapeutic gene is to inhibit the growth of or kill the cancer cell or produce cytokines or other cytotoxic agents which directly or indirectly inhibit the growth of or kill the cancer cells.

Suitable prodrug enzymes include thymidine kinase (TK), xanthine-guanine phosphoribosyltransferase (GPT) gene from *E. coli* or *E. coli* cytosine deaminase (CD), or hypoxanthine phosphoribosyl transferase (HPRT).

Suitable oncogenes and tumor suppressor genes include nen,EGF, ras(including H, K, and N ras), p53, Retinoblastoma tumor suppressor gene (Rb), Wilm's Tumor Gene Product, Phosphotyrosine Phosphatase (PTPase), and mn23. Suitable toxins include Pseudomonas exotoxin A and S; diphtheria toxin (DT); *E. coli* LT toxins, Shiga toxin, Shiga-like toxins (SLT-1, -2), ricin, abrin, supporin, and gelonin.

Suitable cytokines include interferons, GM-CSF interleukins, tumor necrosis factor (TNF) (Wong G, et al., Human GM-CSF: Molecular cloning of the complementary DNA and purification of the natural and recombinant proteins. *Science* 1985; 228:810); WO9323034 (1993); Horisberger Mass., et al., Cloning and sequence analyses of cDNAs for interferon-and virus-induced human Mx proteins reveal that they contain putative guanine nucleotide-binding sites: functional study of the corresponding gene promoter. *Journal of Virology,* 1990, Mar., 64(3):1171–81; Li YP et al., Proinflammatory cytokines tumor necrosis factor-alpha and IL-6, but not IL-1, down-regulate the osteocalcin gene promoter. *Journal of Immunology*, Feb. 1, 1992, 148(3) :788–94; Pizarro TT, et al. Induction of TNF alpha and TNF beta gene expression in rat cardiac transplants during allograft rejection. *Transplantation,* 1993 Aug., 56(2) :399–404). (Breviario F, et al., Interleukin-1-inducible genes in endothelial cells. Cloning of a new gene related to C-reactive protein and serum amyloid P component. *Journal of Biological Chemistry*, Nov. 5, 1992, 267(31):22190–7; Espinoza-Delgado I, et al., Regulation of IL-2 receptor subunit genes in human monocytes. Differential effects of IL-2 and IFN-gamma. *Journal of Immunology*, Nov. 1, 1992, 149(9):2961–8; Algate PA, et al., Regulation of the interleukin-3 (IL-3) receptor by IL3 in the fetal liver-derived FL5.12 cell line. *Blood,* May 1, 1994, 83(9):2459–68; Cluitmans FH, et al., IL-4 down-regulates IL-2-, IL-3-, and GM-CSF-induced cytokine gene expression in peripheral blood monocytes. *Annals of Hematology,* 1994 Jun, 68(6) :293–8; Lagoo, AS, et al., IL-2, IL-4, and IFN-gamma gene expression versus secretion in superantigen-activated T cells. Distinct requirement for costimulatory signals through adhesion molecules. *Journal of Immunology, Feb.* 15, 1994, 152(4):1641–52; Martinez OM, et al., IL-2 and IL-5 gene expression in response to alloantigen in liver allograft recipients and in vitro. *Transplantation,* 1993 May, 55(5) :1159–66; Pang G, et al., GM-CSF, IL-1 alpha, IL-1 beta, IL-6, IL-8, IL-10, ICAM-1 and VCAM-1 gene expression and cytokine production in human duodenal fibroblasts stimulated with lipopolysaccharide, IL-1 alpha and TNF-alpha. *Clinical and Experimental Immunology,* 1994 Jun, 96(3):437–43; Ulich TR, et al., Endotoxin-induced cytokine gene expression in vivo. III. IL-6 mRNA and serum protein expression and the in vivo hematologic effects of IL-6. *Journal of Immunology*, Apr. 1, 1991, 146(7):2316–23; Mauviel A, et al., Leukoregulin, a T cell-derived cytokine, induces IL-8 gene expression and secretion in human skin fibroblasts. Demonstration and secretion in human skin fibroblasts. Demonstration of enhanced NF-kappa B binding and NF-kappa B-driven promoter activity. *Journal of Immunology*, Nov. 1, 1992, 149(9):2969–76).

Growth factors include Transforming Growth Factor-α (TGFα) and β (TGFβ), cytokine colony stimulating factors (Shimane M, et al., Molecular cloning and characterization of G-CSF induced gene cDNA. *Biochemical and Biophysical Research Communications*, Feb. 28, 1994, 199(1) :26–32; Kay AB, et al., Messenger RNA expression of the cytokine gene cluster, interleukin 3 (IL-3), IL-4, IL-5, and granulocyte/macrophage colony-stimulating factor, in allergen-induced late-phase cutaneous reactions in atopic subjects. *Journal of Experimental Medicine*, Mar. 1, 1991, 173(3):775–8; de Wit H, et al., Differential regulation of M-CSF and IL-6 gene expression in monocytic cells. *British Journal of Haematology,* 1994 Feb, 86(2):259–64; Sprecher E, et al., Detection of IL-1 beta, TNF-alpha, and IL-6 gene transcription by the polymerase chain reaction in keratinocytes, Langerhans cells and peritoneal exudate cells during infection with herpes simplex virus-1. *Archives of Virology,* 1992, 126(14):253–69).

Vectors suitable for use in the methods of the present invention are viral vectors including adenoviruses, lentivirus, retroviral vectors, adeno-associated viral (AAV) vectors.

Preferably, the viral vector selected should meet the following criteria: 1) the vector must be able to infect the tumor cells and thus viral vectors having an appropriate host range must be selected; 2) the transferred gene should be capable of persisting and being expressed in a cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells for correction of disorders include retroviruses such as Moloney murine leukemia virus (MoMuLV); papovaviruses such as JC, SV40, polyoma; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles (Bachettis et al.: Transfer of gene for thymidine kinase-deficient human cells by purified herpes simplex viral DNA. *PNAS USA,* 1977 74:1590; Berkner, K. L.: Development of adenovirus vectors for expression of heterologous genes. *Biotechniques,* 1988 6:616; Ghosh-Choudhury G, et al., Human adenovirus cloning vectors based on infectious bacterial plasmids. *Gene* 1986; 50:161; Hag-Ahmand Y, et al., Development of a helper-independent human adenovirus vector and its use in the transfer of the herpes simplex virus thymidine kinase gene. *J Virol* 1986; 57:257; Rosenfeld M, et al., Adenovirus-mediated transfer of a recombinant $\alpha_1$-antitrypsin gene to the lung epithelium invivo. *Science* 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; identification of the component necessary for adenovirus translational control and their utilization in cDNA expression vectors. *PNAS USA,* 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduce genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. *PNAS USA,* 1990 87:8950).

Another vector for mammalian gene transfer is the bovine papilloma virus-based vector (Sarver N, et al., Bovine papilloma virus DNA: A novel eukaryotic cloning vector. Mol *Cell Biol* 1981; 1:486).

Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. *Proc Natl Acad Sci USA* 1982; 79:4927; Smith et al. infectious vaccinia virus recombinants that express hepatitis B virus surface antigens. *Nature,* 1983 302:490.)

Retroviruses are packages designed to insert viral genes into host cells (Guild B, et al., Development of retrovirus vectors useful for expressing genes in cultured murine embryonic cells and hematopoietic cells in vivo. *J Virol* 1988; 62:795; Hock RA, et al., Retrovirus mediated transfer and expression of drug resistance genes in human hemopoietic progenitor cells. *Nature* 1986; 320:275).

The basic retrovirus consists of two identical strands of RNA packaged in a proviral protein. The core surrounded by a protective coat called the envelope, which is derived from the membrane of the previous host but modified with glycoproteins contributed by the virus.

Preferably, for treating defects, disease or damage of cells in, for example, the prostate, vectors of the invention include a therapeutic gene or transgenes, for example a gene encoding TK. The genetically modified vectors are administered into the prostate to treat defects, disease such as prostate cancer by introducing a therapeutic gene product or products into the prostate that enhance the production of endogenous molecules that have ameliorative effects in vivo. The same principles apply with respect to the treatment of other cancers, such as pancreatic, bladder or other cancers expressing PSCA.

The basic tasks in this embodiment of the present method of the invention are isolating the gene of interest, attaching it to a fragment having gene regulatory activity, selecting the proper vector vehicle to deliver the gene of interest to the body, administering the vector having the gene of interest into the body, and achieving appropriate expression of the gene of interest to a target cell. The present invention provides packaging the cloned genes, i.e. the genes of interest, in such a way that they can be injected directly into the bloodstream or relevant organs of patients who need them. The packaging will protect the foreign DNA from elimination by the immune system and direct it to appropriate tissues or cells.

Along with the human or animal gene of interest another gene, e.g., a selectable marker, can be inserted that will allow easy identification of cells that have incorporated the modified retrovirus. The critical focus on the process of gene therapy is that the new gene must be expressed in target cells at an appropriate level with a satisfactory duration of expression.

The methods described below to modify vectors and administering such modified vectors into the target organ (e.g., prostate) are merely for purposes of illustration and are typical of those that might be used. However, other procedures may also be employed, as is understood in the art.

Most of the techniques used to construct vectors and the like are widely practiced in the art, and most practitioners are familiar with the standard resource materials which describe specific conditions and procedures. However, for convenience, the following paragraphs may serve as a guideline.

General Methods for Vector Construction

Construction of suitable vectors containing the desired therapeutic gene coding and control sequences employs standard ligation and restriction techniques, which are well understood in the art (see Maniatis et al., in *Molecular Cloning: A Laboratory Manual,* Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 µg of plasmid or DNA sequences is cleaved by one unit of enzyme in about 20 µl of buffer solution. Typically, an excess of restriction enzyme is used to insure complete digestion of the DNA substrate.

Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* 65:499–560(1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° C. to 25° C. in 50 mM Tris (pH 7.6) 50 mM NaCl, 6 mM $MgCl_2$, 6 mM DTT and 5–10 µM dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 10–50 µl volumes under the following standard conditions and temperatures using T4 DNA ligase. Ligation protocols are standard (D. Goeddel (ed.) Gene Expression Technology: Methods in Enzymology (1991)).

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

Suitable vectors include viral vector systems e.g. ADV, RV, and AAV (R. J. Kaufman "Vectors used for expression in mammalian cells" in *Gene Expression Technology,* edited by D. V. Goeddel (1991).

Many methods for inserting functional DNA transgenes into cells are known in the art. For example, non-vector methods include nonviral physical transfection of DNA into cells; for example, microinjection (DePamphilis et al., *BioTechnique* 6:662–680 (1988)); liposomal mediated transfection (Felgner et al., *Proc. Natl. Acad. Sci. USA,* 84:7413–7417 (1987), Feigner and Holm, *Focus* 11:21–25 (1989) and Felgner et al., *Proc. West. Pharmacol. Soc.* 32: 115–121 (1989)) and other methods known in the art.

Administration of Modified Vectors into Subject

One way to get DNA into a target cell is to put it inside a membrane bound sac or vesicle such as a spheroplast or liposome, or by calcium phosphate precipitation ($CaPO_4$) (Graham F. and Van der Eb, A., Virology 52:456 1973; Schaefer-Ridder M., et al., Liposomes as gene carriers: Efficient transduction of mouse L cells by thymidine kinase gene. *Science* 1982; 215:166; Stavridis J C, et al., Construction of transferrin-coated liposomes for in vivo transport of exogenous DNA to bone marrow erythroblasts in rabbits. *Exp Cell Res* 1986; 164:568–572).

A vesicle can be constructed in such a way that its membrane will fuse with the outer membrane of a target cell. The vector of the invention in vesicles can home into the target cells. The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation.

Before administration, the modified vectors are suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the target organ (e.g., prostate), is relatively non-traumatic, allows multiple administrations simultaneously in several different sites or the same site using the same viral suspension. Multiple injections may consist of a mixture of therapeutic genes.

Uses of the Modified Vectors

The present invention provides methods for maintaining and increasing expression of therapeutic genes using a fragment having expression activity.

The methods of the invention are exemplified by embodiments in which modified vectors carrying a therapeutic gene are injected into a subject.

In a first embodiment a protein product is expressed comprising growing the host vector system of the invention so as to produce the protein in the host and recovering the protein so produced. This method permits the expression of genes of interest in both unicellular and multicellular organisms. For example, in an in vitro assay, prostate cells having the vector of the invention comprising a gene of interest (e.g., the ras gene) may be used in microtiter wells as an unlimited for the ras gene product. A sample from a subject would be added to the wells to detect the presence of antibodies directed against the ras gene. This assay can aid in the quantitative and qualitative determination of the presence of ras antibodies in the sample for the clinical assessment of whether the subject's immune system is combatting the disease associated with elevated levels of ras.

In a second embodiment metastatic prostate cancer is treated via gene therapy, i.e., the correction of a disease phenotype in vivo through the use of the nucleic acid molecules of the invention.

In accordance with the practice of this invention, the subject of the gene therapy may be a human, equine, porcine, bovine, murine, canine, feline, or avian subject. Other mammals are also included in this invention.

The most effective mode of administration and dosage regimen for the molecules of the present invention depends upon the exact location of the prostate tumor being treated, the severity and course of the cancer, the subject's health and response to treatment and the judgment of the treating physician. Accordingly, the dosages of the molecules should be titrated to the individual subject. The molecules may be delivered directly or indirectly via another cell, autologous cells are preferred, but heterologous cells are encompassed within the scope of the invention.

The interrelationship of dosages for animals of various sizes and species and humans based on $mg/m^2$ of surface area is described by Freireich, E. J., et al. Cancer Chemother., Rep. 50 (4): 219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided dose may be administered daily or proportionally reduced depending on the specific therapeutic situation).

It would be clear that the dose of the molecules of the invention required to achieve treatment may be further modified with schedule optimization.

Generation of Transgenic Animals

Another aspect of the invention provides transgenic non-human mammals comprising PSCA nucleic acids. For example, in one application, PSCA-deficient non-human animals can be generated using standard knock-out procedures to inactivate a PSCA homologue or, if such animals are non-viable, inducible PSCA homologue antisense molecules can be used to regulate PSCA homologue activity/expression. Alternatively, an animal can be altered so as to contain a human PSCA-encoding nucleic acid molecule or an antisense-PSCA expression unit that directs the expression of PSCA protein or the antisense molecule in a tissue specific fashion. In such uses, a non-human mammal, for example a mouse or a rat, is generated in which the expression of the PSCA homologue gene is altered by inactivation or activation and/or replaced by a human PSCA gene. This can be accomplished using a variety of art-known procedures such as targeted recombination. Once generated, the PSCA homologue deficient animal, the animal that expresses PSCA (human or homologue) in a tissue specific manner, or an animal that expresses an antisense molecule can be used to (1) identify biological and pathological processes mediated by the PSCA protein, (2) identify proteins and other genes that interact with the PSCA proteins, (3) identify agents that can be exogenously supplied to overcome a PSCA protein deficiency and (4) serve as an appropriate screen for identifying mutations within the PSCA gene that increase or decrease activity.

For example, it is possible to generate transgenic mice expressing the human minigene encoding PSCA in a tissue specific-fashion and test the effect of over-expression of the protein in tissues and cells that normally do not contain the PSCA protein. This strategy has been successfully used for other genes, namely bcl-2 (Veis et al. Cell 1993 75:229). Such an approach can readily be applied to the PSCA protein/gene and can be used to address the issue of a potential beneficial or detrimental effect of the PSCA proteins in a specific tissue.

Further, in another embodiment, the invention provides a transgenic animal having germ and somatic cells comprising an oncogene which is linked to a PSCA upstream region effective for the expression of said gene in the tissues of said mouse for the promotion of a cancer associated with the oncogene, thereby producing a mouse model of that cancer.

Compositions

The invention provides a pharmaceutical composition comprising a PSCA nucleic acid molecule of the invention or an expression vector encoding a PSCA protein or encoding a fragment thereof and, optionally, a suitable carrier. The invention additionally provides a pharmaceutical composition comprising an antibody or fragment thereof which recognizes and binds a PSCA protein. In one embodiment, the antibody or fragment thereof is conjugated or linked to a therapeutic drug or a cytotoxic agent.

Suitable carriers for pharmaceutical compositions include any material which when combined with the nucleic acid or other molecule of the invention retains the molecule's activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Such compositions may also be formulated within various lipid compositions, such as, for example, liposomes as well as in various polymeric compositions, such as polymer microspheres.

The invention also provides a diagnostic composition comprising a PSCA nucleic acid molecule, a probe that specifically hybridizes to a nucleic acid molecule of the invention or to any part thereof, or a PSCA antibody or fragment thereof. The nucleic acid molecule, the probe or the antibody or fragment thereof can be labeled with a detectable marker. Examples of a detectable marker include, but are not limited to, a radioisotope, a fluorescent compound, a bioluminescent compound, a chemiluminescent compound, a metal chelator or an enzyme. Further, the invention provides a diagnostic composition comprising a PSCA-specific primer pair capable of amplifying PSCA-encoding sequences using polymerase chain reaction methodologies, such as RT-PCR.

EXAMPLES

Example 1

Identification And Molecular Characterization Of A Novel Prostate Cell Surface Antigen (PSCA)

MATERIALS AND METHODS

LAPC-4 Xenografts: LAPC-4 xenografts were generated as described in Klein et al, 1997, Nature Med. 3: 402–408.

RDA, Northern Analysis and RT-PCR: Representational difference analysis of androgen dependent and independent LAPC-4 tumors was performed as previously described (Braun et al., 1995, Mol. Cell. Biol. 15: 4623–4630). Total RNA was isolated using Ultraspec$^R$ RNA isolation systems (Biotecx, Houston, Tex.) according to the manufacturer's instructions. Northern filters were probed with a 660 bp RDA fragment corresponding to the coding sequence and part of the 3' untranslated sequence of PSCA or a ~400 bp fragment of PSA. The human multiple tissue blot was obtained from Clontech and probed as specified. For reverse transcriptase (RT)-PCR analysis, first strand cDNA was synthesized from total RNA using the GeneAmp RNA PCR core kit (Perkin Elmer-Roche, New Jersey). For RT-PCR of human PSCA transcripts, primers 5'-tgcttgccctgttgatggcag- and 3'-ccagagcagcaggccgagtgca- were used to amplify a ~320 bp fragment. Thermal cycling was performed by 25—25 cycles of 95° for 30 sec, 60° for 30 sec and 72° for 1 min, followed by extension at 72° for 10 min. Primers for GAPDH (Clontech) were used as controls. For mouse PSCA, the primers used were 5'-ttctcctgctggccacctac- and 3'-gcagctcatcccttcacaat-.

In Situ Hybridization Assay for PSCA mRNA: For mRNA in situ hybridization, recombinant plasmid pCR II (1 ug, invitrogen, San Diego, Calif.) containing the full-length PSCA gene was linearized to generate sense and antisense digoxigenin labeled riboprobes. In situ hybridization was performed on an automated instrument (Ventana Gen II, Ventana Medical Systems) as previously described (Magi-Galluzzi et al., 1997, Lab. Invest. 76: 37–43). Prostate specimens were obtained from a previously described database which has been expanded to ~130 specimens (Magi-Galluzzi et al., supra). Slides were read and scored by two pathologists in a blinded fashion. Scores of 0–3 were assigned according to the percentage of positive cells (0=0%; 1=<25%; 2=25–50%; 3=>50%) and the intensity of staining (0=0; 1=1+; 2=2+; 3=3+). The two scores were multiplied to give an overall score of 0–9.

Results

Figure 9A:
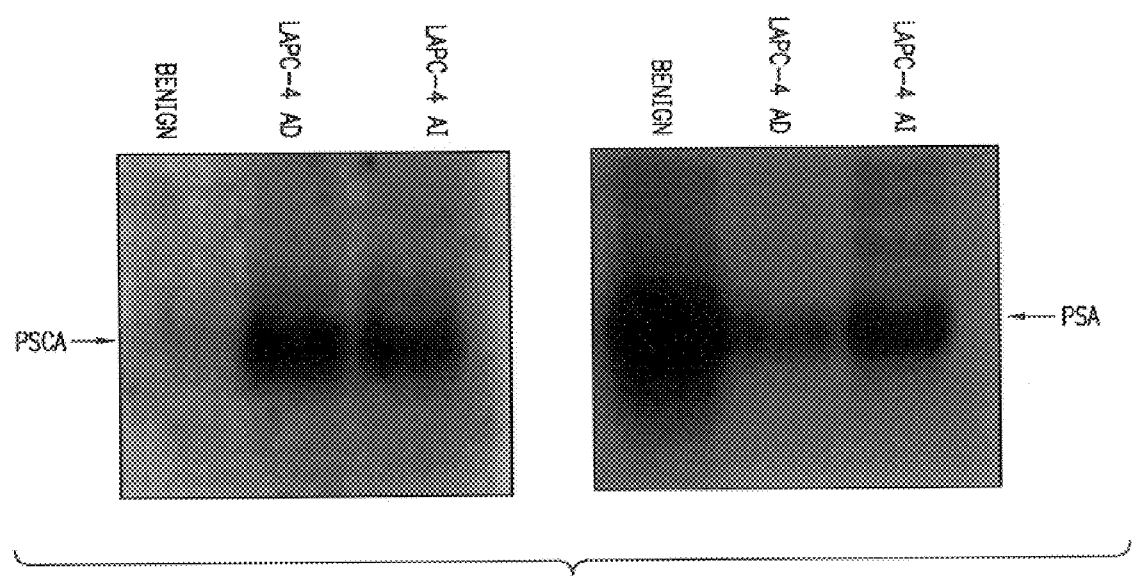
FIG. 9A. Northern blot analysis of PSCA expression. Total RNA from normal prostate and LAPC-4 androgen dependent (AD) and independent (AI) prostate cancer xenografts were analyzed using PSCA or PSA specific probes. Equivalent RNA loading and RNA integrity were demonstrated separately by ethidium staining for 18S and 28S RNA.

Human PSCA cDNA: Representational Difference Analysis (RDA), a PCR-based subtractive hybridization technique, was used to compare gene expression between hormone dependent and hormone independent variants of a human prostate cancer xenograft (LAPC-4) and to isolate cDNAs upregulated in the androgen-independent LAPC-4 subline. Multiple genes were cloned, sequenced, and checked for differential expression. One 660 bp fragment (clone #15) was identified which was found to be highly overexpressed in xenograft tumors when compared with normal prostate. Comparison of the expression of this clone to that of PSA in normal prostate and xenograft tumors suggested that clone #15 was relatively cancer specific (FIG. 9).

Sequence analysis revealed that clone #15 had no exact match in the databases, but shared 30% nucleotide homology with stem cell antigen 2, a member of the Thy-1/Ly-6 superfamily of glycosylphosphatidylinositol (GPI)-anchored cell surface antigens. Clone #15 encodes a 123 amino acid protein (SEQ ID NO:2) which is 30% identical to SCA-2 (SEQ ID NO:5) (also called RIG-E) and contains a number of highly conserved cysteine residues characteristic of the Ly-6/Thy-1 gene family (FIG. 3). Consistent with its homology to a family of GPI-anchored proteins, clone #15 contains both an amino-terminal hydrophobic signal sequence and a carboxyl-terminal stretch of hydrophobic amino acids preceded by a group of small amino acids defining a cleavage/binding site for GPI linkage (Udenfriend and Kodukula, 1995, Ann. Rev. Biochem. 64: 563–591). It also contains four predicted N-glycosylation sites. Because of its strong homology to the stem cell antigen-2, clone #15 was renamed prostate stem cell antigen (PSCA). 5' and 3' PCR RACE analysis was then performed using cDNA obtained from the LAPC-4 androgen independent xenograft and the full length cDNA nucleotide sequence (including the coding and untranslated regions) was obtained. The nucleotide sequence of the full length cDNA (SEQ ID NO:1) encoding human PSCA is shown in FIG. 1A and the translated amino acid sequence (SEQ ID NO:2) is shown in FIG. 1B and in FIG. 3.

Figure 7A:
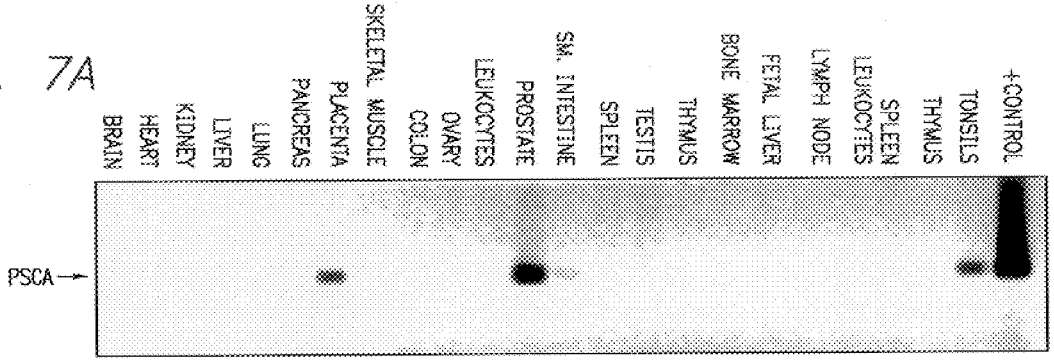
FIG. 7A. Restricted Expression of PSCA mRNA in normal and cancerous tissues. RT-PCR analysis of PSCA expression in normal human tissues demonstrating high expression in prostate, placenta, and tonsils. 1 ng of reverse-transcribed first strand cDNA (Clontech, Palo Alto, Calif.) from the indicated tissues was amplified with PSCA gene specific primers. Data shown are from 30 cycles of amplification.
Figure 7B:
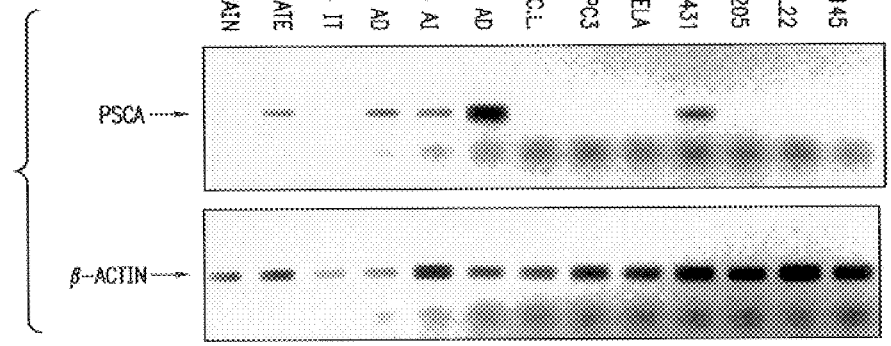
FIG. 7B. Restricted Expression of PSCA mRNA in normal and cancerous tissues. RT-PCR analysis of PSCA expression demonstrating high level in prostate cancer xenografts and normal tissue. 5 ng of reverse-transcribed cDNA from the indicated tissues was amplified with PSCA gene specific primers. Amplification with β-actin gene specific primers demonstrate normalization of the first strand cDNA of the various samples. Data shown are from 25 cycles of amplification. AD, androgen-dependent; AI, androgen-independent; IT, intratibial xenograft; C.L., cell line.
Figure 9B:
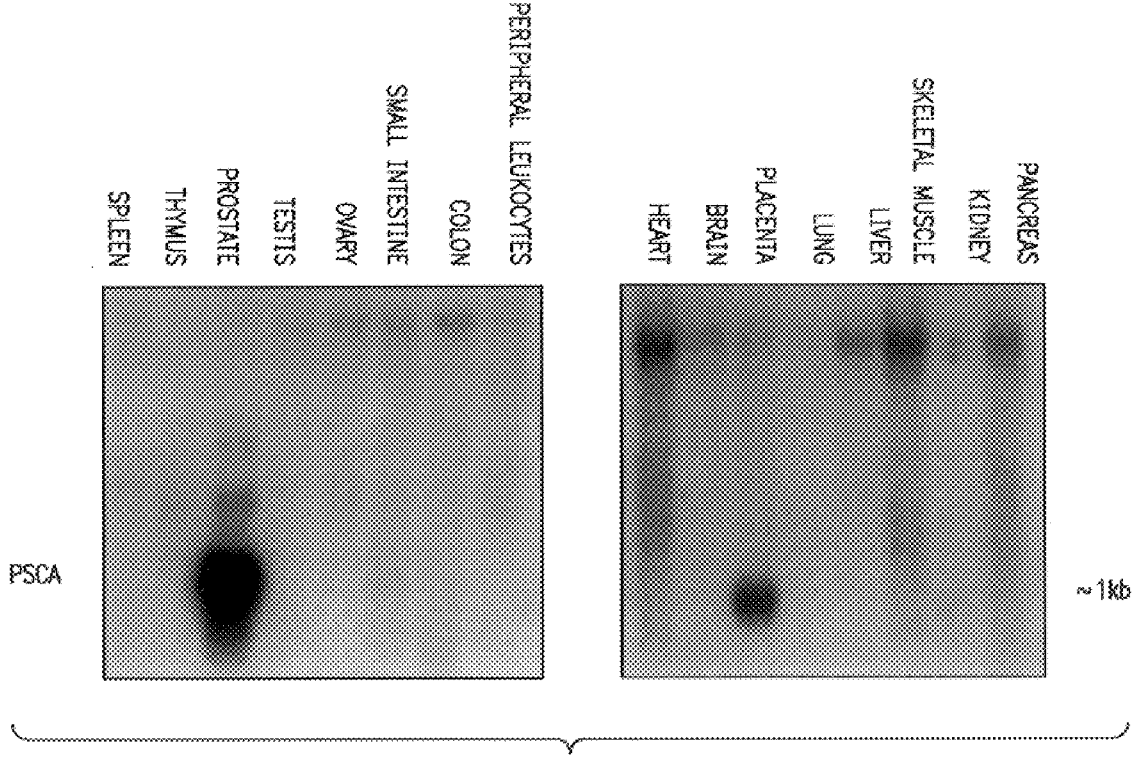
FIG. 9B. Northern blot analysis of PSCA expression. Human multiple tissue Northern blot analysis of PSCA. The filter was obtained from Clontech (Palo Alto, Calif.) and contains 2 ug of polyA RNA in each lane.

PSCA is expressed in prostate cells: The distribution of PSCA mRNA in normal human tissues was examined by Northern blot analysis. The results, shown in FIG. 9B, demonstrate that PSCA is expressed predominantly in prostate, with a lower level of expression present in placenta. Small amounts of mRNA can be detected in kidney and small intestine after prolonged exposure and at approximately 1/100 th of the level seen in prostate tissue. RT-PCR analysis of PSCA expression in normal human tissues also demonstrates that PSCA expression is restricted. In a panel of normal tissues, high level PSCA mRNA expression was detected in prostate, with significant expression detected in placenta and tonsils (FIG. 7A). RT-PCR analysis of PSCA mRNA expression in a variety of prostate cancer xenografts prostate cancer cell lines and other cell lines, and normal prostate showed high level expression restricted to normal prostate, the LAPC-4 and LAPC-9 prostate cancer xenografts, and the ovarian cancer cell line A431 (FIG. 7B). The major PSCA transcript in normal prostate is ~1kb (FIG. 9B). Mouse PSCA expression was analyzed by RT-PCR in mouse spleen, liver, lung, prostate, kidney and testis. Like human PSCA, murine PSCA is expressed predominantly in prostate. Expression can also be detected in kidney at a level similar to that seen for placenta in human tissues.

The expression of PSCA, PSMA and PSA in prostate cancer cell lines and xenografts was compared by Northern blot analysis. The results shown in FIG. 10 demonstrate high level prostate cancer specific expression of both PSCA and PSMA, whereas PSA expression is not prostate cancer specific.

PSCA is Expressed by a Subset of Basal Cells in Normal Prostate: Normal prostate contains two major epithelial cell populations--secretory luminal cells and subjacent basal cells. In situ hybridizations were performed on multiple sections of normal prostate using an antisense riboprobe specific for PSCA to localize its expression. As shown in FIG. 11, PSCA is expressed exclusively in a subset of normal basal cells. Little to no staining is seen in stroma, secretory cells or infiltrating lymphocytes. Hybridization with sense PSCA riboprobes showed no background staining. Hybridization with an antisense probe for GAPDH confirmed that the RNA in all cell types was intact. Because basal cells represent the putative progenitor cells for the terminally differentiated secretory cells, these results suggest that PSCA may be a prostate-specific stem/progenitor cell marker (Bonkhoff et al., 1994, Prostate 24: 114–118). In addition, since basal cells are androgen-independent, the association of PSCA with basal cells raises the possibility that PSCA may play a role in androgen-independent prostate cancer progression.

PSCA is Overexpressed in Prostate Cancer Cells: The initial analysis comparing PSCA expression in normal prostate and LAPC-4 xenograft tumors suggested that PSCA was overexpressed in prostate cancer. As demonstrated by the Northern blot analysis as shown in FIG. 9, LAPC-4 prostate cancer tumors strongly express PSCA; however, there is almost no detectable expression in sample of BPH. In contrast, PSA expression is clearly detectable in normal prostate, at levels 2–3 times those seen in the LAPC-4 tumors. Thus, the expression of PSCA in prostate cancer appears to be the reverse of what is seen with PSA. While PSA is expressed more strongly in normal than malignant prostate tissue, PSCA is expressed more highly in prostate cancer.

Figure 11C:
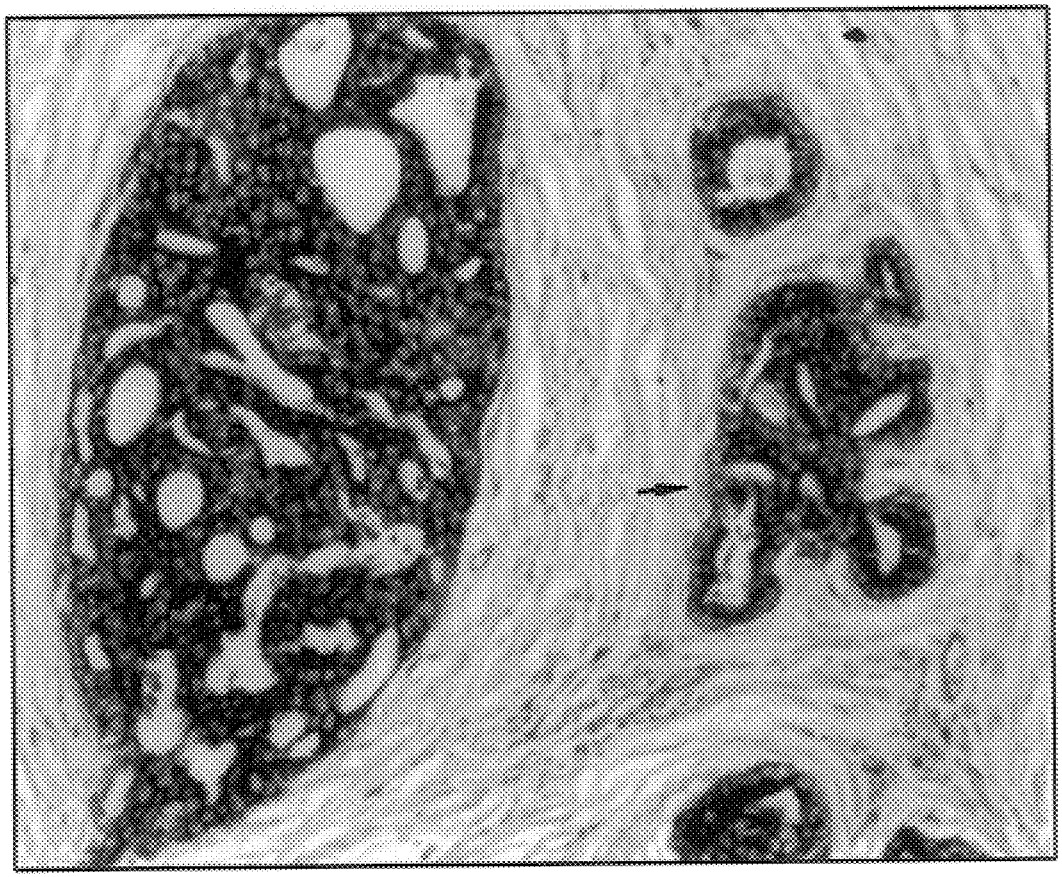
FIG. 11C. In situ hybridization with antisense riboprobe for human PSCA on malignant prostate specimens. Strong expression of PSCA in a case of high grade carcinoma (200× magnification).

To confirm the PSCA expression and its value in diagnosing prostate cancer, one hundred twenty six paraffin-embedded prostate cancer specimens were analyzed by mRNA in situ hybridization for PSCA expression. Specimens were obtained from primary tumors removed by radical prostatectomy or transurethral resection in all cases except one. All specimens were probed with both a sense and antisense construct in order to control for background staining. Slides were assigned a composite score as describe under Materials and Methods, with a score of 6 to 9 indicating strong expression and a score of 4 meaning moderate expression. 102/126 (81%) of cancers stained strongly for PSCA, while another 9/126 (7%) displayed moderate staining (FIGS. 11B and 11C). High grade prostatic intraepithelial neoplasia, the putative precursor lesion of invasive prostate cancer, stained strongly positive for PSCA in 82% (97/118) of specimens (FIG. 11B) (Yang et al., 1997, Am. J. Path. 150: 693–703). Normal glands stained consistently weaker than malignant glands (FIG. 11B). Nine specimens were obtained from patients treated prior to surgery with hormone ablation therapy. Seven of nine (78%) of these residual presumably androgen-independent cancers overexpressed PSCA, a percentage similar to that seen in untreated cancers. Because such a large percentage of specimens expressed PSCA mRNA, no statistical correlation could be made between PSCA expression and pathological features such as tumor stage and grade. These results suggest that PSCA mRNA overexpression is a common feature of androgen-dependent and independent prostate cancer.

PSCA is Expressed in Androgen Independent Prostate Cancer Cell Lines: Although PSCA was initially cloned using subtractive hybridization, Northern blot analysis demonstrated strong PSCA expression in both androgen-dependent and androgen-independent LAPC-4 xenograft tumors (FIG. 9). Moreover, PSCA expression was detected in all prostate cancer xenografts, including the LAPC-4 and LAPC-9 xenografts. PSCA expression in the androgen-independent, androgen receptor-negative prostate cancer cell lines PC3 and DU145 was also detected by reverse-transcriptase polymerase chain reaction analysis. These data suggest that PSCA can be expressed in the absence of functional androgen receptor.

Example 2

Biochemical Characterization Of PSCA

This experiment shows that PSCA is a glycosylated, GPI-anchored cell surface protein.

MATERIALS AND METHODS

Polyclonal Antibodies and Immunoprecipitations: Rabbit polyclonal antiserum was generated against the synthetic peptide -TARIRAVGLLTVISK- and affinity purified using a PSCA-glutathione S transferase fusion protein. 293T cells were transiently transfected with pCDNA II (Invitrogen, San Diego, Calif.) expression vectors containing PSCA, CD59, E25 or vector alone by calcium phosphate precipitation. Immunoprecipitation was performed as previously described (Harlow and Lane, 1988, Antibodies: A Laboratory Manual. (Cold Spring Harbor Press)). Briefly, cells were labeled with 500 uCi of trans35S label (ICN, Irvine, Calif.) for six hours. Cell lysates and conditioned media were incubated with 1ug of purified rabbit anti-PSCA antibody and 20 ul protein A sepharose CL-4B (Pharmacia Biotech, Sweden) for two hours. For deglycosylation, immunoprecipitates were treated overnight at 37° with 1u N-glycosidase F (Boehringer Mannheim) or 0.1 u neuraminidase (Sigma, St. Louis, Mo.) for 1 hour followed by overnight in 2.5 mU O-glycosidase (Boehringer Mannheim).

Flow Cytometry: For flow cytometric analysis of PSCA cell surface expression, single cell suspensions were stained with 2 ug/ml of purified anti-PSCA antibody and a 1:500 dilution of fluorescein isothiocyanate (FITC) labeled anti-rabbit IgG (Jackson Laboratories, West Grove, Pa.). Data was acquired on a FACScan (Becton Dickinson) and analyzed using LYSIS II software. Control samples were stained with secondary antibody alone. Glycosylphosphatidyl inositol linkage was analyzed by digestion of $2 \times 10^6$ cells with 0.5 units of phosphatidylinositol-specific phospholipase C (PI-PLC, Boehringer Mannheim) for 90 min at 37° C. Cells were analyzed prior to and after digestion by either FACS scanning or immunoblotting.

Results

Figures 12A, 12B:
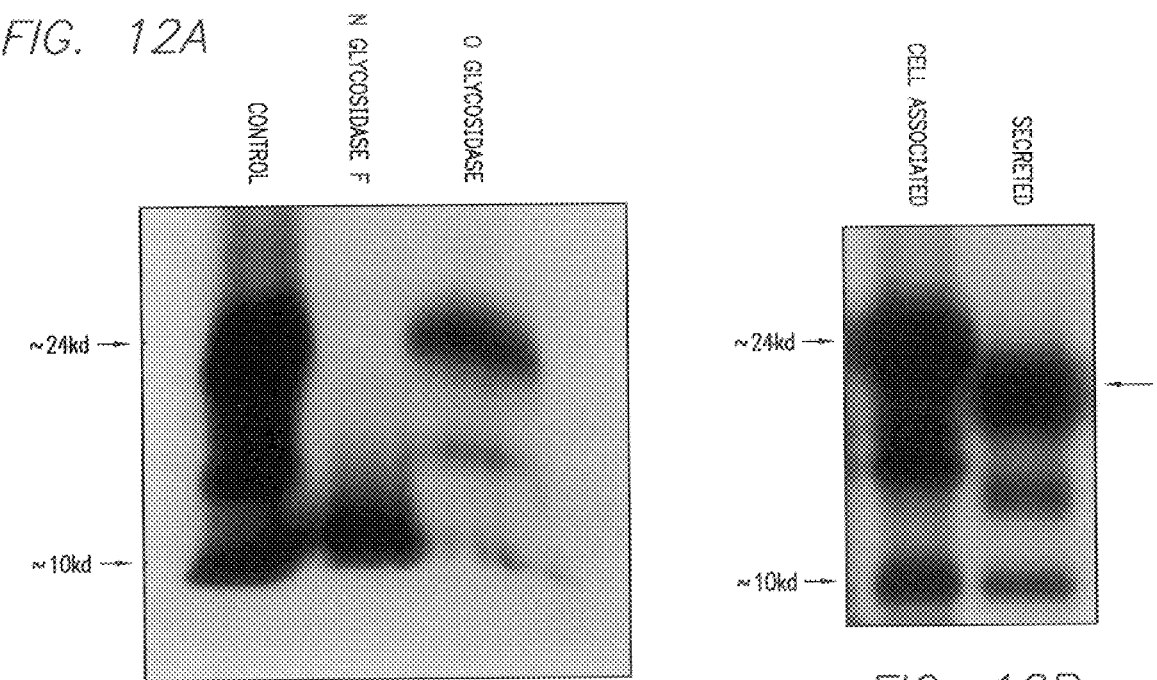
FIG. 12A. Biochemical analysis of PSCA. PSCA was immunoprecipitated from 293T cells transiently transfected with a PSCA construct and then digested with either N-glycosidase F or O-glycosidase, as described in Materials and Methods.
FIG. 12B. Biochemical analysis of PSCA. PSCA was immunoprecipitated from 293T transfected cells, as well as from conditioned media of these cells. Cell-associated PSCA migrates higher than secreted or shed PSCA on a 15% polyacrylamide gel.

PSCA is a GPI-Anchored Glycoprotein Expressed on the Cell Surface: The deduced PSCA amino acid sequence predicts that PSCA is heavily glycosylated and anchored to the cell surface through a GPI mechanism. In order to test these predictions, we produced an affinity purified polyclonal antibody raised against a unique PSCA peptide (see Materials and Methods). This peptide contains no glycosylation sites and was predicted, based on comparison to the three dimensional structure of CD59 (another GPI-anchored PSCA homologue), to lie in an exposed portion of the mature protein (Kiefer et al., 1994, Biochem. 33: 4471–4482). Recognition of PSCA by the affinity-purified antibody was demonstrated by immunoblot and immunoprecipitation analysis of extracts of 293T cells transfected with PSCA and a GST-PSCA fusion protein. The polyclonal antibody immunoprecipitates predominantly a 24 kd band from PSCA-transfected, but not mock-transfected cells (FIG. 12A). Three smaller bands are also present, the smallest being ~10 kd. The immunoprecipitate was treated with N and O specific glycosidases in order to determine if these bands represented glycosylated forms of PSCA. N-glycosidase F deglycosylated PSCA, whereas O-glycosidase had no effect (FIG. 12A). Some GPI-anchored proteins are known to have both membrane-bound and secreted forms (Fritz and Lowe, 1996, Am. J. Physiol. 270:G176-G183). FIG. 12B indicates that some PSCA is secreted in the 293T-overexpressing system. The secreted form of PSCA migrates at a lower molecular weight than the cell surface-associated form, perhaps reflecting the absence of the covalent GPI-linkage. This result may reflect the high level of expression in the 293T cell line and needs to be confirmed in prostate cancer cell lines and in vivo.

Figure 12C:
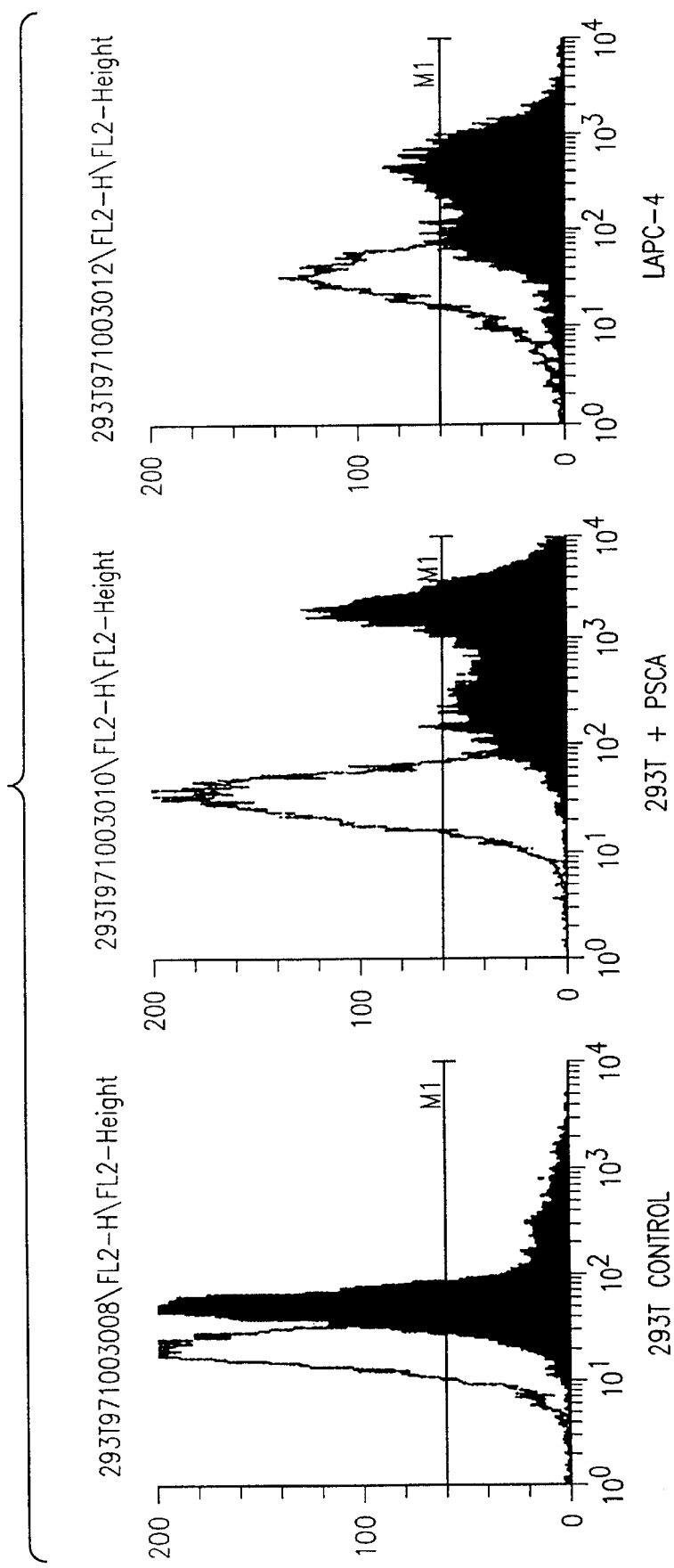
FIG. 12C. Biochemical analysis of PSCA. FACS analysis of mock-transfected 293T cells, PSCA-transfected 293T cells and LAPC-4 prostate cancer xenograft cells using an affinity purified polyclonal anti-PSCA antibody. Cells were not permeabilized in order to detect only surface expression. The y axis represents relative cell number and the x axis represents fluorescent staining intensity on a logarithmic scale.

Fluorescence activated cell sorting (FACS) analysis was used to localize PSCA expression to the cell surface. Nonpermeabilized mock-transfected 293T cells, PSCA-expressing 293T cells and LAPC-4 cells were stained with affinity purified antibody or secondary antibody alone. FIG. 12C shows cell surface expression of PSCA in PSCA-transfected 293T and LAPC-4 cells, but not in mock-transfected cells. To confirm that this cell surface expression is mediated by a covalent GPI-linkage, cells were treated with GPI-specific phospholipase C (PLC). Release of PSCA from the cell surface by PLC was indicated by a greater than one log reduction in fluorescence intensity. Recovery of PSCA in post digest conditioned medium was also confirmed by immunoblotting. The specificity of phospholipase C digestion for GPI-anchored proteins was confirmed by performing the same experiment on 293T cells transfected with the GPI-linked antigen CD59 or the non-GPI linked transmembrane protein E25a (Deleersnijder et al., 1996, J. Biol. Chem 271: 19475–19482). PLC digestion reduced cell surface expression of CD59 to the same degree as PSCA but had no effect on E25. These results support the prediction that PSCA is a glycosylated, GPI-anchored cell surface protein.

Example 3

Isolation Of cDNA Encoding Murine PSCA Homologue

The human PSCA cDNA was used to search murine EST databases in order to identify homologues for potential transgenic and knockout experiments. One EST obtained from fetal mouse and another from neonatal kidney were 70% identical to the human cDNA at both the nucleotide and amino acid levels. The homology between the mouse clones and human PSCA included regions of divergence between human PSCA and its GPI-anchored homologues, indicating that these clones likely represented the mouse homologue of PSCA. Alignment of these ESTs and 5' extension using RACE-PCR provided the entire coding sequence (SEQ ID NO:4) (FIG. 2).

Example 4

Isolation Of Human And Murine PSCA Genes

This experiment shows that PSCA is located at chromosome 8, band q24.2.
MATERIALS AND METHODS Genomic Cloning: Lambda phage clones containing the human PSCA gene were obtained by screening a human genomic library (Stratagene) with a human PSCA cDNA probe (Sambrook et al., 1989, Molecular Cloning (Cold Spring Harbor)). BAC (bacterial artificial chromosome) clones containing the murine PSCA gene were obtained by screening a murine BAC library (Genome Systems, Inc., St. Louis, Mo.) with a murine PSCA cDNA probe. A 14 kb human Not I fragment and a 10 kb murine Eco RI fragment were subcloned into pBluescript (Stratagene), sequenced, and restriction mapped.

Chromosome Mapping by Fluorescence In Situ Hybridization: Fluorescence in situ chromosomal analysis (FISH) was performed as previously described using overlapping human lambda phage clones (Rowley et al., 1990, PNAS USA 87: 9358–9362, H. Shizuya, PNAS USA, 89:8794).

Results

Structure of PSCA Gene: Human and murine genomic clones of approximately 14 kb and 10 kb, respectively, were obtained and restriction mapped. A schematic representation of the gene structures of human and murine PSCA and Ly-6/Thy-1 is shown in FIG. 8. Both the human and murine genomic clones contain three exons encoding the translated and 3' untranslated regions of the PSCA gene. A fourth exon encoding a 5' untranslated region is presumed to exist based on PSCA's homology to other members of the Ly-6 and Thy-1 gene families (FIG. 8).

Figure 13:
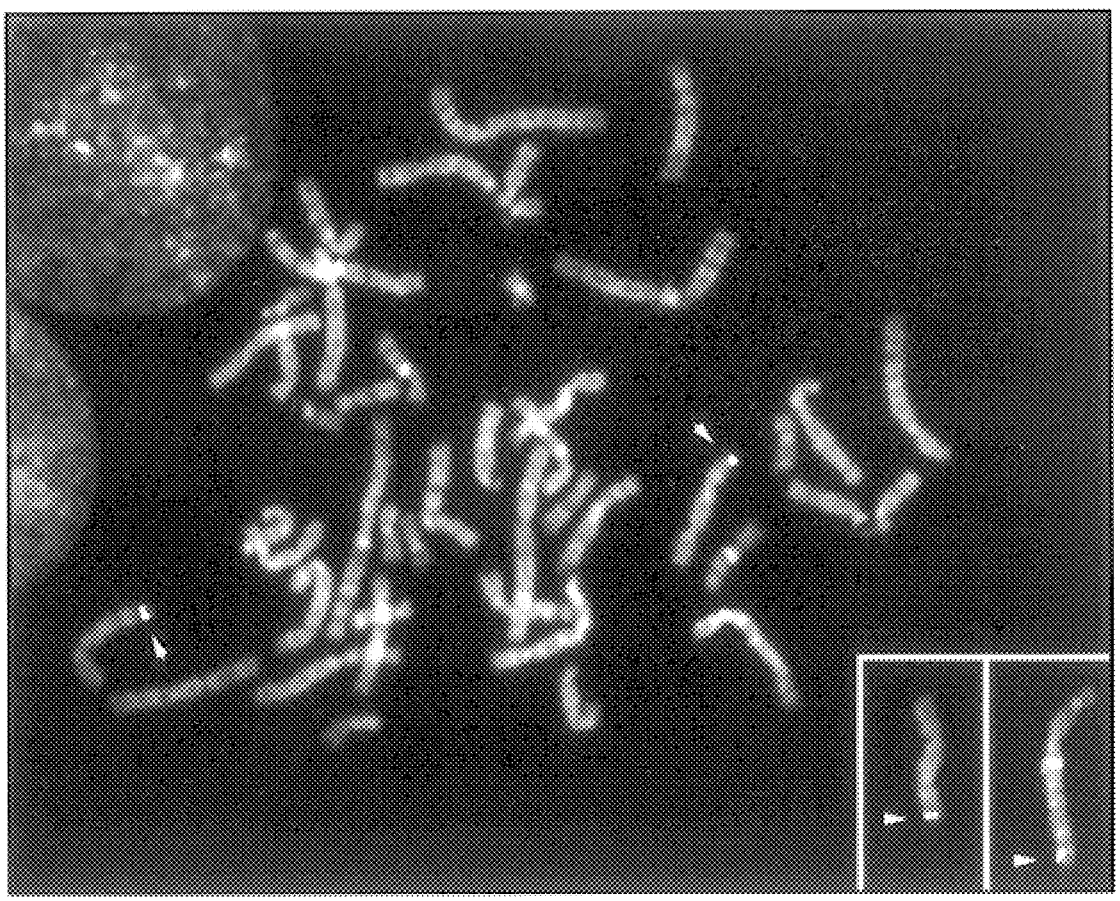
FIG. 13. In situ hybridization of biotin-labeled PSCA probes to human metaphase cells from phytohemagglutinin-stimulated peripheral blood lymphocytes. The chromosome 8 homologues are identified with arrows; specific labeling was observed at 8q24.2. The inset shows partial karyotypes of two chromosome 8 homologues illustrating specific labeling at 8q24.2 (arrowheads). Images were obtained using a Zeiss Axiophot microscope coupled to a cooled charge coupled device (CCD) camera. Separate images of DAPI stained chromosomes and the hybridization signal were merged using image analysis software (NU200 and Image 1.57).
Figure 14A:
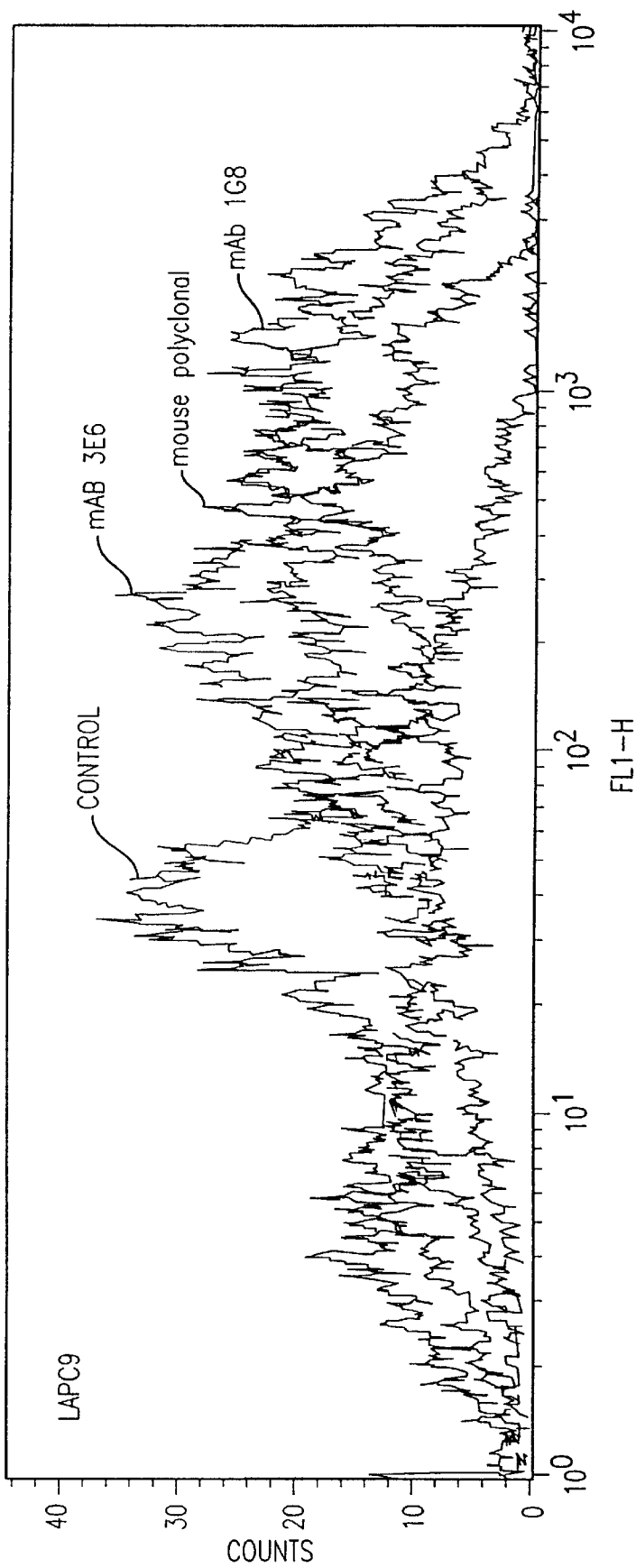
FIG. 14A. Flow Cytometric analysis of cell surface PSCA protein expression on prostate cancer xenograft (LAPC-9) using anti-PSCA monoclonal antibodies 1G8 and 3E6, mouse anti-PSCA polyclonal serum, or control secondary antibody. See Example 5 for details.
Figure 14C:
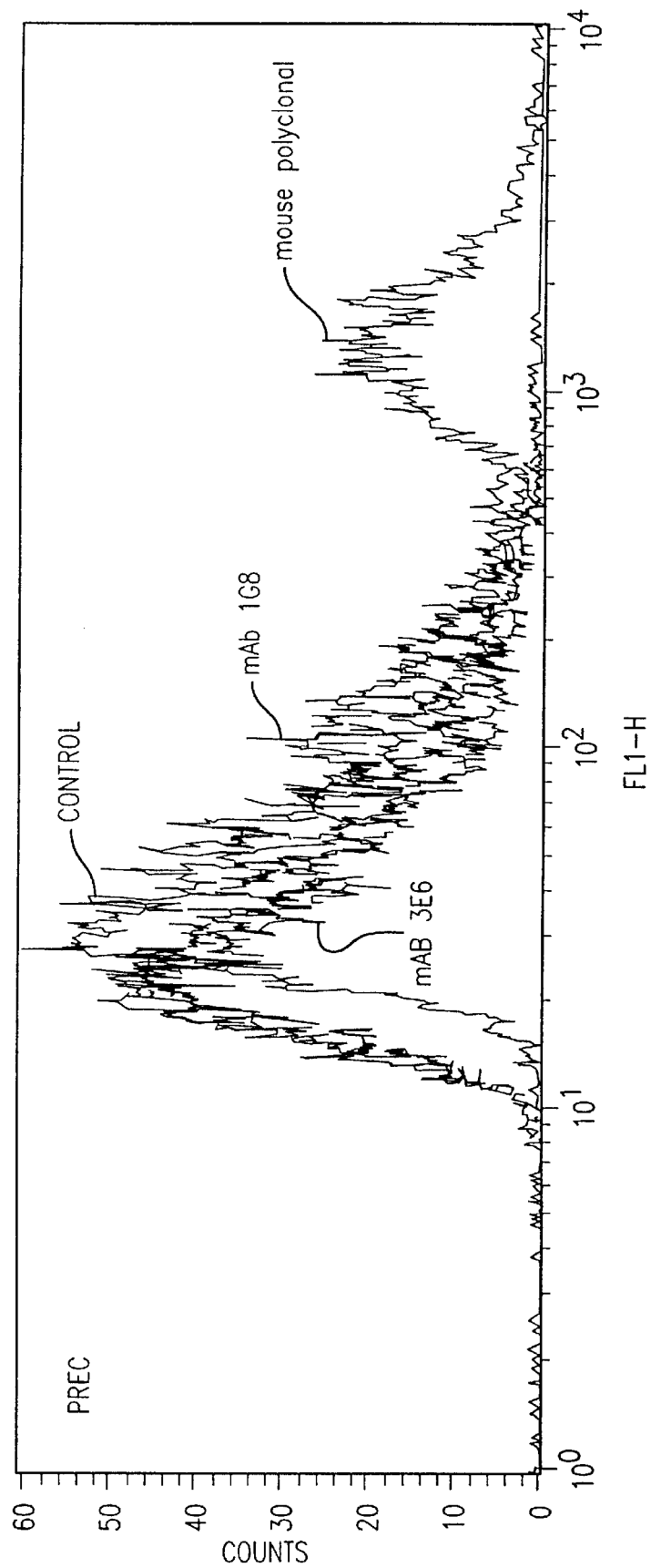
FIG. 14C. Flow Cytometric analysis of cell surface PSCA expression on normal prostate epithelial cells (PreC) using anti-PSCA monoclonal antibodies 1G8 and 3E6, mouse anti-PSCA polyclonal serum, or control secondary antibody. See Example 5 for details.

Human PSCA Gene Maps to Chromosome 8g24.2: Southern blot analysis of LAPC-4 genomic DNA revealed that PSCA is encoded by a single copy gene. Other Ly-6 gene family members contain four exons, including a first exon encoding a 5' untranslated region and three additional exons encoding the translated and 3' untranslated regions. Genomic clones of human and murine PSCA containing all but the presumed 5' first exon were obtained by screening lambda phage libraries. Mouse and human PSCA clones had a similar genomic organization. The human clone was used to localize PSCA by fluorescence in situ hybridization analysis. Cohybridization of overlapping human PSCA lambda phage clones resulted in specific labeling only of chromosome 8 (FIG. 13). Ninety seven percent of detected signals localized to chromosome 8q24, of which 87% were specific for chromosome 8q24.2. These results show that PSCA is located at chromosome 8, band q24.2.

Example 5

Generation Of Monoclonal Antibodies Recognizing Different Epitopes Of PSCA

MATERIALS AND METHODS

Generation and Production of Monoclonal Antibodies. BALB/c mice were immunized three times with a purified PSCA-glutathione S-transferase (GST) fusion protein containing PSCA amino acids 22–99 (SEQ ID NO:2) (FIG. 1B). Briefly, the PSCA coding sequence corresponding to amino acids 18 through 98 of the human PSCA amino acid sequence was PCR-amplified using the primer pair:

5'-GGAGAATTCATGGCACTGCCCTGCTGTGCTAC
3'-GGAGAATTCCTAATGGGCCCCGCTGGCGTT

The amplified PSCA sequence was cloned into pGEX-2T (Pharmacia), used to transform *E. coli,* and the fusion protein isolated.

Spleen cells were fused with HL-1 myeloma cells using standard hybridoma technique. Hybridomas that were positive for PSCA by ELISA and FACS analysis (see Results) were subcloned. Ascites fluid was produced in C.B. 17 scid/scid mice and monoclonal antibodies (mAbs) purified using a protein G affinity column (Pharmacia Biotech, Piscataway, N.J.). PSCA mAb 1G8 was also produced in Cell-Pharm System 100 as recommended by the manufacturer (Unisyn Technologies, Hopkinton, Mass.).

ELISA for Hybridoma Screening: GST or PSCA-GST were immobilized on Reacti-Bind maleic anhydride-activated polystyrene plates (Pierce, Rockford, Ill.). 50 ul of hybridoma media were added to each well and incubated for 1 hour at room temperature. Wells were washed 3 times with 200 ul PBS containing 0.1% BSA and 0.05% Tween 20 and incubated for 1 hour with 100 ul anti-mouse IgG (1:4000) labeled with alkaline phosphatase (Promega, Madison, Wis.). Plates were developed with an alkaline phosphatase substrate (Bio-Rad, Hercules, Calif.).

Cell Culture: LNCaP was obtained from ATCC and stably transfected with a pCDNA II (Invitrogen) expression vector containing PSCA or vector alone (Reiter, R. et al., 1998). 293T cells transiently transfected with PSCA or vector alone were prepared as described previously (Reiter, R. et al., 1998). LAPC-9 xenograft explants were propagated in PrEGM media (Clonetics, San Diego, Calif.) after digestion in 1% pronase for 18 min. at room temperature. Before FACS analysis, LAPC-9 cells were passed though a 40 um cell strainer to obtain single cell suspensions.

Immunofluorescence: Cells were grown on glass coverslips coated with poly-L-lysine. Immunofluorescence assays were carried out on permeabilized and nonpermeabilized fixed cells. For fixation, cells were treated with 2% paraformaldehyde in PBS-CM (PBS, 100 uM $CaCl_2$, 1 mM $MgCl_2$) for 30 minutes in the dark, quenched with 50 uM $NH_4Cl$ in PBS-CM-BSA (PBS, 100 uM $CaCl_2$, 1 mM $MgCl_2$, 0.2% BSA) for 10 minutes, and washed twice with PBS-CM-BSA. For permeabilization, cells were treated additionally with PBS-CM-BSA-Saponin (0.075% saponin (Sigma) in PBS-CM-BSA) for 15 minutes at room temperature. Primary mAb at 2–5 mg/ml in PBS-CM-BSA (plus saponin in cases of permeabilization) was added for 60 minutes and washed twice with PBS-CM-BSA. FITC-conjugated goat antimouse IgG antibody (1:500 diluted in PBS-CM-BSA+/− saponin; Southern Biotechnology, Birmingham, Ala.) was added for 30 minutes and washed 3 times with PBS-CM. Slides were mounted in vectashield (Vector Laboratory, Inc., Burlingame, Calif.).

Flow Cytometry: Cells ($1\times10^6$) were incubated for 30 minutes at 4° C. with 100 ul mAb at 2 ug/ml in PBS containing 2% fetal bovine serum or hybridoma conditioned medium. After washing, cells were stained with a 1:500 dilution of FITC-conjugated goat antimouse IgG (Southern Biotechnology, Birmingham, Ala.). Data was acquired on a FACScan (Becton Dickinson) and analyzed by using LYSIS II software.

Immunoblotting and Immunoprecipitation: Immunoprecipitation was performed as described (Harlow, E. and Lane, D., 1988). Briefly, cells were labeled with 500 uCi of trans35 label (ICN) for 6 hours. Cell lysates were incubated with 3 ug mAb and 20 ul of protein A-Sepharose CL-4B (Pharmacia Biotech) for 2 hours. For immunoblotting, protein extracts were prepared by lysing cells in 1×SDS Laemmli sample buffer and boiling for 5 min. Proteins were separated on 12.5% SDS polyacrylamide gels and transferred to nitrocellulose membranes, washed and incubated with 2 ug mAb in 10 ml blocking buffer (5% nonfat milk in TBST). Blots were developed using the Amersham enhanced chemiluminescence detection system (Amersham, Arlington Heights, Ill.).

Immunohistochemistry: Normal formalin-fixed, paraffin-embedded tissue samples were obtained from the Departments of Pathology at Beth-Israel Deaconess Medical Center-Harvard Medical School and UCLA. Primary radical prostatectomy specimens were selected from a previously described database (Magi-Galluzzi, C. et al., 1997). Bone metastases and matched primary biopsy specimens were obtained from the UCLA Department of Pathology. Normal tissues were stained and scored independently at two institutions in order to ensure reproducibility. Specimens obtained from UCLA were stained using modifications of an immunoperoxidase technique previously described (Said, J. W. et al., 1998). Antigen retrieval was performed on paraffin sections using a commercial steamer and 0.01M citrate buffer pH 6.0. After incubation with PSCA mAbs for 50 min. (see below), slides were treated sequentially with rabbit anti-mouse IgG, swine anti-rabbit IgG and rabbit anti-swine IgG, all biotin conjugated. Slides were then incubated with strepavidin-peroxidase and antibody localization performed using the diaminobenzidene reaction. Specimens obtained from Beth-Israel-Deaconess-Harvard Medical School were stained as previously described using an automated Ventana NexES instrument (Ventana Medical Systems, Tucson, Ariz.) (Magi-Galluzzi, C. et al., 1997). Antigen retrieval was done by microwave for 15 min. in EDTA, pH 8.05 at 750W. mAbs purified at a concentration of ~1 ug/ul from SCID ascites were used at the following concentrations: 1G8=1:20; 3E6=1:30; 2H9=1:50; 4A10=1:100; 3C5=1:100. mAb 1G8 was produced in CellPharm System 100 and used at a concentration of 1:10. Positive controls included LAPC-9 and LNCaP-PSCA and negative controls were LNCaP and isotype-matched irrelevant antibody. Primary biopsy specimens were available for three patients with bone metastases. To approximate conditions of decalcification, slides from these specimens were treated for 20 min. in Decal-Stat (Lengers, NY) prior to staining with PSCA mAbs.

Monoclonal antibodies (mAbs) were raised against a PSCA-GST fusion protein lacking both the amino and carboxyl terminal signal sequences of PSCA. Positive fusions were selected by ELISA using the PSCA-GST fusion protein and GST alone. Out of 400 hybridomas screened, 28 recognized the PSCA-GST fusion but not GST alone. These fusions were screened secondarily by flow cytometry of nonpermeabilized 293T cells transfected with PSCA and mock transfected 293T cells. Secondary screening by FACS was done in order to select clones capable of recognizing PSCA on the cell surface, hypothesizing that these might later become useful for in vivo targeting applications. Seven positive fusions were identified in this manner (mAbs 2A2, 3G3, 4A10, 1G8, 3E6, 3C5 and 2H9), of which five (mAbs 4A10, 1G8, 3E6, 3C5 and 2H9) were subcloned and purified.

The mAbs were tested for their ability to immunoprecipitate PSCA and/or to recognize PSCA on immunoblots. All mAbs were able to immunoprecipitate PSCA from 293T-PSCA cells, as well as from LAPC-9 prostate cancer xenograft tumors that express high levels of endogenous PSCA (FIG. 37). Likewise, all mAbs detected PSCA by immunoblotting, although mAbs 2H9 and 3E6 recognized only the ~12 kd deglycosylated form of PSCA (FIG. 34).

Figures 15A, 15B:
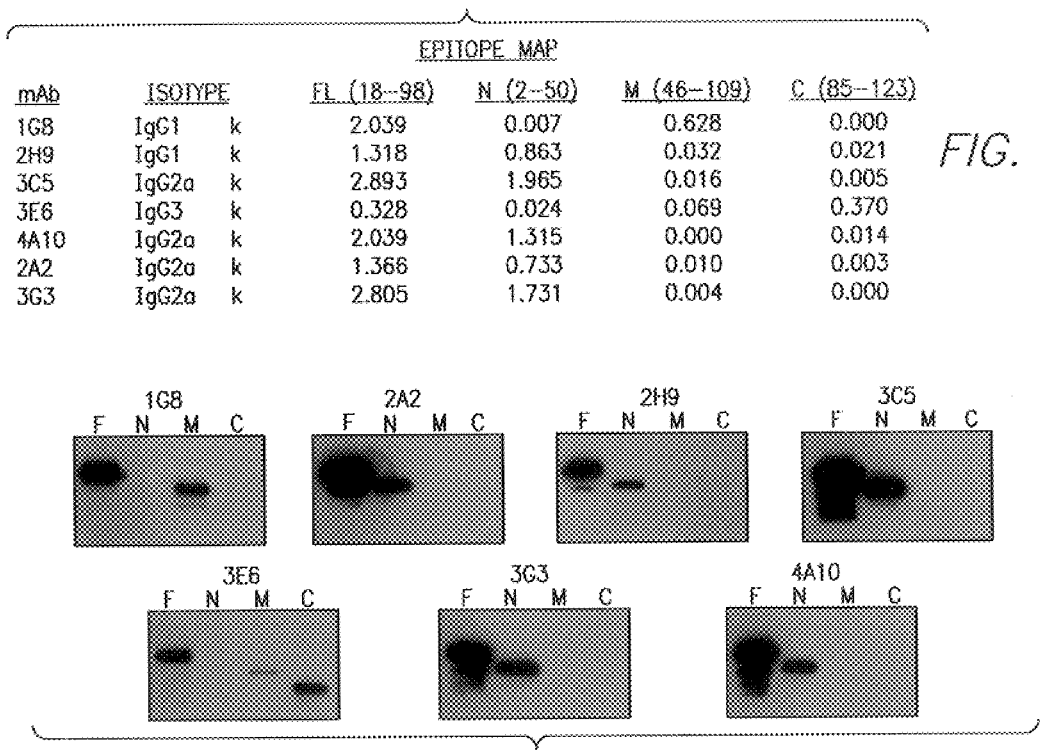
FIG. 15A. An epitope map for each of the seven disclosed antibodies.
FIG. 15B. Epitope mapping of anti-PSCA monoclonal antibodies conducted by Western blot analysis of GST-PSCA fusion proteins.

The location on PSCA of the epitopes recognized by the five mAbs was determined by immunoblot analysis using three truncated PSCA-GST fusions proteins. mAbs 4A10, 2H9 and 3C5 recognize an epitope residing within the amino-terminal portion of PSCA (i.e., amino acids 21–50); mAb 1G8 recognizes an epitope within the middle region of PSCA (i.e., amino acids 46–85); and mAb 3E6 reacts within the carboxyl-terminal portion of PSCA (amino acids 85–99) (FIG. 15). All five mAbs are IgG as described in FIG. 15. These results demonstrate that the five mAbs can detect PSCA in multiple assays and recognize at least three distinct epitopes on PSCA.

PSCA mAbs Stain the Cell Surface of Prostate Cancer Cells

The utility of mAbs for studying PSCA biology and for potential clinical applications such as in vivo targeting applications is dependent on their ability to recognize the antigen of interest on the plasma membrane (Liu, H. et al., 1997; McLaughlin, P. et al., 1998; Wu, Y. et al., 1995; Tokuda, Y. et al., 1996). In order to determine the ability of mAbs 2H9, 3E6, 1G8, 4A10 and C5 to recognize PSCA specifically on the cell surface of prostate cancer cells, LNCaP cells transfected with PSCA (LNCaP-PSCA) and LAPC-9 cells were examined by flow cytometry and indirect immunofluorescence. As with 293T-PSCA cells, all five mAbs were able to detect PSCA on the cell surface of nonpermeabilized LNCaP-PSCA and/or LAPC-9 cells by flow cytometry (FIG. 33). Mock-transfected LNCaP and LNCaP transfected with a neomycin-alone containing vector (LNCaP-neo), neither of which expresses detectable PSCA mRNA, were both negative.

Immunofluorescent analysis was performed on both permeabilized and nonpermeabilized cells in order to ascertain whether PSCA protein localizes to the cell surface (Liu, H. et al., 1997). Nonpermeabilized LNCaP-PSCA showed clear cell surface reactivity with mAbs 1G8, 3E6, 4A10 and 3C5, but did not stain with mAb 2H9 (mAb 2H9 also did not detect PSCA on LNCaP-PSCA cells by FACS). LAPC-9 cells showed cell surface reactivity with all five mAbs (FIG. 35). LNCaP-neo, as predicted, was negative both with and without permeabilization. Permeabilization of LNCaP-PSCA and LAPC-9 resulted in both membrane and cytoplasmic staining. All mAbs produced a punctate staining pattern on the cell surface, which was most pronounced with mAbs 3E6, 3C5 and 4A10 (FIG. 35). This pattern may reflect aggregation or clustering of PSCA to regions of the cell surface. These results demonstrate that all five mAbs react with PSCA on the cell surface of intact prostate cancer cells.

Immunohistochemical Staining of PSCA in Normal Prostate

PSCA mRNA localizes to a subset of basal cells in normal prostate, suggesting that PSCA may be a cell surface marker for prostate stem/progenitor cells (Reiter, R. et al., 1998). In order to test the possibility that PSCA protein may be a marker of basal cells, PSCA expression was examined immunohistochemically in paraffin-embedded sections of normal prostate. mAbs 1G8 and 2H9 stained the cytoplasm of both basal and secretory cells, while mAb 3E6 reacted predominantly with basal cells (FIG. 38). Atrophic glands, which express basal cell cytokeratins, stained strongly with all three mAbs (FIG. 38) (O'Malley, F. P. et al., 1990). mAbs 3C5 and 4A10 gave strong background staining and/or nonspecific nuclear staining in paraffin sections and were not used further. These results suggest that although PSCA mRNA is detected specifically in basal cells, PSCA protein can be detected in both epithelial cell layers (i.e. basal and secretory) of the prostate, although there are some differences in the staining patterns of individual antibodies.

Immunohistochemical Analysis of Normal Tissues

Our initial studies indicated that PSCA expression in men was largely prostate-specific, with low levels of detectable RNA in kidney and small intestine. PSCA mRNA was also detected in placenta. The prostate-specificity of PSCA protein expression was tested by immunohistochemical staining of 20 tissues using mAb 1G8 (see Table 1). Positive tissue staining with mAb 1G8 was confirmed with mAbs 2H9 and/or 3E6 in order to ensure reproducibility with mAbs directed against distinct epitopes. Staining was also performed and scored independently at two institutions in order to confirm the results. As predicted by the RNA analysis, placenta was positive with all mAbs tested, with cytoplasmic staining detected in the trophoblasts (FIG. 39A). In kidney staining was detected in the collecting ducts and distal convoluted tubules, but not in glomeruli (FIG. 39A). Transitional epithelium of the bladder and ureter, which had not been examined previously at the mRNA level, was positive with all mAbs tested (FIG. 39A). The only other tissue with significant immunoreactivity was colon, in which single cells deep within the crypts stained intensely positive (FIG. 39A). Double staining with chromogranin indicated that these cells are of neuroendocrine origin.

In order to confirm that mAb reactivity in bladder represented PSCA, Northern blot analysis was performed on three normal bladder samples obtained at radical cystectomy and compared with PSCA expression in prostate, kidney and the LAPC-9 xenograft (FIG. 39B). PSCA mRNA was detected in bladder at levels lower than those seen in prostate, confirming the immunohistochemical result. No signal was detected in the three kidney specimens, consistent with our previous observation that PSCA expression in kidney is significantly lower than prostate (Reiter, R et al., 1998). LAPC-9, a prostate cancer xenograft established from a bone metastasis, expresses very high levels of PSCA mRNA compared with normal bladder and prostate (Whang, Y. E. et al., 1998). These results confirm that PSCA expression in men is largely prostate-predominant; however, there is also detectable PSCA protein expression in urothelium, renal collecting ducts and colonic neuroendocrine cells.

PSCA Protein is Expressed by a Majority of Localized Prostate Cancers

In our previous study, mRNA was expressed in ~80% of tumors and appeared to be expressed more highly in normal than malignant glands (Reiter, R. et al., 1998). In order to determine if PSCA protein can be detected in prostate cancers and if PSCA protein levels are increased in malignant compared with benign glands, paraffin-embedded pathological specimens of primary and metastatic prostate cancers were immunostained with mAb 1G8 (FIGS. 21 and 28). Isolated cases were also stained with mAbs 3E6 or 2H9 in order to confirm the specificity of the staining. Twelve of 15 primary cancers stained positive (FIG. 21), including 2/2 cases containing foci of high grade prostatic intraepithelial neoplasia. Staining intensity varied, with 7 cases showing equivalent staining in cancer and adjacent normal glands and 5 showing significantly stronger staining in cancer. In some cases there was strong expression in the malignant glands and undetectable staining in adjacent normal tissue (FIG. 21; patient 1). Also, there were some cases in which staining was heterogeneous, with some malignant glands staining more strongly than others (FIG. 21; patient 2). Overall, poorly differentiated tumors stained more strongly than well differentiated ones, suggesting that PSCA overexpression may correlate with increasing tumor grade (FIG. 21; patient 3). These results demonstrate that PSCA protein is expressed in prostate cancer. Consistent with our previous mRNA in situ studies, PSCA appears to be overexpressed in a significant percentage of cancers, perhaps in concert with increasing tumor grade.

This study describes the first characterization of PSCA protein expression using five monoclonal antibodies directed against PSCA. Because these mAbs recognize epitopes on the exterior of the cell surface, they may have utility for prostate cancer diagnosis and therapy (Liu, H. et al., 1997). One possibility is that these mAbs could be used to locate sites of metastatic disease, similar to the Prostascint scan which uses an antibody directed against PSMA (Sodee, D. B. et al., 1996). Another possibility is that they may be used to target prostate cancer cells therapeutically, either alone or conjugated to a radioisotope or other toxin. Similar approaches are currently being evaluated using antibodies directed against extracellular epitopes on PSMA (Murphy, G. P. et al., 1998; Liu, H. et al., 1997; Liu, H. et al., 1998).

PSCA mAbs stain the cell surface in a punctate manner, suggesting that PSCA may be localized to specific regions of the cell surface. GPI-anchored proteins are known to cluster in detergent-insoluble glycolipid-enriched microdomains (DIGS) of the cell surface (Varma, R. and Mayor, S., 1998). These microdomains, which include caveolae and sphingolipid-cholesterol rafts, are believed to play critical roles in signal transduction and molecular transport (Anderson, R. Caveolae, 1993; Friedrichson, T. and Kurzchalia, T. V., 1998; Hoessli, D. C. and Robinson, P. J., 1998). Thy-1, a homologue of PSCA, has previously been shown to transmit signals to src kinases through interaction in lipid-microdomains (Thomas, P. M. and Samuelson, L. E., 1992; Stefanova, I. et al., 1991). Preliminary subcellular fractionation experiments in our laboratory confirm the presence of PSCA in DIGS (Xavier, R. et al., 1998). GPI-anchored proteins have also been reported to localize to prostasomes, membrane-bound storage vesicles released by prostate epithelial cells (Ronquist, G. and Brody, I., 1985). CD59, a GPI-anchored inhibitor of complement-mediated cytolysis, is found in high concentrations in prostasomes of normal prostate epithelial cells and prostatic secretions (Rooney, I. et al., 1993). PSCA protein is detected in prostate secretory cells.

Contrary to our previous finding that PSCA mRNA localized exclusively to basal cells, the current results suggest that PSCA protein may be present in both basal and secretory cells. Similar differences between mRNA and protein localization in prostate have been described for PSMA and androgen receptor (Magi-Galuzzi, C. et al., 1997; Kawakami, M. and Nakayama, J., 1997). One possible explanation for the presence of PSCA protein in secretory cells is that PSCA mRNA is transcribed in basal progenitor cells but that PSCA protein expression persists as basal cells differentiate into secretory cells. Another possibility is that PSCA protein may be transferred from basal to secretory cells posttranslationally.

Differences in staining intensity of basal and secretory cells by mAbs 3E6, 1G8 and 2H9 may reflect the distinct epitopes recognized by the antibodies and/or differences in posttranslational modification of PSCA in basal and secretory cells. Supporting this possibility is the observation that the five mAbs do not react equally with PSCA in all assays or cell lines. mAb 2H9 recognizes PSCA on the cell surface of LAPC-9 but not LNCaP-PSCA, suggesting that the epitope recognized by this antibody may be altered or obscured in the latter cell type. We have also observed that mAb 3E6 does not stain cancers as strongly as mAbs 1G8 and 2H9 in some cases, suggesting that it may react with certain forms of PSCA preferentially.

Although largely prostate-specific in men, PSCA is also expressed at lower levels in urothelium, colonic neuroendocrine cells, and renal tubules and collecting ducts. The staining seen in renal tubules and collecting ducts is interesting in that these structures derive embryologically from the ureteric bud of the mesonephric duct, suggesting a possible reason for the staining patterns seen in kidney. The absence of detectable PSCA mRNA in kidney specimens may reflect either low levels of expression or the possibility that the samples were obtained primarily from the renal cortex, whereas the collecting ducts are located in the renal medulla.

The primary impetus for identifying prostate-specific cell surface genes is the desire to develop selective, nontoxic therapies. PSMA, another "prostate-restricted" protein, has also been shown to be expressed in duodenum, colonic neuroendocrine cells and proximal renal tubules (Silver, D. A. et al., 1997). Preliminary reports of PSMA vaccine therapy have not produced significant toxicity (Tjoa, B. A. et al., 1998).

Expression of PSCA in urothelium and kidney appears to be lower than in normal prostate and significantly less than that seen in many of the prostate cancers evaluated. Therapies directed against PSCA may therefore be relatively selective for cancer, much as Her-2/neu antibodies primarily target breast cancers that overexpress Her-2/neu (Disis, M. L. and Cheever, M. A., 1997).

Expression of PSCA in urothelium and kidney raises the possibility that it may be expressed in transitional and renal cell carcinomas. Two bladder cancers examined do express PSCA, one at levels similar to LAPC-9, suggesting that PSCA may be overexpressed in some cases of transitional cell carcinoma. A more complete survey of bladder cancer specimens will be required to test this possibility.

The data herein supports our earlier observation that PSCA is expressed in a majority of prostate cancers. Likewise, PSCA protein is overexpressed in some prostate tumors when compared to adjacent normal glands, supporting its use as a target for prostate cancer therapy. In contrast to the mRNA in situ studies, the current results suggest that PSCA protein expression may correlate with cancer stage and/or grade. Similar differences between RNA and protein expression have been noted for thymosin Beta-15 (Bao, L., et al., 1996).

TABLE 1

PSCA expression in normal tissues.

| Staining | Tissue |
| --- | --- |
| Positive | Prostate (epithelium) |
| | Bladder (transitional epithelium) |
| | Placenta (trophoblasts) |
| | Colon (neuroendocrine cells) |
| | Kidney (tubules and collecting duct)* |
| Negative | Kidney (glomeruli) |
| | Prostate (stroma) |
| | Bladder (smooth muscle) |
| | Testis |
| | Endometrium |
| | Small intestine |
| | Liver |
| | Pancreas |
| | Breast |
| | Gallbladder |
| | Skeletal muscle |
| | Brain |
| | Peripheral nerve |
| | Bone marrow |
| | Thymus |
| | Spleen |
| | Lung |
| | Bronchus |
| | Heart |

*mAb 3E6 reacts with the distal convoluted tubule, while mAb 1G8 reacts with distal tubules and, in some cases, proximal tubules.
**subsequent experimental analysis also showed PSCA expression in normal stomach tissue.

Example 6

PSCA Expression in Prostate Cancer Bone Metastases

This experiment shows that PSCA expression is amplified in bone metastases of prostate cancer.
MATERIALS AND METHODS
Horse Serum (NHS) (GIBCO #26050-070) was diluted (1/20 dilution) in 1% Casein, PBST. The antibodies of the invention that recognize PSCA were diluted in 1/100 NHS, PBST.

The detection system included HRP-rabbit anti-mouse Ig (DAKO P260), HRP-swine anti-rabbit Ig (DAKO P217), HRP-rabbit anti-swine Ig (DAKO P164). Each were diluted 1/100 in 1/100 NHS, PBST.

3,3'-diaminobenzidine tetrahyrochloride (DAB) (Fluka) stock was made by dissolving 5 gm in 135 ml of 0.05 M Tris, pH 7.4. DAB was aliquoted into 1 ml/vial and frozen at $-20°$ C. A working solution of DAB was made by adding 1 ml of DAB to 40 ml of DAB buffer and 40 microliters of 50% $H_2O_2$.

DAB buffer was prepared by combining 1.36 gm Imidazole (Sigma #I-0125) with 100 ml $D^2$- $H_2O$, then adjusting the pH to 7.5 with 5 N HCl. After the pH adjustment 20 ml of 0.5 M Tris pH 7.4 and 80 ml of $D^2$- $H_2O$ were added.

A section of a tissue/tumor known and previously demonstrated to be positive for the antibody was run with the patient slide. This slide served as a "positive control" for that antibody. A section of the patient's test specimen was incubated with a negative control antibody in place of the primary antibody. This slide served as a "negative control" for the test.

The staining procedure was as follows. Bone samples were applied to slides. The slides were then baked overnight at 60° C. Slides were deparaffinize in 4 changes of xylene for 5 minutes each and passed through a graded series of ethyl alcohol (100%×4, 95%×2) to tapwater then transferred to NBF, and fixed for 30 minutes. The fixed slides were placed in running tapwater for 15 minutes, transferred to 3% $H_2O_2$-MeOH, incubated for 10 minutes, and washed in running tapwater for 5 minutes, then rinse in deionized water.

Slides were then subjected to 0.01 M citrate buffer pH 6.0, heated at 45° C. for 25 minutes, cooled for 15 min and then washed in PBS. The slides were then rinsed in PBS and placed onto programmed DAKO Autostainer, using the following four step program. The four step program is as follows. The slide is rinsed in PBS and blocked with 1/20 NHS in 1% Casein in PBST for 10 minutes. Primary antibody is then applied and incubated for 30 minutes followed by a buffer rinse. HRP-Rabbit anti-Mouse Ig is then applied and incubated for 15 minutes followed by another buffer rinse. HRP-Swine anti-Rabbit Ig is applied and incubated for 15 minutes followed by a buffer rinse. HRP-Rabbit anti-Swine Ig is applied and incubated for 15 minutes followed by a buffer rinse.

DAB is then applied to the slide and incubated for 5 minutes followed by a buffer rinse. A second DAB is applied and incubated for 5 minutes followed by a buffer rinse.

The slides are removed from the Autostainer and placed into slide holders, rinsed in tapwater and counter stained with Harris hematoxylin (15 seconds). The slide is then washed in tapwater, dipped in acid-alcohol, washed in tapwater, dipped in sodium bicarbonate solution, and washed in tapwater. The slides are then dehydrated in graded ethyl alcohols (95%×2, 100%×3) and Propar×3 and coverslipped with Permount.

PSCA Protein is Expressed Strongly in Prostate Cancers Metastatic to Bone

Prostate cancer is unique among human tumors in its propensity to metastasize preferentially to bone and to induce osteoblastic responses. Nine sections of prostate cancer bone metastases were examined immunohistochemically (FIG. 28). All reacted intensely and uniformly with mAb 1G8 (and/or 3E6). In two instances, micrometastases not readily detectable on hematoxylin and eosin sections could be seen after staining with mAb 1G8 (FIG. 28; patient 5). Overall, staining in bone metastases was stronger and more uniform than in the primary tumors. In three cases, biopsy specimens from the primary tumors were available for comparison. All were weakly positive for PSCA when compared with the matched bone metastasis, suggesting that PSCA expression was increased in bone. In one biopsy specimen, weak staining was present in only a small focus of malignant glands, while the remaining tumor was negative (FIGS. 21 and 28; Patient 4). In two cases, the biopsy specimens were obtained 10 and 15 years prior to the bone metastasis, indicative of a long latency period between the development of the primary and metastatic lesions. To rule out the possibility that the strong staining in bone was caused by the decalcification process used to prepare bone sections, the three primary biopsy specimens were also treated with decalcification buffer. Although this treatment increased background staining, it did not alter epithelial reactivity significantly, indicating that the strong signal in bone was unlikely to be caused by the decalcification process. These results suggest that PSCA may be selected for or upregulated in prostate cancer metastases to bone.

FIGS. 21–23 show the bone samples of bone metastases of prostate cancer were positive for PSCA. Nine sections of prostate cancer bone metastases were examined. Consistent, intense staining was seen in nine prostate cancer bone metastases and all reacted intensely and uniformly with mAb 1G8 (and/or 3E6). In two instances, the pathologist could not readily identify the metastasis until staining with 1G8 highlighted the lesion. Overall, staining in bone metastases appeared stronger and more uniform than in the primary tumors.

These results suggest that PSCA may be greatly overexpressed in prostate cancer metastases to bone. This is particularly interesting since Sca-2, a close homologue of PSCA, was recently reported to suppress osteoclast activity in bone marrow. If PSCA had similar activity, it might provide one explanation for the tendency of prostate cancer metastases to produce an osteoblastic response, since inhibition of osteoclast activity would tilt the balance of activity in bone to bone formation. Another possibility is that PSCA might be involved in adhesion to bone, since other Ly-6/Thy-1 family members are involved in similar processes. There was heterogeneous expression of PSCA in a number of primary prostate cancers. These results further support the use of PSCA as a novel target for advanced disease.

One of the most intriguing results of the present study was the consistent, intense staining seen in the nine prostate cancer bone metastases. LAPC-9, a xenograft established from a bony metastasis, also stained intensely for PSCA. In three patients, matched primary biopsy specimens showed low levels of PSCA expression compared to the bony metastases. Areas of strong PSCA expression in the primary tumors of the three patients examined may have been missed since only biopsies were available for analysis. Heterogeneous expression of PSCA was detected in at least one matched primary tumor, as well as in number of primary tumors for whom matched metastatic lesions were not available. Also, in two cases the primary tumor was sampled at least a decade prior to the bone metastasis, raising the possibility that clones expressing high levels of PSCA within the primary could have developed subsequent to the initial biopsy. These results clearly demonstrate PSCA expression in bone metastases, further supporting it as a novel target for advanced disease.

Example 7

PSCA Overexpression in Bladder and Pancreatic Carcinomas

This experiment shows that PSCA expression is higher in bladder carcinomas than normal bladder.

Tissues from prostate, bladder, kidney, testes, and small intestine (including prostate cancer and bladder and kidney carcinomas) were obtained from patients. These tissues were then examined for binding to PSCA using northern and western blot analyses as follows.

For northern blot analyses, tissue samples were excised and a less than 0.5×0.5 cm tissue sample was quick frozen in liquid nitrogen. The samples were homogenized in 7 mls of Ultraspec (Biotecx, Houston, Tex.), using a polytron homogenizer using the protocol provided by Biotecx (Ultraspec™ RNA Isolation System, Biotecx Bulletin No: 27, 1992).

After quantification, 20 µg of purified RNA from each sample were loaded onto a 1% agarose formaldehyde gel. Running and blotting conditions were the same as was used in Example 1. The filters were separately probed with labeled PSCA and an internal control, actin. Filters were washed and exposed for several hours-overnight.

For western blot analyses, tissue samples were excised and a less than 0.5×0.5 cm tissue sample was taken and quickly minced and vortexed in equal volume of hot 2×Sample Buffer (5% SDS, 20% glycerol). Samples were incubated at 100° for 5 mins, vortexed and clarified for 30 min. Protein concentrations were determined by Biorad's DC Protein Assay kit (Richmond, Calif.). 40 g/sample was loaded on a 12% polyacrylamide protein gel. Transfer to a nitrocellulose filter was done by standard methods (Towbin et al. PNAS 76:4350 (1979). A western blot was performed by incubating the filter with 1G8 primary antibody followed by a secondary antibody, i.e., a goat αmouse IgG HRP. Detection was by Amersham ECL Detection kit (Arlington Heights, Ill.).

1G8 recognized and bound the PSCA on the cells surface of LAPC9 and a bladder carcinoma (designated bladder (Rob)) in a western blot analysis (FIG. 6). In FIG. 6, all tissues except LAPC9 were normal. A northern blot analysis confirmed elevated PSCA in the bladder carcinoma tissue (designated bladder (Rob) (also referred to as Rob's Kid CA) and LAPC9) (FIG. 25).

A Northern blot analysis was performed, testing transcripts isolated from pancreatic cancer cell lines: PANC-1 (epithelioid, ATCC No. CRL-1469), BxPC-3 (adenocarcinoma, ATCC No. CRL-1687), HPAC (epithelial adenocarcinoma, ATCC No. CRL-2119), and Capan-1 (adenocarcinoma, liver metastasis, ATCC No. HTB-79). The Northern blot was probed with a full length cDNA clone of PSCA which detected PSCA transcripts in two pancreatic cancer cell lines, HPAC and Capan-1 (FIG. 63).

A Western blot analysis using the PSCA mAb 1G8 detected high levels of PSCA protein in the HPAC cell line and lower levels in Capan-1 and ASPC-1 (adenocarcinoma, ascites, ATCC No. CRL-1682) (FIG. 64).

Example 8

PSCA Gene Amplification in Prostate Cancer

This experiment shows that PSCA gene copy number is increased similar to an increase in copy number of c-myc (FIG. 17). This is important because c-myc amplification correlates with poor outcome. Thus, the data suggests that PSCA amplification may also be a predictor for poor outcome.

FISH with Chromosome Enumeration Probes and a Probe for c-Myc.

The method of FISH is well known (Qian, J. et al., "Chromosomal Anomalies in Prostatic Intraepithelial Neoplasia and Carcinoma Detected by Fluorescence in vivo Hybridization," *Cancer Research,* 1995, 55:5408–5414.) Briefly, tissue sections (samples 34 and 75 were from two patients) were deparaffinized, dehydrated, incubated in 2×SSC at 75° C. for 15 min, digested in pepsin solution [4 mg/ml in 0.9% NaCl (pH 1.5)] for 15 min at 37° C., rinsed in 2×SSC at room temperature for 5 min, and air-dried.

Directly labeled fluorescent DNA probes for PSCA and for the 8q24 (c-myc) region were chosen. The PSCA cDNA (SEQ ID NO:1) (FIG. 1A) was used to identify a 130 kb bacterial artificial chromosome (bac) clone (PSCA probe) that in turn was used in the FISH analysis in accordance with the manufacturer's protocol (Genome Systems Inc.) The bac clone so identified and used in the FISH analysis was BACH-265B12 (Genome Systems, Inc. control number 17424).

Dual-probe hybridization was performed on the serial 5-μm sections using a SG-labeled PSCA probe together with a SO-labeled probe for 8q24 (c-myc). Probes and target DNA were denatured simultaneously in an 80° C. oven for 5 min. and each slide was incubated at 37° C. overnight.

Posthybridization washes were performed in 1.5 M urea/ 0.1×SSC at 45° C. for 30 min and in 2×SSC at room temperature for 2 min. Nuclei were counter-stained with 4.6-diamidino-2-phenylindole and anilfade compound p-phenylenediamine.

The number of FISH signals was counted with a Zeiss Axioplan microscope equipped with a triple-pass filter (I02-104-1010; VYSIS). The number of c-myc signals and PSCA signals were counted for each nucleus, and an overall mean c-myc:PSCA ratio was calculated. Results are shown in FIG. 17.

The results show that PSCA gene copy number increased in prostate cancer samples (FIG. 17). The PSCA gene is located at 8q24.2. The increase in gene copy number is due to both a gain in chromosome 8, and amplification of the PSCA gene (FIG. 17). Interestingly, the increase in PSCA gene copy number is similar to an increase in gene copy number of c-myc (FIG. 17) which is also located at 8q24. A previous study has demonstrated that a gain of chromosome 8 and amplification of c-myc are potential markers of prostate carcinoma progression (R B Jenkins et al 1997 *Cancer Research* 57: 524–531).

Example 9

Reporter Gene Construct using the hPSCA 9 kb Upstream Region to Drive Luciferase Expression The 14 kb Not I genomic fragment encoding the human PSCA gene was isolated from λFIXII library encoding human genomic DNA (Stratagene), by screening the library with a full length human PSCA cDNA probe, as described in example 4 (Sambrook et al., 1989, Molecular Cloning (Cold Spring Harbor). The 14 kb human PSCA genomic fragment includes 9 kb of PSCA upstream sequences that was used to drive expression of a reporter gene.

The reporter gene vectors are depicted in FIG. 42 and were constructed as follows. The 14 kb Not I fragment was sub-cloned from the λ vector into a Bluescript KS vector (Stratagene), resulting in the pBSKS-PSCA (14 kb) construct. The PSCA upstream sequence was subcloned from pBSKS-PSCA (14 kb) by PCR amplification using a primer corresponding to the T7 sequence contained within the Bluescript vector, and a primer corresponding to a sequence contained within PSCA exon 1 (primer H3hPSCA3'-5, the sequence of this primer is as follows: The sequence of H3hPSCA3'-5 is 5'-gggaagcttgcacagccttcagggtc-3'. The primer corresponding to PSCA exon 1 contained an introduced HindIII sequence to allow further subcloning following PCR amplification. The resulting amplified fragment was digested with HindIII and was subcloned into the pGL3-basic vector (Promega) to generate pGL3-PSCA (7 kb) which was used to generate a series of deletion reporter gene constructs containing varying lengths of PSCA upstream sequences operatively linked to the luciferase gene (FIG. 42). The deleted portions of the PSCA upstream regions were obtained by subcloning restriction fragments from pGL3-PSCA (7 kb). The PSCA upstream region between -9 kb and -7 kb was subcloned from the pBSKS-PSCA (14 kb) construct, the Not I site was converted into a blunt end by Klenow and the fragment was cloned into the SacI/HindIII sites of pGL-PSCA (7 kb) in order to obtain the pGL3-PSCA (9 kb) construct. The reference to the sequences upstream of the PSCA coding region, such as -9 kb and -6 kb (etc.), are relative to the ATG start translation codon. The reporter gene constructs pGL3-PSCA (9 kb), pGL3-PSCA (6 kb), pGL3-PSCA (3 kb), and pGL3-PSCA (1 kb) were operatively linked to the luciferase gene (FIG. 42). Plasmid, pGL3-CMV contains the cytomegalovirus promoter (Boshart, M. et al., 1985 *Cell* 41:521–530) linked to the luciferase gene and was used as a positive control. Also, plasmid pGL3 contains no promoter sequence and was used as a negative control plasmid.

Example 10

Transfection Assay using a Reporter Gene Construct Containing the hPSCA Upstream Region Triplicate dishes of prostate and non-prostate cell lines were transfected by Tfx50 (Boeringer Manheim) with the PSCA construct pGL3-PSCA (9 kb), or the positive control construct, pGL3-CMV both described in Example 9 above, and assayed for luciferase activity (FIG. 43). The cells and cell lines transfected include PrEC (androgen-independent prostate basal cell), LNCaP (androgen-dependent prostate secretory cell line), LAPC4 (androgen-dependent prostate cell line), HT1376 (bladder cell line), and 293T (kidney cell line). Expression activities of the constructs are expressed as a percentage of the activity of the CMV promoter. Standard errors are indicated above the bars.

Figure 10A:
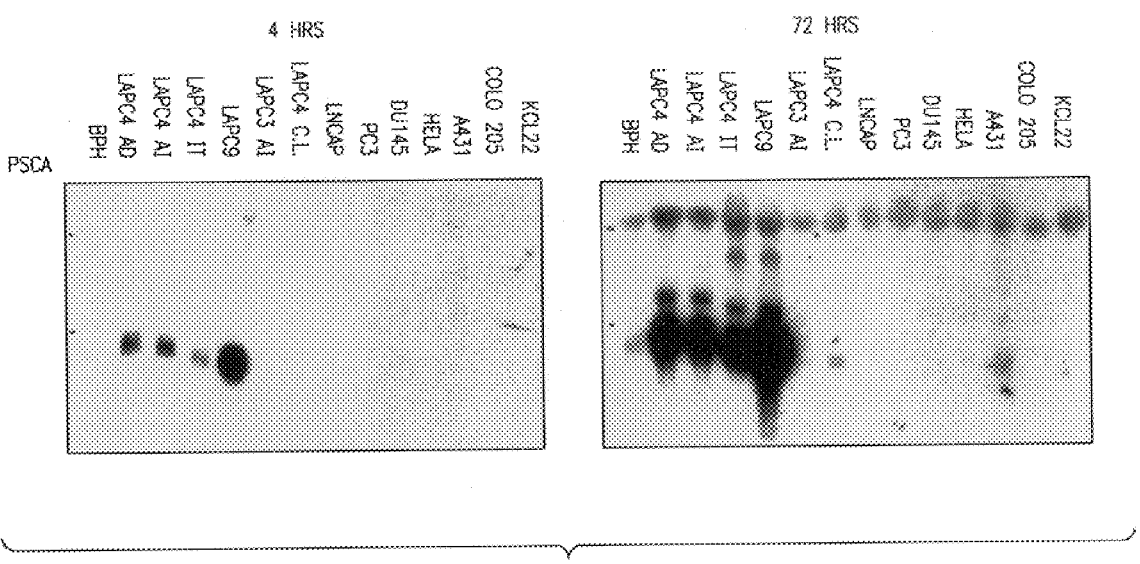
FIG. 10A. Northern blot comparison of PSCA expression in prostate cancer xenografts and tumor cell lines. PSCA demonstrate high level prostate cancer specific gene expression. 10 μg of total RNA from the indicated tissues were size fractionated on an agarose/formaldehyde gel, transferred to nitrocellulose, and hybridized sequentially with $^{32}$P-labelled probes representing PSCA cDNA fragments. Shown are 4 hour and 72 hour autoradiographic exposures of the membrane. BPH, benign prostatic hyperplasia; AD, androgen-dependent; AI, androgen-independent; IT, intratibial xenograft; C.L., cell line.
Figure 10B:
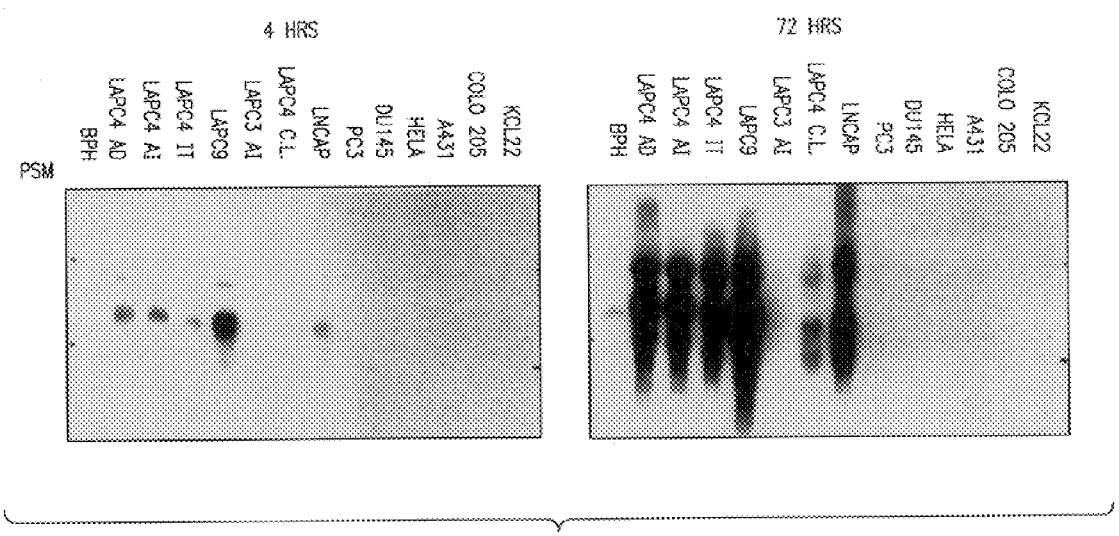
FIG. 10B. Northen blot analysis of PSM expression in prostate cancer xenografts and tumor cell lines. PSM demonstrate high level prostate cancer specific gene expression. 10 μg of total RNA from the indicated tissues were size fractionated on an agarose/formaldehyde gel, transferred to nitrocellulose, and hybridized sequentially with $^{32}$P-labelled probes representing PSM cDNA fragments. Shown are 4 hour and 72 hour autoradiographic exposures of the membrane. BPH, benign prostatic hyperplasia; AD, androgen-dependent; AI, androgen-independent; IT, intratibial xenograft; C.L., cell line.
Figure 10C:
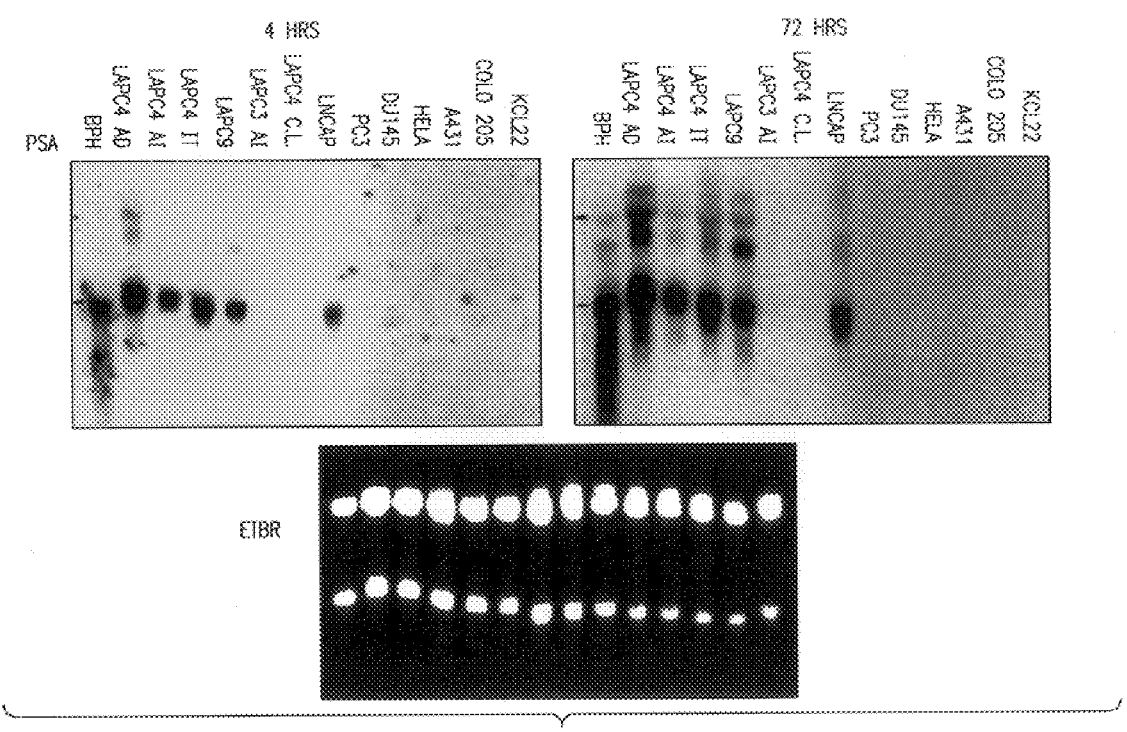
FIG. 10C. Northern blot analysis of PSA expression in prostate cancer xenografts and tumor cell lines. 10 μg of total RNA from the indicated tissues were size fractionated on an agarose/formaldehyde gel, transferred to nitrocellulose, and hybridized sequentially with $^{32}$P-labelled probes representing PSA cDNA fragments. Shown are 4 hour and 72 hour autoradiographic exposures of the membrane and the ethidium bromide gel demonstating equivalent loading of samples. BPH, benign prostatic hyperplasia; AD, androgen-dependent; AI, androgen-independent; IT, intratibial xenograft; C.L., cell line.

The results show that 9 kb of human PSCA upstream sequences drives expression of the luciferase gene in a tissue-specific manner similar to the mRNA expression patterns seen for native hPSCA shown in FIG. 10 (Example 1). Luciferase was readily detectable in both androgen-dependent and androgen-independent prostate cell lines and bladder. Luciferase was also detectable, although at a lower level, in kidney cells.

Example 11

Identification of Regulatory Elements within the PSCA Upstream Region

Triplicate dishes of PrEC (Clonetech) or LNCaP cells were transfected with the reporter gene constructs or the positive control construct described in Example 9 above, and assayed for luciferase activity. The reporter gene constructs comprise various lengths of the hPSCA upstream region operatively linked to the luciferase gene. The positive control construct, pGL3-CMV, comprises the CMV promoter operatively linked to the luciferase. The cells were transfected using a Tfx50 transfection system (Promega). Expression of luciferase in the transfected cells were assayed using a Dual Luciferase Reporter Assay System (Promega), and the level of luciferase expression was measure a relative luciferase unit (RLU).

The ability of the various lengths of the hPSCA upstream region to drive luciferase expression are expressed as a percentage of the activity of the positive control construct containing the CMV promoter. Standard errors are indicated.

The results shown in FIG. 44 demonstrate that 3 kb of hPSCA upstream sequences drives expression of luciferase in both PrEc and LNCAP cells, but the level of detectable luciferase is 6 times higher in the LNCaP cells compared to the PrEC cells. This comparison was based on the level of detectable luciferase. In contrast, 1 kb of hPCSA upstream sequences did not drive expression of luciferase in either cell line.

Example 12

A Targeting Vector

A targeting vector was designed to delete the endogenous PSCA coding region, by homologous recombination. FIG. 40 depicts a targeting vector for the mouse PSCA gene, and the strategy for using the targeting vector to delete the endogenous PSCA gene contained in a mouse cell. A targeting vector comprising a 12 kb SpeI fragment containing mouse PSCA upstream sequences, a Not I/EcoRI fragment containing the PGK promoter operatively linked to a $neo^r$ gene from the pGT-N29 vector (New England BioLabs), and a 3.5 kb BstXI/XhoI fragment containing mouse PSCA downstream sequences. Constitutive expression of the neomycin resistance gene is controlled by the PGK promoter, and allows antibiotic selection of the targeted cells that contain the targeting vector.

As understood by one skilled in the art, the targeting vector described here includes but is not limited to the $neo^r$ gene for selection of the cells that contain the targeting vector or can contain no selectable reporter gene. The targeting vector can also be used to generate transgenic mice, known in the art as knock-in or knock-out mice, depending on whether the targeting vector contains a reporter gene or not, respectively. The transgenic mice can be used as an animal model to study the function of the PSCA gene in prostate development of mice.

As an example that is not intended to be limiting, the targeting vector was used to delete the wild type endogenous genomic mouse PSCA coding sequences in embryonic stem cells (ES) cells to generate cells that are heterozygous, containing a deleted PSCA gene. For example, the heterozygous cells generated using the targeting vector are PSCA+/$neo^r$ as shown by the results in FIG. 40. The phenotype of the heterozygous cells or transgenic mice can be compared with that of wild type PSCA cells or animals.

The targeting vector was constructed as follows. The ends of the 12 kb SpeI fragment containing the PSCA upstream and part of exon 1 sequences was blunt-ended and linked to the blunt-ended NotI/EcoRI fragment from pGT-N29 (BioLabs) containing the neomycin-resistance gene. The 3' end of the neomycin-resistance gene was linked to a blunt-ended 3.5 kb BstXI/XhoI fragment containing part of PSCA exon 3 and the downstream sequences. The resulting fragment was cloned into pGT-N29 to generate the targeting vector pGT-N29-mPSCA5'/3'.

The targeting vector was transfected into ES cells by electroporation using the method described in the following: Teratocarcinomas and Embryonic Stem Cells; A Practical Approach. IRL Press, Oxford (1987). Neomycin-resistant cells were selected and genomic DNA was isolated from the selected cells. A genomic Southern analysis was performed to determine the outcome of the homologous recombination reaction. 10 μg of DNA from the homologous recombination reaction and non-targeted ES cells were digested with EcoRI and analyzed by the Southern blot method (Southern, EM 1975 J. Molec. Biol. 98:503). The blot was probed with a XhoI/EcoRI fragment that contains sequences 3' to the PSCA coding region. The results show that the probe detects a 10 kb fragment that corresponds to the control non-targeted cells that are PSCA+/PSCA+, and a 4 kb fragment that corresponds to the targeted cells that are heterozygous and contain PSCA+/$neo^r$.

Example 13

Transgenic Mouse Models for Prostate Cancer

The present invention contemplates a strategy to generate transgenic mouse models for prostate cancer, using the upstream regions of the PSCA gene to drive expression of an oncogene, to induce tumor formation in prostate basal cells. As shown in FIG. 41, the strategy involves administration, e.g., microinjection, of a chimeric oncogene vector, comprising the upstream region of the PSCA gene operatively linked to a transgene that encodes a gene product that induces formation of a tumor. Other researchers have used this technique, using different prostate and non-prostate regulatory sequences operatively linked to an oncogene. For example, C3(1) is a prostate-predominant regulatory sequence (Moroulakou et al 1994 Proc. Nat. Acad. Sci. 91: 11236–11240) and probasin is a prostate-specific regulatory sequence (Greenberg et al 1995 Proc. Nat. Acad. Sci. 92: 3439–3443), and both of these regulatory sequences drive expression of a transgene in prostate secretory cells. Cryptdin2 is a small-intestine predominant regulatory sequence (Garagenian et al Proc. Nat. Acad. Sci. 95: 15382–15387) that caused expression of an oncogene in prostate endocrine cells. In contrast, the present invention contemplates using the PSCA upstream region to drive expression of an oncogene in prostate basal cells, in order to generate a transgenic mouse model for prostate cancer.

The clinical characteristics of the induced prostate tumor can be analyzed and compared with known characteristics of tumors caused by the particular oncogene used in constructing the chimeric oncogene vector. In addition, various tissues and organs of the transgenic mouse can be analyzed by DNA, RNA and proteins analyses to ascertain the presence and expression patterns of the chimeric oncogene vector.

Example 14

Transgenic Mice Carrying Chimeric Vectors Comprising hPSCA Upstream Sequences and a Transgene The expression patterns of transgenes under the control of hPSCA upstream regions will be tested. Toward this end, chimeric mice carrying chimeric vectors comprising hPSCA upstream sequences and a transgene have been generated. Chimeric vectors comprising 9 kb or 6 kb of hPSCA upstream sequences operatively linked to a transgene were constructed, and are schematically represented in FIG. 45. The transgenes included green fluorescent protein cDNA (GFP, Clontech) linked to the SV40 polyadenylation sequence (PSCA (9 kb)-GFP and PSCA (6 kb)-GFP), green fluorescent protein cDNA linked to a 3' region of the human growth hormone that contains an intron cassette that confers stability to mRNA (PSCA (9 kb)-GFP-3'hGH and PSCA (6 kb)-GFP-3'hGH) (Brinster et al 1988 PNAS 85: 836–840), and the genomic fragment encoding SV40 small and large T antigen including an intron (PSCA (9 kb)-SV40TAG and PSCA (6 kb)-SV40TAG) (Brinster et al 1984 Cell 37:367–379).

The chimeric vectors were used to generate a line of founder transgenic mice. Linearized chimeric vectors were microinjected into fertilized mouse eggs derived from intercrosses of C57BL/6X C3H hybrid mice. Founder mice that carried the chimeric vector were identified by Southern analysis of tail DNA, using GFP cDNA or SV40 genomic DNA as a probe. The number of founders of each transgenic mouse line is indicated on the right panel of FIG. 45.

Example 15 hPSCA Upstream Sequences Drives Expression of Transgene in Transgenic Mice

Two independent founder mice carrying PSCA (9 kb)-GFP transgene were bred to Balb/c mice to obtain their offspring. At age of 8 weeks and 12 weeks, male and female transgenic or non-transgenic littermates were sacrificed. After sacrifice, all urogenital and other tissues were tested for GFP expression by observing the fixed tissues under fluorescent illumination. The results shown in FIG. 46 show green fluorescent images of prostate, bladder and skin tissues from a non transgenic and a transgenic mouse. One out of two founder lines expressed GFP protein in prostate, bladder and skin (FIG. 46). Tissues that did not express GFP include: seminal vesicle, liver, stomach, kidney, lung, brain, testis, pancreas, heart, skeletal muscle, small intestine, colon, placenta.

Example 16

Transcript Expression Pattern of PSCA in Human and Mouse Tissue

The upper panel of FIG. 47 shows a human multiple tissue Northern blot (obtained from Clonetech), probed with a full length human PSCA cDNA probe. The results demonstrate that human PSCA transcripts are abundant in prostate, and less abundant but readily detectable in placenta, but not detectable in spleen, thymus, testis ovary, small intestine, colon, peripheral blood leukocytes (PBL), heart, brain, lung, liver, muscle, kidney and pancreas.

The lower panel of FIG. 47 shows an ethidium bromide-stained agarose gel of RT-PCR analysis of murine PSCA transcript expression patterns in various mouse tissues. The RT-PCR was prepared using Ultraspec.RNA (Biotex), and cDNA cycle kit (Invitrogen). Primers corresponding to a region within exon 1 and exon 3 of PSCA were used to amplify a 320 bp fragment. The exon 1 primer sequence is as follows: 5' primer: 5'-TTCTCCTGCTGGCCACCTAC-3' (SEQ ID NO:8). The exon 3 primer sequence is as follows: 3' primer: 5'-GCAGCTCATCCCTTCACAAT-3' (SEQ ID NO:9). As a control, to demonstrate the integrity of the RNA samples isolated from the various mouse tissues, a 300 bp G3PD fragment was amplified.

The results shown in the lower panel of FIG. 47 demonstrate that murine PSCA transcripts are detectable in dorsal/lateral prostate, ventral prostate, bladder, stomach (cardiac, body and pyloric), and skin. In contrast, murine PSCA transcripts are not detectable in anterior prostate, ventral prostate, seminal vesicle, urethra, testis, kidney, duodenum, small intestine, colon, salivary gland, spleen, thymus, bone marrow, skeletal muscle, heart, brain, eye, lung and liver. The G3PDH results demonstrate that the transcripts isolated from various mouse tissue were intact.

Example 17

Immunohistochemical Evidence of High Level Overexpression of PSCA in Bladder Cancer The following example demonstrates that PSCA protein is highly overexpressed in various grades of bladder carcinoma as determined by immunohistochemical staining of paraffin-embedded bladder and bladder carcinoma tissue sections using PSCA mAb 1G8. Specifically, the following four tissues were examined: (A) normal bladder, (B) non-invasive superficial papillar, (C) carcinoma in situ (a high grade pre-cancerous lesion, (D) invasive bladder cancer.

Figure 62:
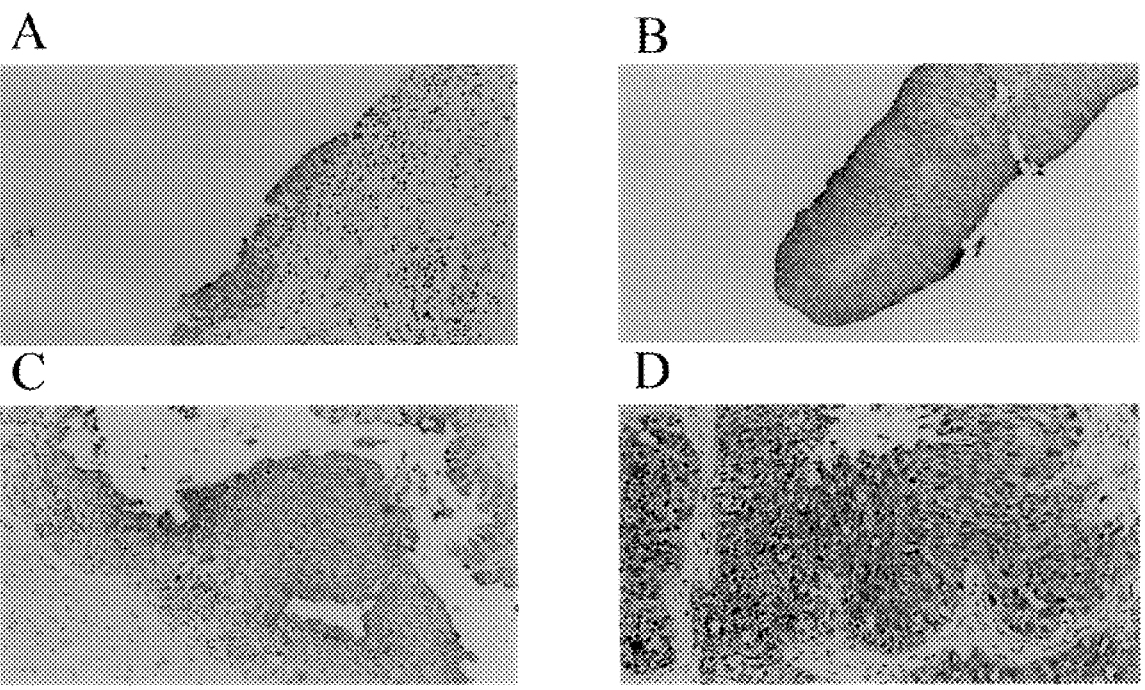

The results are shown in FIG. 62. PSCA is expressed at low levels in the transitional epithelium of normal bladder tissue. Very high level expression was detected in the carcinoma in situ sample, in all cell layers. In the invasive bladder carcinoma sample, very strong staining was seen, again in all cells. Lower level staining was observed in the superficial papillar sample. These results suggest that PSCA expression levels may correlate with increasing grade.

In addition to the above study, preliminary results from an immunohistochemical analysis of PSCA expression in a large number of bladder and bladder carcinoma tissue specimens indicates the following (1) normal bladder expresses low levels of PSCA in the transitional eptihelium; similar levels of expression are seen in low grade, papillary, non-invasive lesions; (2) carcinoma in situ, a high grade, often quite aggressive precancerous lesion, is almost always (90%) intensely positive for PSCA in all cells; (3) PSCA is expressed intensely by ~30% of invasive cancers, i.e. overexpressed when compared to normal bladder; and (4) metastases are intensely positive for PSCA.

Example 18

PSCA Monoclonal Antibody Mediated Inhibition of Prostate Tumors in vivo

The following examples demonstrate that unconjugated PSCA monoclonal antibodies inhibit the growth of human prostate tumor xenografts grown in SCID mice, both when administered alone or in combination.

A. Tumor inhibition using multiple unconjugated PSCA mAbs—Study 1

MATERIALS AND METHODS

Anti-PSCA Monoclonal Antibodies

Murine monoclonal antibodies were raised against a GST-PSCA fusion protein comprising PSCA amino acid residues 18–98 of the PSCA amino acid sequence (SEQ ID NO:2) (FIG. 1B) and expressed in *E. coli*, utilizing standard monoclonal antibody production methods. The following seven anti-PSCA monoclonal antibodies, produced by the corresponding hybridoma cell lines deposited with the American Type Culture Collection on Dec. 11, 1998, were utilized in this study:

| Antibody | Isotype | ATCC No. |
| --- | --- | --- |
| 1G8 | IgG1 | HB-12612 |
| 2H9 | IgG1 | HB-12614 |
| 2A2 | IgG2a | HB-12613 |
| 3C5 | IgG2a | HB-12616 |
| 3G3 | IgG2a | HB-12615 |

-continued

| Antibody | Isotype | ATCC No. |
|---|---|---|
| 4A10 | IgG2a | HB-12617 |
| 3E6 | IgG3 | HB-12618 |

Antibodies were characterized by ELISA, Western blot, FACS and immunoprecipitation for their capacity to bind PSCA. FIG. 49 shows epitope mapping data for the above seven anti-PSCA mAbs as determined by ELISA and Western analysis, as described in the accompanying figure legend, demonstrating that the seven antibodies recognize different epitopes on the PSCA protein. Immunohistochemical analysis of prostate cancer tissues and cells with these antibodies is described in Examples 5 and 6 infra.

Antibody Formulation

The monoclonal antibodies described above were purified from hybridoma tissue culture supernatants by Protein-G Sepharose chromatography, dialyzed against PBS, and stored at −20° C. Protein determinations were performed by a Bradford assay (Bio-Rad, Hercules, Calif.).

A therapeutic antibody cocktail comprising a mixture of the seven individual monoclonal antibodies, as indicated in Table 2, below, was prepared and used for the treatment of SCID mice receiving subcutaneous injections of LAPC-9 prostate tumor xenografts. Mouse IgG, purchased from ICN (Costa Mesa, Calif.) was used as non-specific control antibody. Prior to injection into mice, all antibodies were sterilized using a 0.22-micron filter.

TABLE 2

Anti-PSCA Antibody Cocktail

| Monoclonal Antibody | Isotype | Amount (% of total) |
|---|---|---|
| 1G8 | IgG1 | 2.0 mg (16.7%) |
| 2H9 | IgG1 | 1.0 mg (8.3%) |
| 2A2 | IgG2a | 2.5 mg (20.8%) |
| 3C5 | IgG2a | 2.0 mg (16.7%) |
| 3G3 | IgG2a | 2.5 mg (20.8%) |
| 4A10 | IgG2a | 1.5 mg (12.5%) |
| 3E6 | IgG3 | 0.5 mg (4.2%) |

Introduction of Prostate Cancer Xenografts into SCID Mice

The human prostate cancer xenograft line LAPC-9, which expresses very high levels of PSCA, was used to produce tumors in SCID mice (PCT Application No. WO98/16628, supra; Klein et al., 1987, supra).

For injection into IcR-SCID mice (Taconic Farms, Germantown, N.Y.), a single-cell suspension of LAPC-9 was prepared as follows. An LAPC-9 xenograft tumor of approximately 2.0 g in size was harvested from a SCID mouse, minced into very small pieces using scissors and forceps, washed once in RPMI, and digested in a 1% solution of pronase for 20 minutes. After digestion, the cell suspension was washed twice in RPMI, and resuspended in 10 ml of PrEGM medium (Clonetics, Walkersville, Md.). After overnight incubation, the cells were harvested and washed once in PrEGM, then passed through a 200-micron nylon filter to remove large clumps and debris. Cells passing through the filter were collected, centrifuged, and resuspended in PrEGM medium. Cells were then counted, and the appropriate number of cells was transferred to a new tube, centrifuged, and resuspended at 2×concentration in RPMI. An equal volume of ice cold Matrigel was then added to the cell suspension, and the suspension was kept on ice prior to injection. For injection, male IcR-SCID mice were shaved on their flanks, and each mouse received a single subcutaneous (s.c.) injection of $1\times10^6$ cells in a volume of 100 μl on the right flank. Mice injected with tumor cells were treated with either control antibodies or the anti-PSCA monoclonal antibody preparation as described below.

Treatment Protocol

Twenty SCID mice injected with tumor cells were treated with either control antibodies (mouse IgG) or the anti-PSCA monoclonal antibody cocktail (above) as follows. Ten mice were treated with mouse IgG control antibody and ten mice were treated with the anti-PSCA monoclonal antibody preparation. Injections of 200 μg of the mouse IgG control antibody or the anti-PSCA monoclonal antibody cocktail were administered intraperitoneally on days −1, +3, +7, +11, +14, and +21 relative to the injection of the tumor cells. Growth of LAPC-9 tumors was followed by caliper measurements to determine tumor volumes on days +32, +35, +39, +42, +47, +54 and +61 relative to injection of tumor cells. In addition, mice were periodically bled for assaying circulating PSA levels using a commercially available PSA test (American Qualex, San Clemente, Calif.).

One of the mice in the control group (mouse #2) expired during the course of the study and had no detectable tumor at the time.

Results

SCID mice receiving a subcutaneous injection of the LAPC-9 prostate cancer xenograft were treated with either the anti-PSCA mAb preparation or mouse IgG control antibody, as described above. Palpable tumors first appeared in the mouse IgG control group at 4 weeks after tumor cell injection. Tumor volume measurements were initiated on day +32.

The results, which are tabulated in Table 3, below, as well as presented graphically in FIG. 48, show that all of the control mAb-treated mice developed tumors (9 out of 9 surviving, mouse #1, #3–10), but that none of the anti-PSCA mAb treated mice developed any detectable tumor growth (0 out of 10, mouse #11–20). The control-treated animals developed significant tumors rapidly in most instances, and these mice experienced constant tumor growth leading to progressively larger tumor sizes with time. By day 54, all control-treated mice had developed detectable tumors. In sharp contrast to the control-treated group, none of the ten mice treated with the anti-PSCA mAb preparation developed detectable tumors, even after 61 days post xenograft injection.

TABLE 3

Recorded tumor volume ($mm^3$) measurements

| | DAYS | | | | | | |
|---|---|---|---|---|---|---|---|
| MOUSE #* | 32 | 35 | 39 | 42 | 47 | 54 | 61 |
| 1 | 416 | 576 | 578 | 720 | 810 | 1045 | 1080 |
| 2 | 0 | 0 | 0 | 0 | | | |
| 3 | 100 | 269.5 | 450 | 476 | 544 | 648 | 810 |
| 4 | 0 | 0 | 0 | 0 | 0 | 87.5 | 151.3 |
| 5 | 338 | 420 | 800 | 900 | 1087 | 1265 | 2002 |

TABLE 3-continued

Recorded tumor volume (mm³) measurements

| MOUSE #* | DAYS | | | | | | |
|---|---|---|---|---|---|---|---|
| | 32 | 35 | 39 | 42 | 47 | 54 | 61 |
| 6 | 216 | 250.3 | 504 | 476 | 612 | 850.5 | 1050 |
| 7 | 252 | 472.5 | 637.5 | 720 | 720 | 720 | 1306 |
| 8 | 336 | 532 | 560 | 693 | 1080 | 1365 | 1617 |
| 9 | 0 | 160.9 | 225 | 294 | 478 | 640 | 900 |
| 10 | 0 | 0 | 195 | 294 | 341 | 504 | 769.5 |
| 11 | 0 | 0 | 0 | 0 | 0 | 0 | 0 |
| 12 | 0 | 0 | 0 | 0 | 0 | 0 | 0 |
| 13 | 0 | 0 | 0 | 0 | 0 | 0 | 0 |
| 14 | 0 | 0 | 0 | 0 | 0 | 0 | 0 |
| 15 | 0 | 0 | 0 | 0 | 0 | 0 | 0 |
| 16 | 0 | 0 | 0 | 0 | 0 | 0 | 0 |
| 17 | 0 | 0 | 0 | 0 | 0 | 0 | 0 |
| 18 | 0 | 0 | 0 | 0 | 0 | 0 | 0 |
| 19 | 0 | 0 | 0 | 0 | 0 | 0 | 0 |
| 20 | 0 | 0 | 0 | 0 | 0 | 0 | 0 |

*Mice #1–10 represent the group treated with the mouse IgG control antibody. Mice #11–20 represents the group treated with the anti-PSCA mAb cocktail.
*Tumor volume corresponds to length (L) × width (W) × height (H) measurements in mm. To determine the ellipsoid volume represented in FIG. 1, which accurately represents tumor mass (Tomayko and Reynolds, 1989), we used the formula L × W × H × ½.

Clinically, the control treated mice all displayed visual symptoms of progressively poor health as tumors developed and expanded. In contrast, the mice in the anti-PSCA mAb treatment group remained active, vigorous, and generally healthy in appearance throughout the treatment period, suggesting no apparent toxicity or obvious side-effects were associated with the treatment.

In addition to tumor volume, mice were bled for determination of circulating PSA. Circulating PSA levels correlated with increasing tumor volumes in the control group, whereas no detectable PSA was observed in the anti-PSCA mAb treated group throughout the experiment.

B. Tumor inhibition using multiple unconjugated PSCA mAbs—Study 2

To verify the results described in Example 18, supra, a newly prepared anti-PSCA mAb cocktail was evaluated for growth inhibition of LAPC-9 tumor xenografts in vivo, essentially as described above. Briefly, a new batch of each mAb was prepared and mixed together according to the proportions presented in Table 4. All antibodies were tested for PSCA reactivity. SCID mice received a subcutaneous injection of LAPC-9 xenograft cells as described above. The mice were treated with either a cocktail of anti-PSCA mAb, or control preparations of mouse IgG or purified bovine IgG. A bovine IgG control group was included in this study in order to study the effect of bovine IgG co-purified with the anti-PSCA antibodies on protein G-sepharose. Two hundred micrograms of antibody was administered to each mouse by intraperitoneal injection on days −1, +3, +7, +11, +14, and +21 relative to the injection of the tumor cells. Tumor volume corresponding to length (L)×(W)×(H) in mm was monitored by caliper measurements, and serum was collected at weekly intervals. To determine the ellipsoid volume of the tumors, which accurately represents tumor mass, we used the formula L×W×H×½ (Tomayko and Reynolds, 1989).

TABLE 4

Anti-PSCA antibody cocktail 2

| Monoclonal Antibody | Isotype | Amount (% of total) |
|---|---|---|
| 1G8 | IgG1 | 8.0 mg (16.7%) |
| 2H9 | IgG1 | 4.0 mg (8.3%) |
| 2A2 | IgG2a | 10.0 mg (20.8%) |
| 3C5 | IgG2a | 8.0 mg (16.7%) |
| 3G3* | IgG2a | 10.0 mg (20.8%) |
| 4A10 | IgG2a | 6.0 mg (12.5%) |
| 3E6 | IgG3 | 2.0 mg (4.2%) |

*One of the monoclonal antibody preparations used to formulate this cocktail, 3G3, demonstrated weak activity.

The results of this study are presented in FIG. 53 and confirm the results generated from the study described in Example 18-A, supra. Animals in the anti-PSCA treated group experienced significant inhibition of tumor cell growth compared with both of the control groups. No detectable difference in tumor growth was observed in mice that received either bovine IgG or murine IgG. The tumors in the control groups grew at equal rates and with similar latency. In contrast, LAPC-9 tumors in mice receiving the anti-PSCA antibody cocktail exhibited a longer latency, a significantly slower rate of growth and smaller sizes at the end of the experiment. The average tumor volume at the final time point was 1,139 mm³ for mice treated with murine IgG (day 46), 1091 mm³ for mice treated with bovine IgG (day 42) and 391 mm³ for anti-PSCA treated mice (day 46). Due to the large tumor sizes in the bovine IgG treated group, these mice were sacrificed earlier than mice in the other groups. In addition, tumor volume correlated with PSA levels in the serum of the treated mice. Some mice receiving anti-PSCA antibodies showed very small tumors or no tumor growth at all, as was previously observed in the study described in Example 1, supra. No apparent toxicity was associated with administration of any of this antibody cocktail preparation, consistent with the study described in Example 18-A.

C. Tumor inhibition in vivo using single unconjugated PSCA mAbs

Materials and Methods

Several of the monoclonal antibodies described herein were studied for their ability to inhibit the growth of prostate tumor xenografts in their unconjugated (or, "naked") form using the previously described tumor challenge assay (see Examples 18-A and 18-B, above). Generally, the studies were conducted as described above, with slight modifications as described in the results sections presented below for each of the antibodies assayed.

C1: PSCA mAb 1G8

Anti-PSCA monoclonal antibody 1G8 is an IgGI isotype antibody. The antitumor effect of 1G8 was evaluated using the LAPC-9 xenograft and mouse IgG as a control. The results presented in FIG. 54 demonstrate that treatment of mice with the 1G8 antibody inhibited tumor growth. Specifically, the average tumor volume at the final time point for the control group was 854 mm³ versus an average tumor volume of 335 mm³ for the 1G8 antibody treated group. These results show that the 1G8 monoclonal antibody can inhibit the growth of prostate tumors when used alone. As with the studies described supra, there was no apparent toxicity associated with the treatment of these animals with the 1G8 mAb.

The effect of the 1G8 monoclonal antibody on the growth of prostate cancers generated with PC-3 cells was also determined. PC-3 cells do not express PSCA. As shown in FIG. 65, the 1G8 antibody had no effect on the development of PC-3 xenograft tumors, in sharp contrast to its effect on PSCA-expressing LAPC-9 xenografts. These results clearly show that the 1G8 antibody is inhibiting tumor cell growth through the PSCA antigen.

C2: PSCA mAbs 2A2 and 2H9

Two anti-PSCA monoclonal antibodies of different isotypes were evaluated simultaneously for prostate tumor growth inhibition in vivo. Anti-PSCA mAbs 2A2 (IgG2a isotype) and 2H9 (IgG1 isotype) were tested for prostate tumor inhibition as described in Example 18-C1, immediately above. The results presented in FIG. 55 demonstrate striking inhibition of tumor cell growth in the anti-PSCA mAb treated groups versus the control groups. Specifically, the average tumor volume at the final time point was 483 mm$^3$ for mice treated with murine IgG (day 42), 49 mm$^3$ for mice treated with the 2A2 mAb (day 42), and 72 mm$^3$ for the mice treated with 2H9 mAb (day 42). More significantly, tumor incidence was 6/6 mice in the mouse IgG control group, versus 2/7 for the 2A2-treated group and 1/7 for the 2H9-treated group. In the 2A2 treated group, the first tumor appeared at day 25 and the second tumor at day 42. In the 2H9 treated group the single tumor present appeared at day 21. In the mouse IgG control group, 4/6 of the mice had developed tumors by day 21. As with the in vivo studies described above, there was no apparent toxicity associated with the treatment of these animals with the 2A2 or 2H9 mAbs.

PSA levels in the serum of the treated mice were significantly lower than in control mice, and correlated directly with tumor volume (FIG. 56). At week 6, the mean PSA serum level in the mouse IgG control group was 35 ng/ml, 2 ng/ml in the 2A2 group, and 8 ng/ml in the 2H9 group.

This study further supports the conclusion that a single "naked" anti-PSCA monoclonal antibody is sufficient for anti-tumor activity. In addition, these data demonstrate that mAbs recognizing different PSCA epitopes are effective, and that the anti-tumor effect is not dependent upon a single IgG isotype since both IgG1 (1G8, 2H9) and IgG2a (2A2) mAbs inhibited tumor growth.

C3: PSCA mAbs exert growth inhibitory effect specifically through PSCA

In order to demonstrate that PSCA mAbs exert tumor growth inhibition specifically through the PSCA protein, a tumor inhibition study with the 1G8 mAb and PC-3 tumor xenografts was conducted. PC-3 cells do not express endogenous PSCA. This study was conducted as described in Section C1 of this Example, above. The results, shown in FIG. 65, show that the PSCA mAb 1G8 had no effect on the growth of PC-3 tumors in mice over a 40 day period. The results are shown, for comparison, together with a parallel study of the effect of 1G8 on LAPC-9 prostate tumor xenografts (Example C1, above).

C4: PSCA mAb 3C5 inhibits the growth of established LAPC-9 prostate tumors in vivo In order to determine whether PSCA mAbs could effect growth of established tumors, the following study was conducted. Briefly, a cohort of SCID mice were injected with 10$^6$ LAPC-9 cells SQ, essentially as described in examples C1 and C2. After tumors reached a size of approximately 100 cubic millimeters, mice were segregated into two groups, a control group receiving mouse IgG and a treatment group receiving PSCA mAb 3C5. Each mouse was injected IP with control IgG or 3C5 mAb according to the following protocol: 1 mg per injection, three times per week for the first 2 weeks, followed by two times per week in the third week. Tumor volume and PSA measurements were determined as above. The results, shown in FIG. 57, indicate that the 3C5 mAb inhibits the growth of established LAPC-9 prostate tumors in vivo. In at least some of the treatment group mice, tumor regression up to 50% of the initial, pre-treatment size of the tumor was observed.

Example 19

In vitro Assays for Characterizing PSCA Monoclonal Antibodies

19-A: Antibody-dependent cell cytotoxicity assay

To determine if the anti-PSCA mAbs sensitize tumor cells to ADCC, the following assay is performed. First, for NK cell mediated ADCC, spleen cells from SCID mice are cultured for 5 days in vitro as described by Hooijberg et al., 1995, Cancer Res. 55: 2627-2634. The activated cells are then co-cultured with $^{51}$Cr-labeled LAPC-9, LNCaP-PSCA, or LNCaP target cells for four hours in the presence of either anti-PSCA mAbs or a control mouse IgG. LNCaP serves as a negative control in all assays since it does not express PSCA. If single mAbs are used, the respective mouse IgG isotype control is also used. NK activity of the activated spleen cells is determined by incubation with the murine NK-sensitive target YAC-1. In all cases, killing is determined by $^{51}$Cr-release into the medium. Spontaneous release is determined after incubation of labeled cells only, and total release by incubation of labeled cells with 5% Triton X-100. The percent of specific cell lysis is determined by:

$$\% \text{ Cell Lysis} = \frac{\text{Experimental}^{51}Cr \text{ release} - \text{spontaneous}^{51}Cr \text{ release}}{\text{Total}^{51} Cr \text{ release} - \text{spontaneous}^{51} Cr \text{ release}}$$

19-B: Antibody-dependent macrophage-mediated cytotoxicity assay

To determine whether the anti-PSCA mAbs sensitize tumor cells to ADMMC, the following assay is performed. Peritoneal macrophages are activated by intraperitoneal injection of SCID mice with Brewer's thioglycollate medium as described by Larson et al., 1988, Int. J. Cancer 42: 877–882. After four days, cells are collected by intraperitoneal lavage, and the percent of activated macrophages determined by Mac-1 staining. For the assay, the activated macrophages are co-cultured with $^3$H-thymidine labeled LAPC-9, LNCaP-PSCA, and LNCaP target cells for 48 hours in the presence of either anti-PSCA mAbs or control mouse IgG. At the end of the assay, supernatants are harvested from the wells and killing is determined by the amount of $^3$H-thymidine released as described above for $^{51}$Cr release.

19-C: Complement-mediated tumor cell lysis assay

Destruction of tumor targets by complement-dependent lysis may be performed according to the method described by Huang et al., 1995, Cancer Res. 55: 610–616. For example, LAPC-9, LNCaP-PSCA, and LNCaP cells are labeled with $^{51}$Cr and then incubated on ice for 30' with either anti-PSCA mAbs or a mouse IgG control. After washing to remove unbound antibody, the cells are incubated with rabbit complement at 37° C. for 2 hr, and cell lysis measured by $^{51}$Cr-release into the supernatant. The percent cell lysis will be determined as described above.

19-D: Cell proliferation assay

The effect of anti-PSCA mAbs on cell proliferation may be determined by an MTT assay. Briefly, LNCaP-PSCA or LNCaP cells are cultured for 72 hr with varying amounts of either anti-PSCA mAbs or mouse IgG as a control. At the end of the incubation period, the cells are washed and incubated in a solution of MTT for 4 hr. Proliferation is indicated by dehydrogenase mediated conversion of the MTT solution to a purple color and measured at a wavelength of 570 nm.

19-E: Assay for colony formation in soft agar

Colony formation in the presence of anti-PSCA mAbs may be measured by growth of cells in soft agar. Briefly, $1 \times 10^4$ LNCaP-PSCA or LNCAP cells are plated in medium containing Nobel agar. A dilution series of anti-PSCA mAbs is then added to plates in duplicate to determine the effect on colony growth. Mouse IgG is used as a control. Macroscopic colonies are counted after 14–21 days in culture.

Example 20

PSCA capture ELISA

A PSCA capture ELISA was developed in order to measure PSCA levels in serum prior to treatment with anti-PSCA mAbs and provides information useful in determining the therapeutic dosage regimen. The assay may also be useful in monitoring patient response to the therapy.

A schematic representation of the assay format is shown in FIG. 50B. Briefly, affinity purified anti-PSCA peptide sheep polyclonal antibody (directed against amino acids 67-81 of the PSCA protein) and anti-PSCA monoclonal antibody 1G8 are used as capture antibodies and are coated microtiter wells. After coating, incubation with a dilution series of test antigen is conducted in order to generate a standard curve. Patient serum is added to the wells and incubated at room temperature. After incubation, unbound antibody is washed with PBS. Anti-PSCA monoclonal antibodies 2A2, 3C5 and 4A10 (IgG2a isotype), which recognize different epitopes on the PSCA protein, are used as detection antibodies, and are added to the wells, incubated, and the wells washed to remove unbound antibody. The captured reaction is then visualized by the addition of an anti-mouse Ig2a-horseradish peroxidase-conjugated secondary antibody followed by development with 3,3' 5,5' tetramethylbenzidine base substrate and OD determinations taken.

A schematic representation of the standardization and control antigens are shown in FIG. 50A. Briefly, a GST-fusion protein encoding amino acids 18–98 of PSCA is used for generating a standard curve for quantification of unknown samples. A secreted recombinant mammalian expressed form of PSCA is used for quality control of the ELISA assay. This protein contains an Ig leader sequence to direct secretion of the recombinant protein and MYC and 6XHIS epitope tags for affinity purification.

Figure 51:
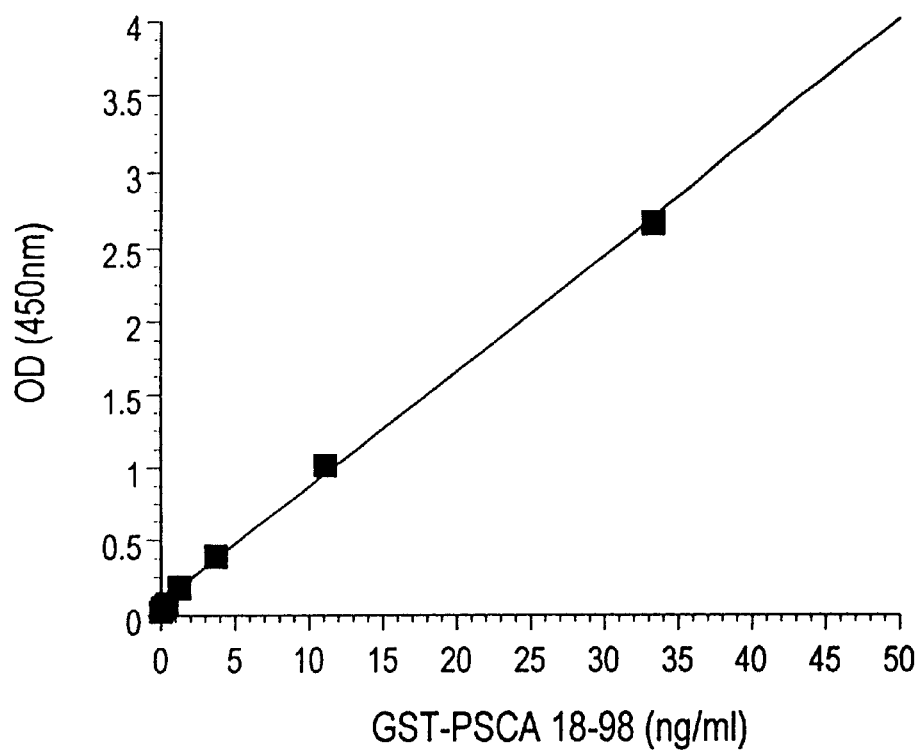

Quantification of recombinant PSCA secreted from 293T cells engineered to express and secrete PSCA is shown in FIG. 51.

Example 21

Sequence of PSCA mAb Genes

The nucleotide sequences of the genes encoding the heavy chain variable regions of murine monoclonal antibodies 1G8, 4A10 and 2H9 were determined using the methods described in Coloma et al., 1992, J Immunol. Methods 153: 89–104. Primers for heavy chain variable region sequencing of mAbs 1G8 and 4A10 were as follows:

HLEAD.1: ggc gat atc cac cat ggR atg Sag ctg Kgt Mat Sct ctt

CH3': agg gaa ttc aYc tcc aca cac agg RRc cag tgg ata gac

Primers for heavy chain variable region sequencing of mAb 2H9 were as follows:

HLEAD.2: ggg gat atc cac cat gRa ctt cgg gYt gag ctK ggt ttt

CH3': agg gaa ttc aYc tcc aca cac agg RRc cag tgg ata gac

Total RNA was isolated from 1G8, 2H9, and 4A10 hybridoma cells using the Trizol Reagent (Gibco-BRL cat#15596). First strand synthesis reactions on 5 pg of RNA were generated using the Gibco-BRL Superscript II reverse transcriptase reaction according to manufacturers protocols and CH3'. Two μl of the 30 μl first strand reaction was used in the PCR to amplify the variable regions.

First strand cDNA was synthesized from hybridoma RNA using a primer from the constant region of the heavy chain (CH3'). The variable region was amplified using CH3' and a primer designed to the leader sequence (HLEAD.1 and HLEAD.2). The resulting PCR product is sequenced and the complementarity determining regions (CDRs) are determined using the Kabat rules. The nucleotide (SEQ ID NOS:10, 12, and 14) and amino acid (SEQ. ID NO:11, 13, and 15) sequences are shown in FIGS. 58, 59 and 60. An amino acid alignment of the CDRs of these three Mabs is shown in FIG. 61.

Example 22

PSCA mAb Binding Affinity

The affinity of PSCA monoclonal antibody 1G8 (described above) was determined using BIAcore™ instrumentation (Uppsala, Sweden), which uses surface plasmon resonance (SPR, Welford K. 1991, Opt. Quant. Elect. 23:1; Morton and Myszka, 1998, Methods in Enzymology 295: 268) to monitor biomolecular interactions in real time. On the basis of general procedures outlined by the manufacturer (Pharmacia), kinetic analysis of the antibody was performed using a recombinant PSCA immobilized onto the sensor surface at a low density (30 RU). Recombinant PSCA was generated as follows. 293T cells transiently transfected or 293 cells stably expressing a CMV-driven expression vector encoding PSCA with a C-terminal 6XHis and MYC tag (pcDNA3.1/mycHIS, Invitrogen) served as source of secreted soluble PSCA protein for purification. The HIS-tagged PSCA protein was purified over a nickel column using standard techniques. The association and dissociation rates were determined using the software provided by the manufacturer. The results, tabulated below (Table 5), show that 1G8 has a 1 nanomolar $K_D$, indicating a strong affinity for the PSCA antigen.

TABLE 5

BIOCORE AFFINITY DETERMINATION OF PSCA mAb 1G8

| mAb in solution | | |
| --- | --- | --- |
| $k_a(M^{-1}s^{-1})$ | $k_d(M^{-1}s^{-1})$ | $K_D(nM)$ |
| $1.68 \times 10^5$ | $1.69 \times 10^{-4}$ | 1.0 |

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Example 23

Immunohistochemical Analysis

This example describes immunohistochemical (IHC) analysis of various formalin-fixed, paraffin-embedded tissues with the seven anti-PSCA mAbs described supra.

MATERIALS AND METHODS

Each of the seven anti-PSCA monoclonal antibodies was tested against: (1) a cell pellet consisting of LNCaP over-expressing PSCA, LNCaP parental, and 293T cells; (2) LAPC9AD xenograft; and (3) benign prostatic hyperplasia (BPH), prostate carcinoma, and normal prostate tissues. All tissue staining was performed by QualTek Molecular Laboratories, Inc (Santa Barbara, Calif.). Tissue blocks were sectioned at 4 microns and placed onto positively charged Capillary Gap microscope slides (Ventana Medical Systems, Inc., Tucson, Ariz.). After dewaxing in xylene, followed by hydration through alcohol series, tissue sections were pre-treated in a steamer for 20 minutes in the presence of sodium citrate (10 mM, pH 6.0) in order to optimize antibody reactivity.

After cooling for 5 minutes, the slides were immunostained using an ABC-peroxidase technique. Briefly, slides were incubated in blocking serum (normal goat) for 5 minutes, followed by 2 µg/ml anti-PSCA monoclonal primary antibody or 2 µg/ml mouse IgG for the negative control (25 minutes), biotinylated secondary antibody-goat-anti-mouse IgG (25 min) and avidin-biotin complex (ABC) conjugated to peroxidase enzyme, Vector Labs, Burlingame, Calif. (25 minutes). Between the incubation steps, sections were rinsed in buffer. DAB—Diaminobenzidine chromogen (QualTek Molecular Labs) was used to develop the reaction—yielding a brown precipitate. Slides were subsequently counterstained with hematoxylin and then cover-slipped. Staining was performed on a TechMate 1000 automated staining instrument (Ventana Medical Systems, Inc., Tucson, Ariz.) at room temperature.

Results

FIG. 52 shows the IHC results for the anti-PSCA monoclonal antibody 3C5 in the cell pellet, LAPC9AD xenograft, a BPH sample, and a prostate carcinoma tissue (left panel). The cell pellet mix contains three cell types of which only one, the LNCaP-PSCA cells, are expected to stain with anti-PSCA monoclonal. As expected, 3C5 stains strongly approximately ⅓ of the cells. This staining conveniently shows positive and negatively staining cell types on the same slide. The LAPC9AD xenograft is very strongly stained with 3C5 antibodies. Basal and epithelia cells in the ducts of the BPH tissue stain well but the basal cells are especially prominent. Finally, the prostate carcinoma tissue shows strong staining in the neoplastic ducts. The panel on the right represents the background control consisting of pre-immune mouse serum. No background staining was detectable in any of the samples evaluated.

Example 24

Inhibition of established LAPC-9 tumor growth and prolonged survival following anti-PSCA antibody treatment. The LAPC-9 xenograft was generated from a bone tumor biopsy of a patient with hormone-refractory metastatic prostate cancer.

The following examples demonstrate that anti-PSCA monoclonal antibodies, 1G8 and 3C5, inhibit the growth of established orthotopic, LAPC-9 prostate tumors, in SCID mice and significantly prolonged their survival. The growth of the tumors was monitored by tracking the level of serum PSA.

Orthotopic Injections

A single cell suspension of LAPC-9 tumors was prepared according to the methods described in Example 18-A. The cell suspension was mixed, at a 1:1 dilution, with Matrigel. The cell suspension was kept on ice prior to the orthotopic injections. The orthotopic injections were performed on male IcR-SCID mice, under anesthesia, using ketamine/xylazine. The anesthetized mice were shaved in the lower abdomen, a 5–8 mm incision was made just above the penis to expose the abdominal wall and muscles. An incision was made through the abdominal muscles to expose the bladder and seminal vescicles, which were then delivered through the incision to expose the dorsal prostate. The LAPC-9 cell suspension was injected into each dorsal lobe using a 500 µl Hamilton syringe. Each lobe was injected with 10 µl of cell suspension corresponding to about $5 \times 10^5$ cells. After the injections, both incisions were closed using a running suture and the mice were kept under a heat lamp to recover. After the injections, the serum level of PSA was monitored. The mice were treated with a different regimen of 1G8 or 3C5 antibody, depending on the serum level of PSA. After the antibody treatments, the mice were kept alive, to determine the PSA levels as a measure of the tumor growth, and to determine the survival of the mice in each treatment group.

Monitoring the Serum Levels of PSA

The level of serum PSA was used to track the tumor size. The mice were bled on an approximate weekly basis, to monitor the levels of serum PSA, which were measured using a commercially-available PSA kit (American Qualex, San Clemente, Calif.). The mice were segregated into two treatment groups, based on the levels of serum PSA. For example, the groups included: low levels of PSA (e.g., 2–3 ng/ml; FIG. 66A); and moderate levels of PSA (e.g., 64–78 ng/ml; FIG. 66B). The serum PSA levels were monitored until the tumors were visible through the abdomen.

The serum PSA levels were monitored on days +9, +15, +22, +30, +37, +44, and +51, relative to the day of injection of the tumor cells (FIG. 66A). Similarly, the serum PSA levels were monitored on days +13, +21, +27, and +34 (FIG. 66B), on days +9, +16, +22, +29, and +36 (FIG. 68A), and on days +7, +14, +21, and +28 (FIG. 68B).

Treatment with 1G8

Orthotopic, tumor-bearing mice were established according to the methods described above. Two groups of animals, exhibiting (i) low levels of serum PSA (2–3 ng/ml), or (ii) moderate levels of serum PSA (64–78 ng/ml) were selected for treatment.

The mice having low levels of PSA (e.g., 2–3 ng/ml) were treated with intraperitoneal injection of 2 mg of 1G8 antibody, three times per week for one week, followed by 1 mg of 1G8 three times per week for the next two weeks, followed by 1 mg of 1G8 once per week for the next three weeks (as indicated by the arrows in FIG. 66A).

The mice having moderate levels of PSA (e.g., 64–78 ng/ml) were treated with intraperitoneal injection of 1 mg of 1G8 antibody, three times per week for three consecutive weeks, followed by a single injection of 1 mg of 1G8 the following week (as indicated by the arrows in FIG. 66B).

The control mice, having low or moderate levels of PSA, were treated with about 0.5 to 0.8 ml of phosphate buffer solution (Gibco) (FIGS. 66A and B).

Treatment with 3C5

Similar treatments were performed on orthotopic tumor-bearing mice, using the 3C5 antibody. In the first experiment, 1 mg of 3C5 antibody was administered intraperitoneally three times per week for three consecutive weeks, followed by a single injection of 1 mg of 3C5 (FIG. 68A). In the second experiment, 2 mg of 3C5 was administered three times per week for the first week, followed by 1 mg three times per week for the next two weeks (FIG. 68B). The injections were administered on the days indicated by the arrows in FIGS. 68A and B.

Results—Treatment with 1G8 Results in Inhibition of Tumor Growth and Increased Survival The serum PSA levels of the tumor-bearing mice were used to track the growth of the tumors, since the serum PSA levels correlated well with the tumor size. The mice bearing LAPC-9 AD tumors, treated with the anti-PSCA monoclonal antibody, 1G8, exhibited a reduction in the rate of increase in serum PSA levels (FIGS. 66A and B). This result indicates that 1G8 inhibits growth of tumors expressing PSCA.

In FIG. 66A, each data point represents the mean PSA level for mice receiving PBS (n=6) or 1G8 (n=6). The mice were bled on the days indicated on the X-axis for PSA determinations.

As shown in FIG. 66B, the mice were bled on the days indicated on the X-axis for PSA determinations. Each data point represents the mean PSA level for mice receiving PBS (n=4) or 1G8 (n=5). In FIG. 67, 4 mice in the PBS-treated group and 5 mice in the 1G8-treated group.

Additionally, the mice having lower serum PSA levels that were treated with the 1G8 antibody exhibited a reduced rate of increase in the level of serum PSA, compared to the mice having higher serum PSA levels that were treated with the 1G8 antibody (e.g., compare the data described by (■) in FIGS. 66A and B). This result suggests that the 1G8 antibody was more effective at reducing tumor growth, when there was a smaller tumor burden, under the administration protocol of this study.

The affect of the 1G8 treatment on survival of the tumor-bearing mice was also monitored. In general, the mice treated with only PBS began to die within 5–6 weeks post-injection, due to local tumor growth and metastasis. In contrast, the mice treated with 1G8 antibody exhibited a prolonged life. For example, the effect on survival was more dramatic in the mice having low serum PSA levels (FIG. 67A), where the median survival time in the PBS-treated mice was 56.5 days (range 42–71 days) and the median survival time in the 1G8-treated mice was 89 days (range 77–101). In the mice having moderate serum PSA levels (FIG. 67B) the median survival time in PBS-treated mice was 40 days (range 32–48 days) compared to a median survival time of 78.5 days (range 52–105 days) in the 1G8-treated mice. This indicates an increase of median survival time of 38.5 days in 1G8-treated mice.

The inhibition of tumor growth correlated with prolonged life. Collectively, these results demonstrate that 1G8 treatment inhibited tumor growth and increased the survival time of orthotopic tumor-bearing mice. Thus, these results suggest that treatment with 1G8 increased survival time, by inhibiting tumor growth.

Treatment with 1G8 effectively inhibited tumor growth on smaller orthotopic tumors. Thus, 1G8 may represent an effective therapeutic treatment for minimal residual disease, in recurrent local disease, after primary treatment and in metastatic tumor formation. The results of mice treated with the 3C5 antibody are similar to the data obtained from mice treated with the 1G8 antibody. The mice bearing LAPC-9 AD tumors, treated with the anti-PSCA monoclonal antibody, 3C5, exhibited a decrease in serum PSA levels. This result indicates that 3C5 inhibits growth of tumors expressing PSCA.

Two separate experiments were conducted to evaluate the effect of 3C5 treatment. The mice treated with 3C5 antibody exhibited a lower rate of increase in the level of serum PSA, compared to the mice treated with phosphate buffer solution (FIGS. 68A and B).

This result suggests that the 3C5 antibody inhibited tumor growth. In FIG. 68A, each data point represents the mean PSA level for mice receiving PBS (n=4) or 3C5 (n=5). In FIG. 68B, each data point represents the mean PSA level for mice receiving PBS (n=6) or 3C5 (n=6).

The mice treated with 3C5 antibody exhibited prolonged life (FIG. 69A), compared to the mice treated with PBS (FIG. 69B). In the first experiment, the median survival time of the PBS-treated mice was 52 days (range 45–59 days), compared to more than 92 days (range 59 to +125 days) in the 3C5-treated group (FIG. 69A) (one mouse is still alive). In the second experiment, the median survival time in PBS-treated mice was 43 days (range 29–57), compared to 57.5 days in the 3C5-treated mice (range 33–82 days) (FIG. 69B).

The inhibition of tumor growth correlated with prolonged life. Collectively, these results demonstrate that 3C5 treatment inhibited tumor growth and thereby increased the survival time of orthotopic tumor-bearing mice. Thus, these results indicate that treatment with 3C5 increased survival time, by inhibiting tumor growth.

Example 25

Inhibition of established PC3-PSCA tumor growth and prolonged survival following anti-PSCA antibody treatment alone or in combination with doxorubicin.

The following examples demonstrate that 1G8, an anti-PSCA monoclonal antibody, inhibited the growth of established subcutaneous, PC3-PSCA prostate tumors (AI), growing in SCID mice. Additionally, 1G8, when administered alone or in combination with doxorubicin, inhibited the growth of prostate tumors. Furthermore, treatment with 1G8 prolonged the survival of these mice, when administered alone or in combination with doxorubicin. Treatment with 1G8 and doxorubicin appears to result in a synergistic inhibitory effect on tumor growth and survival.

PSCA-expressing PC3 cells

PC3-PSCA cells were derived by retroviral gene transfer. Briefly, PSCA cDNA was inserted into the retroviral vector pSR-α (Muller, et al., 1991 *Molec. Cell. Biol.* 11:1785-1792)). Amphotropic retrovirus was generated by co-transfection of 293T cells with pSR-α containing PSCA and a retroviral helper plasmid containing the amphotropic envelope protein. PC3 cells were subsequently infected with the PSCA containing amphotropic retrovirus, and 48 hours after infection the cells were selected by growth in medium containing the neomycin analogue G418. After 2–3 weeks of selection and expansion, a Western blot was performed to confirm that the PC3-PSCA cells express PSCA protein. Parental PC3 or PC3 cells infected with an empty vector that did not contain PSCA were both negative for PSCA protein expression.

Subcutaneous Injections

PC3-PSCA cells were grown in T-150 flasks in DMEM+ 10% FBS prior to the injections. The cells were grown to log phase, harvested, washed, counted, then mixed with Matrigel at a 1:1 dilution, and kept on ice. For injection, male IcR-SCID mice were shaved on their flanks, and each mouse received a single subcutaneous injection of about $1 \times 10^6$ cells in a volume of 100 µl on the right flank. The growth of PC3-PSCA tumors was followed by caliper measurements of the growing tumors. The mice were selected for treatment when the tumor reached the size of 100–200 mm$^3$, at approximately 9 days after the subcutaneous injection. The tumor size was measured at days +9, +15, +23, +29, +36, and +43 post injection.

Treatment with PBS

The control mice were treated with about 0.5 to 0.8 ml of phosphate buffer solution (Gibco) (FIGS. 66A and B).

Treatment with 1G8

The mice treated with 1G8, were administered 1 mg of 1G8, three times per week for three consecutive weeks.

Treatment with Doxorubicin

An LD$_{50}$ experiment was performed to determine the maximum tolerable dose of doxorubicin. Doxorubicin (Sigma) and was resuspended in sterile PBS. Doxorubicin was administered by intraperitoneal injection, at the following doses: 50 µg, 25 µg, 12.5 µg, and 6.75 µg. At the highest dose, 50 µg, all the mice died within 2 weeks. At the lower dose ranges, the mice survived for more than 4 weeks. The maximal tolerable dose was 25 µg.

The mice treated with only doxorubicin, were administered 25 µg, once weekly for three consecutive weeks.

Treatment with 1G8 and doxorubicin

The mice treated with 1G8 and doxorubicin, were administered 1 mg of 1G8 three times per week for three consecutive weeks (FIG. 70; 1G8=arrows), and were administered 25 µg of doxorubicin once weekly for three consecutive weeks (FIG. 70; doxorubicin=( )).

Results—Treatment with 1G8 alone or in Combination with Doxorubicin Results in Inhibition of Tumor Growth The mice bearing PC3-PSCA tumors, treated with anti-PSCA monoclonal antibody, 1G8, alone or in combination with doxorubicin, exhibited a decrease in tumor growth compared to mice treated with phosphate buffer solution or doxorubicin alone (FIG. 70). These results indicate that 1G8 inhibits the growth of tumors expressing PSCA. These results also suggest that the combination of 1G8 and doxorubicin act synergistically to inhibit tumor growth.

Each data point represents the mean tumor volume for mice receiving PBS (n=5), doxorubicin (n=6), 1G8 (n=6), or 1G8+doxorubicin (n=6).

The mice treated with doxorubicin exhibited a slightly lower tumor growth rate, compared to mice treated with PBS (e.g., 4% growth inhibition at day 43). In contrast, mice treated with 1G8 antibody alone exhibited a greater reduction in tumor growth rate, compared to the mice treated with PBS (e.g., 20% growth inhibition at day 43). The mice treated with the combination of 1G8 and doxorubicin exhibited a slightly greater reduction in tumor growth rate, compared to the mice treated with PBS (e.g., 36% growth inhibition at day 43).

Treatment with 1G8 alone, in this subcutaneous model using PC3-PSCA xenografts, effectively inhibited tumor growth on established androgen-independent tumors (e.g., PC3 cells are hormone refractory). Furthermore, the combination of 1G8 and doxorubicin showed augmented tumor growth inhibitory effects. Thus, treatment with the combination of 1G8 and doxorubicin represents an effective therapeutic treatment for prostate cancer patients with metastatic disease who have failed hormone ablation therapy.

Example 26

Anti-PSCA Monoclonal Antibodies Circulate and Target PSCA-Expressing Tumors

In one study, SCID mice bearing established, subcutaneous, LAPC-9 AD tumors, described in Example 18 C4 above, were treated with either control mouse IgG or 3C5 anti-PSCA mAb as described. On day 34, 6 days after the last antibody treatment, the mice were sacrificed and the tumors were explanted. In a different study, tumor-bearing SCID mice were treated with control mouse IgG or 1G8. The presence of antibody in the tumor samples from both studies was detected by either Western blot analysis or immunohistochemistry (IHC).

Immunohistochemistry

Explanted tumors were fixed in formalin and embedded in paraffin for immunohistochemical analysis (performed by QualTek Molecular Labs, Santa Barbara, Calif.). The paraffin blocks were sliced, the slices were fixed on slides, and the slides were probed with biotinylated goat anti-mouse IgG followed by an avidin-biotin complex (ABC) conjugated to peroxidase enzyme (Vector Labs, Burlingame, Calif.). DAB (diaminobenzidine) chromogen was used to develop the reaction which yielded a brown precipitate. Slides were subsequently counterstained with hematoxylin and then coverslipped. Staining was performed on a TechMate 1000 automated staining instrument (Ventana Medical Systems, Inc., Tucson, Ariz.) at room temperature (FIG. 71).

Results—Immunohistochemistry

FIG. 71 demonstrates that the 3C5 antibody localized in the LAPC-9 AD tumors from the 3C5-treated mice, but not with control IgG-treated mice. Additionally, antibody could be detected throughout the tumor.

Western Blotting

Explanted tumors from 3 mice in the IgG-treated group and the 3C5-treated group, (e.g., the mice as described in Example 18 C4 above), were lysed in boiling SDS sample 5 buffer. The cell lysates were electrophoresed in SDS-PAGE gels, transferred to nitrocellulose filters, probed with goat anti-mouse IgG-HRP antibodies (Southern Biotech, Birmingham, Ala.), and visualized by enhanced chemiluminescence. The mouse IgG control antibody and 3C5 were also run on the gel as controls (FIG. 72).

In a similar experiment, LAPC-9 AD subcutaneous tumor-bearing mice were treated with either control mouse IgG or the 1G8 anti-PSCA mAb. On day 30, which was 7 days after the last antibody treatment, the mice were sacrificed and tumors were explanted. Western blot analysis was performed on explanted tumors from 3 mice in each group. The explanted tumors were lysed in boiling SDS sample buffer, the cell lysates were electrophoresed in SDS-PAGE gels, transferred to nitrocellulose, probed with goat antimouse IgG-HRP antibodies (Southern Biotech, Birmingham, Ala.), and visualized by enhanced chemiluminescence. The mouse IgG control antibody and 1G8 were also run on the gel as controls (FIG. 73).

Results—Western Blotting

FIG. 72 demonstrates that IgG heavy and light chains were readily detected in tumor lysates from the 3C5 treated mice, but not in the mouse IgG control treated mice.

FIG. 73 demonstrates that IgG heavy and light chains were readily detected in tumor lysates from the 1G8 treated mice, but not in the mouse IgG control treated mice.

These results demonstrate that anti-PSCA mAbs, such as 3C5 and 1G8, can circulate and target a PSCA-expressing tumor, after administration to tumor-bearing mice. Furthermore the antibody localization is specific since control mouse IgG, which does not recognize PSCA, is either absent from the tumors, or present at very low levels when compared to tumors from anti-PSCA treated mice. These results suggest that anti-PSCA mAbs have the potential to circulate through the body and localize to primary and metastatic, PSCA-expressing tumors in cancer patients. Furthermore, conjugated anti-PSCA mAbs may be capable of effectively destroying PSCA-expressing tumors for local, locally recurring and metastatic disease.

What is claimed is:

1. A method for detecting a Prostate Stem Cell Antigen (PSCA) protein of bone (SEQ ID NO:2), said method comprising:
   obtaining a sample;
   contacting the sample with an antibody that recognizes and binds the PSCA protein; and,
   detecting binding of the antibody with the PSCA protein in the sample.

2. The method of claim 1, wherein the sample is a bone tissue sample.

3. The method of claim 1, wherein the detecting step comprises determining whether a complex is formed between the PSCA protein and the antibody, wherein the presence of a complex indicates that PSCA protein is in the sample.

4. The method of claim 1, wherein the sample is a cell, tissue or biological fluid.

5. The method of claim 4, wherein the biolofical fluid is urine, blood, serum, or phlegm.

6. The method of claim 1, wherein the antibody is labeled, so as to produce a detectable signal, with a compound selected from the group consisting of a radiolabel, an enzyme, a chromophore and a fluorescer.

7. The method of claim 1, wherein the antibody is produced by a hybridoma designated HB-12612, as deposited with the American Type Culture Collection.

8. The method of claim 1, wherein the antibody is produced by a hybridoma designated HB-12613, as deposited with the American Type Culture Collection.

9. The method of claim 1, wherein the antibody is produced by a hybridoma designated HB-12614, as deposited with the American Type Culture Collection.

10. The method of claim 1, wherein the antibody is produced by a hybridoma designated HB-12615, as deposited with the American Type Culture Collection.

11. The method of claim 1, wherein the antibody is produced by a hybridoma designated HB-12616, as deposited with the American Type Culture Collection.

12. The method of claim 1, wherein the antibody is produced by a hybridoma designated HB-12617, as deposited with the American Type Culture Collection.

13. The method of claim 1, wherein the antibody is produced by a hybridoma designated HB-12618, as deposited with the American Type Culture Collection.

* * * * *

UNITED STATES PATENT AND TRADEMARK OFFICE
CERTIFICATE OF CORRECTION

PATENT NO.       : 6,541,212 B2
APPLICATION NO.  : 09/564329
DATED            : April 1, 2003
INVENTOR(S)      : Robert E. Reiter et al.

It is certified that error appears in the above-identified patent and that said Letters Patent is hereby corrected as shown below:

Column 1, Line 5, after 1999, please insert --claiming the priority of provisional applications, U.S. Ser. Nos. 60/124,658 filed Mar. 16, 1999; 60/120,536 filed Feb. 17, 1999; and 60/113,230 filed Dec. 21, 1998--.

Column 1, Lines 17-20, please delete "This application further claims the benefit of the filing dates of U.S. Ser. Nos. 60/124,658 filed Mar. 16, 1999; 60/120,536 filed Feb. 17, 1999; and 60/113,230 filed Dec. 21, 1998".

Signed and Sealed this

Eighth Day of July, 2008

JON W. DUDAS
*Director of the United States Patent and Trademark Office*